(12) United States Patent
    Erickson et al.

(10) Patent No.: US 11,813,196 B2
(45) Date of Patent: Nov. 14, 2023

(54) DIAGNOSTIC METHODS AND APPARATUS

(71) Applicant: ForSight Vision4, Inc., South San Francisco, CA (US)

(72) Inventors: Signe Erickson, San Francisco, CA (US); Darren Doud, Los Altos, CA (US); Eugene de Juan, Jr., Brisbane, CA (US); Yair Alster, San Francisco, CA (US); Cary J. Reich, San Francisco, CA (US); Kathleen Cogan Farinas, Los Altos, CA (US)

(73) Assignee: ForSight Vision4, Inc., South San Francisco, CA (US)

( * ) Notice: Subject to any disclaimer, the term of this patent is extended or adjusted under 35 U.S.C. 154(b) by 1085 days.

(21) Appl. No.: 16/540,617

(22) Filed: Aug. 14, 2019

(65) Prior Publication Data
    US 2020/0030142 A1    Jan. 30, 2020

Related U.S. Application Data

(63) Continuation of application No. 14/129,200, filed as application No. PCT/US2012/044695 on Jun. 28, 2012, now Pat. No. 10,398,592.

(60) Provisional application No. 61/595,618, filed on Feb. 6, 2012, provisional application No. 61/538,736, filed on Sep. 23, 2011, provisional application No. 61/503,492, filed on Jun. 30, 2011, provisional application No. 61/502,157, filed on Jun. 28, 2011.

(51) Int. Cl.
    *A61F 9/00*     (2006.01)
    *A61B 10/00*    (2006.01)

(52) U.S. Cl.
    CPC ........ *A61F 9/0017* (2013.01); *A61B 10/0045* (2013.01); *A61F 2250/0067* (2013.01)

(58) Field of Classification Search
    CPC ........... A61F 9/0017; A61F 2250/0067; A61B 10/0045
    USPC ......................................................... 604/294
    See application file for complete search history.

(56) References Cited

U.S. PATENT DOCUMENTS

| | | |
|---|---|---|
| 1,747,814 A | 2/1930 | Bradley |
| 2,564,977 A | 8/1951 | Hu et al. |
| 2,585,815 A | 2/1952 | McLintock |
| 2,646,042 A | 7/1953 | Hu |
| 2,886,497 A | 5/1959 | Butler |
| 3,232,117 A | 2/1966 | Gilmont |
| 3,416,530 A | 12/1968 | Ness |
| 3,612,089 A | 10/1971 | Beguiristain |

(Continued)

FOREIGN PATENT DOCUMENTS

| | | |
|---|---|---|
| CN | 101505683 A | 8/2009 |
| EP | 0033042 B1 | 8/1984 |

(Continued)

OTHER PUBLICATIONS

U.S. Appl. No. 13/814,466, filed Jun. 28, 2013, 2013/0274691.

(Continued)

*Primary Examiner* — Andrew J Mensh
(74) *Attorney, Agent, or Firm* — Mintz Levin Cohn Ferris Glovsky and Popeo, P.C.

(57) ABSTRACT

An apparatus to treat a patient comprises a container to receive fluid of a device implanted in the eye. The fluid of the device can be analyzed to determine a component of the vitreous humor of the eye.

18 Claims, 65 Drawing Sheets

(56) References Cited

U.S. PATENT DOCUMENTS

| | | |
|---|---|---|
| 3,618,604 A | 11/1971 | Ness |
| 3,641,237 A | 2/1972 | Gould et al. |
| 3,734,095 A | 5/1973 | Santomieri |
| 3,828,777 A | 8/1974 | Ness |
| 3,831,583 A | 8/1974 | Edmunds, Jr. et al. |
| 3,845,201 A | 10/1974 | Haddad et al. |
| 3,902,495 A | 9/1975 | Weiss et al. |
| 3,914,402 A | 10/1975 | Shell |
| 3,916,899 A | 11/1975 | Theeuwes et al. |
| 3,926,188 A | 12/1975 | Baker et al. |
| 3,949,748 A | 4/1976 | Malmin |
| 3,949,750 A | 4/1976 | Freeman |
| 3,961,628 A | 6/1976 | Arnold |
| 3,977,404 A | 8/1976 | Theeuwes |
| 3,995,635 A | 12/1976 | Higuchi et al. |
| 4,008,719 A | 2/1977 | Theeuwes et al. |
| 4,014,333 A | 3/1977 | McIntyre |
| 4,014,334 A | 3/1977 | Theeuwes et al. |
| 4,014,335 A | 3/1977 | Arnold |
| 4,034,756 A | 7/1977 | Higuchi et al. |
| 4,034,758 A | 7/1977 | Theeuwes |
| 4,077,407 A | 3/1978 | Theeuwes et al. |
| 4,111,201 A | 9/1978 | Theeuwes |
| 4,111,203 A | 9/1978 | Theeuwes |
| 4,135,514 A | 1/1979 | Zaffaroni et al. |
| 4,160,452 A | 7/1979 | Theeuwes |
| 4,164,559 A | 8/1979 | Miyata et al. |
| 4,179,497 A | 12/1979 | Cohen et al. |
| 4,186,184 A | 1/1980 | Zaffaroni |
| 4,200,098 A | 4/1980 | Ayer et al. |
| 4,220,152 A | 9/1980 | Dresback |
| 4,220,153 A | 9/1980 | Dresback |
| 4,256,108 A | 3/1981 | Theeuwes |
| 4,298,000 A | 11/1981 | Thill et al. |
| 4,300,557 A | 11/1981 | Refojo et al. |
| 4,309,776 A | 1/1982 | Berguer |
| 4,326,525 A | 4/1982 | Swanson et al. |
| 4,327,725 A | 5/1982 | Cortese et al. |
| 4,343,787 A | 8/1982 | Katz |
| 4,439,196 A | 3/1984 | Higuchi |
| 4,439,198 A | 3/1984 | Brightman, II et al. |
| 4,475,916 A | 10/1984 | Himmelstein |
| 4,484,922 A | 11/1984 | Rosenwald |
| 4,519,801 A | 5/1985 | Edgren |
| 4,609,374 A | 9/1986 | Ayer |
| 4,627,850 A | 12/1986 | Deters et al. |
| 4,634,418 A | 1/1987 | Binder |
| 4,634,427 A | 1/1987 | Hannula et al. |
| 4,673,405 A | 6/1987 | Guittard et al. |
| 4,693,886 A | 9/1987 | Ayer |
| 4,712,550 A | 12/1987 | Sinnett |
| 4,730,013 A | 3/1988 | Bondi et al. |
| 4,737,150 A | 4/1988 | Baeumle et al. |
| 4,774,091 A | 9/1988 | Yamahira et al. |
| 4,777,049 A | 10/1988 | Magruder et al. |
| 4,781,675 A | 11/1988 | White |
| 4,851,228 A | 7/1989 | Zentner et al. |
| 4,853,229 A | 8/1989 | Theeuwes |
| 4,863,457 A | 9/1989 | Lee |
| 4,865,846 A | 9/1989 | Kaufman |
| 4,883,459 A | 11/1989 | Calderon |
| 4,959,217 A | 9/1990 | Sanders et al. |
| 4,979,938 A | 12/1990 | Stephen et al. |
| 5,049,142 A | 9/1991 | Herrick et al. |
| 5,053,030 A | 10/1991 | Herrick et al. |
| 5,084,021 A | 1/1992 | Baldwin |
| 5,098,443 A | 3/1992 | Parel et al. |
| 5,128,145 A | 7/1992 | Edgren et al. |
| 5,141,748 A | 8/1992 | Rizzo |
| 5,147,647 A | 9/1992 | Darougar |
| 5,164,188 A | 11/1992 | Wong |
| 5,171,270 A | 12/1992 | Herrick |
| 5,174,999 A | 12/1992 | Magruder et al. |
| 5,238,687 A | 8/1993 | Magruder et al. |
| 5,273,530 A | 12/1993 | del Cerro et al. |
| 5,277,912 A | 1/1994 | Lowe et al. |
| 5,282,829 A | 2/1994 | Hermes |
| 5,300,114 A | 4/1994 | Gwon et al. |
| 5,322,504 A | 6/1994 | Doherty et al. |
| 5,322,691 A | 6/1994 | Darougar et al. |
| 5,324,518 A | 6/1994 | Orth et al. |
| 5,334,189 A | 8/1994 | Wade |
| 5,336,175 A | 8/1994 | Mames |
| 5,358,473 A | 10/1994 | Mitchell |
| 5,364,343 A | 11/1994 | Apolet et al. |
| 5,378,475 A | 1/1995 | Smith et al. |
| 5,413,572 A | 5/1995 | Wong et al. |
| 5,443,505 A | 8/1995 | Wong et al. |
| 5,466,233 A | 11/1995 | Weiner et al. |
| 5,476,448 A | 12/1995 | Urich |
| 5,476,511 A | 12/1995 | Gwon et al. |
| 5,554,132 A | 9/1996 | Straits et al. |
| 5,562,915 A | 10/1996 | Lowe et al. |
| 5,578,042 A | 11/1996 | Cumming |
| 5,674,193 A | 10/1997 | Hayes |
| 5,681,572 A | 10/1997 | Seare, Jr. |
| 5,725,493 A | 3/1998 | Avery et al. |
| 5,755,684 A | 5/1998 | Chen |
| 5,766,242 A | 6/1998 | Wong et al. |
| 5,770,076 A | 6/1998 | Chu et al. |
| 5,773,019 A | 6/1998 | Ashton et al. |
| 5,792,099 A | 8/1998 | DeCamp et al. |
| 5,797,898 A | 8/1998 | Santini, Jr. et al. |
| 5,807,581 A | 9/1998 | Rosenblatt et al. |
| 5,817,075 A | 10/1998 | Giungo |
| 5,824,072 A | 10/1998 | Wong |
| 5,830,173 A | 11/1998 | Avery et al. |
| 5,830,546 A | 11/1998 | Ehret et al. |
| 5,836,935 A | 11/1998 | Ashton et al. |
| 5,868,697 A | 2/1999 | Richter et al. |
| 5,902,598 A | 5/1999 | Chen et al. |
| 5,916,584 A | 6/1999 | O'Donoghue et al. |
| 5,928,662 A | 7/1999 | Phillips |
| 5,951,512 A | 9/1999 | Dalton |
| 5,968,008 A | 10/1999 | Grams |
| 5,972,369 A | 10/1999 | Roorda et al. |
| 5,985,328 A | 11/1999 | Chu et al. |
| 6,001,386 A | 12/1999 | Ashton et al. |
| 6,123,861 A | 9/2000 | Santini, Jr. et al. |
| 6,196,993 B1 | 3/2001 | Cohan et al. |
| 6,251,090 B1 | 6/2001 | Avery et al. |
| 6,303,290 B1 | 10/2001 | Liu et al. |
| 6,331,313 B1 | 12/2001 | Wong et al. |
| 6,331,523 B1 | 12/2001 | Kljavin et al. |
| 6,375,972 B1 | 4/2002 | Guo et al. |
| 6,395,300 B1 | 5/2002 | Straub et al. |
| 6,413,540 B1 | 7/2002 | Yaacobi |
| 6,416,777 B1 | 7/2002 | Yaacobi |
| 6,420,399 B1 | 7/2002 | Graff et al. |
| 6,468,264 B1 | 10/2002 | Gillis et al. |
| 6,472,162 B1 | 10/2002 | Coelho et al. |
| 6,605,066 B1 | 8/2003 | Gravagna et al. |
| 6,620,139 B1 | 9/2003 | Plicchi et al. |
| 6,663,668 B1 | 12/2003 | Chaouk et al. |
| 6,669,950 B2 | 12/2003 | Yaacobi |
| 6,685,940 B2 | 2/2004 | Andya et al. |
| 6,695,821 B1 | 2/2004 | Sjaarda |
| 6,713,081 B2 | 3/2004 | Robinson et al. |
| 6,719,750 B2 | 4/2004 | Varner et al. |
| 6,740,077 B1 | 5/2004 | Brandau et al. |
| 6,756,049 B2 | 6/2004 | Brubaker et al. |
| 6,756,058 B2 | 6/2004 | Brubaker et al. |
| 6,869,412 B2 | 3/2005 | Ross |
| 6,932,983 B1 | 8/2005 | Straub et al. |
| 6,976,982 B2 | 12/2005 | Santini, Jr. et al. |
| 6,986,900 B2 | 1/2006 | Yaacobi |
| 7,026,329 B2 | 4/2006 | Crain et al. |
| 7,074,426 B2 | 7/2006 | Kochinke |
| 7,077,848 B1 | 7/2006 | de Juan, Jr. et al. |
| 7,090,681 B2 | 8/2006 | Weber et al. |
| 7,094,222 B1 | 8/2006 | Siekas et al. |
| 7,094,226 B2 | 8/2006 | Yaacobi |
| 7,117,870 B2 | 10/2006 | Prescott |
| 7,141,023 B2 | 11/2006 | Diermann et al. |

(56) References Cited

U.S. PATENT DOCUMENTS

| | | |
|---|---|---|
| 7,141,152 B2 | 11/2006 | Le Febre |
| 7,181,287 B2 | 2/2007 | Greenberg |
| 7,195,774 B2 | 3/2007 | Carvalho et al. |
| 7,195,778 B2 | 3/2007 | Fleshner-Barak et al. |
| 7,211,272 B2 | 5/2007 | Renner et al. |
| 7,276,050 B2 | 10/2007 | Franklin |
| 7,468,065 B2 | 12/2008 | Weber et al. |
| 7,476,510 B2 | 1/2009 | Kapur et al. |
| 7,585,517 B2 | 9/2009 | Cooper et al. |
| 7,615,141 B2 | 11/2009 | Schwartz et al. |
| 7,621,907 B2 | 11/2009 | Rodstrom |
| 7,625,927 B2 | 12/2009 | Klimko et al. |
| 7,678,078 B1 | 3/2010 | Peyman et al. |
| 7,686,016 B2 | 3/2010 | Wharton et al. |
| 7,699,820 B1 | 4/2010 | French |
| 7,709,049 B2 | 5/2010 | Chappa |
| 7,883,717 B2 | 2/2011 | Varner et al. |
| 7,893,040 B2 | 2/2011 | Loftsson et al. |
| 7,906,136 B2 | 3/2011 | Wong et al. |
| 7,909,800 B2 | 3/2011 | Cazzini |
| 7,914,442 B1 | 3/2011 | Gazdzinski |
| 7,939,094 B2 | 5/2011 | Schwarz et al. |
| 7,973,068 B2 | 7/2011 | Demopulos et al. |
| 8,795,712 B2 | 8/2014 | de Juan, Jr. et al. |
| 8,808,727 B2 | 8/2014 | de Juan, Jr. et al. |
| 8,905,963 B2 | 12/2014 | de Juan, Jr. et al. |
| 9,066,779 B2 | 6/2015 | de Juan, Jr. et al. |
| 9,861,521 B2 | 1/2018 | de Juan, Jr. et al. |
| 9,883,968 B2 | 2/2018 | Doud et al. |
| 10,398,592 B2 * | 9/2019 | Erickson ............... A61P 27/02 |
| 2002/0026176 A1 | 2/2002 | Varner et al. |
| 2002/0049389 A1 * | 4/2002 | Abreu .................. G02C 7/04 600/318 |
| 2002/0086051 A1 | 7/2002 | Viscasillas |
| 2002/0106395 A1 | 8/2002 | Brubaker |
| 2002/0110591 A1 | 8/2002 | Brubaker et al. |
| 2002/0110592 A1 | 8/2002 | Brubaker et al. |
| 2002/0110635 A1 | 8/2002 | Brubaker et al. |
| 2002/0188244 A1 | 12/2002 | Smith |
| 2003/0003129 A1 | 1/2003 | Yaacobi |
| 2003/0005945 A1 | 1/2003 | Onishi et al. |
| 2003/0014036 A1 | 1/2003 | Varner et al. |
| 2003/0047011 A1 | 3/2003 | Diermann et al. |
| 2003/0118649 A1 | 6/2003 | Gao et al. |
| 2003/0119177 A1 | 6/2003 | Gruber et al. |
| 2003/0120217 A1 | 6/2003 | Abergel |
| 2003/0176854 A1 | 9/2003 | Rodstrom |
| 2003/0185872 A1 | 10/2003 | Kochinke |
| 2003/0212383 A1 | 11/2003 | Cote et al. |
| 2003/0233067 A1 | 12/2003 | McIntosh et al. |
| 2003/0235603 A1 | 12/2003 | Schwarz et al. |
| 2004/0011651 A1 | 1/2004 | Becker et al. |
| 2004/0019325 A1 | 1/2004 | Shekalim |
| 2004/0024371 A1 | 2/2004 | Plicchi et al. |
| 2004/0029832 A1 | 2/2004 | Zeldis |
| 2004/0092911 A1 | 5/2004 | Yaacobi |
| 2004/0106906 A1 | 6/2004 | Yaacobi |
| 2004/0131654 A1 | 7/2004 | Yaacobi |
| 2004/0131655 A1 | 7/2004 | Yaacobi |
| 2004/0171997 A1 | 9/2004 | Wilson et al. |
| 2004/0209359 A1 | 10/2004 | Yayon et al. |
| 2004/0230183 A1 * | 11/2004 | Breegi ................. A61F 9/0017 604/891.1 |
| 2004/0247487 A1 | 12/2004 | Commercon et al. |
| 2004/0260240 A1 * | 12/2004 | Beyerlein ............. A61B 5/489 604/117 |
| 2004/0260380 A1 | 12/2004 | Marco et al. |
| 2004/0260381 A1 | 12/2004 | Marco et al. |
| 2005/0064010 A1 | 3/2005 | Cooper et al. |
| 2005/0074497 A1 | 4/2005 | Schultz |
| 2005/0112175 A1 | 5/2005 | Yaacobi |
| 2005/0112759 A1 | 5/2005 | Radisic et al. |
| 2005/0113806 A1 | 5/2005 | De Carvalho et al. |
| 2005/0119737 A1 | 6/2005 | Bene et al. |
| 2005/0143363 A1 | 6/2005 | De Juan et al. |
| 2005/0154399 A1 | 7/2005 | Weber et al. |
| 2005/0163711 A1 | 7/2005 | Nycz et al. |
| 2005/0171491 A1 * | 8/2005 | Minh Miner ........ A61M 5/1411 604/257 |
| 2005/0181018 A1 | 8/2005 | Peyman |
| 2005/0244467 A1 | 11/2005 | Nivaggioli et al. |
| 2005/0244469 A1 | 11/2005 | Whitcup et al. |
| 2005/0255144 A1 | 11/2005 | Schultz |
| 2005/0256499 A1 | 11/2005 | Pettis et al. |
| 2005/0271703 A1 | 12/2005 | Anderson et al. |
| 2005/0271706 A1 | 12/2005 | Anderson et al. |
| 2005/0276837 A1 | 12/2005 | Anderson et al. |
| 2005/0277802 A1 | 12/2005 | Larsen et al. |
| 2005/0281861 A1 | 12/2005 | Hughes et al. |
| 2005/0281863 A1 | 12/2005 | Anderson et al. |
| 2005/0287188 A1 | 12/2005 | Anderson et al. |
| 2006/0013835 A1 | 1/2006 | Anderson et al. |
| 2006/0039952 A1 | 2/2006 | Yaacobi |
| 2006/0052754 A1 | 3/2006 | Fields |
| 2006/0057277 A1 | 3/2006 | Chappa |
| 2006/0073182 A1 | 4/2006 | Wong et al. |
| 2006/0104969 A1 | 5/2006 | Oray et al. |
| 2006/0110428 A1 | 5/2006 | deJuan et al. |
| 2006/0129215 A1 | 6/2006 | Helmus et al. |
| 2006/0154981 A1 | 7/2006 | Klimko et al. |
| 2006/0172941 A1 | 8/2006 | Rastelli et al. |
| 2006/0182783 A1 | 8/2006 | Hughes et al. |
| 2006/0200097 A1 | 9/2006 | Humayun et al. |
| 2006/0233858 A1 | 10/2006 | Tzekov et al. |
| 2006/0246112 A1 | 11/2006 | Snyder et al. |
| 2006/0257450 A1 | 11/2006 | Mudumba et al. |
| 2006/0258000 A1 | 11/2006 | Allen et al. |
| 2006/0258994 A1 | 11/2006 | Avery |
| 2007/0020336 A1 | 1/2007 | Loftsson et al. |
| 2007/0021357 A1 | 1/2007 | Tobia et al. |
| 2007/0026037 A1 | 2/2007 | Kloke et al. |
| 2007/0059336 A1 | 3/2007 | Hughes et al. |
| 2007/0071756 A1 | 3/2007 | Peyman |
| 2007/0072933 A1 | 3/2007 | Peyman |
| 2007/0077270 A1 | 4/2007 | Wen |
| 2007/0078359 A1 | 4/2007 | Luloh et al. |
| 2007/0083155 A1 | 4/2007 | Muller |
| 2007/0088414 A1 | 4/2007 | Campbell et al. |
| 2007/0119450 A1 | 5/2007 | Wharton et al. |
| 2007/0128644 A1 | 6/2007 | Munenaka |
| 2007/0131610 A1 | 6/2007 | Peng et al. |
| 2007/0131611 A1 | 6/2007 | Peng et al. |
| 2007/0134305 A1 | 6/2007 | Zilberman |
| 2007/0141111 A1 | 6/2007 | Suokas et al. |
| 2007/0191863 A1 | 8/2007 | De Juan et al. |
| 2007/0197491 A1 | 8/2007 | Robin et al. |
| 2007/0203174 A1 | 8/2007 | Klimko et al. |
| 2007/0212388 A1 | 9/2007 | Patravale et al. |
| 2007/0212397 A1 | 9/2007 | Roth |
| 2007/0233037 A1 | 10/2007 | Gifford, et al. |
| 2007/0235331 A1 | 10/2007 | Simpson et al. |
| 2007/0243230 A1 | 10/2007 | de Juan et al. |
| 2007/0260201 A1 | 11/2007 | Prausnitz et al. |
| 2007/0265599 A1 | 11/2007 | Castillejos |
| 2007/0269487 A1 | 11/2007 | de Juan et al. |
| 2008/0003219 A1 | 1/2008 | Peyman |
| 2008/0004329 A1 | 1/2008 | Jamieson et al. |
| 2008/0015545 A1 | 1/2008 | Sanchez et al. |
| 2008/0020045 A1 | 1/2008 | Chappa et al. |
| 2008/0038316 A1 | 2/2008 | Wong et al. |
| 2008/0057561 A1 | 3/2008 | Takahashi et al. |
| 2008/0066739 A1 | 3/2008 | LeMahieu et al. |
| 2008/0066741 A1 | 3/2008 | LeMahieu et al. |
| 2008/0069854 A1 | 3/2008 | Xiao et al. |
| 2008/0089923 A1 | 4/2008 | Burkstrand et al. |
| 2008/0108954 A1 | 5/2008 | Mathias et al. |
| 2008/0111282 A1 | 5/2008 | Xie et al. |
| 2008/0124372 A1 | 5/2008 | Hossainy et al. |
| 2008/0139674 A1 | 6/2008 | Archambeau et al. |
| 2008/0145406 A1 | 6/2008 | Asgharian et al. |
| 2008/0146679 A1 | 6/2008 | Archambeau et al. |
| 2008/0147021 A1 | 6/2008 | Jani |
| 2008/0152694 A1 | 6/2008 | Lobl et al. |
| 2008/0154241 A1 | 6/2008 | Burkstrand et al. |

(56) References Cited

U.S. PATENT DOCUMENTS

| | | |
|---|---|---|
| 2008/0161741 A1 | 7/2008 | Bene et al. |
| 2008/0167600 A1 | 7/2008 | Peyman |
| 2008/0172014 A1 | 7/2008 | Whitcup et al. |
| 2008/0181930 A1 | 7/2008 | Rodstrom et al. |
| 2008/0195218 A1 | 8/2008 | Jones |
| 2008/0207502 A1 | 8/2008 | Rastelli et al. |
| 2008/0213611 A1 | 9/2008 | Asgari |
| 2008/0216736 A1 | 9/2008 | David |
| 2008/0228127 A1 | 9/2008 | Burns et al. |
| 2008/0233053 A1 | 9/2008 | Gross et al. |
| 2008/0233171 A1 | 9/2008 | Whitcup et al. |
| 2008/0233172 A1 | 9/2008 | Whitcup et al. |
| 2008/0233173 A1 | 9/2008 | Whitcup et al. |
| 2008/0241219 A1 | 10/2008 | Whitcup et al. |
| 2008/0241220 A1 | 10/2008 | Whitcup et al. |
| 2008/0241221 A1 | 10/2008 | Whitcup et al. |
| 2008/0241222 A1 | 10/2008 | Whitcup et al. |
| 2008/0241223 A1 | 10/2008 | Nivaggioli et al. |
| 2008/0249501 A1 | 10/2008 | Yamasaki |
| 2008/0286338 A1 | 11/2008 | Rosenthal et al. |
| 2008/0292679 A1 | 11/2008 | Lyons et al. |
| 2009/0005864 A1 | 1/2009 | Eggleston |
| 2009/0012485 A1 | 1/2009 | Michaels et al. |
| 2009/0036827 A1 | 2/2009 | Cazzini |
| 2009/0043253 A1 | 2/2009 | Podaima |
| 2009/0047335 A1 | 2/2009 | Rastelli et al. |
| 2009/0081271 A1 | 3/2009 | Clarke et al. |
| 2009/0081272 A1 | 3/2009 | Clarke et al. |
| 2009/0082631 A1 | 3/2009 | Cronin et al. |
| 2009/0087494 A1 | 4/2009 | Kompella et al. |
| 2009/0092654 A1 | 4/2009 | de Juan, Jr. et al. |
| 2009/0093752 A1 | 4/2009 | Richard et al. |
| 2009/0099626 A1 | 4/2009 | de Juan, Jr. et al. |
| 2009/0104243 A1 | 4/2009 | Utkhede et al. |
| 2009/0105749 A1 | 4/2009 | de Juan et al. |
| 2009/0124986 A1 | 5/2009 | Hayakawa |
| 2009/0124997 A1 | 5/2009 | Pettis et al. |
| 2009/0192493 A1 | 7/2009 | Meng et al. |
| 2009/0196903 A1* | 8/2009 | Kliman ............ A61P 27/02 424/423 |
| 2009/0214601 A1 | 8/2009 | Chappa et al. |
| 2009/0220572 A1 | 9/2009 | Deschatelets et al. |
| 2009/0224064 A1 | 9/2009 | Brodbeck et al. |
| 2009/0234449 A1 | 9/2009 | De Juan, Jr. et al. |
| 2009/0240208 A1 | 9/2009 | Cowan |
| 2009/0240215 A1 | 9/2009 | Humayun et al. |
| 2009/0247458 A1 | 10/2009 | Watson et al. |
| 2009/0258069 A1 | 10/2009 | Burnier et al. |
| 2009/0259212 A1 | 10/2009 | Sabbah |
| 2009/0263346 A1 | 10/2009 | Taft et al. |
| 2009/0263495 A1 | 10/2009 | Watson et al. |
| 2009/0274730 A1 | 11/2009 | Watson et al. |
| 2009/0274771 A1 | 11/2009 | Watson et al. |
| 2009/0280470 A1 | 11/2009 | Fare et al. |
| 2009/0306025 A1 | 12/2009 | Lane |
| 2009/0306595 A1 | 12/2009 | Shih et al. |
| 2009/0318545 A1 | 12/2009 | Silver et al. |
| 2009/0324686 A1 | 12/2009 | Cooper et al. |
| 2009/0324687 A1 | 12/2009 | Cooper et al. |
| 2009/0324688 A1 | 12/2009 | Cooper et al. |
| 2009/0324689 A1 | 12/2009 | Cooper et al. |
| 2009/0324690 A1 | 12/2009 | Cooper et al. |
| 2009/0326448 A1 | 12/2009 | Huo et al. |
| 2009/0326489 A1 | 12/2009 | Kensy et al. |
| 2010/0003333 A1 | 1/2010 | Watson et al. |
| 2010/0004189 A1 | 1/2010 | Watson et al. |
| 2010/0008997 A1 | 1/2010 | Watson et al. |
| 2010/0009008 A1 | 1/2010 | Watson et al. |
| 2010/0010452 A1 | 1/2010 | Paques et al. |
| 2010/0011888 A1 | 1/2010 | Pawliszyn et al. |
| 2010/0015157 A1 | 1/2010 | Andya et al. |
| 2010/0015158 A1 | 1/2010 | Robinson et al. |
| 2010/0016786 A1 | 1/2010 | Drews et al. |
| 2010/0021464 A1 | 1/2010 | Archambeau et al. |
| 2010/0022943 A1 | 1/2010 | Mauch et al. |
| 2010/0022945 A1 | 1/2010 | Rodstrom |
| 2010/0023033 A1 | 1/2010 | Mauch et al. |
| 2010/0028442 A1 | 2/2010 | Archambeau et al. |
| 2010/0028443 A1 | 2/2010 | Watson et al. |
| 2010/0030136 A1 | 2/2010 | Dacquay et al. |
| 2010/0034870 A1 | 2/2010 | Sim et al. |
| 2010/0083963 A1 | 4/2010 | Wharton et al. |
| 2010/0100054 A1 | 4/2010 | Cormier et al. |
| 2010/0114017 A1 | 5/2010 | Lenker et al. |
| 2010/0114309 A1 | 5/2010 | de Juan, Jr. et al. |
| 2010/0158980 A1 | 6/2010 | Kopczynski et al. |
| 2010/0168535 A1 | 7/2010 | Robinson et al. |
| 2010/0174272 A1 | 7/2010 | Weiner |
| 2010/0185205 A1 | 7/2010 | Novakovic et al. |
| 2010/0189765 A1 | 7/2010 | Erickson et al. |
| 2010/0191176 A1 | 7/2010 | Ho et al. |
| 2010/0197512 A1 | 8/2010 | Trinkle et al. |
| 2010/0211041 A1 | 8/2010 | Omori et al. |
| 2010/0216702 A1 | 8/2010 | Szkudlinski et al. |
| 2010/0221309 A1 | 9/2010 | Myers et al. |
| 2010/0227904 A1 | 9/2010 | Kabra et al. |
| 2010/0255061 A1* | 10/2010 | de Juan, Jr. ............ A61P 27/02 604/93.01 |
| 2010/0256597 A1 | 10/2010 | Prausnitz et al. |
| 2010/0266664 A1 | 10/2010 | Asgharian et al. |
| 2010/0286121 A1 | 11/2010 | Rohrs et al. |
| 2010/0286791 A1 | 11/2010 | Goldsmith |
| 2010/0297046 A1 | 11/2010 | Schwartz et al. |
| 2010/0297120 A1 | 11/2010 | Beliveau et al. |
| 2010/0297193 A1 | 11/2010 | Archambeau et al. |
| 2010/0303917 A1 | 12/2010 | Watson et al. |
| 2010/0303918 A1 | 12/2010 | Watson et al. |
| 2010/0310664 A1 | 12/2010 | Watson et al. |
| 2010/0310665 A1 | 12/2010 | Watson et al. |
| 2010/0316723 A1 | 12/2010 | Watson et al. |
| 2010/0330146 A1 | 12/2010 | Chauhan et al. |
| 2011/0009571 A1 | 1/2011 | Taft et al. |
| 2011/0014264 A1 | 1/2011 | Helmus et al. |
| 2011/0033933 A1 | 2/2011 | Gharib et al. |
| 2011/0034448 A1 | 2/2011 | Chang et al. |
| 2011/0081384 A1 | 4/2011 | Archambeau et al. |
| 2011/0098686 A1 | 4/2011 | Varner et al. |
| 2011/0104155 A1 | 5/2011 | Rekik |
| 2011/0108025 A1 | 5/2011 | Fink et al. |
| 2011/0111006 A1 | 5/2011 | Wong et al. |
| 2011/0112188 A1 | 5/2011 | Tobia et al. |
| 2011/0117083 A1 | 5/2011 | Bais et al. |
| 2011/0125178 A1 | 5/2011 | Drews et al. |
| 2011/0159073 A1 | 6/2011 | deJuan et al. |
| 2011/0190723 A1 | 8/2011 | Fangrow |
| 2011/0206646 A1 | 8/2011 | Alfonso et al. |
| 2012/0029445 A1 | 2/2012 | de Juan, Jr. et al. |
| 2012/0029470 A1 | 2/2012 | Juan, Jr. et al. |
| 2012/0095439 A1 | 4/2012 | de Juan, Jr. et al. |
| 2013/0165860 A1 | 6/2013 | Doud et al. |
| 2013/0218081 A1 | 8/2013 | Roth |
| 2013/0245544 A1 | 9/2013 | de Juan, Jr. et al. |
| 2013/0274691 A1 | 10/2013 | de Juan, Jr. et al. |
| 2013/0274692 A1 | 10/2013 | Alster et al. |
| 2013/0304031 A1 | 11/2013 | Varner et al. |
| 2013/0324918 A1 | 12/2013 | de Juan, Jr. et al. |
| 2013/0324942 A1 | 12/2013 | de Juan, Jr. et al. |
| 2014/0031769 A1 | 1/2014 | de Juan, Jr. et al. |
| 2014/0073714 A1 | 3/2014 | Reich et al. |
| 2014/0276482 A1 | 9/2014 | Astafieva et al. |
| 2014/0296800 A1 | 10/2014 | Erickson et al. |
| 2014/0358125 A1 | 12/2014 | de Juan, Jr. et al. |
| 2015/0080846 A1 | 3/2015 | de Juan, Jr. et al. |
| 2015/0297402 A1 | 10/2015 | de Juan, Jr. et al. |
| 2016/0101046 A1 | 4/2016 | Reich et al. |
| 2016/0184134 A1 | 6/2016 | Varner et al. |
| 2016/0258855 A1 | 9/2016 | Farinas et al. |
| 2016/0302965 A1 | 10/2016 | Erickson et al. |
| 2017/0165110 A1 | 6/2017 | Erickson et al. |
| 2017/0172794 A1 | 6/2017 | Varner et al. |
| 2017/0258634 A1 | 9/2017 | de Juan, Jr. et al. |
| 2018/0161202 A1 | 6/2018 | de Juan, Jr. et al. |
| 2018/0243130 A1 | 8/2018 | Doud et al. |
| 2018/0243131 A1 | 8/2018 | Erickson et al. |

(56) References Cited

U.S. PATENT DOCUMENTS

| | | |
|---|---|---|
| 2018/0289542 A1 | 10/2018 | de Juan, Jr. et al. |
| 2018/0292403 A1 | 10/2018 | de Juan, Jr. et al. |
| 2019/0336335 A1 | 11/2019 | de Juan, Jr. et al. |

FOREIGN PATENT DOCUMENTS

| | | |
|---|---|---|
| EP | 0 228 185 A1 | 11/1986 |
| EP | 0498471 A2 | 8/1992 |
| EP | 0500143 A2 | 8/1992 |
| EP | 0671165 A2 | 9/1995 |
| EP | 0295248 B2 | 4/1999 |
| EP | 0944658 B1 | 6/2003 |
| EP | 1671624 | 6/2006 |
| EP | 1385452 B1 | 9/2006 |
| EP | 1409065 B1 | 1/2007 |
| EP | 1337284 B1 | 12/2007 |
| EP | 1911481 | 4/2008 |
| EP | 1521572 B1 | 3/2009 |
| JP | 01-149716 A | 6/1989 |
| JP | 01-197429 A | 8/1989 |
| JP | 08509636 A | 10/1996 |
| WO | WO-8804573 | 6/1988 |
| WO | WO-9007545 | 7/1990 |
| WO | WO-94/24969 A1 | 11/1994 |
| WO | WO-95/28984 A1 | 11/1995 |
| WO | WO-97/29850 | 8/1997 |
| WO | WO-98/25982 | 6/1998 |
| WO | WO-99/11244 | 3/1999 |
| WO | WO-00/48660 | 8/2000 |
| WO | WO-01/26714 | 4/2001 |
| WO | WO-01/50943 | 7/2001 |
| WO | WO-0168016 | 9/2001 |
| WO | WO-02/100318 | 12/2002 |
| WO | WO-03028765 | 4/2003 |
| WO | WO-03/077972 | 9/2003 |
| WO | WO-03/082188 | 10/2003 |
| WO | WO-2004/000267 | 12/2003 |
| WO | WO-2004/112653 | 12/2004 |
| WO | WO-2005/016401 | 2/2005 |
| WO | WO-2005025413 A2 | 3/2005 |
| WO | WO-2005027906 | 3/2005 |
| WO | WO-2005028006 | 3/2005 |
| WO | WO-2005091922 | 10/2005 |
| WO | WO-2005107705 | 11/2005 |
| WO | WO-2005110362 | 11/2005 |
| WO | WO-2005110436 | 11/2005 |
| WO | WO-2005110473 | 11/2005 |
| WO | WO-2005117780 | 12/2005 |
| WO | WO-2006014484 | 2/2006 |
| WO | WO-2006015385 | 2/2006 |
| WO | WO-2006023530 | 3/2006 |
| WO | WO-2006031358 | 3/2006 |
| WO | WO-2006031388 | 3/2006 |
| WO | WO-2006044614 | 4/2006 |
| WO | WO-2006050221 | 5/2006 |
| WO | WO-2006068838 | 6/2006 |
| WO | WO-2006071554 | 7/2006 |
| WO | WO-2006082588 | 8/2006 |
| WO | WO-2006108054 | 10/2006 |
| WO | WO-2006127962 | 11/2006 |
| WO | WO-2006138609 | 12/2006 |
| WO | WO-2007012974 | 2/2007 |
| WO | WO-2007035473 | 3/2007 |
| WO | WO-2007035621 | 3/2007 |
| WO | WO-2007038453 | 4/2007 |
| WO | WO-2007044534 | 4/2007 |
| WO | WO-2007047744 | 4/2007 |
| WO | WO-2007/066339 | 6/2007 |
| WO | WO-2007/084582 | 7/2007 |
| WO | WO-2007/084765 | 7/2007 |
| WO | WO-2007101204 | 9/2007 |
| WO | WO-2007/115259 A2 | 10/2007 |
| WO | WO-2007117394 | 10/2007 |
| WO | WO-2007131050 | 11/2007 |
| WO | WO-2007133761 | 11/2007 |
| WO | WO-2007133762 | 11/2007 |
| WO | WO-2008003043 | 1/2008 |
| WO | WO-2008005240 | 1/2008 |
| WO | WO-2008011125 | 1/2008 |
| WO | WO-2008019265 | 2/2008 |
| WO | WO-2008033924 | 3/2008 |
| WO | WO-2008040062 | 4/2008 |
| WO | WO-2008045272 | 4/2008 |
| WO | WO-2008/061043 A2 | 5/2008 |
| WO | WO-2008052145 | 5/2008 |
| WO | WO-2008060359 | 5/2008 |
| WO | WO-2008076544 | 6/2008 |
| WO | WO-2008094989 | 8/2008 |
| WO | WO-2008115290 | 9/2008 |
| WO | WO-2008116165 | 9/2008 |
| WO | WO-2008144340 | 11/2008 |
| WO | WO-2008144919 | 12/2008 |
| WO | WO-2009012075 | 1/2009 |
| WO | WO-2009023615 | 2/2009 |
| WO | WO-2009046164 | 4/2009 |
| WO | WO-2009055620 | 4/2009 |
| WO | WO-2009055671 | 4/2009 |
| WO | WO-2009055729 | 4/2009 |
| WO | WO-2009055824 | 4/2009 |
| WO | WO-2009061607 | 5/2009 |
| WO | WO-2009073192 | 6/2009 |
| WO | WO-2009086112 | 7/2009 |
| WO | WO-2009089409 | 7/2009 |
| WO | WO-2009094466 | 7/2009 |
| WO | WO-2009112878 | 9/2009 |
| WO | WO-2009117112 | 9/2009 |
| WO | WO-2009124096 | 10/2009 |
| WO | WO-2009128932 | 10/2009 |
| WO | WO-2009134929 | 11/2009 |
| WO | WO-2009137777 | 11/2009 |
| WO | WO-2009137780 A2 | 11/2009 |
| WO | WO-2010008424 | 1/2010 |
| WO | WO-2010021993 | 2/2010 |
| WO | WO-2010047753 | 4/2010 |
| WO | WO-2010062628 | 6/2010 |
| WO | WO-2010066714 | 6/2010 |
| WO | WO-2010/075565 | 7/2010 |
| WO | WO-2010078063 | 7/2010 |
| WO | WO-2010088548 | 8/2010 |
| WO | WO-2010093945 | 8/2010 |
| WO | WO-2010095940 | 8/2010 |
| WO | WO-2010125416 | 11/2010 |
| WO | WO-2010126908 | 11/2010 |
| WO | WO-2010135369 | 11/2010 |
| WO | WO-2010/141729 | 12/2010 |
| WO | WO-2010147661 | 12/2010 |
| WO | WO-2011008896 | 1/2011 |
| WO | WO-2011008897 | 1/2011 |
| WO | WO-2011028850 | 3/2011 |
| WO | WO-2011034627 | 3/2011 |
| WO | WO-2011079232 | 6/2011 |
| WO | WO-2012/019047 A2 | 2/2012 |
| WO | WO-2012019136 | 2/2012 |
| WO | WO-2013/003620 | 1/2013 |
| WO | WO-2013022801 | 2/2013 |

OTHER PUBLICATIONS

U.S. Appl. No. 14/753,574, filed Jun. 29, 2015, 2015/0297402.
U.S. Appl. No. 14/937,754, filed Nov. 10, 2015, 2016/0128867.
U.S. Appl. No. 15/102,191, filed Jun. 6, 2016, 2016/0302965.
U.S. Appl. No. 15/606,647, filed May 26, 2017, 2017/0258634.
U.S. Appl. No. 15/730,537, filed Oct. 11, 2017, 2018/0243131.
U.S. Appl. No. 15/807,396, filed Nov. 8, 2017, 2018/0292403.
U.S. Appl. No. 15/877,146, filed Jan. 22, 2018, 2018/0243130.
U.S. Appl. No. 16/004,085, filed Jun. 8, 2018, 2018/0289542.
U.S. Appl. No. 16/091,493, filed Oct. 4, 2018, 2019/0117454.
U.S. Appl. No. 16/386,854, filed Apr. 17, 2019, 2019/0336335.
PCT/US2018/61262, Nov. 15, 2018, WO 2019/10396.
"Juvederm", FDA, 2006, XP002670727, Retrieved from the Internet: URL:http://www.accessdata.fda.gov/cdrh_docs/pdf5/P050047b.pdf [retrieved on Mar. 1, 2012] p. 1, last paragraph.

(56) References Cited

OTHER PUBLICATIONS

"MAbPac SCX-10 Column for Monoclonal Antibody Variant Analysis." Dionex. Aug. 2010. [http://www.dionex.com/en-us/webdocs/87008-DS-MAbPac-SCX-10-Column-20Aug2010-LPN2567-03.pdf]. Web. Retrieved May 2012. 4 pages.

Andrews, "Effect of nonsteroidal anti-inflammatory drugs on LFA-1 and ICAM-1 expression in gastric mucosa," Am J Physiol. Apr. 1994;266(4 Pt 1):G657-664.

Arvo, Agenda for the Summer Eye Research Conference, (Jul. 2009). 7 pages.

Avery et al., "Intravitreal bevacizumab (Avastin) in the treatment of proliferative diabetic retinopathy," Ophthalmology. Oct. 2006, 113(10):1695-1705.e6.

Bakri et al., "The effect of intravitreal triamcinolone acetonide on intraocular pressure," Ophthalmic Surgery, Lasers and Imaging, Sep./Oct. 2003; 34(5): 386-390.

Bird et al., Transport Phenomena, John Wiley & Sons, Inc., New York, 1960, pp. 196-201.

Block et al., "Solubility and dissolution of triamcinolone acetonide," Journal of Pharmaceutical Sciences, Apr. 1973; 62(4):617-621.

Breslin, C.W., et al., "Chapter 7. Slow Release Artificial Tears", Symposium on Ocular Therapy pp. 77-83, 1977.

Castro et al., "Effect of COX inhibitors on VEGF-induced retinal vascular leakage and experimental corneal and choroidal neovascularization," Exp Eye Res. Aug. 2004;79(2):275-285.

Chirila et al., "The Vitreous Humor" in Handbook of Biomaterial Properties, eds. Black & Hastings. Chapman & Hall, London, 1998; pp. 125-131.

Cousins et al., "Program # 1251—Targeting Complement Factor 5 in Combination with Vascular Endothelial Growth Factor (VEGF) Inhibition for Neovascular Age Related Macular Degeneration (AMD): Results of a Phase 1 Study," [Presentation Abstract], AMD Clinical Trials Session # 220, May 3, 2010. 2 pages.

Deissler et al., "VEGF-induced effects on proliferation, migration and tight junctions are restored by ranibizumab (Lucentis) in microvascular retinal endothelial cells," Br J Ophthalmol 2008;92:839-843.

Del Amo, et al., Current & future ophthalmic drug delivery systems . . . , Drug Discovery Today, vol. 13, Nos. 3/4, Feb. 2008. pp. 135-143.

Donoso et al., "The role of inflammation in the pathogenesis of age-related macular degeneration," Surv Ophthalmol. Mar.-Apr. 2006;51(2):137-52.

Duvvuri et al., Drug Delivery to the Retina: Challenges and Opportunities, Expert Opinion on Biological Therapy, 2003, vol. 3(1): 45-56.

Duvvuri, S. et al. "Microdialysis assessment of drug delivery systems for vitreoretinal targets." Advanced Drug Delivery Reviews. 57(2005):2080-2091.

European Medicine Agency, Scientific Discussion; retrieved from the Internet; <http://www.ema.europa.eu/docs/en_GB/document_library/EPAR_-_Scientific_Discussion/human/000715/WC500043550.pdf>, EMEA 2007, 54 pages total. 2007.

Funatsu et al. "Association of vitreous inflammatory factors with diabetic macular edema," Ophthalmology 2009;116:73-79.

Gaudana et al., Recent Perspectives in Ocular Drug Delivery, Pharmaceutical Research, 2008. 20 pages.

Gaudreault et al., "Preclinical Pharmacokinetics of Ranibizumab (rhuFabV2) after a Single Intravitreal Administration," Investigative Ophthalmology and Visual Science. 2005;46:726-733. Retrieved from the Internet: <<http://www.iovs.org/cgi/reprint/46/2/726>>.

Gillies et al., "Intravitreal triamcinolone for refractory diabetic macular edema: two-year results of a double-masked, placebo-controlled, randomized clinical trial," Ophthalmology. Sep. 2006;113(9):1533-1538.

Haller, An Overview of Sustained-release Drug Implants, Retinal Physician, Jan. 2008. 4 pages.

Hastedt & Wright, "Diffusion in porous materials above the percolation threshold," Pharm. Res. Sep. 1990; 7(9):893-901 (1990).

Heier et al, "Ketorolac versus prednisolone versus combination therapy in the treatment of acute pseudophakic cystoid macular edema," Ophthalmology. Nov. 2000;107(11):2034-2038;discussion 2039.

International Search Report dated Jan. 28, 2013, for PCT application No. PCT/US2012/044695. 4 pages.

Janoria et al., Novel Approaches to Retinal Drug Delivery, Expert Opinion Drug Delivery, 2007, 4 (4):371-388.

Jena et al., "A Novel Technique for Surface Area and Particle Size Determination of Components of Fuel Cells and Batteries," Porous Materials, Inc., Dec. 2006, 3 pages total. Downloaded from the Internet: <<http://www.pmiapp.com/publications/docs/A_Novel_technique_for_surface_area.pdf>>.

Kang et al., "Inhibitory effects of anti-inflammatory drugs on interleukin-6 bioactivity," Biol Pharm Bull. Jun. 2001;24(6):701-703.

Katz, I.M., et al., "A Soluble Sustained-Release Ophthalmic Delivery Unit", 8:5 (May 1977) pp. 728-734.

Lamberts, D.W., M.D., et al., "A Clinical Study of Slow-Releasing Artificial Tears", Ophthalmology 85 (1978) pp. 794-800.

Lee, D.A., et al., "Glaucoma Filtration Surgery in Rabbits Using Bioerodible Polymers and 5-Fluorouracil", Ophthalmology 94:12 (1987) pp. 1523-1530.

Lee, D.A., et al., "The Use of Bioerodible Polymers and 5-Fluorouracil in Glaucoma Filtration Surgery", Investigative Ophthalmology & Visual Science 29-11 (1988) pp. 1692-1697.

Li, et al., An electrochemical introculardrug delivery device, Science Direct, Sensors and Actuators, www.sciencedirect.com,Jul. 4, 2007. pp. 41-48.

Lopez-Armada et al., "Modulation of cell recruitment by anti-inflammatory agents in antigen-induced arthritis," Ann Rheum Dis Nov. 2002;61(11):1027-1030.

Luncentis, INN-Ranibizumab, "Scientific Discussion," European Medicines Agency; retrieved from the Internet:<http://www.ema.europa.eu/docs/en_GB/document_library/EPAR_-_Assessment_Report_-_Variation/human/000715/WC500101009.pdf>. Oct. 21, 2010. 32 pages.

Metal Powder Industries Federation, Porous Metal Design Guidebook, 2007, 24 pages total. Downloaded from the Internet: <<http://www.mpif.org/DesignCenter/porous.pdf>>.

Miller, DP, et al., Thermophysical Properties of Trehalose and Its Concentrated Aqueous Solutions,Pharmaceutical Research, vol. 14, No. 5, 1997, pp. 578-590.

Molokhia et al., "Transscleral iontophoretic and intravitreal delivery of a macromolecule: Study of ocular distribution in vivo and postmortem with MRI", Experimental Eye Research 88 (2009) 418-425.

Moritera, T., et al., "Microspheres of Biodegradable Polymers as a Drug-Delivery System in the Vitreous", Investigative Ophthalmology & Visual Science 32-6 (1991) pp. 1785-1790.

MOTT Corporation, "Sintered Metal Powder Media," American Filtration & Separation Society 2007, 2 pages total. Downloaded from the Internet:<<http://www.afssociety.org/education/0907oneminute.htm>>.

Navarro, "The Optical Design of the Human Eye: a Critical Review," J Optom, Jan.-Mar. 2009 2(1): 3-18.

Nutan, MTH, et al., General Principles of Suspensions, in Pharmaceutical Suspensions From Formulation Development to Manufacturing, editors AK Kulshreshtha, et al., Spinger, 2010. 29 pages.

Okabe et al., "Intraocular tissue distribution of betamethasone after intrascleral administration using a non-biodegradable sustained drug delivery device," Investigative Ophthalmology and Visual Science. 2003;44:2702-2707. Downloaded from the Internet: <<http://www.iovs.org/cgi/reprint/44/6/2702>>.

Rosenfeld, "The Latest Research: Intravitreal Bevacizumab for Proliferative Diabetic Retinopathy," Review of Ophthalmology's Retina Online, Feb. 2006. 2 pages. Retrieved from the Internet: http://www.revophth.com/archive/newsletter/0206_retina.htm.

SALINE (medicine)—Wikipedia, the free encyclopedia. http://web.archive.org/web/20110205192937/http://en.wikipedia.org/wiki/Saline_(medicine). Apr. 27, 2012. 4 pages.

(56) References Cited

OTHER PUBLICATIONS

Sanborn G.E., et al., Sustained-Release Ganciclovir Therapy for Treatment of Cytomegalovirus Retinitis, Use of an Intravitreal Device, Arch. Ophthalmol, vol. 110, 188-195 (Feb. 1992).
Sharma, Rajesh K., Anna T. Rogojina, and K.V. Chalam. "Bevacizumab Therapy Normalizes the Pathological Intraocular Environment beyond Neutralizing VEGF." Molecular Vision 16 (2010): 2175-2184. Print.
Sheardown and Saltzman, Novel Drug Delivery Systems for Posterior Segment Ocular Disease, *Opthalmology: Ocular Angiogenesis: Diseases, Mechanisms and Therapeutics*, 2007, pp. 393-408.
Smith et al., "Spectrophotometric determination of pKa values for fluorescein using activity coefficient corrections," WaterSA 2002; 28(4):395-402.
Smith, T.J., et al., "Intravitreal Sustained-Release Ganciclovir", *Arch. Ophthamol* 110 (1992) pp. 255-258.
Soheilian et al., "Pilot Study of Intravitreal Injection of Diclofenac for Treatment of Macular Edema of Various Etiologies," Retina, Mar. 2010; 30(3): 509-515.
Stay et al. Computer Simulation of Convective and Diffusive Transport of Controlled-Release Drugs in the vitreous Humor, *Pharm Res* 2003,20(1), pp. 96-102.
Theodossiadis et al., "Intravitreal administration of the anti-tumor necrosis factor agent infliximab for neovascular age-related macular degeneration," Am J Ophthalmol. May 2009;147(5):825-830.
Weiner, A.L., "Chapter 13: Polymeric Drug Delivery Systems for the Eye", *Polymeric Site—Specific Pharmacotherapy*, pp. 315-346, Edited by A.J. Domb (1994) John Wiley & Sons Ltd.
Williams et al., "Treating Diabetic Macular Edema With Ocular NSAIDs," Retinal Physician, Nov. 2007; retrieved from the Internet Nov. 11, 2007. http://www.retinalphysician.com/article.aspx?article=101096>, 5 pages total.
Wright, P., et al. "Slow-Release Artificial Tear Inserts in the Treatment of Dry Eyes Resulting from the Oculomucocutaneous Syndrome", *British Journal of Ophthalmology* 67(1983) pp. 393-397.
Yao et al. (Prevention of Laser Photocoagulation Induced Choroidal Neovascularization Lesions by Intravitreal Doses of Ranibizumab in Cynomolgus Monkeys, ARVO 2009 abstract D906). 2 pages.

\* cited by examiner

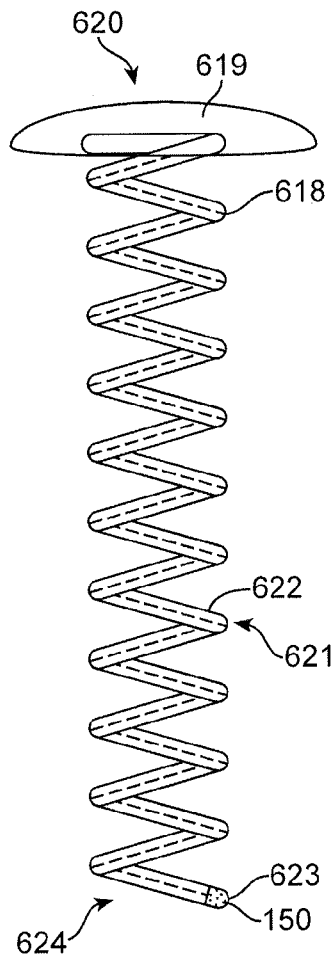
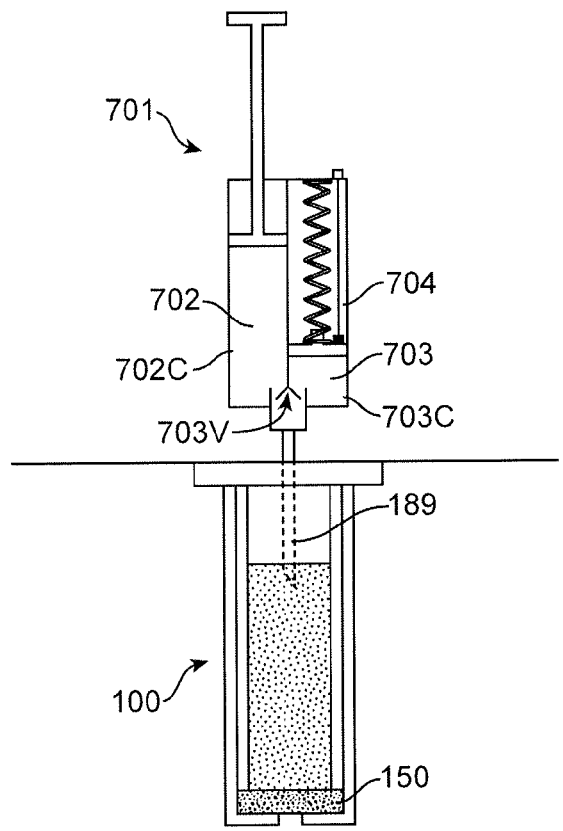
FIG. 44
FIG. 46
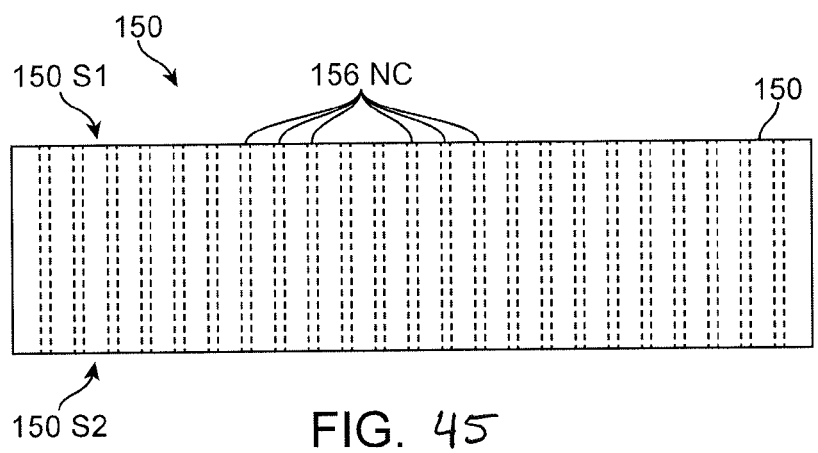
FIG. 45

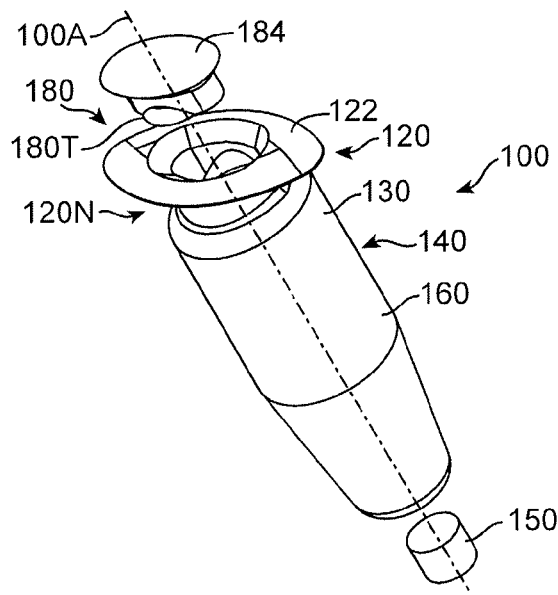
FIG. 75
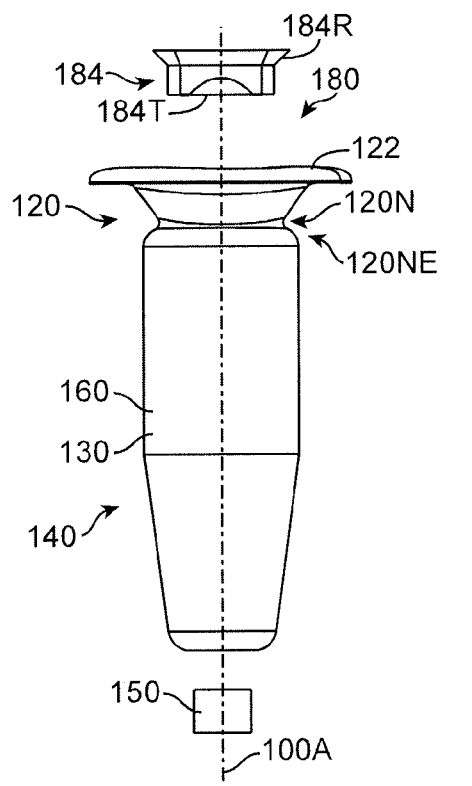 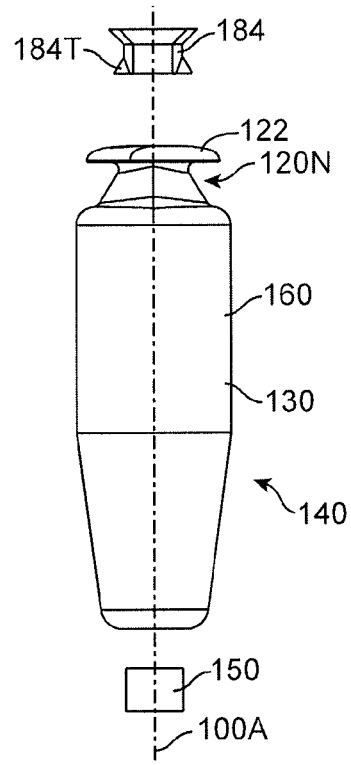
FIG. 76   FIG. 77

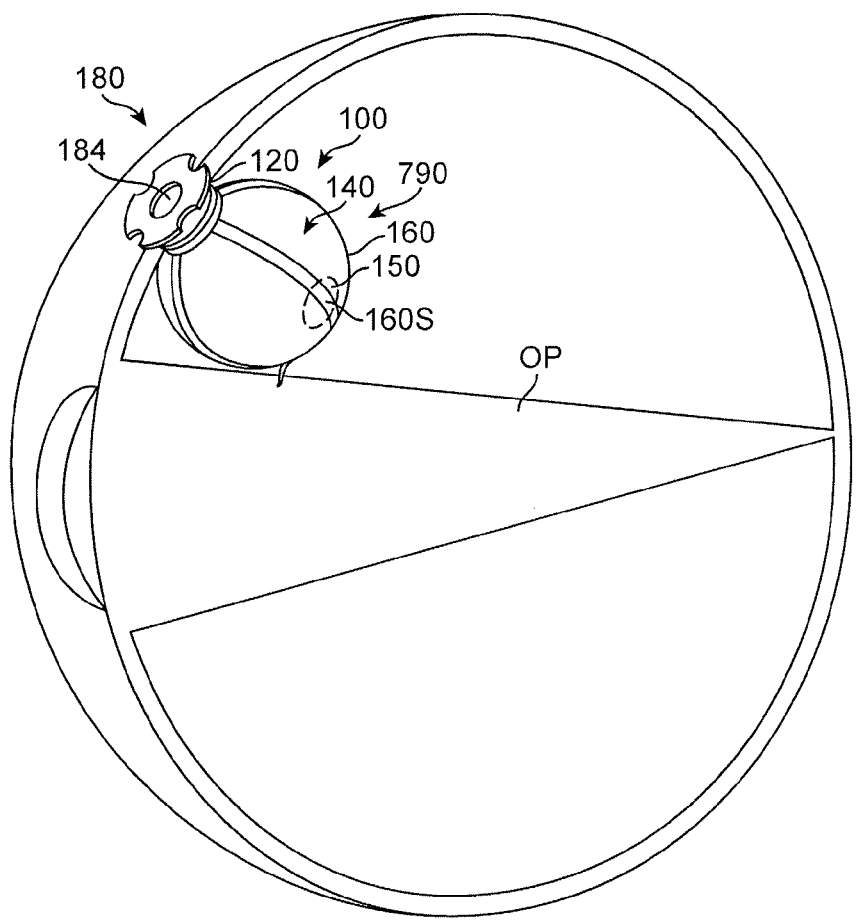
FIG. 78
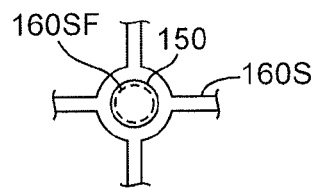 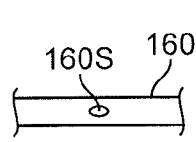 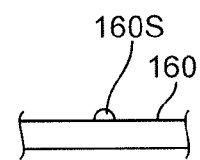
FIG. 79  FIG. 80  FIG. 81

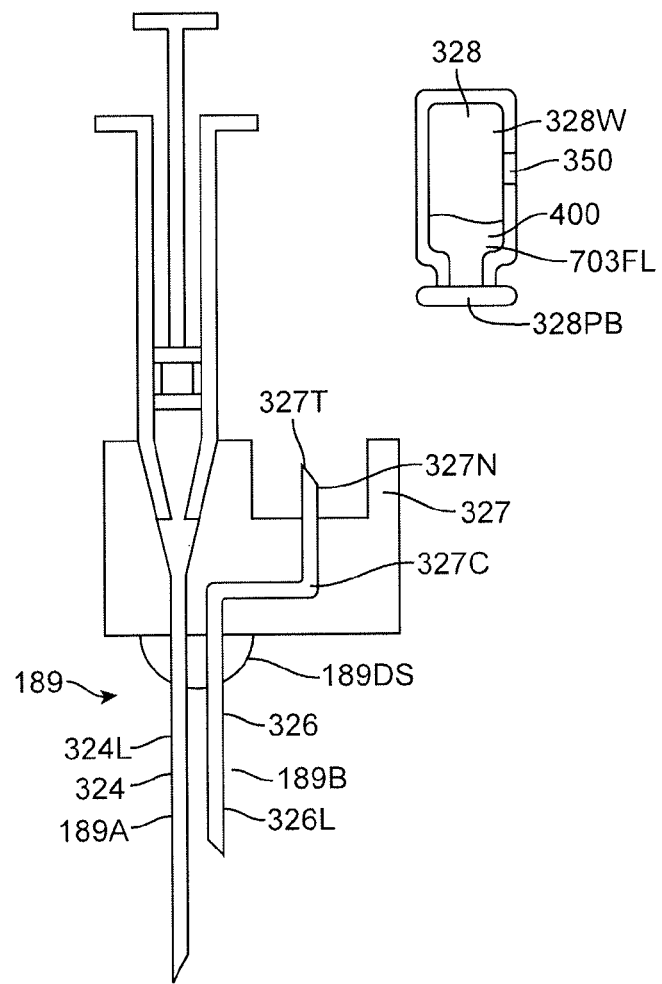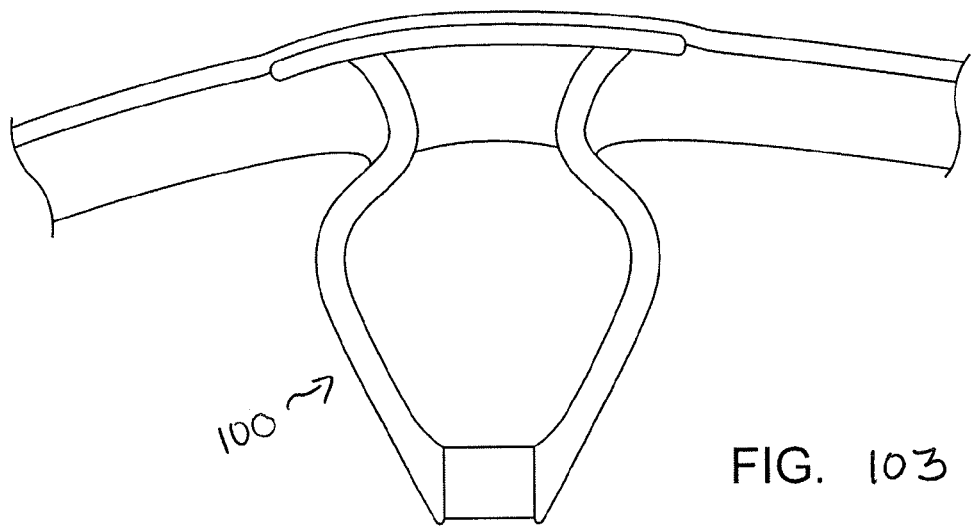
FIG. 103

Marker 1 Ranibizumab bound VEGF, MW = 93 kDa
Marker 2 GAPDH, MW = 37 kDa

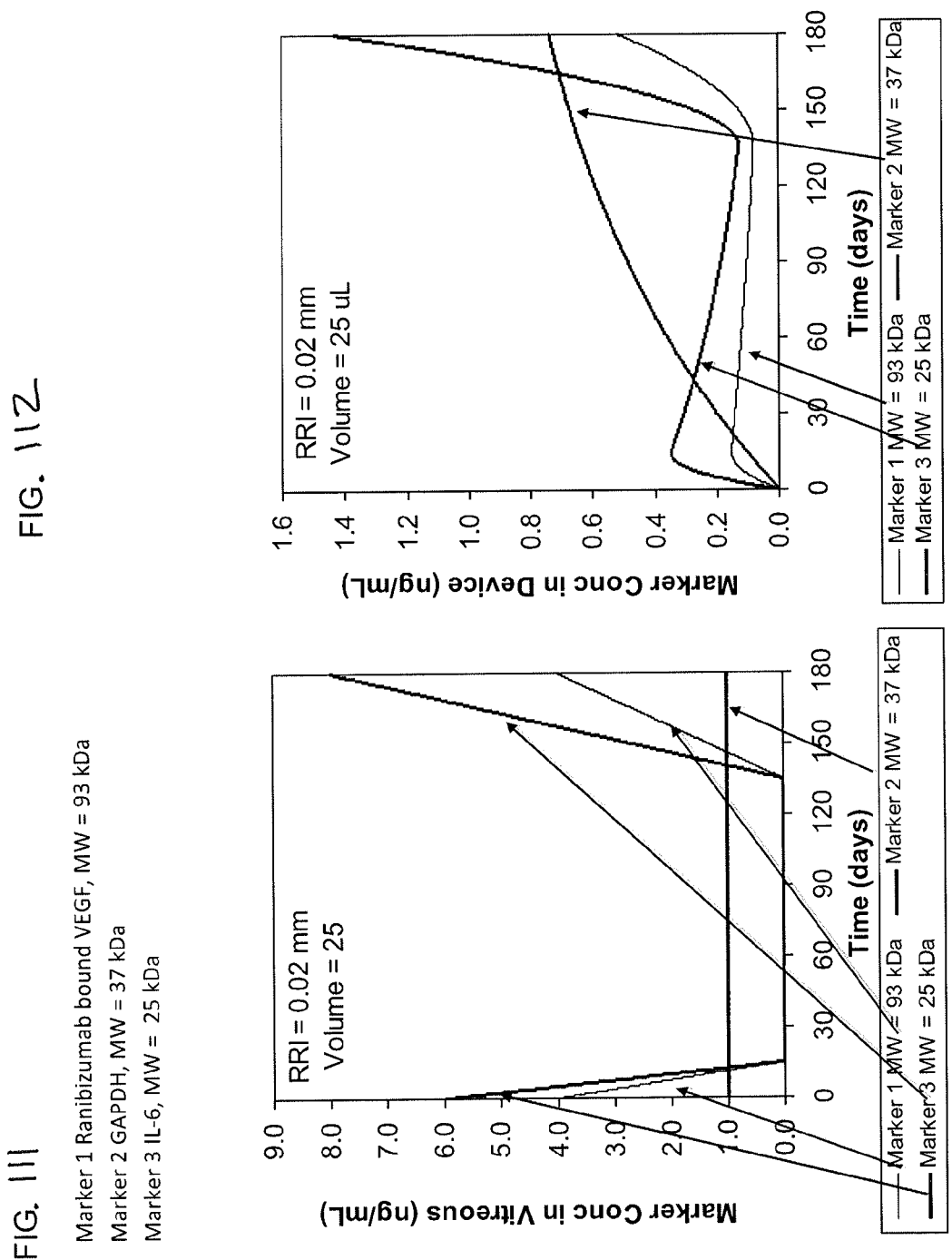

Marker 1 Ranibizumab bound VEGF, MW = 93 kDa
Marker 2 GAPDH, MW = 37 kDa
Marker 4 IL-8, MW = 9 kDa Marker 1 Ranibizumab bound VEGF, MW = 93 kDa
Marker 2 GAPDH, MW = 37 kDa
Marker 3 IL-6, MW = 25 kDa
Marker 4 IL-8, MW = 9 kDa Marker 5 C-Reactive Protein, MW = 125 kDa

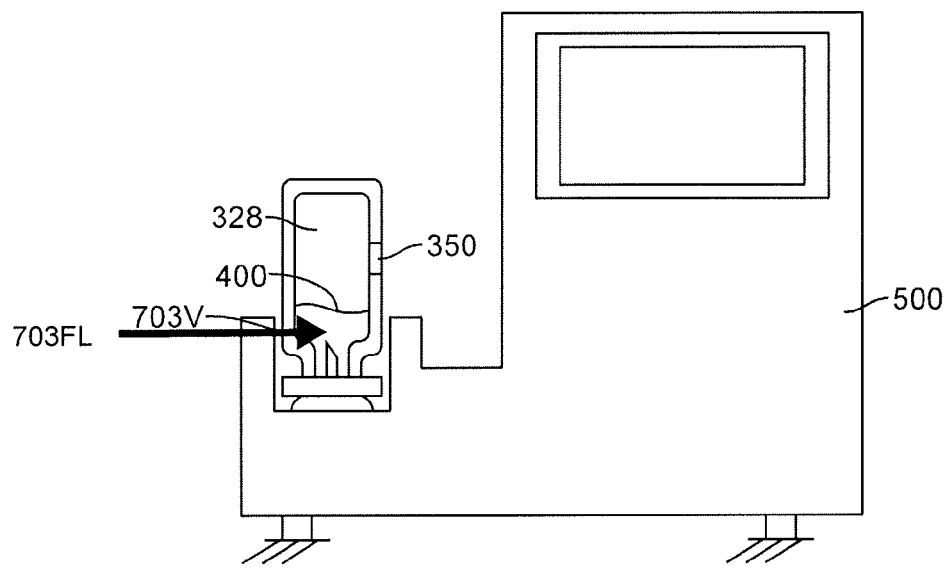
FIG. 124
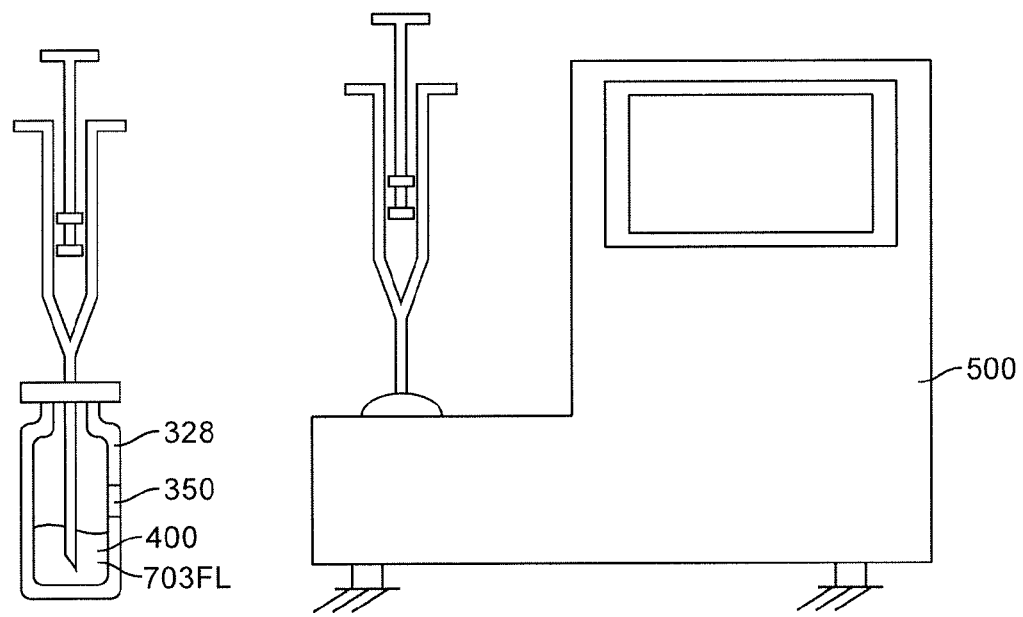
FIG. 125
FIG. 126

DIAGNOSTIC METHODS AND APPARATUS

CROSS-REFERENCES TO RELATED APPLICATIONS

This application is a continuation of U.S. application Ser. No. 14/129,200, filed Apr. 10, 2014, which is a 371 Application of PCT Application Serial No. PCT/US2012/044695, filed Jun. 28, 2012, which claims priority to U.S. Provisional Application Ser. No. 61/502,157, filed Jun. 28, 2011; U.S. Provisional Application Ser. No. 61/503,492, filed Jun. 30, 2011; U.S. Provisional Application Ser. No. 61/538,736, filed Sep. 23, 2011; and U.S. Provisional Application Ser. No. 61/595,618, filed Feb. 6, 2012, the full disclosures of which are incorporated herein by reference.

BACKGROUND

The present disclosure is generally directed to diagnosis and treatment of disease such as disease of the eye.

Prior methods and apparatus for treating tissue of the eye can be less than ideal in at least some instances. Although examination of the tissues of the eye can provide an indication of the condition of the eye, in at least some instances the tissue of the eye may indicate disease progression later than would be ideal. In at least some instances, it may be beneficial to treat the eye or modify treatment before tissue of the eye is altered by a disease of the eye. In at least some instances, the tissue of the eye can be damaged with progression of an eye disease and treatment of the eye may not occur until at least some damage to tissue has occurred.

At least some of the current methods to access the vitreous humor of the eye can be more invasive than would be ideal. Intravitreal taps and microdialysis can rely on insertion of a needle into the vitreous humor of the eye, and may not be well suited to diagnose the condition of the eye of a patient in at least some instances.

In light of the above, it would be desirable to provide improved diagnosis and treatment of diseases such as diseases of the eye. Ideally, these treatments would decrease at least some of the deficiencies of the prior art, and provide diagnosis and treatment.

SUMMARY

Some embodiments described herein provide improved methods and apparatus to treat diseases such as diseases of the eye. In many embodiments, a fluid of a device implanted in the eye is received in a container, and one or more components of the fluid of the implanted device identified to treat the eye. The components of the fluid of the implanted device may comprise one or more components of the eye or one or more components of a formulation placed in the device implanted in the eye. The components of the eye identified from the liquid of the implanted device can be used in many ways to treat the eye, and may comprise one or more components of the aqueous humor or the vitreous humor of the eye. In many embodiments, the eye can be treated based on one or more markers of a disease of the eye, such that the eye can be treated based on the markers prior to substantial damage to tissue of the eye. The marker may comprise one or more of a genetic marker, a genomic marker, or a protein marker. In many embodiments, the marker comprises a protein corresponding to one or more of a genetic marker or a protein marker. In many embodiments, the device implanted in the eye comprises a reservoir chamber to store a therapeutic agent and a porous structure coupled to the reservoir chamber to release the therapeutic agent into the vitreous humor or the aqueous humor of the eye. The volume of the chamber and the release rate of the porous structure can be tuned to an amount of therapeutic agent injected into the device. The amount of therapeutic agent in the reservoir chamber and the amount of the component in the eye can be related to the volume of the reservoir chamber and the release rate of the porous structure.

The components of the fluid of the implanted device may comprise one or more of a pathogen of the eye, an autogenic component of the eye, or a component placed in the implanted device such as a therapeutic agent or a stabilizer such as a surfactant, or combinations thereof. The eye can be diagnosed based on one or more of the pathogen, the autogenic component, or the component placed in the implanted device, or combinations thereof. In many embodiments, the treatment of the eye can be determined based on an autogenic component of the eye such as a growth factor. The therapeutic agent may interact with the autogenic component, and the amount of an autogenic component can be determined based on one or more of the amount of autogenic component, the amount of therapeutic agent, or an amount of therapeutic agent bound to the autogenic component. The autogenic component may comprise a growth factor such as vascular endothelial growth factor (hereinafter "VEGF"), and the therapeutic agent may comprise an antibody fragment such as ranibizumab to bind to the growth factor.

In many embodiments, the component placed in the implanted device comprises one or more components of a formulation placed in the implanted device, for example placed in the implanted device with injection. The injected formulation may comprise a therapeutic fluid comprising the therapeutic agent and a stabilizer. The amount of therapeutic agent and the amount of stabilizer in the fluid received from the implanted device can be measured and used to determine one or more of an amount of mixing of the therapeutic fluid with the implantable device fluid during placement, an amount of therapeutic agent in the implanted device prior to placement of the therapeutic fluid, rate of release of the therapeutic agent from the implant, or an amount of therapeutic fluid placed in the device and an amount of implantable device fluid remaining in the implanted device. In many embodiments, the amount of time since the prior injection of therapeutic fluid and the ratio of therapeutic agent and stabilizer can be used to determine the rate of release of the therapeutic agent from the implant.

The components of the eye identified from the liquid of the implanted device may comprise a plurality of markers. The plurality of markers may comprise a first plurality of markers from a first sample and a second plurality of markers from a second sample, and the first plurality of markers may comprise a first marker profile of the eye measured at a first time, and the second plurality of markers may comprise a second marker profile of the eye measured at a second time. The first marker profile can be compared to the second marker profile to one or more of diagnose or treat the patient.

BRIEF DESCRIPTION OF THE DRAWINGS

FIG. 44 shows a rigid porous structure as in FIG. 35 comprising a non-linear helical structure for sustained release, in accordance with embodiments.

FIG. 45 shows porous nanostructures, in accordance with embodiments, in accordance with embodiments.

FIG. 46 shows a therapeutic device coupled to an injector that removes material from the device and injects therapeutic agent into the device, according to embodiments, in accordance with embodiments.

FIG. 75, FIG. 76, and FIG. 77 show exploded assembly drawings for the therapeutic device as in FIGS. 70 to 74, in accordance with embodiments.

FIG. 78 shows an expandable therapeutic device comprising an expandable barrier material and support in an expanded configuration for extended release of the therapeutic agent, in accordance with embodiments.

FIG. 79 shows the distal end portion of the support 160S as in FIG. 78, in accordance with embodiments.

FIG. 80 shows the support 160S disposed inside the barrier 160, in accordance with embodiments.

FIG. 81 shows the support 160S disposed along the inner surface of the barrier 160, in accordance with embodiments.

FIG. 103 shows the cartridge assembly as in FIGS. 101-102 removed from the implanted therapeutic device and the container having the fluid of the implanted removed from the cartridge, in accordance with embodiments.

FIG. 110 shows concentrations of a first marker, a second housekeeping marker and a third marker in the vitreous humor over time in response to therapeutic agent, in which the third marker is more sensitive than the first marker to amounts of therapeutic agent, in accordance with embodiments.

FIG. 111 shows concentrations in the vitreous humor of a first marker having a molecular weight corresponding to Ranibizumab bound to VEGF, a second housekeeping marker having a molecular weight corresponding to GADPH and a third marker having a molecular weight corresponding to IL-6 in response to therapeutic agent, in which the third marker is more sensitive than the first and second markers to amounts of therapeutic agent, in accordance with embodiments.

FIG. 112 shows concentrations in the reservoir chamber of the implanted device corresponding to the marker concentration in the vitreous humor as in FIG. 111, in accordance with embodiments.

FIG. 124 shows the sample container coupled to the apparatus to analyze the sample of the device, in accordance with embodiments.

FIGS. 125 and 126 show fluid of the implanted device being drawn from the sample container into a syringe and the fluid from the sample container being injected to the apparatus to analyze the sample of the implanted therapeutic device, in accordance with embodiments.

DETAILED DESCRIPTION

Figure 1:
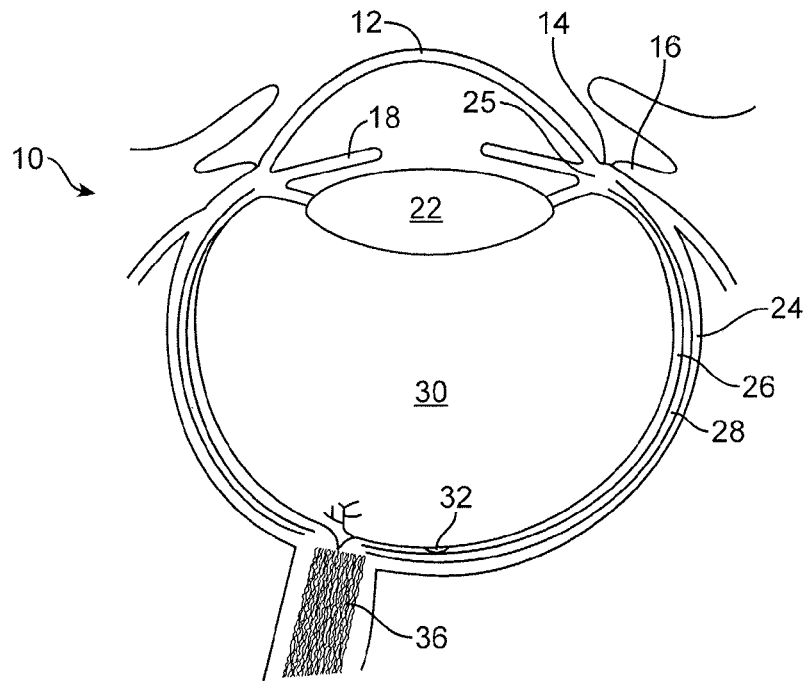
FIG. 1 shows an eye suitable for incorporation of the therapeutic device, in accordance with embodiments.

Embodiments as described herein can be combined in many ways to treat one or more of many diseases such as diseases of the eye. The embodiments can be beneficially combined with many known diagnostics, medicines and procedures, for example combined with known methods of diagnosing and treating the eye with a device implanted in the eye, and combinations thereof. Examples of implantable devices suitable for combination in accordance with embodiments of the present disclosure are described in U.S. patent application Ser. No. 12/696,678, filed 29 Jan. 2010, entitled "Posterior Segment Drug Delivery", published as U.S. Pub. No. 2010/0255061 on Oct. 7, 2010, the full disclosure of which is incorporated herein by reference.

Although specific reference is made to the delivery of macromolecules comprising antibodies or antibody fragments to the posterior segment of the eye, embodiments can be used to diagnose the patient and to deliver many therapeutic agents to one or more of many tissues of the body. For example, embodiments can be used to diagnose the patient based on a sample from an implantable device and to deliver therapeutic agent for an extended period to one or more of the following tissues: intravascular, intra articular, intrathecal, pericardial, intraluminal and gut.

Embodiments provide sampling of a component of the eye from a device implanted in the eye and sustained release of a therapeutic agent to the posterior segment of the eye or the anterior segment of the eye, or combinations thereof. Therapeutic amounts of a therapeutic agent can be released into the vitreous humor of the eye, such that the therapeutic agent can be transported by at least one of diffusion or convection to the retina or other ocular tissue, such as the choroid or ciliary body, for therapeutic effect.

The diagnostic methods and apparatus as described herein can be used in many ways to one or more of treat or diagnose the patient, and can be combined in many ways with known treatments. In many embodiments, a diagnostic sample can be measured at a plurality of time points, such as when the therapeutic device is implanted, and one or more samples at a plurality of time points from the therapeutic device. A baseline sample can be measured from the patient when the device is implanted, for example prior to implantation with removal of a portion of the vitreous humor similar to a vitreal tap. When the device has been implanted, the fluid of the therapeutic device can be exchanged with a therapeutic fluid and analyzed, for example every 3-8 months.

As used herein the release rate index (PA/FL) encompasses where P comprises the porosity, A comprises an effective area, F comprises a curve fit parameter corresponding to an effective length, and L comprises a length or thickness of the porous structure. The units of the release rate index (RRI) comprise units of mm unless indicated otherwise and can be determined by a person of ordinary skill in the art in accordance with the teachings described herein.

As used herein, sustained release encompasses the release of therapeutic amounts of an active ingredient of a therapeutic agent for an extended period of time. The sustained release may encompass a first order release of the active ingredient, zero order release of the active ingredient, or other kinetics of release such as intermediate to zero order and first order, or combinations thereof.

As used herein, a therapeutic agent referred to with a trade name encompasses one or more of the formulation of the therapeutic agent commercially available under the tradename, the active ingredient of the commercially available formulation, the generic name of the active ingredient, or the molecule comprising the active ingredient. In addition, as used herein, similar numerals indicate similar structures and/or similar steps.

As used herein, terms of sequence such as first, second, and third can be used to illustrate combinations in accordance with embodiments merely by way of non-limiting example. Although terms of sequence may be used in accordance with one or more embodiments, a person of ordinary skill in the art will recognize many adaptations and variations based on the teachings described herein. For example, the order can be changed or one or more terms of sequence removed, or combinations thereof.

Measurement of One or More Ocular Components to Diagnose and Treat the Eye

Based on diagnostic tests of samples from a reservoir container of the device, the therapeutic treatment can be adjusted accordingly. For example, the patient may be diagnosed as a non-responder and the therapeutic agent changed, or the time interval at which the therapeutic agent is exchanged can be adjusted. For example, the exchange of the therapeutic fluid may be sooner e.g. every 3 months, or later, e.g. every 8 months, based on the components of the sample from the therapeutic device and patient response.

The components of the eye from the device may correspond to one or more pathways. For example, based on the diagnostic tests as described herein, amounts of pro-inflammatory cytokines that may upregulate VEGF can be measured and compared to one or more markers as described herein, such as VEGF. The embodiments as described herein can be well suited to determine one or more of a genotype of a patient, a phenotype of a patient, or combinations thereof, that can be used to diagnose and treat the patient. The sample may be combined with genetic testing to evaluate genes and phenotypes associated with a disease. For example, the sample may be combined with a DNA sample, such as from a swab of the sample used to determine a genotype of the patient, such as complement factor H-genotype. A patient having the compliment factor H genotype can be identified as more likely to get AMD, and the treatment and marker data interpreted based on one or more of the genotype of the phenotype of the patient. The one or more markers may comprise markers capable of binding to each other, such as complement factor H and c-reactive protein.

The marker measured from the implantable device sample may comprise one or more proteins having a substantial fluctuation in amount in response to the therapeutic agent. For example intra-vitreal amounts of the markers IL6 and GCSF can each have high ratios of mean pre-treatment to mean post treatment, such that these markers can be well suited to diagnose and treat the eye. The marker from the vitreous may correspond to a component of blood, such as serum amyloid, and may comprise a component of blood plasma. The marker may comprise one or more of the markers of Table I, herein below. The marker may comprise a protein, or alternatively a non-protein such as a carbohydrate, for example glucose or lactose, for example.

The marker can be a marker corresponding to a diagnosed condition of the patient. For example, insulin may be measured from the sample of the implantable device for patients having diabetic retinopathy, for example. Alternatively or in combination, the marker may comprise a marker corresponding to a target of the therapeutic agent, such as VEGF, and amounts of the marker bound to the therapeutic agent may be measured. For example, the therapeutic agent and marker can be bound when diffusing into the reservoir chamber of the device so as to decrease the rate of diffusion into the reservoir chamber, and the patient can be one or more of diagnosed or treated based on amounts of the therapeutic agent bound to the target and corresponding rates of diffusion of the bound components through the porous structure of the implantable device. For example, Ranibizumab when bound to VEGF can have a molecular weight of about 93 kilo Daltons (hereinafter "kDa") and diffuse about 20% slower than unbound VEGF.

The plurality of markers measured from the implanted device as described herein can be combined with statistical analysis from a population of patients to one or more of diagnose or treat the patient. The sample from the implanted device can be measured so as to provide a marker profile of the plurality of components that can be compared with marker profiles determined from a variety of patients. For example, data from a population of patients can provide correlations, statistical metrics, and statistical significance to the amounts of markers of the profile. The marker profile may comprise a plurality of markers from the implantable device, at least about 10 markers, or 20 or more markers measured from the implantable device, for example.

Table 1 (see Appendix I) shows examples of markers that can be received from the implanted device and used to diagnose the eye or treat the eye, or both. The markers can be used to determine a course of treatment for the patient, and may be combined in many ways with the therapeutic agent as described herein. In many embodiments, the marker comprises a molecule that is a component of the eye which can diffuse through the porous structure into the reservoir structure. In many embodiments, the marker comprises a large molecule that can diffuse through the porous structure of the implanted device into the reservoir chamber. The therapeutic agent may comprise a large molecule or a small molecule that can diffuse through the porous structure, or combinations of large and small molecules. Work in relation to embodiments indicate that marker molecules having a lower molecular weight may accumulate in the implanted device more rapidly than larger molecular weight marker molecules, and that marker molecules having a molecular weight of no more than about 500 kDa can be used in many embodiments. In many embodiments the molecular weight can be smaller than 500 kDa, for example 100 kDa or less, so that the accumulation rate is increased. The molecular weight values of Table 1 can be combined in many ways to provide ranges of molecular weights of the measured marker. Alternatively or in combination, a plurality of markers of different molecular weight can be used to diagnose and treat the patient. Examples of markers and amounts similar to Table 1 can be used and are shown in Molecular Vision (Mol Vis. 2010; 16: 2175-2184, Published online 2010 Oct. 27) available on the world wide web (at the address http://www.ncbi.nlm.nih.gov/pmc/articles/PMC2994336/table/t1/)

A ratio of pre-treatment mean concentration to post-treatment mean concentration is shown for the markers of Table 1. This ratio can be used to determine markers suitable to indicate efficacy of treatment and markers suitable for use as housekeeping genes. The markers having a ratio above about 1.2, for example, can be suitable for use as housekeeping markers. Markers having a ratio above about 1.2 may be suitable for use as efficacy markers. In many embodiments, the one or more markers from the therapeutic device correspond to a pre/post ratio above of about 1.5, for example. Alternatively or in combination, the pre/post ratio can be less than 0.8, for example, and the marker risk may correspond to under-expression of protective factors, for example. The marker profile to diagnose the patient from a sample of the implanted device may comprise a plurality of up-regulation of pathogenic factor markers corresponding to a ratio above about 1.2 and a plurality of under-expression of protective factor markers corresponding to a ratio below about 0.8, for example.

A list of known Hugo symbols is provided in Appendix II of this disclosure, and can be used to determine genetic markers and corresponding genetic mapping in accordance with embodiments. This appendix includes genes and code-names for genes whose expression may change upon VEGF treatment of the eye.

The markers of Table 1 and the therapeutic agent of Table 1A (see Appendix I) can be combined in many ways to treat the eye. For example, one or more of the markers of Table 1 can be combined with one or more therapeutic agents of Table 1A to treat the eye. The efficacy of a treatment with the therapeutic agent can be evaluated based on the marker, and the therapeutic agent can be changed or the amount of therapeutic agent adjusted based on one or more of the presence or amount of the marker. The many combinations corresponding to each marker of Table 1 with one or more therapeutic agents of Table 1A provide many embodiments. A person of ordinary skill in the art can conduct experiments to determine empirically which of the one or more markers can be combined with which of the one or more therapeutic agents to beneficially treat the patient or the eye, or both. Further, one or more marker may be combined with a plurality of therapeutic agents, in accordance with embodiments. Alternatively, a plurality of markers may be combined with one or more therapeutic agents, in accordance with many embodiments. A person of ordinary skill in the art will recognize many embodiments in accordance with the teachings and embodiments described herein.

The molecular weights of the markers of Table 1 can be used to determine the rate of diffusion of the marker through the porous structure in accordance with the teachings described herein. The rate of accumulation of the marker can be determined based on the RRI and volume of the reservoir chamber of the device implanted in the eye. For example, markers having low molecular weight may accumulate in the reservoir chamber more rapidly than molecules with high molecular weight, and the time for the marker to accumulate in the reservoir chamber can be used to diagnose the eye and determine the effectiveness of the treatment. The molecular weights of the markers of Table 1 range from about 2.5 kDa for Endothelium-1 to about 540 kDa for fibrinogen, for example. The lower end of the range may comprise a low molecular weight cytokine, for example a MIP-1 alpha or MIP-1 beta. Alternatively or in combination, the lower end of the range may correspond to Endothelium-1. Based on the values of Table 1, the range of the molecular weight of the marker can be within a range from about 1 kDa to about 540 kDa, for example within a range from about 2.5 kDa to about 540 kDa.

The marker may comprise a molecular weight corresponding to a molecular weight of the therapeutic agent. For example, the molecular weight of the marker may correspond to a diffusion coefficient of at least about half of the diffusion coefficient of the therapeutic agent. For example, with Lucentis™ the molecular weight is about 48 kDa and a marker having a molecular weight of about 500 kDa can have a diffusion coefficient and corresponding accumulation rate that is about half of Lucentis™. In many embodiments, the molecular weight of the marker comprises no more than the molecular weight of the therapeutic agent, for example no more than about half of the molecular weight of the therapeutic agent.

For some entries in the table, ranges are shown that represent variations that may be due to glycosylation, subunits vs. association into soluble aggregates, and binding to other molecules. Hence, these are representative values that may be adjusted to account for the actual size of the moiety diffusing into the device during use.

Therapeutic Agent Delivery

The therapeutic agent may be contained within a chamber of a container, for example within a reservoir comprising the container and chamber. The therapeutic agent may comprise a formulation such as solution of therapeutic agent, a suspension of a therapeutic agent or a dispersion of a therapeutic agent, for example. Examples of therapeutic agents suitable for use in accordance with embodiments of the therapeutic device are described herein, for example with reference to Table 1A below and elsewhere.

The therapeutic agent may comprise a macromolecule, for example an antibody or antibody fragment. The therapeutic macromolecule may comprise a VEGF inhibitor, for example commercially available Lucentis™. The VEGF (Vascular Endothelial Growth Factor) inhibitor can cause regression of the abnormal blood vessels and improvement of vision when released into the vitreous humor of the eye. Examples of VEGF inhibitors include Lucentis™, Avastin™, Macugen™, and VEGF Trap.

The therapeutic agent may comprise small molecules such as of a corticosteroid and analogues thereof. For example, the therapeutic corticosteroid may comprise one or more of trimacinalone, trimacinalone acetonide, dexamethasone, dexamethasone acetate, fluocinolone, fluocinolone acetate, or analogues thereof. Alternatively or in combination, he small molecules of therapeutic agent may comprise a tyrosine kinase inhibitor comprising one or more of axitinib, bosutinib, cediranib, dasatinib, erlotinib, gefitinib, imatinib, lapatinib, lestaurtinib, nilotinib, semaxanib, sunitinib, toceranib, vandetanib, or vatalanib, for example.

The therapeutic agent may comprise an anti-VEGF therapeutic agent. Anti-VEGF therapies and agents can be used in the treatment of certain cancers and in age-related macular degeneration. Examples of anti-VEGF therapeutic agents suitable for use in accordance with the embodiments described herein include one or more of monoclonal antibodies such as bevacizumab (Avastin™) or antibody derivatives such as ranibizumab (Lucentis™), or small molecules that inhibit the tyrosine kinases stimulated by VEGF such as lapatinib (Tykerb™), sunitinib (Sutent™), sorafenib (Nexavar™), axitinib, or pazopanib.

The therapeutic agent may comprise a therapeutic agent suitable for treatment of dry AMD such as one or more of Sirolimus™ (Rapamycin), Copaxone™ (Glatiramer Acetate), Othera™, Complement C5aR blocker, Ciliary Neurotrophic Factor, Fenretinide or Rheopheresis.

The therapeutic agent may comprise a therapeutic agent suitable for treatment of wet AMD (age-related macular degeneration) such as one or more of REDD14NP (Quark), Sirolimus™ (Rapamycin), ATG003; Regeneron™ (VEGF Trap) or complement inhibitor (POT-4).

The therapeutic agent may comprise a kinase inhibitor such as one or more of bevacizumab (monoclonal antibody), BIBW 2992 (small molecule targeting EGFR/Erb2), cetuximab (monoclonal antibody), imatinib (small molecule), trastuzumab (monoclonal antibody), gefitinib (small molecule), ranibizumab (monoclonal antibody), pegaptanib (small molecule), sorafenib (small molecule), dasatinib (small molecule), sunitinib (small molecule), erlotinib (small molecule), nilotinib (small molecule), lapatinib (small molecule), panitumumab (monoclonal antibody), vandetanib (small molecule) or E7080 (targeting VEGFR2/VEGFR2, small molecule commercially available from Esai, Co.)

The amount of therapeutic agent within the therapeutic device may comprise from about 0.01 mg to about 1 mg, for example Lucentis™, so as to provide therapeutic amounts of the therapeutic agent for the extended time, for example at least 30 days. The extended time may comprise at least 90 days or more, for example at least 180 days or for example at least 1 year, at least 2 years or at least 3 years or more. The target threshold therapeutic concentration of a therapeutic agent such as Lucentis™ in the vitreous may comprise at least a therapeutic concentration of 0.1 ug/mL. For example the target threshold concentration may comprise from about 0.1 ug/mL to about 5 ug/mL for the extended time, where the upper value is based upon calculations shown in Example 9 of in U.S. patent application Ser. No. 12/696,678, filed 29 Jan. 2010, entitled "Posterior Segment Drug Delivery", published as U.S. Pub. No. 2010/0255061 on Oct. 7, 2010, the full disclosure of which has been previously incorporated herein by reference. The target threshold concentration is drug dependent and thus may vary for other therapeutic agents.

The delivery profile may be configured in many ways to obtain a therapeutic benefit from the sustained release device. For example, an amount of the therapeutic agent may be inserted into the container at monthly intervals so as to ensure that the concentration of therapeutic device is above a safety protocol or an efficacy protocol for the therapeutic agent, for example with monthly or less frequent injections into the container. The sustained release can result in an improved delivery profile and may result in improved results. For example, the concentration of therapeutic agent may remain consistently above a threshold amount, for example 0.1 ug/mL, for the extended time.

The insertion method may comprise inserting a dose into the container of the therapeutic device. For example, a single injection of Lucentis™ may be injected into the therapeutic device.

The duration of sustained delivery of the therapeutic agent may extend for twelve weeks or more, for example four to six months from a single insertion of therapeutic agent into the device when the device is inserted into the eye of the patient.

The therapeutic agent may be delivered in many ways so as to provide a sustained release for the extended time. For example, the therapeutic device may comprise a therapeutic agent and a binding agent. The binding agent may comprise small particles configured to couple releasably or reversibly to the therapeutic agent, such that the therapeutic agent is released for the extended time after injection into the vitreous humor. The particles can be sized such that the particles remain in the vitreous humor of the eye for the extended time.

The therapeutic agent may be delivered with a device implanted in the eye. For example, the drug delivery device can be implanted at least partially within the sclera of the eye, so as to couple the drug delivery device to the sclera of the eye for an extended period of time. The therapeutic device may comprise a drug and a binding agent. The drug and binding agent can be configured to provide the sustained release for the extended time. A membrane or other diffusion barrier or mechanism may be a component of the therapeutic device to release the drug for the extended time.

The lifetime of the therapeutic device and number of injections can be optimized for patient treatment. For example, the device may remain in place for a lifetime of 30 years, for example with AMD patients from about 10 to 15 years. For example, the device may be configured for an implantation duration of at least two years, with 8 injections (once every three months) for sustained release of the therapeutic agent over the two year duration. The device may be configured for implantation of at least 10 years with 40 injections (once every three months) for sustained release of the therapeutic agent.

The therapeutic device can be refilled in many ways. For example, the therapeutic agent can be refilled into the device in the physician's office.

The therapeutic device may comprise many configurations and physical attributes, for example the physical characteristics of the therapeutic device may comprise at least one of a drug delivery device with a suture, positioning and sizing such that vision is not impaired, and biocompatible material. The device may comprise a reservoir capacity from about 0.005 cc to about 0.2 cc, for example from about 0.01 cc to about 0.1 cc, and a device volume of no more than about 2 cc. A vitrectomy may be performed for device volumes larger than 0.1 cc. The length of the device may not interfere with the patient's vision and can be dependent on the shape of the device, as well as the location of the implanted device with respect to the eye. The length of the device may also depend on the angle in which the device is inserted. For example, a length of the device may comprise from about 4 to 6 mm. Since the diameter of the eye is about 24 mm, a device extending no more than about 6 mm from the sclera into the vitreous may have a minimal effect on patient vision.

Embodiments may comprise many combinations of implanted drug delivery devices. The therapeutic device may comprise a drug and binding agent. The device may also comprise at least one of a membrane, an opening, a diffusion barrier, and a diffusion mechanism so as to release therapeutic amounts of therapeutic agent for the extended time.

Measurements to Determine Implantable Device Performance and Exchange Efficiency As described herein, the amount of therapeutic agent in the exchanged implantable device fluid can be measured to evaluate the release of the therapeutic agent from the device and to determine the amount of therapeutic fluid placed in the device. In many embodiments, the therapeutic fluid placed in the eye comprises one or more components of a formulation of the therapeutic agent. The components of the formulation of the therapeutic fluid can be measured to determine the amount of therapeutic agent present in the implantable device fluid and the efficiency of placement of the therapeutic fluid in the implantable device. In many embodiments, a non-pharmacologic component of the implantable device fluid can be measured to determine one or more of the following; the amount of therapeutic agent released since a previous placement of a therapeutic fluid in the device; performance of the porous structure to release the therapeutic agent; leakage of the therapeutic agent from the reservoir chamber away from the porous structure; the efficiency of placement of the therapeutic fluid within the implantable device; or the amount of implantable fluid displaced with the therapeutic agent. For example, the ratio of a component of the formulation to the amount of therapeutic agent can be determined.

The measured component of the formulation may comprise a stabilizer, and a ratio of the stabilizer to the therapeutic agent can be measured, for example. The measured component comprises a diffusion coefficient and a molecular weight proportional to the therapeutic agent, such that the ratio of the therapeutic agent to the component in the implantable device fluid can be compared to determine the amount of therapeutic agent release since a prior placement of therapeutic fluid.

In many embodiments, the stabilizer increases an amount of time the therapeutic agent has a therapeutic effect when placed in a therapeutic device placed in a patient. The stabilizer may comprise one or more of the following; a buffer to maintain a pH of the formulation, hydrophilic functional groups; a hydrophilic functional group to provide a co-solvent stabilization; a charged functional group to provide charge interaction; or a functional group to form a complex with the therapeutic agent, so as to increase one or more of physical stability or chemical stability of the therapeutic agent and maintain biological activity of the therapeutic agent. The stabilizer can be soluble and may comprise one or more of a sugar, an alcohol, a polyol, or a carbohydrate and the functional group may comprise a hydroxyl group.

In some embodiments, the stabilizer comprises a molecular weight of at least about 3 k Daltons. The stabilizer may comprise a molecular weight of at least about 5 k Daltons, and may comprise a molecular weight of at least about 10 k Daltons, for example at least about 25 k Daltons.

In many embodiments, the stabilizer comprises a molecular weight of at least about 25% of a molecular weight of the therapeutic agent. The stabilizer and the therapeutic agent may each comprise a half-life when placed, for example injected, into a therapeutic device, and the half-life of the stabilizer may comprise at least about 25% of the half-life of the therapeutic agent. The half-life of the stabilizer may be comprised of at least about 50% of the half-life of the therapeutic agent.

In many embodiments, the therapeutic agent may comprise ranibizumab. The therapeutic agent may comprise ranibizumab and degradation products of ranibizumab, and the degradation products may comprise one or more of deamidized ranibizumab or oxidized ranibizumab.

In many embodiments, the stabilizer comprising the molecular weight comprises one or more of: HA (hyaluronic acid) having the molecular weight of at least 2 kDa, histidine polymer buffer having the molecular weight of at least 2 kDa, sugar having the molecular weight of at least 2 kDa, polysaccharides having the molecular weight of at least 2 kDa, carbohydrate having the molecular weight of at least 2 kDa, starch having the molecular weight of at least 2 kDa, alcohol having the molecular weight of at least 2 kDa, polyol having the molecular weight of at least 2 kDa, or polyethylene oxide having the molecular weight of at least 2 kDa, so as to stabilize the therapeutic agent and decrease release of the therapeutic agent when placed in a therapeutic device.

In some embodiments, the stabilizer comprising the molecular weight comprises one or more of: a phenol, a protein, or a charged stabilizers such as a metal comprising one or more of zinc ion, calcium ion, or iron ion, so as to form a reversible complex with the therapeutic agent.

In some embodiments, the stabilizer comprises a plurality of micelles and wherein the molecular weight of the stabilizer corresponds to a weight of each micelle of the plurality such that diffusion of the plurality of micelles corresponds to the weight of said each micelle. The plurality of micelles may comprise a reservoir of the stabilizer. The stabilizer may comprise a surfactant, and a concentration of surfactant may comprise at least about two times a critical micelle concentration of the surfactant. The concentration of surfactant may comprise at least about two times the critical micelle concentration, and may comprise at least about four times the critical micelle concentration.

In some embodiments, a stabilizer, may comprise a polysorbate.

In some embodiments, an amount of the stabilizer may correspond to at least about 0.05% by weight of a formulation when injected into the eye.

Ocular Anatomy, Therapeutic Devices and Placement

FIG. 1 shows an eye 10 suitable for incorporation of the therapeutic device 100. The eye has a cornea 12 and a lens 22 configured to form an image on the retina 26. The cornea 12 can extend to a limbus 14 of the eye 10, and the limbus 14 can connect to a sclera 24 of the eye 10. A conjunctiva 16 of the eye can be disposed over the sclera 24. The lens 22 can accommodate to focus on an object seen by the patient. The eye 10 has an iris 18 that may expand and contract in response to light. The eye 10 also comprises a choroid 28 disposed the between the sclera 24 and the retina 26. The retina 26 comprises the macula 32, and an optic nerve 36 extends from the retina 26. The eye 10 comprises a pars plana 25, which comprises an example of a region of the eye 10 suitable for placement and retention, for example anchoring, of the therapeutic device 100 as described herein. The pars plana region 25 may comprise the sclera 24 and conjunctiva 16 disposed between the retina 26 and cornea 12. The therapeutic device 100 can be positioned so as to extend from the pars plana region 25 into the vitreous humor 30 to release the therapeutic agent. The therapeutic agent can be released into the vitreous humor 30, such that the therapeutic agent arrives at the retina 26 and choroids 28 for therapeutic effect on the macula 32. The vitreous humor of the eye 30 comprises a liquid disposed between the lens 22 and the retina 26. The vitreous humor 30 may comprise convection currents to deliver the therapeutic agent to the macula 32.

Figure 2:
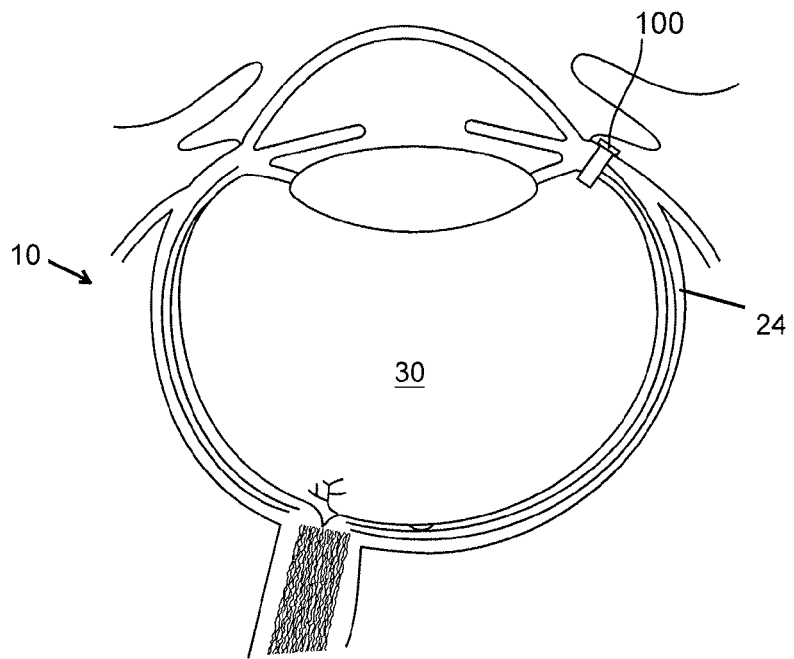
FIG. 2 shows a therapeutic device implanted at least partially within the sclera of the eye as in FIG. 1, in accordance with embodiments.

FIG. 2 shows a therapeutic device 100 implanted at least partially within the sclera 24 of the eye 10 as shown in FIG. 1. The therapeutic device 100 may comprise a retention structure, for example a protrusion, to couple the device 100 to the sclera 24. The therapeutic device 100 may extend through the sclera 24 into vitreous humor 30, such that the therapeutic device 100 can release the therapeutic agent into the vitreous humor 30.

Figure 3:
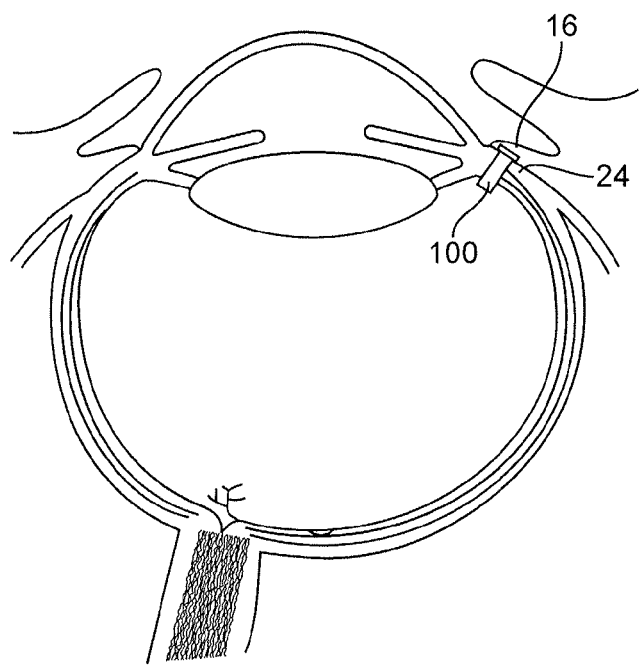
FIG. 3 shows a therapeutic device implanted under the conjunctiva and extending through the sclera to release a therapeutic agent into vitreous humor of the eye so as to treat the retina of the eye, in accordance with embodiments.
Figure 6:
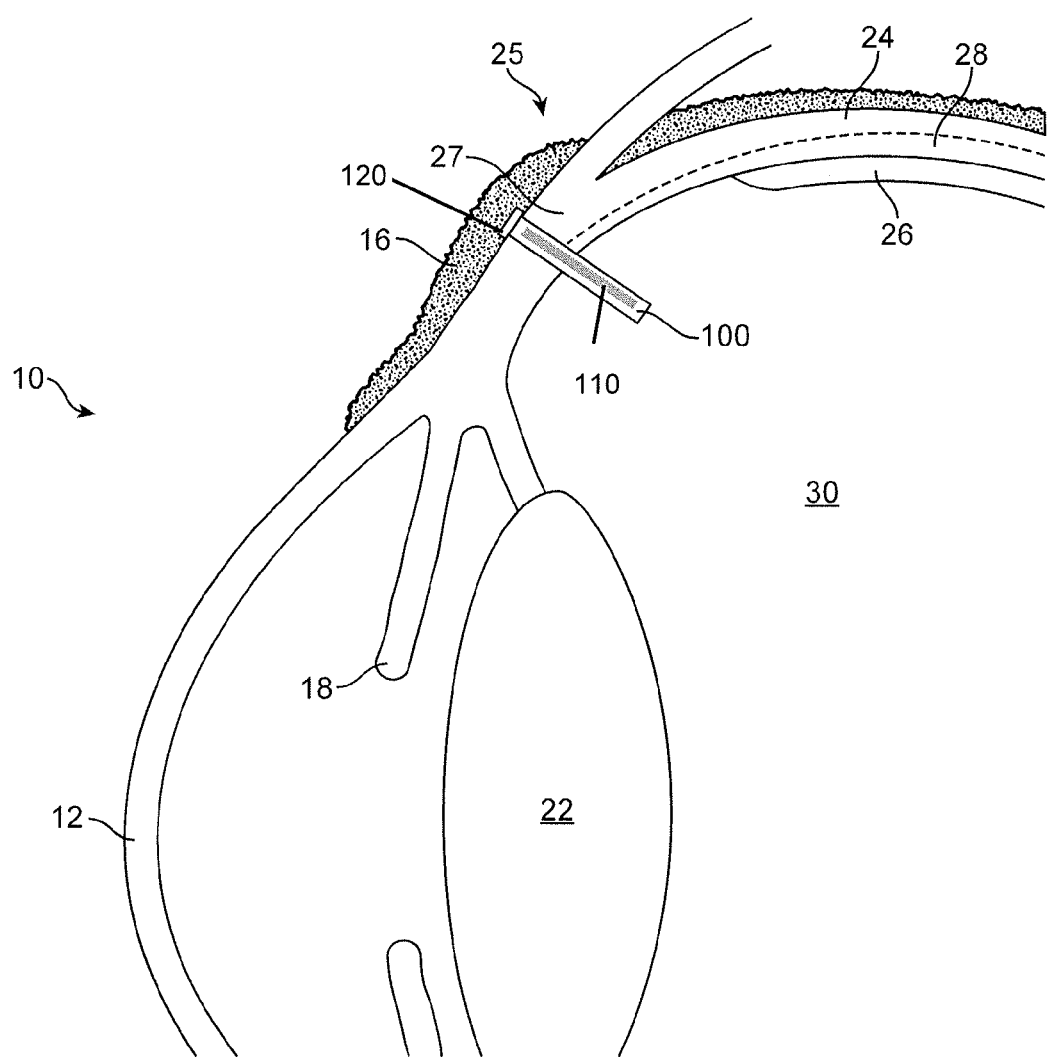
FIG. 6 shows a therapeutic device implanted under the conjunctiva and extending through the sclera to release a therapeutic agent into vitreous humor of the eye so as to treat the retina of the eye, in accordance with embodiments.

FIGS. 3 and 6 show a therapeutic device 100 implanted under the conjunctiva 16 and extending through the sclera 24 to release a therapeutic agent 110 into vitreous humor 30 of the eye 10 so as to treat the retina 26 of the eye 10. The therapeutic device 100 may comprise a retention structure 120 such as a smooth protrusion configured for placement along the sclera 24 and under the conjunctiva 16, such that the conjunctiva 16 can cover the therapeutic device 100 and protect the therapeutic device 100. When the therapeutic agent 110 is inserted into the device 100, the conjunctiva 16 may be lifted away, incised, or punctured with a needle to access the therapeutic device 100. The eye 10 may comprise an insertion of the tendon 27 of the superior rectus muscle to couple the sclera 24 of the eye 10 to the superior rectus muscle. The device 100 may be positioned in many locations of the pars plana region 25, for example away from tendon 27 and one or more of posterior to the tendon 27, anterior to the tendon 27, under the tendon 27, or with nasal or temporal placement of the therapeutic device 100.

While the implant 100 can be positioned in the eye 10 in many ways, placement in the pars plana region 25 can release therapeutic agent 110 into the vitreous to treat the retina 26, for example therapeutic agent 110 comprising an active ingredient composed of large molecules.

Therapeutic agents 110 suitable for use with device 100 may include a variety of therapeutic agents 110, for example as listed in Table 1A, herein below. The therapeutic agent 110 of device 100 may comprise one or more of the following; an active ingredient of the therapeutic agent 110; a formulation of the therapeutic agent; a commercially available formulation of the therapeutic agent; a physician prepared formulation of therapeutic agent; a pharmacist prepared formulation of the therapeutic agent; or a commercially available formulation of therapeutic agent having an excipient. The therapeutic agent 110 may be referred to with a generic name or a trade name, for example as shown in Table 1A.

The therapeutic device 100 can be implanted in the eye 10 to treat the eye 10 for as long as is helpful and beneficial to the patient. For example the device 100 can be implanted for at least about 5 years, such as permanently for the life of the patient. Alternatively or in combination, the device 100 can be removed when no longer helpful or beneficial for treatment of the patient.

Figure 4:
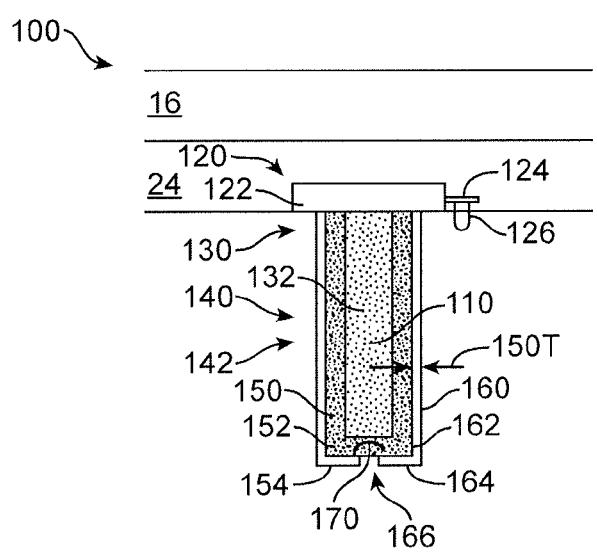
FIG. 4 shows structures of a therapeutic device configured for placement in an eye as in FIGS. 2 and 3, in accordance with embodiments.

FIG. 4 shows structures of therapeutic device 100 configured for placement in an eye 10 as in FIGS. 2, 3 and 6. The device 100 may comprise retention structure 120 to couple the device 100 to the sclera 24, for example a protrusion disposed on a proximal end of the device 100. The device 100 may comprise a container 130 affixed to the retention structure 120. An active ingredient, for example therapeutic agent 110, can be contained within a reservoir 140, for example a chamber 132 defined by a container 130 of the device 100. The container 130 may comprise a porous structure 150 comprising a porous material 152, for example a porous glass frit 154, and a barrier 160 to inhibit release of the therapeutic agent 110, for example non-permeable membrane 162. The non-permeable membrane 162 may comprise a substantially non-permeable material 164.

The non-permeable membrane 162 may comprise an opening 166 sized to release therapeutic amounts of the therapeutic agent 110 for an extended time. The porous structure 150 may comprise a thickness 150T and pore sizes configured in conjunction with the opening 166 so as to release therapeutic amounts of the therapeutic agent 110 for the extended time. The container 130 may comprise the reservoir 140 having a chamber 132 with a volume 142 sized to contain a therapeutic quantity of the therapeutic agent 110 for release over the extended time. The device 100 may comprise a needle stop 170. Proteins in the vitreous humor 30 may enter the device 100 and compete for adsorption sites on the porous structure and thereby may contribute to the release of therapeutic agent 110. The therapeutic agent 110 contained in the reservoir 140 can equilibrate with proteins in the vitreous humor 30, such that the system is driven towards equilibrium and the therapeutic agent 110 is released in therapeutic amounts.

The non-permeable membrane 162, the porous material 152, the reservoir 140, and the retention structure 120, may comprise many configurations to deliver the therapeutic agent 110. The non-permeable membrane 162 may comprise an annular tube joined by a disc having at least one opening formed thereon, such as opening 166, to release the therapeutic agent 110. The porous material 152 may comprise an annular porous glass frit 154 and a circular end disposed thereon. The reservoir 140 may be shape-changing for ease of insertion, i.e., it may assume a thin elongated shape during insertion through the sclera 24 and then assume an extended, ballooned shape, once it is filled with therapeutic agent 110.

The porous structure 150 can be configured in many ways to release the therapeutic agent 110 in accordance with an intended release profile. For example, the porous structure may comprise a porous structure 150 having a plurality of openings on a first side facing the reservoir 140 and a plurality of openings on a second side facing the vitreous humor 30, with a plurality of interconnecting channels disposed therebetween so as to couple the openings of the first side with the openings of the second side, for example a sintered rigid material. The porous structure 150 may comprise one or more of a permeable membrane, a semi-permeable membrane, a material having at least one hole disposed therein, nano-channels, nano-channels etched in a rigid material, laser etched nano-channels, a capillary channel, a plurality of capillary channels, one or more tortuous channels, tortuous microchannels, sintered nano-particles, an open cell foam or a hydrogel such as an open cell hydrogel.

The retention structure 120 may comprise a flange 122 shaped to extend along a surface of the sclera 24 beneath the conjunctiva 16. The implantable device 100 may be retained without sutures. Alternatively, device 100 may comprise a suture tab 124 to couple to a suture 126 to retain the device 100.

Figure 5:
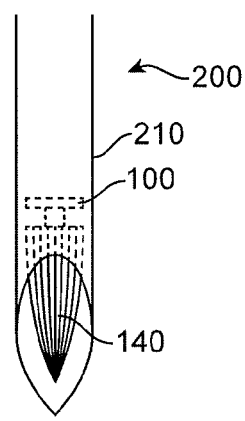
FIG. 5 shows a therapeutic device loaded into an insertion cannula, in which the device comprises an elongate narrow shape for insertion into the sclera, and in which the device is configured to expand to a second elongate wide shape for retention at least partially in the sclera, in accordance with embodiments.

FIG. 5 shows therapeutic device 100 loaded into an insertion cannula 210 of an insertion apparatus 200, in which the device 100 comprises an elongate narrow shape for insertion into the sclera 24, and in which the device, particular the reservoir chamber 140, is configured to expand to a second elongate wide shape for retention at least partially in the sclera 24.

Figure 7:
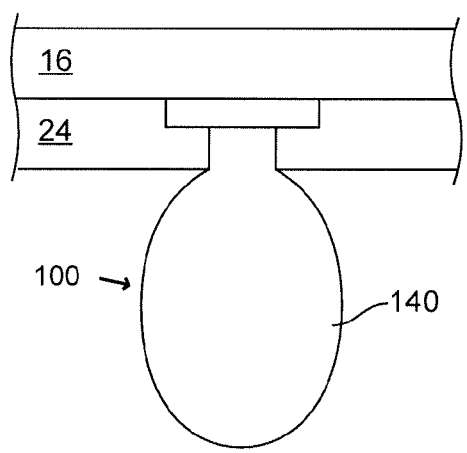
FIG. 7 shows a therapeutic device comprising a reservoir suitable for loading in a cannula, in accordance with embodiments.

FIG. 7 shows a therapeutic device 100 comprising reservoir 140 suitable for loading in a cannula, in which the reservoir 140 comprises an expanded configuration.

Figure 8:
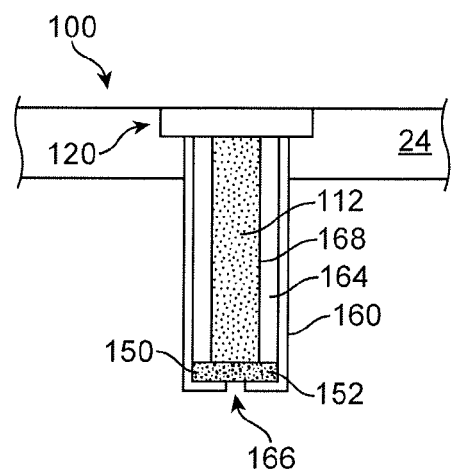
FIG. 8 shows a therapeutic device configured for placement in an eye as in FIGS. 2 and 3, in accordance with embodiments.

FIG. 8 shows therapeutic device 100 configured for placement in an eye 10 as in FIGS. 2 and 3. The device 100 comprises retention structure 120 to couple to the sclera 24, for example flush with the sclera 24, and the barrier 160 comprises a tube 168. An active ingredient 112 comprising the therapeutic agent 110 is contained within tube 168 comprising non-permeable material 164. A porous structure 150 composed of porous material 152 is disposed at the distal end of the tube 168 to provide a sustained release of the therapeutic agent 110 at therapeutic concentrations for the extended period. The non-permeable material 164 may extend distally around the porous material 152 so as to define an opening 166 to couple the porous material 152 to the vitreous humor 30 when the device 100 is inserted into the eye 10.

The tube 168 and retention structure 120 may be configured to receive a glass rod, which may be surface treated, and the glass rod can be injected with therapeutic agent 110. When the therapeutic agent 110 has finished elution for the extended time, the rod can be replaced with a new rod.

The device 100 may comprise therapeutic agent 110 and a carrier, for example a binding medium 192 comprising a binding agent to deliver the therapeutic agent 110. The therapeutic agent 110 can be surrounded with a column comprising a solid support that is eroded away.

Figure 9:
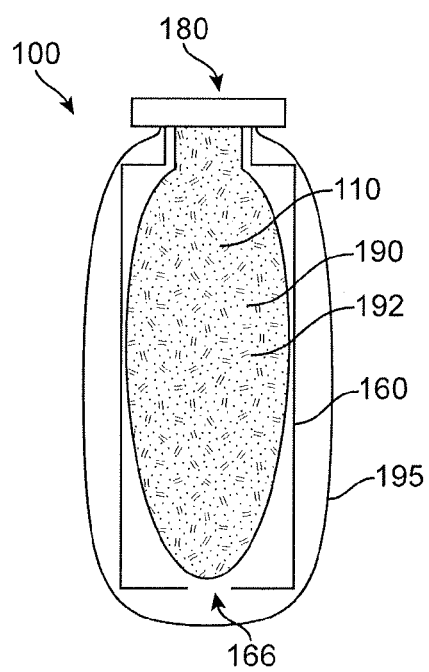
FIG. 9 shows a therapeutic device configured for placement in an eye as in FIGS. 2 and 3, in accordance with embodiments.

FIG. 9 shows a therapeutic device 100 configured for placement in an eye 10 as in FIGS. 2 and 3. A binding medium 192 comprising a binding agent 190, such as glass wool, may be loaded with therapeutic agent 110 prior to injection into the device 100 through an access port 180. The device 100 may comprise binding, leak, and barrier functions to deliver the therapeutic agent 110 for the extended time. The binding medium 192 and therapeutic agent 110 can be aspirated to replace the binding medium 192 and therapeutic agent 110. The binding medium 192 can be at least one of flushed or replaced when at least a majority of the therapeutic agent 110 has been released, such that additional therapeutic agent 110 can be delivered from a second injected binding medium 192 comprising as therapeutic agent 110. A membrane 195 can be disposed over the periphery of the therapeutic device 100. The membrane 195 may comprise methylcellulose, regenerated cellulose, cellulose acetate, nylon, polycarbonate, poly(tetrafluoroethylene) (PTFE), polyethersulfone, and polyvinylidene difluoride (PVDF). The therapeutic device 100 may comprise a barrier 160 shaped such that the opening 166 comprises an exit port. The therapeutic agent 110 may be released through at least one of a diffusion mechanism or convection mechanism. The number, size, and configuration of exit ports may determine the release rate of the therapeutic agent 110. The exit port may comprise a convection port, for example at least one of an osmotically driven convection port or a spring driven convection port. The exit port may also comprise a tubular path to which the therapeutic agent 110 may temporarily attach, and then be released under certain physical or chemical conditions.

Figure 10:
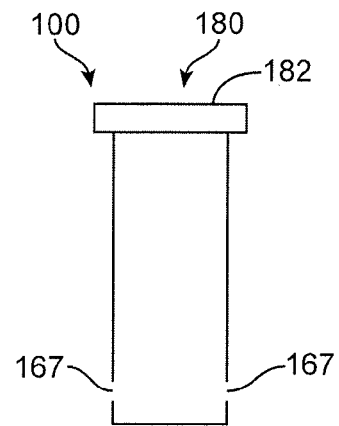
FIG. 10 shows at least one exit port, in accordance with embodiments.

FIG. 10 shows at least one exit port 167, the exit port 167 can be disposed on the device 100 to allow liquid to flow from inside the device 100 outward, for example when fluid is injected into an injection port 182 of the device 100 or when an insert, such as a glass frit, is inserted into the device 100. The therapeutic device 100 may comprise an access port 180 for injection and/or removal, for example a septum. Additionally or in the alternative, when the therapeutic device 100 is refilled, the contents of the device 100 may be flushed into the vitreous 30 of the eye 10.

Figure 11:
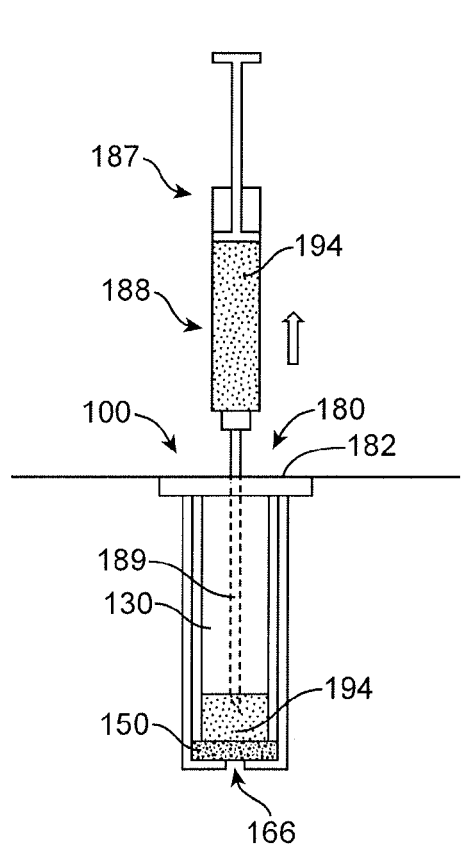
FIG. 11 shows a method of removing a binding material, in accordance with embodiments.

FIG. 11 shows a method of removing a binding agent 194. A needle 189 coupled to a syringe 188 of an injector 187 can be inserted into an access port 180 of the therapeutic device 100. The binding agent 194 can be aspirated with the needle 189.

Figure 12:
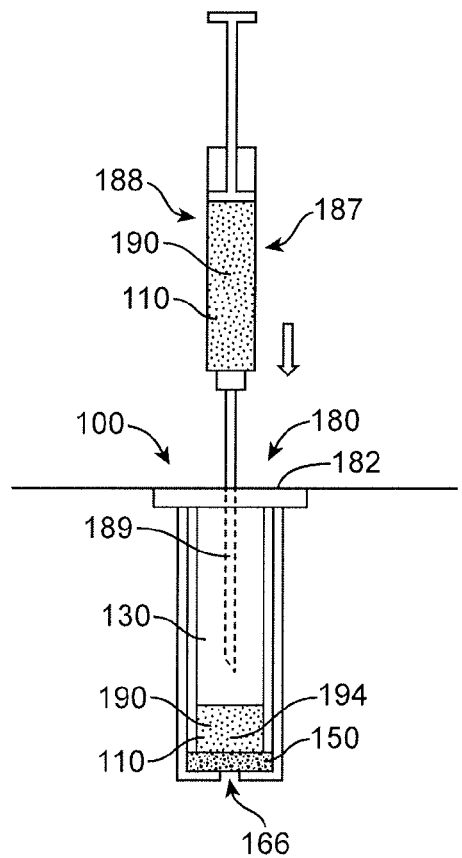
FIG. 12 shows inserting the therapeutic agent with a second insert having the therapeutic agent (TA) bound thereon, in accordance with embodiments.

FIG. 12 shows a method of inserting the therapeutic agent 110 with a second binding agent 190 having the therapeutic agent 110 bound thereon. The therapeutic agent 110 can be injected into a container 130 of the device 100 for sustained release over the extended time.

Figure 13:
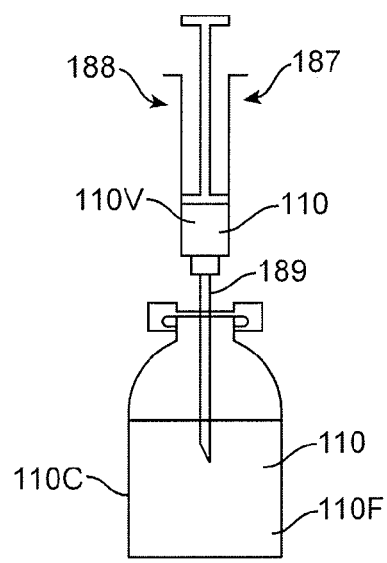
FIG. 13 shows syringe being filled with a commercially available formulation of therapeutic agent for injection into the therapeutic device, in accordance with embodiments.

FIG. 13 shows a syringe 188 being filled with a formulation of therapeutic agent 110 for injection into the therapeutic device 100. The needle 189 coupled to syringe 188 of injector 187 can be used to draw therapeutic agent 110 from a container 110C. The container 110C may comprise a commercially available container, such as a bottle with a septum, a single dose container, or a container suitable for mixing formulations. A quantity 110V of therapeutic agent 110 can be drawn into injector 187 for injection into the therapeutic device 100 positioned within the eye 10. The quantity 110V may comprise a predetermined quantity, for example based on the volume of the container of the therapeutic device 110 and an intended injection into the vitreous humor 30. The example the quantity 110V may exceed the volume of the container 130C so as to inject a first portion of quantity 110V into the vitreous humor 30 through the therapeutic device and to contain a second portion of quantity 110V within the container of the therapeutic device 100. Container 110C may comprise a formulation 110F of the therapeutic agent 110. The formulation 110F may comprise commercially available formulations of therapeutic agent 110, for example therapeutic agents as described herein and with reference to Table 1A. Non-limiting examples of commercially available formulations that may be suitable for use in accordance with the embodiments described herein include Lucentis™ and Triamcinolone, for example. The formulation 110F may be a concentrated or diluted formulation of a commercially available therapeutic agent 110, for example Avastin™. The osmolarity and tonicity of the vitreous humor 30 can be within a range from about 290 to about 320 mOsm. For example, a commercially available formulation of Avastin™ may be diluted so as to comprise a formulation having an osmolarity and tonicity substantially similar to the osmolarity and tonicity of the vitreous humor 30, for example within a range from about 280 to about 340 mOsm, for example about 300 mOsm. While the therapeutic agent 110 may comprise an osmolarity and tonicity substantially similar to the vitreous humor 30, the therapeutic agent 110 may comprise a hyper osmotic solution relative to the vitreous humor 30 or a hypo osmotic solution relative to the vitreous humor 30. A person of ordinary skill in the art can conduct experiments based on the teachings described herein so as to determine empirically the formulation and osmolarity of the therapeutic agent 110 to provide release of therapeutic agent 110 for an extended time.

For example, in the United States of America, Lucentis™ (active ingredient ranibizumab) is supplied as a preservative-free, sterile solution in a single-use glass vial designed to deliver 0.05 mL of 10 mg/mL Lucentis™ aqueous solution with 10 mM histidine HCl, 10% α, α-trehalose dihydrate, 0.01% polysorbate 20, at pH 5.5. In Europe, the Lucentis™ formulation can be substantially similar to the formulation of the United States.

For example, the sustained release formulation of Lucentis™ developed by Genentech and/or Novartis, may comprise the therapeutic agent 110 injected into the device 100. The sustained release formulation may comprise particles comprising active ingredient.

For example, in the United States, Avastin™ (bevacizumab) is approved as an anticancer drug and in clinical trials are ongoing for AMD. For cancer, the commercial solution is a pH 6.2 solution for intravenous infusion. Avastin™ may be supplied in 100 mg and 400 mg preservative-free, single-use vials to deliver 4 mL or 16 mL of Avastin™ (25 mg/mL). The 100 mg product is formulated in 240 mg α,α-trehalose dihydrate, 23.2 mg sodium phosphate (monobasic, monohydrate), 4.8 mg sodium phosphate (dibasic, anhydrous), 1.6 mg polysorbate 20, and Water for Injection, USP. The 400 mg product is formulated in 960 mg α,α-trehalose dihydrate, 92.8 mg sodium phosphate (monobasic, monohydrate), 19.2 mg sodium phosphate (dibasic, anhydrous), 6.4 mg polysorbate 20, and Water for Injection, USP. The commercial formulations are diluted in 100 mL of 0.9% sodium chloride before administration and the amount of the commercial formulation used varies by patient and indication. Based on the teachings described herein, a person of ordinary skill in the art can determine formulations of Avastin™ to inject into therapeutic device 100. In Europe, the Avastin™ formulation can be substantially similar to the formulation of the United States.

For example, in the United States, there may be two forms of Triamcinolone used in injectable solutions, the acetonide and the hexacetonide. The acetamide may be approved for intravitreal injections in the U.S. The acetamide is the active ingredient in TRIVARIS (Allergan), 8 mg triamcinolone acetonide in 0.1 mL (8% suspension) in a vehicle containing w/w percent of 2.3% sodium hyaluronate; 0.63% sodium chloride; 0.3% sodium phosphate, dibasic; 0.04% sodium phosphate, monobasic; and water, pH 7.0 to 7.4 for injection. The acetamide is also the active ingredient in Triesence™ (Alcon), a 40 mg/ml suspension.

A person of ordinary skill in the art can determine the osmolarity for these formulations. The degree of dissociation of the active ingredient in solution can be determined and used to determine differences of osmolarity from the molarity in these formulations. For example, considering at least some of the formulations may be concentrated (or suspensions), the molarity can differ from the osmolarity.

The formulation of therapeutic agent 110 may be injected into therapeutic device 100 and may comprise many known formulations of therapeutic agents, and the formulation therapeutic agent 110 may comprise an osmolarity suitable for release for an extended time from device 100. Table 1B shows examples of osmolarity (Osm) of saline and some of the commercially formulations of Table 1A.

TABLE 1B

Summary of Calculations

| Description | Osm (M) |
|---|---|
| Saline (0.9%) | 0.308 |
| Phosphate Buffered Saline (PBS) | 0.313 |
| Lucentis ™ | 0.289 |
| Avastin ™ | 0.182 |
| Triamcinolone Acetonide (Trivaris-Allergan) | 0.342 |

TABLE 1B-continued

Summary of Calculations

| Description | Osm (M) |
|---|---|
| Triamcinolone Acetonide (Triessence-Alcon) | Isotonic* |
| Triamcinolone Acetonide (Kenalog-Apothecon) | Isotonic* |

*As described in package insert

The vitreous humor 30 of the eye 10 may comprises an osmolarity of about 290 mOsm to about 320 mOsm. Formulations of therapeutic agent 110 having an osmolarity from about 280 mOsm to about 340 mOsm are substantially isotonic and substantially iso-osmotic with respect to the vitreous humor 30 of the eye 10. Although the formulations listed in Table 1B are substantially iso-osmotic and isotonic with respect to the vitreous of the eye 10 and suitable for injection into the therapeutic device, the formulation of the therapeutic agent 110 injected into the therapeutic device can be hypertonic (hyper-osmotic) or hypotonic (hypo-osmotic) with respect to the tonicity and osmolarity of the vitreous. Work in relation to embodiments suggests that a hyper-osmotic formulation may release the active ingredient of the therapeutic agent 110 into the vitreous somewhat faster initially when the solutes of the injected formulation equilibrate with the osmolarity of the vitreous, and that a hypo-osmotic formulation such as Avastin™ may release the active ingredient of the therapeutic agent 110 into the vitreous somewhat slower initially when the solutes of the injected formulation equilibrate with the eye 10. A person of ordinary skill in the art can conduct experiments based on the teachings described herein to determine empirically the appropriate reservoir 140 chamber 132 volume and porous structure 150 for a formulation of therapeutic agent 110 disposed in the reservoir 140 chamber 132, so as to release therapeutic amounts of the therapeutic agent 110 for an extended time and to provide therapeutic concentrations of therapeutic agent 110 in the vitreous within a range of therapeutic concentrations that is above a minimum inhibitory concentration for the extended time.

Figure 14:
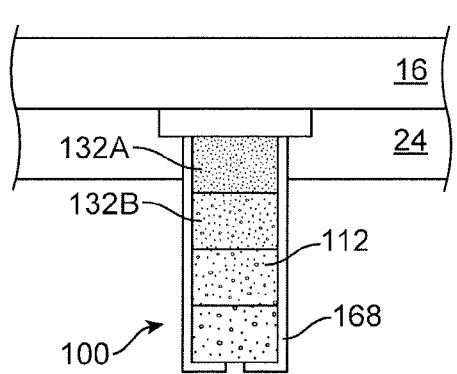
FIG. 14 shows a therapeutic device configured for placement in an eye as in FIGS. 2 and 3, in which the device comprises a plurality of chambers and channels connecting the chambers so as to linearize the release of the therapeutic agent, in accordance with embodiments.

FIG. 14 shows a therapeutic device 100 configured for placement in an eye 10 as in FIGS. 2 and 3, in which the device comprises a tube 168 with a plurality of chambers and channels connecting the chambers so as to linearize the release of the therapeutic agent 110. A first chamber 132A may comprise a reservoir having a first volume to contain the therapeutic quantity of the therapeutic agent 110. For example, the therapeutic agent 110 can comprise the active ingredient 112 contained within the reservoir. A second chamber 132B can be disposed distally to the first chamber 132A, with a first opening connecting the first chamber 132A and the second chamber 132B. For example, the therapeutic agent 110 can diffuse through the first opening into the second chamber 132B. The second chamber 132B may comprise a second volume, such that therapeutic agent 110 is temporarily stored in the second chamber 132B so as to linearize, for example toward zero order, the delivery of the therapeutic agent 110. A second opening can extend from the second chamber 132B toward the vitreous humor 30. The first opening, the second opening and the second volume can be sized so as to linearize the delivery of the therapeutic agent 110 for the sustained release at therapeutic levels for the extended time. More than one therapeutic agent 110 can be inserted into the therapeutic device 100. In such a case the two or more therapeutic agents 110 may be mixed together or injected into separate chambers.

Additional chambers and openings can be disposed on the device in order to linearize the delivery of the drug or therapeutic agent 110. For example, a third chamber 132C can be disposed distally to the second chamber 132B. The second opening can couple the second chamber 132B to the third chamber 132C. For example, a fourth chamber 132D can be disposed distally to the third chamber 132C, and a third opening can connect the third chamber 132C and the fourth chamber 132D.

Additionally or in the alternative, the therapeutic device may comprise at least one gate to provide for sustained drug delivery. The gate can be moved from "closed" to "open" position using magnetism or by applying electrical current. For example the gates can slide or twist. The gates can be spring-loaded, and may comprise a pump that can be re-loaded. The gates may comprise an osmotic pump.

Figure 15:
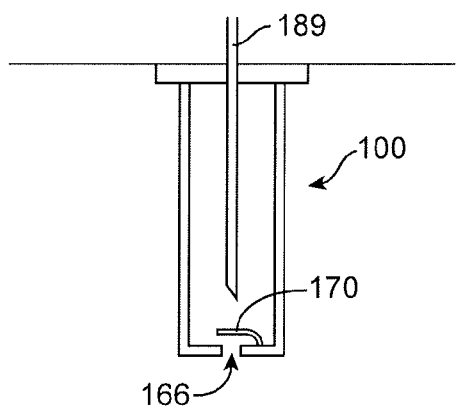
FIG. 15 shows a therapeutic device configured for placement in an eye as in FIGS. 2 and 3, in which the device comprises a needle stop located at the bottom of the therapeutic device, in accordance with embodiments.

FIG. 15 shows a therapeutic device configured for placement in an eye 10 as in FIGS. 2 and 3, in which the device 100 comprises needle stop 170 located at the bottom of the therapeutic device. The needle stop 170 that may be included in the therapeutic device to keep the injection needle 189 from penetrating through and possibly damaging the exit port(s) 166 of the therapeutic device 100. The needle stop 170 will desirably be made of a material of sufficient rigidity to prevent the advancement of the injection needle 189 past a certain level in the therapeutic device. Additionally or in the alternative, the length of the injector's needle 189 may be designed so that it may not penetrate through and possibly damage the exit port(s) 166 of the therapeutic device 100.

Figure 16:
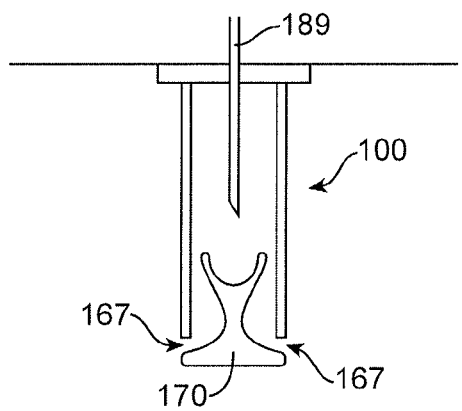
FIG. 16 shows a therapeutic device configured for placement in an eye as in FIGS. 2 and 3, in which the device comprises a needle stop located at the bottom of the therapeutic device and the shape of the device encourages the movement of the therapeutic agent within the chamber of the therapeutic device, in accordance with embodiments.
Figure 17:
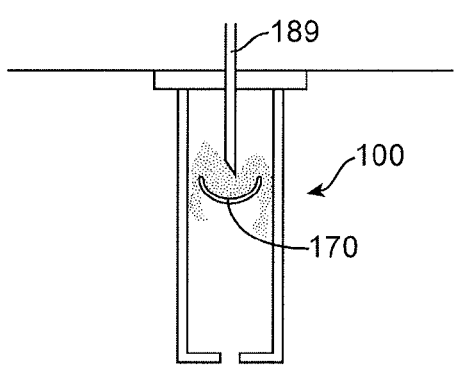
FIG. 17 shows a therapeutic device configured for placement in an eye as in FIGS. 2 and 3, in which the device comprises a needle stop located in the middle of the therapeutic device, in accordance with embodiments.
Figure 18:
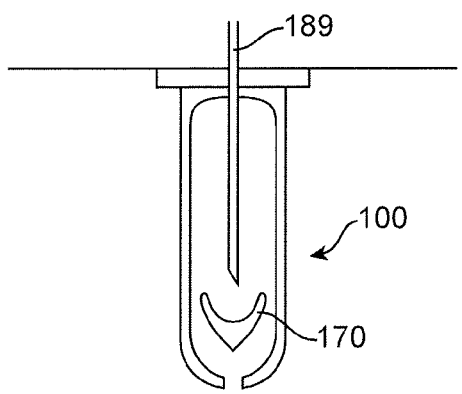
FIG. 18 shows a therapeutic device configured for placement in an eye as in FIGS. 2 and 3, in which the device comprises a needle stop located in the middle of the therapeutic device and the shape of the device encourages the movement of the therapeutic agent within the chamber of the therapeutic device, in accordance with embodiments.
Figure 19:
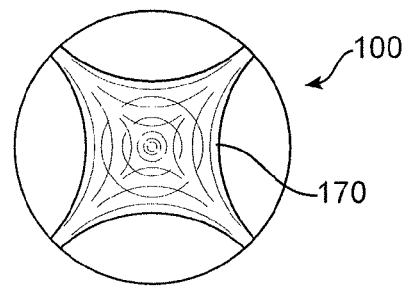
FIG. 19 shows a top view of the therapeutic device configured for placement in an eye as in FIG. 18, in accordance with embodiments.

As shown in FIGS. 15 and 16, the needle stop 170 may be positioned at the posterior end of the therapeutic device. As shown in FIG. 16, the needle stop 170 may partially define the exit ports 167. FIGS. 17, 18 and 19 show additional embodiments that may include needle stops placed in the middle of the device 100. The needle stop 170 may be designed in such a manner as to function as a flow diverter for the therapeutic agent 110. The shape of the needle stop 170 may encourage the mixing of the therapeutic agent 110 with the rest of the fluids present in the inner chamber(s) 132 of the therapeutic device 100.

FIG. 16 shows a therapeutic device 100 configured for placement in an eye 10 as in FIGS. 2 and 3, in which the device 100 comprises a needle stop 170 located at the bottom of the therapeutic device 100 and the shape of the device encourages the movement of the therapeutic agent 110 within the chamber 132 of the therapeutic device 100.

FIG. 17 shows a therapeutic device 100 configured for placement in an eye 10 as in FIGS. 2 and 3, in which the device comprises needle stop 170 located in the middle of the therapeutic device 100.

FIG. 18 shows a therapeutic device 100 configured for placement in an eye 10 as in FIGS. 2 and 3, in which the device comprises needle stop 170 located in the middle of the therapeutic device 100 and the shape of the device encourages the movement of the therapeutic agent 110 within the chamber 132 of the therapeutic device 100.

FIG. 19 shows a top view of the therapeutic device 100 configured for placement in an eye 10 as in FIG. 18.

Figure 20:
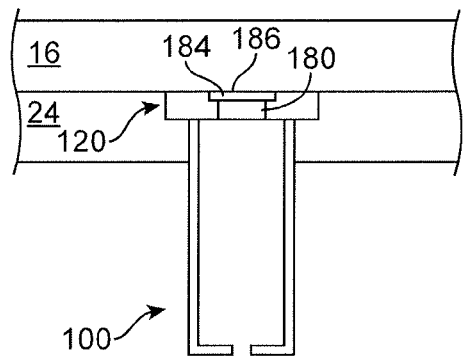
FIG. 20 shows an access port suitable for incorporation with the therapeutic device, in accordance with embodiments.

FIG. 20 shows an access port 180 suitable for incorporation with the therapeutic device 100. The access port 180 may be combined with the therapeutic devices described herein, for example with reference to FIGS. 2 to 14. The access port 180 may be disposed on a proximal end of the device. The access port 180 may comprise an opening formed in the retention structure 120 with a penetrable barrier 184 comprising a septum 186 disposed thereon. The access port 180 may be configured for placement under the conjunctiva 16 of the patient and above the sclera 24.

Figure 21:
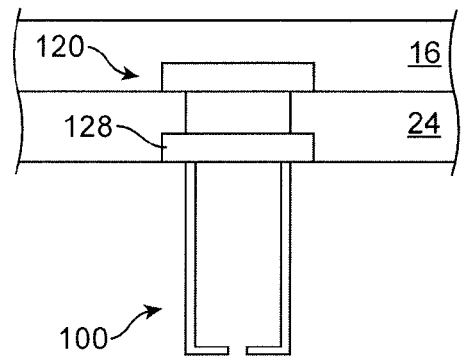
FIG. 21 shows a collar suitable for incorporation with the therapeutic device, in accordance with embodiments.

FIG. 21 shows a collar 128 suitable for incorporation with the therapeutic device 100. The retention structure 120 may be configured to couple to the sclera 24 and may comprise the collar 128. The collar 128 may comprise an expandable collar.

Figure 22:
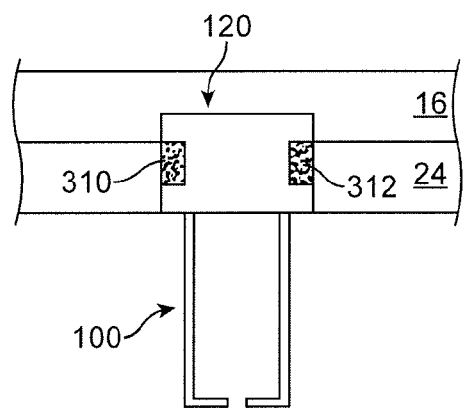
FIG. 22 shows biocompatible material impregnated with an anti-bacterial agent on the therapeutic device to inhibit bacterial growth along the device from the sclera to the vitreous humor, in accordance with embodiments.

FIG. 22 shows biocompatible material impregnated with an anti-bacterial agent 310 on the therapeutic device 100 to inhibit bacterial growth along the device from the sclera 24 to the vitreous humor 30. The biocompatible material may comprise collagen, for example a collagen sponge 312, and the anti-bacterial agent may comprise silver impregnated in the collagen. The biocompatible material impregnated with the bactericide agent 310 may extend around at least a portion of the outer surface of the device 100. The anti-bacterial agent may comprise a portion of the retention structure 120, such that the anti-bacterial agent is disposed at least partially within the sclera 24 when the device 100 is inserted into the eye 10.

Figure 23:
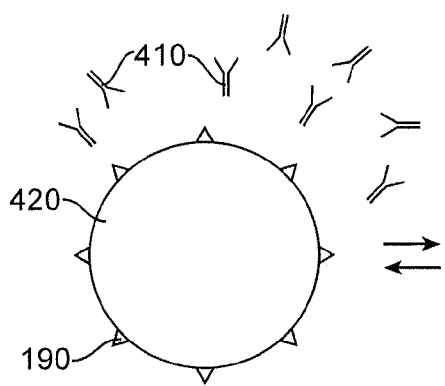
FIG. 23 shows released fragments of antibodies, in accordance with embodiments.
Figure 24:
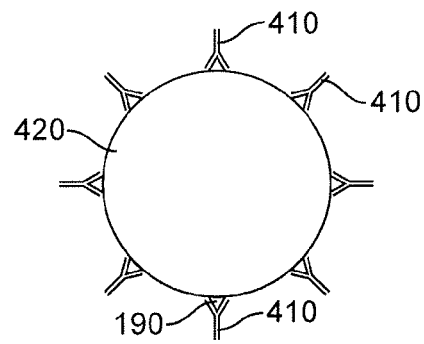
FIG. 24 shows antibody fragments reversibly bound to a substrate, in accordance with embodiments.

FIG. 23 shows released antibodies comprising antibody fragments 410 and a substrate 420 comprising binding agent 190, and FIG. 24 shows antibody fragments 410 reversibly bound to a substrate 420 with binding agent 190, in accordance with embodiments. The antibody fragments 410 can be reversibly bound to the substrate 420 comprising the binding agent 190, such that the bound antibody fragments 410 are in equilibrium with the unbound antibody fragments 410. One of ordinary skill in the art will recognize many substrates comprising binding agent to reversibly bind at least a portion of an antibody based on the teachings described herein. Examples of binding media may include particulates used in chromatography, such as: Macro-Prep t-Butyl HIC Support, Macro-Prep DEAE Support, CHT Ceramic, Hydroxyapatite Type I, Macro-Prep CM Support, Macro-Prep Methyl HIC Support, Macro-Prep Ceramic Hydroxapatite Type II, UNOsphere S Cation Exchange Support, UNOsphere Q Strong Anion Exchange Support, Macro-Prep High-S Support, and Macro-Prep High-Q Support. Additional media to test for binding include ion exchange and bioaffinity chromatography media based on a hydrophilic polymeric support (GE Healthcare) that bind proteins with high capacity, and a hydrophilic packing material from Harvard Apparatus made from poly(vinyl alcohol) that binds more protein than silica. Other candidates would be known to those knowledgeable in the art.

Figure 25:
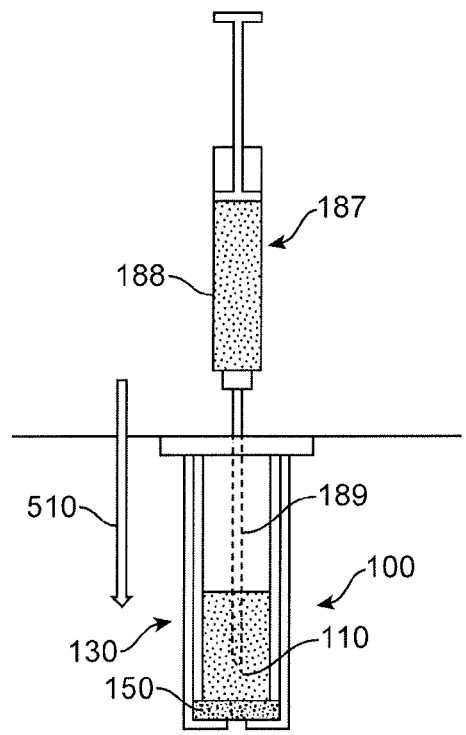
FIG. 25 shows a therapeutic device coupled to an injector to insert therapeutic agent into the device, in accordance with embodiments.

FIG. 25 shows therapeutic device 100 coupled to injector 187 to inject 510 therapeutic agent 110 into container 130 of the device. The injector 187 may comprise needle 189 coupled to a syringe 188.

Figure 26:
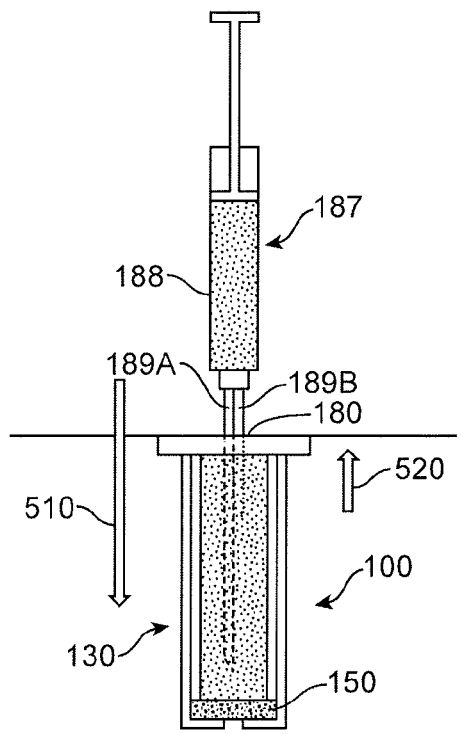
FIG. 26 shows a therapeutic device coupled to an injector to simultaneously inject and remove material from the device, in accordance with embodiments.

FIG. 26 shows a therapeutic device 100 coupled to an injector 187 to inject and remove material from the device. The injector 187 may comprise needle 189 having a first lumen 189A and a second lumen 189B configured to insert into a container 130 of the device 100. The injector 187 may simultaneously inject 510 therapeutic agent 110 into and withdraw 520 liquid from the device 100. The injector 187 may comprise a first one way valve and a second one way valve coupled to the first lumen 189A and the second lumen 189B, respectively.

Figure 27:
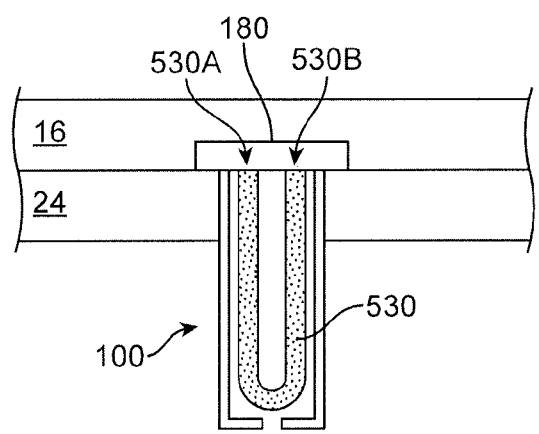
FIG. 27 shows a therapeutic device comprising a micro loop channel, in accordance with embodiments.

FIG. 27 shows a therapeutic device 100 comprising a microloop channel 530. The microloop channel 530 may extend to a first port 530A and a second port 530B, such the therapeutic agent 110 can be injected into the first port, for example with a binding agent, and flowable material, for example liquid comprising binding agent, can be drawn from the microloop channel 530.

Figure 28:
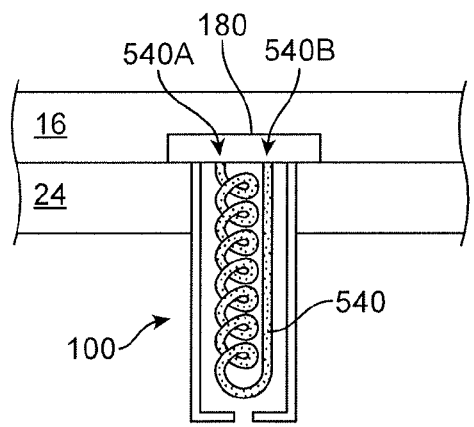
FIG. 28 shows a therapeutic device comprising a tortuous channel, in accordance with embodiments.

FIG. 28 shows therapeutic device 100 comprising a tortuous channel 540. The tortuous channel may extend from a first port 540A to a second port 540B, such that the therapeutic agent 110 can be injected into the first port 540A and flowable material, for example liquid comprising the binding agent, can be drawn from the second channel 540B.

Figure 29:
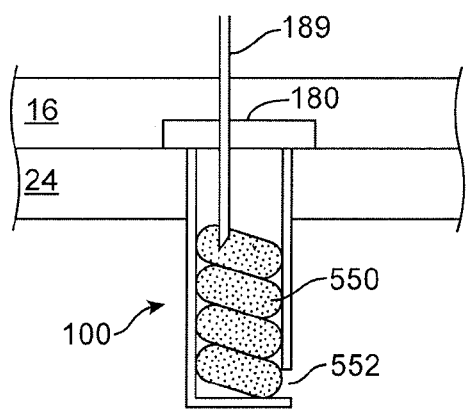
FIG. 29 shows a therapeutic device comprising a coiled channel, in accordance with embodiments.

FIG. 29 shows a therapeutic device 100 comprising a tortuous coiled channel 550. The coiled channel 550 can extend to an exit port 552. A needle 189 can be inserted into the port 180 to inject therapeutic agent 110 into device 100.

Figure 30:
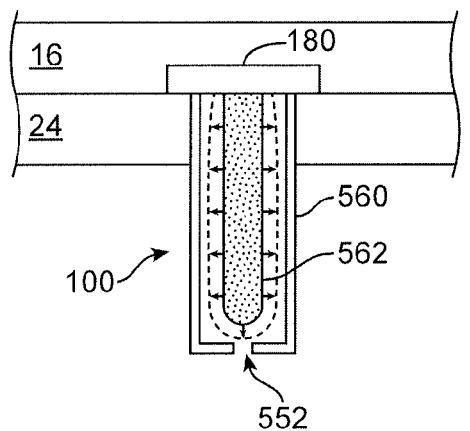
FIG. 30 shows an expandable and contractible structure to retain the therapeutic agent and an outer rigid casing to couple to the sclera, in accordance with embodiments.

FIG. 30 shows an expandable and contactable structure 562 to retain the therapeutic agent 110 and an outer rigid casing 560 to couple to the sclera 24. The expandable structure 562 may comprise a membrane, such as at least one of a bag, a balloon, a flexible reservoir, a diaphragm, or a bag. The outer rigid casing 560 may extend substantially around the structure 562 and may comprise an opening 552 to release liquid into the vitreous humor 30 when the structure 562 is expanded and to draw vitreous humor 30 inside a chamber of the casing when material is drawn from the structure and the structure 562 contacts.

Figure 31:
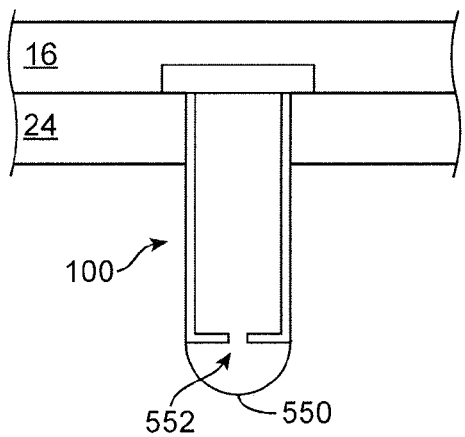
FIG. 31 shows a membrane disposed over an exit port of a therapeutic device, in accordance with embodiments.

FIG. 31 shows a membrane 550 disposed over an exit port 552 of therapeutic device 100.

Figure 32:
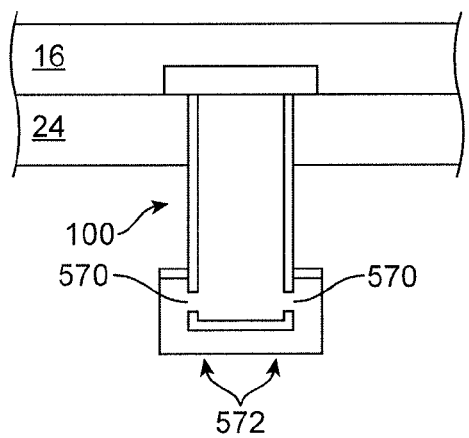
FIG. 32 shows a therapeutic device comprising a tubular membrane clamped onto the therapeutic device, in accordance with embodiments.

FIG. 32 shows therapeutic device 100 comprising a tubular membrane 572 clamped onto the therapeutic device 100 over side ports 570 of device 100.

When protective membranes have pores of 0.2 μm diameter, they can be 20 or more times larger than the proteins of interest, which may comprise a model for delivery of the therapeutic agent 110. For example, molecular weights and diameters of models of proteins of therapeutic interest may include the following:

| (a) | IgG | 150 kDa | 10.5 nm |
| (b) | BSA | 69 kDa | 7.2 nm |
| (c) | Fab fragment of IgG | 49 kDa | hydrodynamic diameter not reported |

Therefore, solutions of therapeutic compounds in the size range of IgG and BSA can flow relatively easily through 0.2 μm pore size protective membranes which may be used to stop passage of bacterial and other cells.

Binding materials/agents may comprise at least one of a chemical binding material/agent, a structural binding agent or material, or an electrostatic binding agent or material. The types of binding agent may comprise a classification composed of non-biodegradable material, for example glass beads, glass wool or a glass rod. A surface can be derivatized with at least one functional group so as to impart the binding agent or material with the potential for at least one of ionic, hydrophobic, or bioaffinity binding to at least one therapeutic compound.

The binding agent may comprise a biodegradable material. For example, the biodegradation, binding, or any combination of the previous processes may control the diffusion rate.

The binding agent may comprise ion exchange, and the ion exchange may comprise at least one of a functional group, a pH sensitive binding or a positive or negative charge. For example, ion exchange may occur with at least one of diethylaminoethyl or carboxymethyl functional groups. Additionally, the ion exchange may comprise positive or negative ion exchange.

The binding agent may comprise a pH sensitive binding agent. For example the binding agent can be configured to elute therapeutic agent 110 at a pH of 7, and to bind the therapeutic agent 110 at a pH from about 4 to about 6.5. A cation exchange binding agent can be configured, for example, such that at a pH of 7, the net negative charge of the binding agent decreases causing a decrease in binding of the positively charged drug and release of the therapeutic agent 110. A target buffer can be provided with the binding agent to reversibly couple the binding agent to the therapeutic agent 110. The rate of release can be controlled, for example slowed down, by using insolubility of the buffer in the vitreous. Alternatively or in combination the elution can be limited by using a porous membrane or a physical property such as a size of an opening.

Furthermore, the binding agent may comprise hydrophobic interaction. For example, the binding agent may comprise at least one binding to hydrophobic pockets, for example at least one of methyl, ethyl, propyl, butyl, t-butyl or phenyl functional groups.

The binding agent may comprise affinity, for example at least one of a macromolecular affinity or a metal chelation affinity. Examples can include a hydroxyapatite, or chelated metal, for example zinc. Iminodiacetic acid can be chelated with zinc.

The binding agent may comprise at least one of the following functions: charging, recharging or elution. The charging may comprise a porous material injected therein so as to release the active ingredient. The porous matter may have an extremely large inert surface area, in which the surface area can be available for binding. The recharging may comprise removing carrier+therapeutic agent; and adding freshly "charged" carrier+therapeutic agent.

The elution may comprise a byproduct, for example unbound binding agent that can be removed. For example, diffusion (plug flow) of vitreous to change conditions, e.g. pH to reduce interaction of therapeutic agent+carriers.

Additionally or in the alternative, a sustained drug delivery system of the therapeutic agent 110 may comprise drug delivery packets, e.g. microspheres, that are activated. The packets can be activated with at least one of photochemical activation, thermal activation or biodegradation.

The therapeutic device 100 may comprise at least one structure configured to provide safety precautions. The device may comprise at least one structure to prevent at least one of macrophage or other immune cell within the reservoir body; bacterial penetration; or retinal detachment.

The therapeutic device 100 may be configured for other applications in the body. Other routes of administration of drugs may include at least one of intraocular, oral, subcutaneous, intramuscular, intraperitoneal, intranasal, dermal, intrathecal, intravascular, intra articular, pericardial, intraluminal in organs and gut, or the like.

Conditions that may be treated and/or prevented using any drug delivery device and method described herein may include at least one of the following: hemophilia and other blood disorders, growth disorders, diabetes, leukemia, hepatitis, renal failure, HIV infection, hereditary diseases such as cerebrosidase deficiency and adenosine deaminase deficiency, hypertension, septic shock, autoimmune diseases such as multiple sclerosis, Graves disease, systemic lupus erythematosus and rheumatoid arthritis, shock and wasting disorders, cystic fibrosis, lactose intolerance, Crohn's disease, inflammatory bowel disease, gastrointestinal or other cancers, degenerative diseases, trauma, multiple systemic conditions such as anemia, and ocular diseases such as, for example, retinal detachment, proliferative retinopathy, proliferative diabetic retinopathy, degenerative disease, vascular diseases, occlusions, infection caused by penetrating traumatic injury, endophthalmitis such as endogenous/systemic infection, post-operative infections, inflammations such as posterior uveitis, retinitis or choroiditis and tumors such as neoplasms and retinoblastoma.

Examples of therapeutic agents 110 that may be delivered by the therapeutic device 100 are described in Table 1A and may include Triamcinolone acetonide, Bimatoprost (Lumigan), Ranibizumab (Lucentis™), Travoprost (Travatan, Alcon), Timolol (Timoptic, Merck), Levobunalol (Betagan, Allergan), Brimonidine (Alphagan, Allergan), Dorzolamide (Trusopt, Merck), Brinzolamide (Azopt, Alcon). Additional examples of therapeutic agents 110 that may be delivered by the therapeutic device 100 include antibiotics such as tetracycline, chlortetracycline, bacitracin, neomycin, polymyxin, gramicidin, cephalexin, oxytetracycline, chloramphenicol kanamycin, rifampicin, ciprofloxacin, tobramycin, gentamycin, erythromycin and penicillin; antifungals such as amphotericin B and miconazole; anti-bacterials such as sulfonamides, sulfadiazine, sulfacetamide, sulfamethizole and sulfisoxazole, nitrofurazone and sodium propionate; antivirals such as idoxuridine, trifluorotymidine, acyclovir, ganciclovir and interferon; antiallergenics such as sodium cromoglycate, antazoline, methapyriline, chlorpheniramine, pyrilamine, cetirizine and prophenpyridamine; anti-inflammatories such as hydrocortisone, hydrocortisone acetate, dexamethasone, dexamethasone 21-phosphate, fluocinolone, medrysone, prednisolone, prednisolone 21-phosphate, prednisolone acetate, fluoromethalone, betamethasone, and triamcinolone; non-steroidal anti-inflammatories such as salicylate, indomethacin, ibuprofen, diclofenac, flurbiprofen and piroxicam; decongestants such as phenylephrine, naphazoline and tetrahydrozoline; miotics and anticholinesterases such as pilocarpine, salicylate, acetylcholine chloride, physostigmine, eserine, carbachol, diisopropyl fluorophosphate, phospholine iodide and demecarium bromide; mydriatics such as atropine sulfate, cyclopentolate, homatropine, scopolamine, tropicamide, eucatropine and hydroxyamphetamine; sypathomimetics such as epinephrine; antineoplastics such as carmustine, cisplatin and fluorouracil; immunological drugs such as vaccines and immune stimulants; hormonal agents such as estrogens, estradiol, progestational, progesterone, insulin, calcitonin, parathyroid hormone and peptide and vasopressin hypothalamus releasing factor; beta adrenergic blockers such as timolol maleate, levobunolol Hcl and betaxolol Hcl; growth factors such as epidermal growth factor, fibroblast growth factor, platelet derived growth factor, transforming growth factor beta, somatotropin and fibronectin; carbonic anhydrase inhibitors such as dichlorophenamide, acetazolamide and methazolamide and other drugs such as prostaglandins, antiprostaglandins and prostaglandin precursors. Other therapeutic agents known to those skilled in the art which are capable of controlled, sustained release into the eye 10 in the manner described herein are also suitable for use in accordance with embodiments.

The therapeutic agent 110 may comprise one or more of the following: Abarelix, Abatacept, Abciximab, Adalimumab, Aldesleukin, Alefacept, Alemtuzumab, Alpha-1-proteinase inhibitor, Alteplase, Anakinra, Anistreplase, Antihemophilic Factor, Antithymocyte globulin, Aprotinin, Arcitumomab, Asparaginase, Basiliximab, Becaplermin, Bevacizumab, Bivalirudin, Botulinum Toxin Type A, Botulinum Toxin Type B, Capromab, Cetrorelix, Cetuximab, Choriogonadotropin alfa, Coagulation Factor IX, Coagulation factor VIIa, Collagenase, Corticotropin, Cosyntropin, Cyclosporine, Daclizumab, Darbepoetin alfa, Defibrotide, Denileukin diftitox, Desmopressin, Dornase Alfa, Drotrecogin alfa, Eculizumab, Efalizumab, Enfuvirtide, Epoetin alfa, Eptifibatide, Etanercept, Exenatide, Felypressin, Filgrastim, Follitropin beta, Galsulfase, Gemtuzumab ozogamicin, Glatiramer Acetate, Glucagon recombinant, Goserelin, Human Serum Albumin, Hyaluronidase, Ibritumomab, Idursulfase, Immune globulin, Infliximab, Insulin Glargine recombinant, Insulin Lyspro recombinant, Insulin recombinant, Insulin, porcine, Interferon Alfa-2a, Recombinant, Interferon Alfa-2b, Recombinant, Interferon alfacon-1, Interferonalfa-n1, Interferon alfa-n3, Interferon beta-1b, Interferon gamma-1b, Lepirudin, Leuprolide, Lutropin alfa, Mecasermin, Menotropins, Muromonab, Natalizumab, Nesiritide, Octreotide, Omalizumab, Oprelvekin, OspA lipoprotein, Oxytocin, Palifermin, Palivizumab, Panitumumab, Pegademase bovine, Pegaptanib, Pegaspargase, Pegfilgrastim, Peginterferon alfa-2a, Peginterferon alfa-2b, Pegvisomant, Pramlintide, Ranibizumab, Rasburicase, Reteplase, Rituximab, Salmon Calcitonin, Sargramostim, Secretin, Sermorelin, Serum albumin iodonated, Somatropin recombinant, Streptokinase, Tenecteplase, Teriparatide, Thyrotropin Alfa, Tositumomab, Trastuzumab, Urofollitropin, Urokinase, or Vasopressin. The molecular weights of the molecules and indications of these therapeutic agents are set forth below in Table 1A.

The therapeutic agent 110 may comprise one or more compounds that act by binding members of the immunophilin family of cellular proteins. Such compounds are known as "immunophilin binding compounds" Immunophilin binding compounds include but are not limited to the "limus" family of compounds. Examples of limus compounds that may be used include but are not limited to cyclophilins and FK506-binding proteins (FKBPs), including sirolimus (rapamycin) and its water soluble analog SDZ-RAD, tacrolimus, everolimus, pimecrolimus, CCI-779 (Wyeth), AP23841 (Ariad), and ABT-578 (Abbott Laboratories).

The limus family of compounds may be used in the compositions, devices and methods for the treatment, prevention, inhibition, delaying the onset of, or causing the regression of angiogenesis-mediated diseases and conditions of the eye 10, including choroidal neovascularization. The limus family of compounds may be used to prevent, treat, inhibit, delay the onset of, or cause regression of AMD, including wet AMD. Rapamycin may be used to prevent, treat, inhibit, delay the onset of, or cause regression of angiogenesis-mediated diseases and conditions of the eye, including choroidal neovascularization. Rapamycin may be used to prevent, treat, inhibit, delay the onset of, or cause regression of AMD, including wet AMD.

The therapeutic agent 110 may comprise one or more of: pyrrolidine, dithiocarbamate (NF.kappa.B inhibitor); squalamine; TPN 470 analogue and fumagillin; PKC (protein kinase C) inhibitors; Tie-1 and Tie-2 kinase inhibitors; inhibitors of VEGF receptor kinase; proteosome inhibitors such as Velcade™ (bortezomib, for injection; ranibuzumab (Lucentis™) and other antibodies directed to the same target; pegaptanib (Macugen™); vitronectin receptor antagonists, such as cyclic peptide antagonists of vitronectin receptor-type integrins; .alpha.-v/.beta.-3 integrin antagonists; .alpha.-v/.beta.-1 integrin antagonists; thiazolidinediones such as rosiglitazone or troglitazone; interferon, including.gamma.-interferon or interferon targeted to CNV by use of dextran and metal coordination; pigment epithelium derived factor (PEDF); endostatin; angiostatin; tumistatin; canstatin; anecortave acetate; acetonide; triamcinolone; tetrathiomolybdate; RNA silencing or RNA interference (RNAi) of angiogenic factors, including ribozymes that target VEGF expression; Accutane™ (13-cis retinoic acid); ACE inhibitors, including but not limited to quinopril, captopril, and perindozril; inhibitors of mTOR (mammalian target of rapamycin); 3-aminothalidomide; pentoxifylline; 2-methoxyestradiol; colchicines; AMG-1470; cyclooxygenase inhibitors such as nepafenac, rofecoxib, diclofenac, rofecoxib, NS398, celecoxib, vioxx, and (E)-2-alkyl-2(4-methanesulfonylphenyl)-1-phenylethene; t-RNA synthase modulator; metalloprotease 13 inhibitor; acetylcholinesterase inhibitor; potassium channel blockers; endorepellin; purine analog of 6-thioguanine; cyclic peroxide ANO-2; (recombinant) arginine deiminase; epigallocatechin-3-gallate; cerivastatin; analogues of suramin; VEGF trap molecules; apoptosis inhibiting agents; Visudyne™, snET2 and other photo sensitizers, which may be used with photodynamic therapy (PDT); inhibitors of hepatocyte growth factor (antibodies to the growth factor or its receptors, small molecular inhibitors of the c-met tyrosine kinase, truncated versions of HGF e.g. NK4).

The therapeutic agent 110 may comprise a combination with other therapeutic agents and therapies, including but not limited to agents and therapies useful for the treatment of angiogenesis or neovascularization, particularly CNV. Non-limiting examples of such additional agents and therapies include pyrrolidine, dithiocarbamate (NF.kappa.B inhibitor); squalamine; TPN 470 analogue and fumagillin; PKC (protein kinase C) inhibitors; Tie-1 and Tie-2 kinase inhibitors; inhibitors of VEGF receptor kinase; proteosome inhibitors such as Velcade™ (bortezomib, for injection; ranibuzumab (Lucentis™) and other antibodies directed to the same target; pegaptanib (Macugen™); vitronectin receptor antagonists, such as cyclic peptide antagonists of vitronectin receptor-type integrins; .alpha.-v/.beta.-3 integrin antagonists; .alpha.-v/.beta.-1 integrin antagonists; thiazolidinediones such as rosiglitazone or troglitazone; interferon, including.gamma.-interferon or interferon targeted to CNV by use of dextran and metal coordination; pigment epithelium derived factor (PEDF); endostatin; angiostatin; tumistatin; canstatin; anecortave acetate; acetonide; triamcinolone; tetrathiomolybdate; RNA silencing or RNA interference (RNAi) of angiogenic factors, including ribozymes that target VEGF expression; Accutane™ (13-cis retinoic acid); ACE inhibitors, including but not limited to quinopril, captopril, and perindozril; inhibitors of mTOR (mammalian target of rapamycin); 3-aminothalidomide; pentoxifylline; 2-methoxyestradiol; colchicines; AMG-1470; cyclooxygenase inhibitors such as nepafenac, rofecoxib, diclofenac, rofecoxib, NS398, celecoxib, vioxx, and (E)-2-alkyl-2(4-methanesulfonylphenyl)-1-phenylethene; t-RNA synthase modulator; metalloprotease 13 inhibitor; acetylcholinesterase inhibitor; potassium channel blockers; endorepellin; purine analog of 6-thioguanine; cyclic peroxide ANO-2; (recombinant) arginine deiminase; epigallocatechin-3-gallate; cerivastatin; analogues of suramin; VEGF trap molecules; inhibitors of hepatocyte growth factor (antibodies to the growth factor or its receptors, small molecular inhibitors of the c-met tyrosine kinase, truncated versions of HGF e.g. NK4); apoptosis inhibiting agents; Visudyne™, snET2 and other photo sensitizers with photodynamic therapy (PDT); and laser photocoagulation.

The therapeutic agents may be used in conjunction with a pharmaceutically acceptable carrier such as, for example, solids such as starch, gelatin, sugars, natural gums such as acacia, sodium alginate and carboxymethyl cellulose; polymers such as silicone rubber; liquids such as sterile water, saline, dextrose, dextrose in water or saline; condensation products of castor oil and ethylene oxide, liquid glyceryl triester of a lower molecular weight fatty acid; lower alkanols; oils such as corn oil, peanut oil, sesame oil, castor oil, and the like, with emulsifiers such as mono- or di-glyceride of a fatty acid, or a phosphatide such as lecithin, polysorbate 80, and the like; glycols and polyalkylene glycols; aqueous media in the presence of a suspending agent, for example, sodium carboxymethylcellulose, sodium hyaluronate, sodium alginate, poly(vinyl pyrrolidone) and similar compounds, either alone, or with suitable dispensing agents such as lecithin, polyoxyethylene stearate and the like. The carrier may also contain adjuvants such as preserving, stabilizing, wetting, emulsifying agents or other related materials.

The therapeutic device 100 may comprise a container configured to hold at least one therapeutic agent 110, the container comprising a chamber 132 to hold the at least one therapeutic agent 110 with at least one opening to release the at least one therapeutic agent 110 to the vitreous humor 30 and porous structure 150 placed within the at least one opening. The porous structure 150 may comprise a fixed tortuous, porous material such as a sintered metal, a sintered glass or a sintered polymer with a defined porosity and tortuosity that controls the rate of delivery of the at least one therapeutic agent 110 to the vitreous humor 30. The rigid porous structures can provide certain advantages over capillary tubes, erodible polymers and membranes as a mechanism for controlling the release of a therapeutic agent 110 or agents from the therapeutic device 100. These advantages include the ability of the rigid porous structure to comprise a needle stop 170, simpler and more cost effective manufacture, flushability for cleaning or de-clogging either prior to or after implantation, high efficiency depth filtration of microorganisms provided by the labyrinths of irregular paths within the structure and greater robustness due to greater hardness and thickness of the structure compared to a membrane or erodible polymer matrix. Additionally, when the rigid porous structure is manufactured from a sintered metal, ceramic, glass or certain plastics, it can be subjected to sterilization and cleaning procedures, such as heat or radiation based sterilization and depyrogenation that might damage polymer and other membranes. In certain embodiments, as illustrated in Example 9 of in U.S. patent application Ser. No. 12/696,678, filed 29 Jan. 2010, entitled "Posterior Segment Drug Delivery", published as U.S. Pub. No. 2010/0255061 on Oct. 7, 2010, the full disclosure of which has been previously incorporated herein by reference, the rigid porous structure may be configured to provide a therapeutically effective concentration of the therapeutic agent 110 in the vitreous for at least 6 months. This release profile provided by certain configurations of the rigid porous structures enables a smaller device which is preferred in a small organ such as the eye 10 where larger devices may alter or impair vision.

Figure 33:
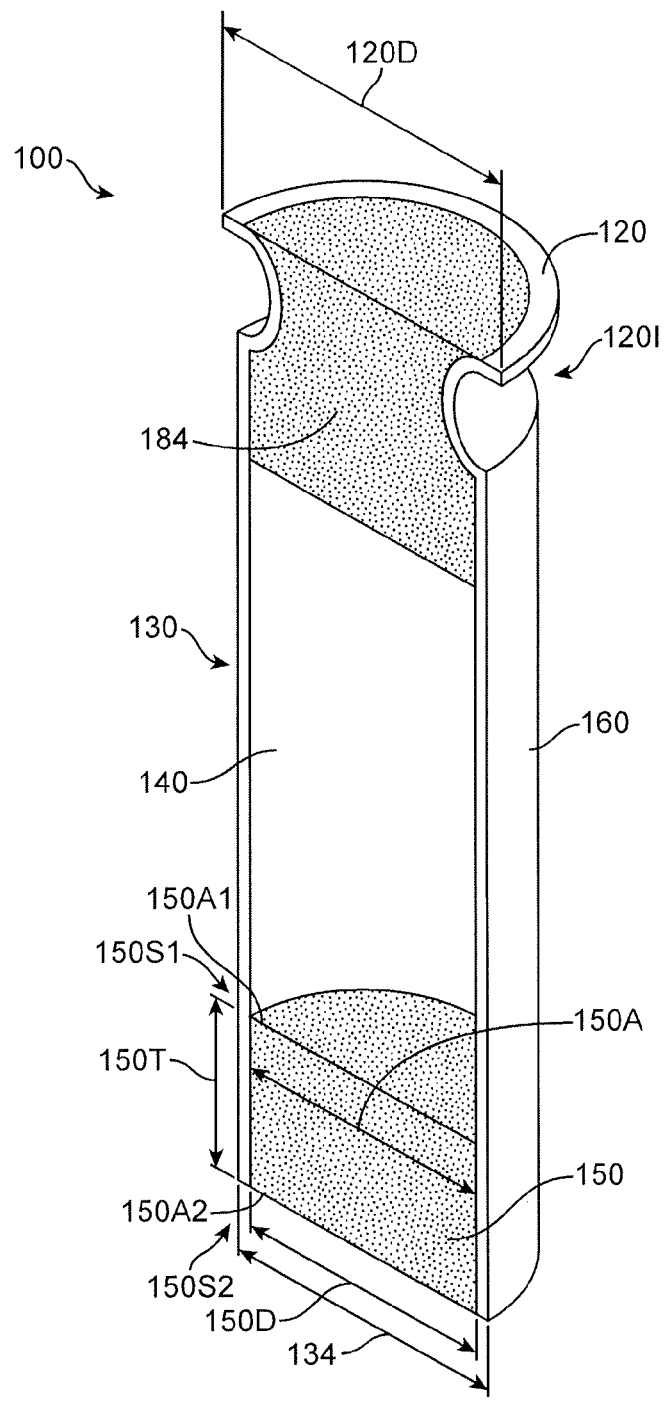
FIG. 33 shows a therapeutic device comprising a container having a penetrable barrier disposed on a first end, a porous structure disposed on a second end to release therapeutic agent for an extended period, and a retention structure comprising an extension protruding outward from the container to couple to the sclera and the conjunctiva, in accordance with embodiments.

FIG. 33 shows a therapeutic device 100 comprising a container 130 having a penetrable barrier 184 disposed on a first end, a porous structure 150 disposed on a second end to release therapeutic agent 110 for an extended period, and a retention structure 120 comprising an extension protruding outward from the container 130 to couple to the sclera 24 and the conjunctiva 16. The extending protrusion of the retention structure 120 may comprise a diameter 120D. The retention structure 120 may comprise an indentation 1201 sized to receive the sclera 24. The container 130 may comprise a tubular barrier 160 that defines at least a portion of the reservoir 140, and the container 130 may comprise a width, for example a diameter 134. The diameter 134 can be sized within a range, for example within a range from about 0.5 to about 4 mm, for example within a range from about 1 to 3 mm and can be about 2 mm, for example. The container 130 may comprise a length 136, sized so as to extend from the conjunctive to the vitreous to release the therapeutic agent 110 into the vitreous. The length 136 can be sized within a range, for example within a range from about 2 to about 14 mm, for example within a range from about 4 to 10 mm and can be about 7 mm, for example. The volume of the reservoir 140 may be substantially determined by an inner cross-sectional area of the tubular structure and distance from the porous structure 150 to the penetrable barrier 184. The retention structure 120 may comprise an annular extension having a retention structure diameter 120D greater than a diameter of the container 130. The retention structure 120 may comprise an indentation 1201 configured to receive the sclera 24 when the extension extends between the sclera 24 and the conjunctive. The penetrable barrier 184 may comprise a septum disposed on a proximal end of the container 130, in which the septum comprises a barrier that can be penetrated with a sharp object such as a needle 189 for injection of the therapeutic agent 110. The porous structure 150 may comprise a cross-sectional area 150A sized to release the therapeutic agent 110 for the extended period.

The porous structure 150 may comprise a first side 150S1 coupled to the reservoir 140 and a second side 150S2 to couple to the vitreous. The first side 150S1 may comprise a first area 150A1 and the second side 150S2 may comprise a second area 150A2. The porous structure 150 may comprise a thickness 150T. The porous structure 150 many comprise a diameter 150D.

The volume of the reservoir 140 may comprise from about 5 uL to about 2000 uL of therapeutic agent 110, or for example from about 10 uL to about 200 uL of therapeutic agent 110.

The therapeutic agent 110 stored in the reservoir 140 of the container 130 comprises at least one of a solid comprising the therapeutic agent 110, a solution comprising the therapeutic agent 110, a suspension comprising the therapeutic agent 110, particles comprising the therapeutic agent 110 adsorbed thereon, or particles reversibly bound to the therapeutic agent 110. For example, reservoir 140 may comprise a suspension of a cortico-steroid such as triamcinolone acetonide to treat inflammation of the retina 26. The reservoir 140 may comprise a buffer and a suspension of a therapeutic agent 110 comprising solubility within a range from about 1 µg/mL to about 100 µg/mL, such as from about 1 µg/mL to about 40 µg/mL. For example, the therapeutic agent 110 may comprise a suspension of triamcinolone acetonide having a solubility of approximately 19 µg/mL in the buffer at 37° C. when implanted.

The release rate index may comprise many values, and the release rate index with the suspension may be somewhat higher than for a solution in many embodiments, for example. The release rate index may be no more than about 5, and can be no more than about 2.0, for example no more than about 1.5, and in many embodiments may be no more than about 1.2, so as to release the therapeutic agent 110 with therapeutic amounts for the extended time.

The therapeutic device 100, including for example, the retention structure 120 and the porous structure 150, may be sized to pass through a lumen of a catheter.

The porous structure 150 may comprise a needle stop 170 that limits penetration of the needle 189. The porous structure 150 may comprise a plurality of channels configured for the extended release of the therapeutic agent 110. The porous structure 150 may comprise a rigid sintered material having characteristics suitable for the sustained release of the material.

Figure 34:
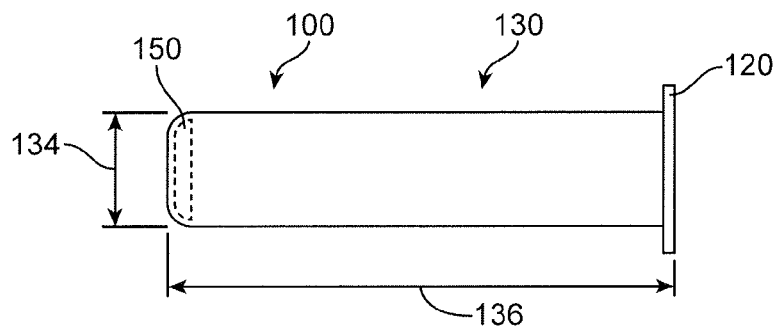
FIG. 34 shows a therapeutic device as in FIG. 33 comprising a rounded distal end, in accordance with embodiments.

FIG. 34 shows a therapeutic device 100 as in FIG. 33 comprising a rounded distal end.

Figure 35:
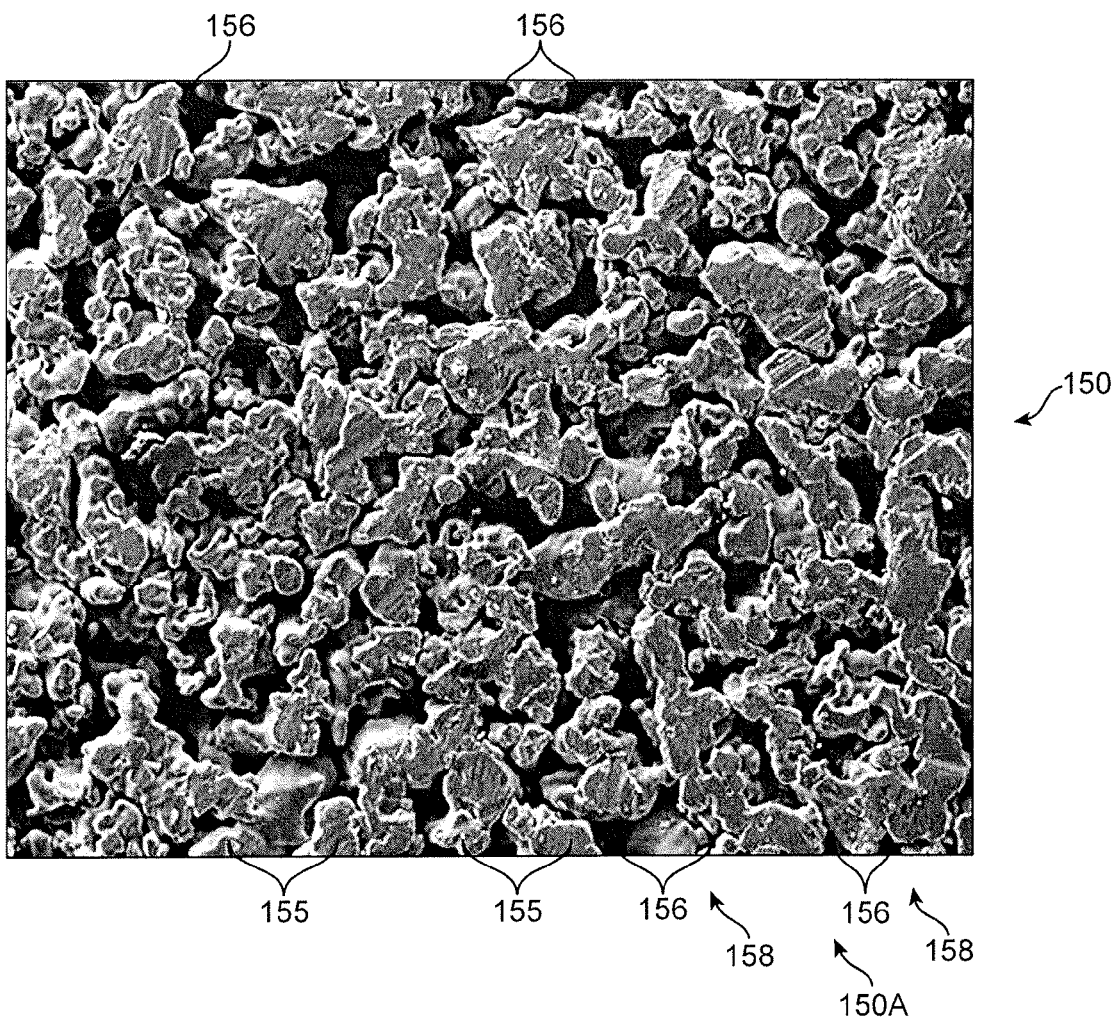
FIG. 35 shows a rigid porous structure configured for sustained release with a device as in FIG. 33 in accordance with embodiments.

FIG. 35 shows a rigid porous structure 150 as in FIG. 33. The rigid porous structure 150 comprises a plurality of interconnecting channels 156. The porous structure 150 comprises a sintered material composed of interconnected grains 155 of material. The interconnected grains 155 of material define channels 156 that extend through the porous material to release the therapeutic agent 110. The channels 156 may extend around the sintered grains of material 155, such that the channels 156 comprise interconnecting channels 156 extending through the porous material.

The rigid porous structure 150 can be configured for injection of the therapeutic agent 110 into the container 130 in many ways. The channels 156 of the rigid porous structure 150 may comprise substantially fixed channels 156 when the therapeutic agent 110 is injected into the reservoir 140 with pressure. The rigid porous structure 150 comprises a hardness parameter within a range from about 160 Vickers to about 500 Vickers. In some embodiments the rigid porous structure 150 is formed from sintered stainless steel and comprises a hardness parameter within a range from about 200 Vickers to about 240 Vickers. In some embodiments it is preferred to inhibit ejection of the therapeutic agent 110 through the porous structure 150 during filling or refilling the reservoir 140 of the therapeutic device 100 with a fluid. In these embodiments the channels 156 of the rigid porous structure 150 comprise a resistance to flow of an injected solution or suspension through a thirty gauge needle such that ejection of said solution or suspension through the rigid porous structure 150 is substantially inhibited when said solution or suspension is injected into the reservoir 140 of the therapeutic device 100. Additionally, these embodiments may optionally comprise an evacuation vent or an evacuation reservoir 140 under vacuum or both to facilitate filling or refilling of the reservoir 140.

The reservoir 140 and the porous structure 150 can be configured to release therapeutic amounts of the therapeutic agent 110 in many ways. The reservoir 140 and the porous structure 150 can be configured to release therapeutic amounts of the therapeutic agent 110 corresponding to a concentration of at least about 0.1 µg per ml of vitreous humor 30 for an extended period of at least about three months. The reservoir 140 and the porous structure 150 can be configured to release therapeutic amounts of the therapeutic agent 110 corresponding to a concentration of at least about 0.1 µg per ml of vitreous humor 30 and no more than about 10 µg per ml for an extended period of at least about three months. The therapeutic agent 110 may comprise at least a fragment of an antibody and a molecular weight of at least about 10 kDa. For example, the therapeutic agent 110 may comprise one or more of ranibizumab or bevacizumab. Alternatively or in combination, the therapeutic agent 110 may comprise a small molecule drug suitable for sustained release. The reservoir 140 and the porous structure 150 may be configured to release therapeutic amounts of the therapeutic agent 110 corresponding to a concentration of at least about 0.1 ug per ml of vitreous humor 30 and no more than about 10 ug per ml for an extended period of at least about 3 months or at least about 6 months. The reservoir 140 and the porous structure 150 can be configured to release therapeutic amounts of the therapeutic agent corresponding to a concentration of at least about 0.1 ug per ml of vitreous humor 30 and no more than about 10 ug per ml for an extended period of at least about twelve months or at least about two years or at least about three years. The reservoir 140 and the porous structure 150 may also be configured to release therapeutic amounts of the therapeutic agent 110 corresponding to a concentration of at least about 0.01 ug per ml of vitreous humor 30 and no more than about 300 ug per ml for an extended period of at least about 3 months or 6 months or 12 months or 24 months.

The channels 156 of the rigid porous structure 150 comprise a hydrogel configured to limit a size of molecules passed through the channels 156 of the rigid porous structure 150. For example, the hydrogel can be formed within the channels 156 and may comprise an acrylamide gel. The hydrogel comprises a water content of at least about 70%. For example, the hydrogel may comprise a water content of no more than about 90% to limit molecular weight of the therapeutic agent 110 to about 30 kDa. The hydrogel comprises a water content of no more than about 95% to limit molecular weight of the therapeutic agent 110 to about 100 kDa. The hydrogel may comprise a water content within a range from about 90% to about 95% such that the channels 156 of the porous material are configured to pass Lucentis™ and substantially not pass Avastin™.

The rigid porous structure 150 may comprise a composite porous material that can readily be formed in or into a wide range of different shapes and configurations. For example, the porous material can be a composite of a metal, aerogel or ceramic foam (i.e., a reticulated inter-cellular structure in which the interior cells are interconnected to provide a multiplicity of pores passing through the volume of the structure, the walls of the cells themselves being substantially continuous and non-porous, and the volume of the cells relative to that of the material forming the cell walls being such that the overall density of the intercellular structure is less than about 30 percent theoretical density) the through pores of which are impregnated with a sintered powder or aerogel. The thickness, density, porosity and porous characteristics of the final composite porous material can be varied to conform with the desired release of the therapeutic agent 110.

Embodiments comprise a method of making an integral (i.e., single-component) porous structure 150. The method may comprise introducing particles into a mold having a desired shape for the porous structure 150. The shape may include a proximal end defining a plurality of proximal porous channel openings to couple to the reservoir 140, a distal end defining a plurality of outlet channel openings to couple to the vitreous humor 30 of the eye 10, a plurality of blind inlet cavities extending into the filter from the proximal openings, and a plurality of blind outlet cavities extending into the porous structure 150 from the outlet channel openings. The method further includes applying pressure to the mold, thereby causing the particles to cohere and form a single component, and sintering the component to form the porous structure 150. The particles can be pressed and cohere to form the component without the use of a polymeric binder, and the porous structure 150 can be formed substantially without machining.

The mold can be oriented vertically with the open other end disposed upwardly, and metal powder having a particle size of less than 20 micrometers can be introduced into the cavity through the open end of the mold while vibrating the mold to achieve substantially uniform packing of the metal powder in the cavity. A cap can be placed on the open other end of the mold, and pressure is applied to the mold and thereby to the metal powder in the cavity to cause the metal powder to cohere and form a cup-shaped powdered metal structure having a shape corresponding to the mold. The shaped powdered metal structure can be removed from the mold, and sintered to obtain a porous sintered metal porous structure 150.

The metal porous structure 150 can be incorporated into the device by a press fit into an impermeable structure with an opening configured to provide a tight fit with the porous structure 150. Other means, such as welding, known to those skilled in the art can be used to incorporate the porous structure 150 into the device. Alternatively, or in combination, the powdered metal structure can be formed in a mold where a portion of the mold remains with the shaped powdered metal structure and becomes part of the device. This may be advantageous in achieving a good seal between the porous structure 150 and the device.

The release rate of therapeutic agent 110 through a porous body, such as a sintered porous metal structure or a porous glass structure, may be described by diffusion of the therapeutic agent 110 within the porous structure 150 with the channel parameter, and with an effective diffusion coefficient equal to the diffusion coefficient of the therapeutic agent 110 in the liquid that fills the reservoir multiplied by the Porosity and a Channel Parameter of the porous body:

Release Rate=$(DP/F)A(c_R-c_V)/L$, where:

$c_R$=Concentration in reservoir
$c_V$=Concentration outside of the reservoir or in the vitreous
D=Diffusion coefficient of the therapeutic agent in the reservoir solution
P=Porosity of porous structure
F=Channel parameter that may correspond to a tortuosity parameter of channels of porous structure
A=Area of porous structure
L=Thickness (length) of porous structure Cumulative Release=$1-cR/cR0=1-\exp((-DPA/FLV_R)t)$, where t=time, Vr=reservoir volume The release rate index can (hereinafter RRI) be used to determine release of the therapeutic agent 110. The RRI may be defined as (PA/FL), and the RRI values herein will have units of mm unless otherwise indicated. Many of the porous structures used in the therapeutic delivery devices described here have an RRI of no more than about 5.0, often no more than about 2.0, and can be no more than about 1.2 mm.

The channel parameter can correspond to an elongation of the path of the therapeutic agent 110 released through the porous structure 150. The porous structure 150 may comprise many interconnecting channels 156, and the channel parameter can correspond to an effective length that the therapeutic agent 110 travels along the interconnecting channels 156 of the porous structure 150 from the reservoir side to the vitreous side when released. The channel parameter multiplied by the thickness (length) of the porous structure 150 can determine the effective length that the therapeutic agent 110 travels along the interconnecting channels 156 from the reservoir side to the vitreous side. For example, the channel parameter (F) of about 1.5 corresponds to interconnecting channels 156 that provide an effective increase in length traveled by the therapeutic agent 110 of about 50%, and for a 1 mm thick porous structure 150 the effective length that the therapeutic agent 110 travels along the interconnecting channels 156 from the reservoir side to the vitreous side corresponds to about 1.5 mm. The channel parameter (F) of at least about 2 corresponds to interconnecting channels 156 that provide an effective increase in length traveled by the therapeutic agent 110 of about 100%, and for a 1 mm thick porous structure 150 the effective length that the therapeutic agent 110 travels along the interconnecting channels 156 from the reservoir side to the vitreous side corresponds to at least about 2.0 mm. As the porous structure 150 comprises many interconnecting channels 156 that provide many alternative paths for release of the therapeutic agent 110, blockage of some of the channels 156 provides no substantial change in the effective path length through the porous structure 150 as the alternative interconnecting channels 156 are available, such that the rate of diffusion through the porous structure 150 and the release of the therapeutic agent 110 are substantially maintained when some of the channels 156 are blocked.

If the reservoir solution is aqueous or has a viscosity similar to water, the value for the diffusion coefficient of the therapeutic agent (TA) in water at the temperature of interest may be used. The following equation can be used to estimate the diffusion coefficient at 37° C. from the measured value of $D_{BSA,20C}$=6.1 e-7 cm2/s for bovine serum albumin in water at 20° C. (Molokhia et al, *Exp Eye Res* 2008):

$$D_{TA,37C}=D_{BSA,20C}(\eta_{20C}/\eta_{37C})(MW_{BSA}/MW_{TA})^{1/3}$$

where

MW refers to the molecular weight of either BSA or the test compound and η is the viscosity of water. The following table lists diffusion coefficients of proteins of interest.

| Compound | MW | Temp C. | Diff Coeff (cm^2/s) |
|---|---|---|---|
| BSA | 69,000 | 20 | 6.1E-07 |
| BSA | 69,000 | 37 | 9.1E-07 |
| Ranibizumab | 48,000 | 20 | 6.9E-07 |
| Ranibizumab | 48,000 | 37 | 1.0E-06 |
| Bevacizumab | 149,000 | 20 | 4.7E-07 |
| Bevacizumab | 149,000 | 37 | 7.1E-07 |

Small molecules have a diffusion coefficient similar to fluorescein (MW=330, D=4.8 to 6 e-6 cm²/s from Stay, M S et al., *Pharm Res* 2003, 20(1), pp. 96-102). For example, the small molecule may comprise a glucocorticoid such as triamcinolone acetonide having a molecular weight of about 435.

The porous structure 150 comprises a porosity, a thickness, a channel parameter and a surface area configured to release therapeutic amounts for the extended period. The porous material may comprise a porosity corresponding to the fraction of void space of the channels 156 extending within the material. The porosity may comprise a value within a range from about 3% to about 70%. In other embodiments, the porosity may comprise a value with a range from about 5% to about 10% or from about 10% to about 25%, or for example from about 15% to about 20%. Porosity can be determined from the weight and macroscopic volume or can be measured via nitrogen gas adsorption The porous structure 150 may comprise a plurality of porous structures, and the area used in the above equation may comprise the combined area of the plurality of porous structures.

The channel parameter may comprise a fit parameter corresponding to the tortuosity of the channels 156. For a known porosity, surface area and thickness of the surface parameter, the curve fit parameter F, which may correspond to tortuosity of the channels 156 can be determined based on experimental measurements. The parameter PA/FL can be used to determine the desired sustained release profile, and the values of P, A, F and L determined. The rate of release of the therapeutic agent 110 corresponds to a ratio of the porosity to the channel parameter, and the ratio of the porosity to the channel parameter can be less than about 0.5 such that the porous structure 150 releases the therapeutic agent 110 for the extended period. For example, the ratio of the porosity to the channel parameter is less than about 0.1 or for example less than about 0.2 such that the porous structure 150 releases the therapeutic agent 110 for the extended period. The channel parameter may comprise a value of at least about 1, such as at least about 1.2. For example, the value of the channel parameter may comprise at least about 1.5, for example at least about 2, and may comprise at least about 5. The channel parameter can be within a range from about 1.1 to about 10, for example within a range from about 1.2 to about 5. A person of ordinary skill in the art can conduct experiments based on the teachings described herein to determine empirically the channel parameter to release the therapeutic agent 110 for an intended release rate profile.

The area in the model originates from the description of mass transported in units of flux; i.e., rate of mass transfer per unit area. For simple geometries, such as a porous disc mounted in an impermeable sleeve of equal thickness, the area corresponds to one face of the disc and the thickness, L, is the thickness of the disc. For more complex geometries, such as a porous body in the shape of a truncated cone, the effective area is a value in between the area where therapeutic agent 110 enters the porous body and the area where therapeutic agent 110 exits the porous body.

A model can be derived to describe the release rate as a function of time by relating the change of concentration in the reservoir 140 to the release rate described above. This model assumes a solution of therapeutic agent 110 where the concentration in the reservoir 140 is uniform. In addition, the concentration in the receiving fluid or vitreous is considered negligible ($c_V$=0). Solving the differential equation and rearrangement yields the following equations describing the concentration in the reservoir as a function of time, t, and volume of the reservoir, $V_R$, for release of a therapeutic agent 110 from a solution in a reservoir though a porous structure 150.

$$c_R = c_{R0} \exp((-DPA/FLV_R)t)$$

and Cumulative Release=$1-c_R/c_{R0}$

When the reservoir 140 contains a suspension, the concentration in reservoir, $c_R$, is the dissolved concentration in equilibrium with the solid (i.e., the solubility of the therapeutic agent). In this case, the concentration in the reservoir is constant with time, the release rate is zero order, and the cumulative release increases linearly with time until the time when the solid is exhausted.

Therapeutic concentrations for many ophthalmic therapeutic agents may be determined experimentally by measuring concentrations in the vitreous humor 30 that elicit a therapeutic effect. Therefore, there is value in extending predictions of release rates to predictions of concentrations in the vitreous. A one-compartment model may be used to describe elimination of therapeutic agent from eye tissue.

Current intravitreal administration of therapeutic agents such as Lucentis™ involves a bolus injection. A bolus injection into the vitreous may be modeled as a single exponential with rate constant, k=0.693/half-life and a cmax=dose/$V_v$ where $V_v$ is the vitreous volume. As an example, the half-life for ranibizumab is approximately 3 days in the rabbit and the monkey (Gaudreault et al) and 9 days in humans (Lucentis™ package insert). The vitreous volume is approximately 1.5 mL for the rabbit and monkey and 4.5 mL for the human eye. The model predicts an initial concentration of 333 ug/mL for a bolus injection of 0.5 mg Lucentis™ into the eye of a monkey. This concentration decays to a vitreous concentration of 0.1 ug/mL after about a month.

For devices with extended release, the concentration in the vitreous changes slowly with time. In this embodiment, a model can be derived from a mass balance equating the release rate from the device (described by equations above) with the elimination rate from the eye, k $c_v$ $V_v$. Rearrangement yields the following equation for the concentration in the vitreous:

$$c_v = \text{Release rate from device}/kV_v.$$

Since the release rate from a device with a solution of therapeutic agent 110 decreases exponentially with time, the concentration in the vitreous decreases exponentially with the same rate constant. In other words, vitreous concentration decreases with a rate constant equal to D PA/FL $V_R$ and, hence, is dependent on the properties of the porous structure 150 and the volume of the reservoir.

Since the release rate is zero order from a device with a suspension of therapeutic agent 110, the vitreous concentration will also be time-independent. The release rate will depend on the properties of the porous structure 150 via the ratio, PA/FL, but will be independent of the volume of the reservoir until the time at which the drug is exhausted.

Exemplary Porous Structures for Release of Therapeutic Agents

Although the porous structure 150 may comprise one or more of many structures as described herein to release the therapeutic agent 110, in many embodiments the porous structure 150 comprises a rigid porous structure 150. The channels 156 of the rigid porous structure 150 can be sized in many ways to release the intended therapeutic agent 110. For example, the channels 156 of the rigid porous structure 150 can be sized to pass therapeutic agent 110 comprising molecules having a molecular weight of at least about 100 Da or for example, at least about 50 kDa. The channels 156 of the rigid porous structure 150 can be sized to pass therapeutic agent 110 comprising molecules comprising a cross-sectional size of no more than about 10 nm. The channels 156 of the rigid porous structure 150 comprise interconnecting channels 156 configured to pass the therapeutic agent 110 among the interconnecting channels 156. The rigid porous structure 150 comprises grains of rigid material and wherein the interconnecting channels 156 extend at least partially around the grains of rigid material to pass the therapeutic agent 110 through the porous material. The grains of rigid material can be coupled together at a loci of attachment and wherein the interconnecting channels 156 extend at least partially around the loci of attachment.

The porous structure 150 and reservoir 140 may be configured to release the glucocorticoid for an extended time of at least about six months with a therapeutic amount of glucocorticoid of corresponding to an in situ concentration within a range from about 0.05 µg/mL to about 4 µg/mL, for example from 0.1 µg/mL to about 4 µg/mL, so as to suppress inflammation in the retina-choroid.

The porous structure 150 can be comprised of a sintered material. The sintered material may comprise grains of material 155 in which the grains comprise an average size of no more than about 20 µm. For example, the sintered material may comprise grains of material 155 in which the grains comprise an average size of no more than about 10

μm, an average size of no more than about 5 μm, or an average size of no more than about 1 μm. The channels 156 are sized to pass therapeutic quantities of the therapeutic agent 110 through the sintered material for the extended time based on the grain size of the sintered material and processing parameters such as compaction force and time and temperature in the furnace. The channels 156 can be sized to inhibit penetration of microbes including bacterial and fungal spores through the sintered material.

The sintered material can be comprised of a wettable material to inhibit bubbles within the channels 156 of the material.

The sintered material can be comprised of at least one of a metal, a ceramic, a glass or a plastic. The sintered material may comprise a sintered composite material, and the composite material can comprise two or more of the metal, the ceramic, the glass or the plastic. The metal can comprise at least one of Ni, Ti, nitinol, stainless steel including alloys such as 304, 304L, 316 or 316L, cobalt chrome, elgiloy, hastealloy, c-276 alloy or Nickel 200 alloy. The sintered material may comprise a ceramic. The sintered material may comprise a glass. The plastic may comprise a wettable coating to inhibit bubble formation in the channels, and the plastic may comprise at least one of polyether ether ketone (PEEK), polyethylene, polypropylene, polyimide, polystyrene, polycarbonate, polyacrylate, polymethacrylate, or polyamide.

The rigid porous structure 150 may comprise a plurality of rigid porous structures coupled to the reservoir and configured to release the therapeutic agent 110 for the extended period. For example, additional rigid porous structure 150 can be disposed along the container 130, for example the end of the container 130 may comprise the porous structure 150, and an additional porous structure 150 can be disposed along a distal portion of the container 130, for example along a tubular sidewall of the container 130.

The therapeutic device 100 can be tuned to release therapeutic amounts of the therapeutic agent 110 above the minimum inhibitory concentration for an extended time based on bolus injections of the therapeutic agent 110. For example, the volume of the chamber 132 of the reservoir 140 can be sized with the release rate of the porous structure 150 based on the volume of the bolus injection. A formulation of a therapeutic agent 110 can be provided, for example a known intravitreal injection formulation. The therapeutic agent 110 can be capable of treating the eye 10 with bolus injections, such that the formulation has a corresponding period between each of the bolus injections to treat the eye 10. For example the bolus injections may comprise monthly injections. Each of the bolus injections comprises a volume of the formulation, for example 50 μL. Each of the bolus injections of the therapeutic agent 110 may correspond to a range of therapeutic concentrations of the therapeutic agent 110 within the vitreous humor 30 over the time course between injections, and the device can be tuned so as to release therapeutic amounts of the therapeutic agent 110 such that the vitreous concentrations of the released therapeutic agent 110 from the device are within the range of therapeutic concentrations of the corresponding bolus injections. For example, the therapeutic agent 110 may comprise a minimum inhibitory concentration to treat the eye 10, for example at least about 3 μg/mL, and the values of the range of therapeutic concentrations can be at least about 3 μg/mL. The therapeutic device 100 can be configured to treat the eye 10 with an injection of the monthly volume of the formulation into the device, for example through the penetrable barrier 184. The reservoir 140 of the container 130 has a chamber 132 to contain a volume of the therapeutic agent 110, for example 35 μL, and a mechanism to release the therapeutic agent 110 from the chamber 132 to the vitreous humor 30.

The volume of the container 130 and the release mechanism can be tuned to treat the eye 10 with the therapeutic agent 110 with vitreous concentrations within the therapeutic range for an extended time with each injection of the quantity corresponding to the bolus injection, such that the concentration of the therapeutic agent 110 within the vitreous humor 30 remains within the range of therapeutic concentrations and comprises at least the minimum inhibitory concentration. The extended time may comprise at least about twice the corresponding period of the bolus injections. The release mechanism comprises one or more of a porous frit, a sintered porous frit, a permeable membrane, a semipermeable membrane, a capillary tube or a tortuous channel, nano-structures, nano-channels or sintered nano-particles. For example, the porous frit may comprise a porosity, cross-sectional area, and a thickness to release the therapeutic agent 110 for the extended time. The volume of the container 130 reservoir 140 can be sized in many ways in relation to the volume of the injected formulation and can be larger than the volume of injected formulation, smaller than the volume of injected formulation, or substantially the same as the volume of injected formulation. For example, the volume of the container 130 may comprise no more than the volume of the formulation, such that at least a portion of the formulation injected into the reservoir passes through the reservoir and comprises a bolus injection to treat the patient immediately. As the volume of the reservoir is increased, the amount of formulation released to the eye 10 through the porous structure 150 upon injection can decrease along with the concentration of active ingredient of the therapeutic agent 110 within the reservoir 140, and the release rate index can be increased appropriately so as to provide therapeutic amounts of therapeutic agent 110 for the extended time. For example, the volume of the reservoir 140 of the container 130 can be greater than the volume corresponding to the bolus injection, so as to provide therapeutic amounts for at least about five months, for example 6 months, with an injection volume corresponding to a monthly injection of Lucentis™. For example, the formulation may comprise commercially available Lucentis™, 50 μL, and the reservoir may comprise a volume of about 100 μL and provide therapeutic vitreous concentrations of at least about 3 μg/mL for six months with 50 μL of Lucentis™ injected into the reservoir.

The chamber may comprise a substantially fixed volume and the release rate mechanism can be comprised of a substantially rigid structure to maintain release of the therapeutic agent 110 above the minimum inhibitory concentration for the extended time with each injection of a plurality of injections.

A first portion of the injection may pass through the release mechanism and treat the patient when the formulation is injected, and a second portion of the formulation can be contained in the chamber when the formulation is injected.

Figure 36:
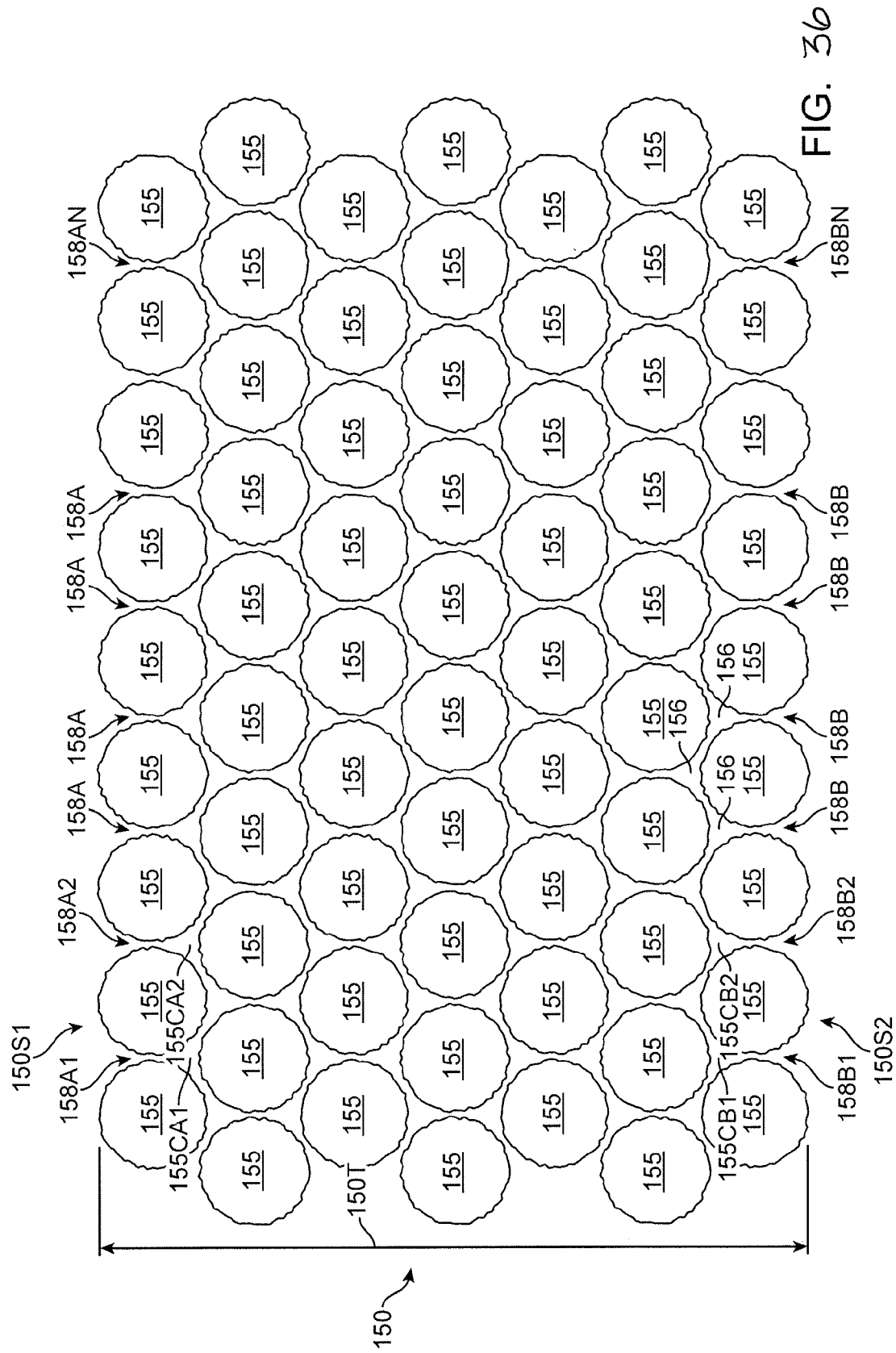
FIG. 36 shows interconnecting channels extending from a first side 150S1 to a second side 150S2 of the porous structure as in FIG. 35, in accordance with embodiments.

FIG. 36 shows a rigid porous structure 150 of grains of material 155 with pores, such as pores 155 CA1, 155CA2, 155CB1, 155CB2, that form interconnecting channels 156 extending from first side 150S1 to second side 150S2 of the porous structure 150 as in FIG. 35. The interconnecting channels 156 extend to a first plurality of openings 158A on the first side 150S1, such as a first opening 158A1, a second opening 158A2 and an Nth opening 158AN. The interconnecting channels 156 extend to a second plurality of openings 158B on the second side 150S2, such as a first opening 158B1, a second opening 158B2 and an Nth opening 158BN. Each of the openings of the plurality of channels 156 on the first side can be connected to each of the openings of plurality of channels 156 on the second side, such that effective length traveled along the channels can be greater than thickness 150T. The channel parameter can be within a range from about 1.1 to about 10, such that the effective length is within a range from about 1.1 to 10 times the thickness 150T. For example, the channel parameter can be about 1 and the porosity about 0.2, such that the effective length corresponds to at least about 5 times the thickness 150T.

Figure 37:
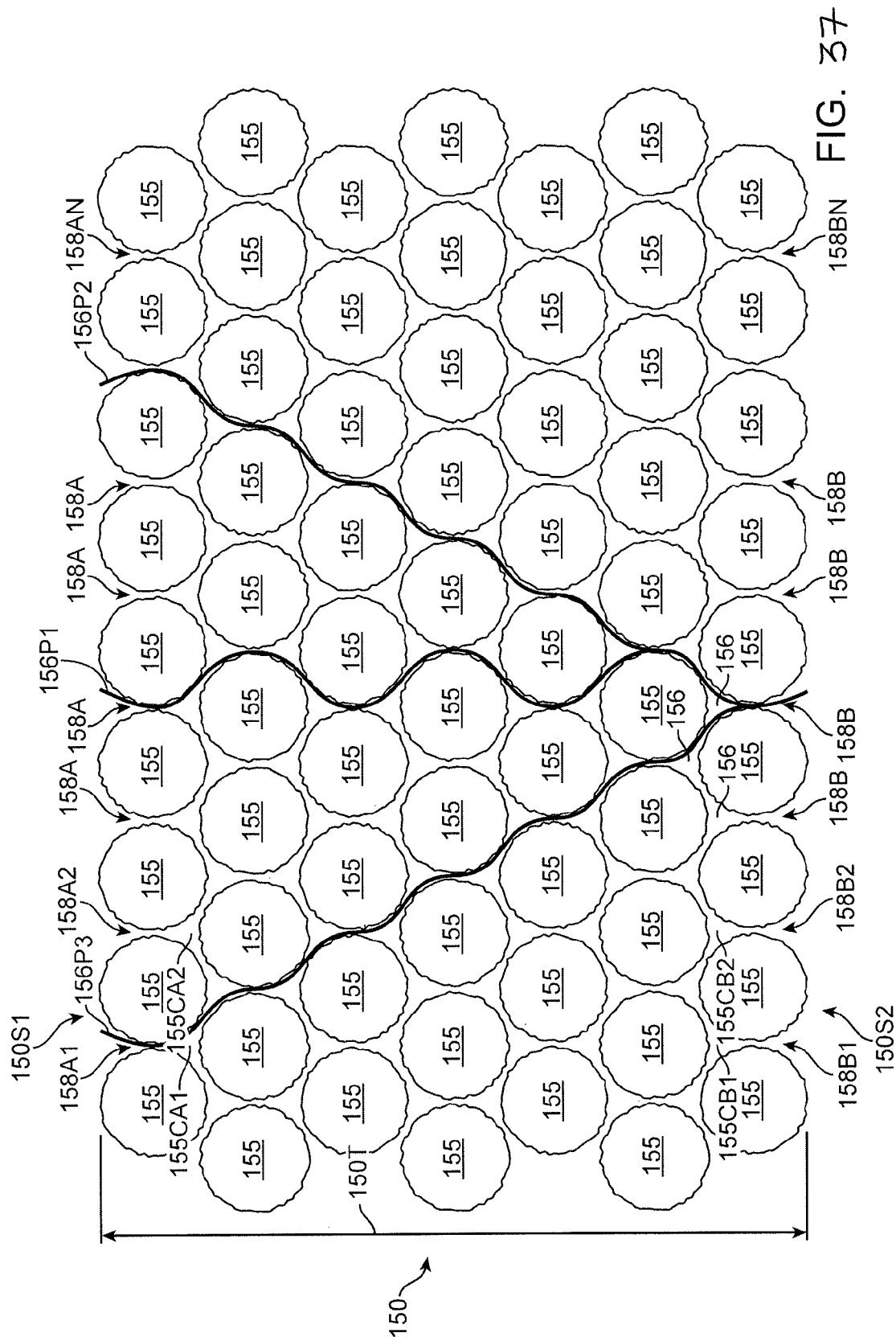
FIG. 37 shows a plurality of paths of the therapeutic agent along the interconnecting channels extending from a first side 150S1 to a second side 150S2 of the porous structure as in FIGS. 35 and 36, in accordance with embodiments.

FIG. 37 shows a plurality of paths of the therapeutic agent 110 along the interconnecting channels 156 extending from a first side 150S1 to a second side 150S2 of the porous structure 150 as in FIGS. 35 and 36. The plurality of paths comprises a first path 156P1 extending from the first side 150S1 to second side 150S2, a second path 156P2 extending from the first side 150S1 to second side 150S2 and a third path 156P3 extending from the first side 150S1 to second side 150S2, and many additional paths. The effect length of each of first path 156P1, second path 156P2 and third path 156P3 is substantially similar, such that each opening on the first side can release the therapeutic agent 110 to each interconnected opening on the second side. The substantially similar path length can be related to the sintered grains of material 155 and the channels 156 that extend around the sintered material. The porous structure 150 may comprise randomly oriented and connected grains of material 155, packed beads of material, or combinations thereof. The channel parameter can be related to the structure of the sintered grains of material 155 and corresponding interconnecting channels 156, porosity of the material, and percolation threshold. Some embodiments allow the percolation threshold of the sintered grains to be below the porosity of the porous frit structure, such that the channels 156 are highly inter-connected. The sintered grains of material 155 can provide interconnected channels 156, and the grains can be selected to provide desired porosity and channel parameters and RRI as described herein.

The channel parameter and effective length from the first side 150S1 to the second side 150S2 can be configured in many ways. The channel parameter can be greater than 1 and within a range from about 1.2 to about 5.0, such that the effective length is within a range about 1.2 to 5.0 times the thickness 150T, although the channel parameter may be greater than 5, for example within a range from about 1.2 to 10. For example, the channel parameter can be from about 1.3 to about 2.0, such that the effective length is about 1.3 to 2.0 times the thickness 150T. For example, experimental testing has shown the channel parameter can be from about 1.4 to about 1.8, such that the effective length is about 1.4 to 1.8 times the thickness 150T, for example about 1.6 times the thickness. These values correspond to the paths of the channels 156 around the sintered grains of material 155 and may correspond, for example, to the paths of channels 156 around packed beads of material.

Figure 38:
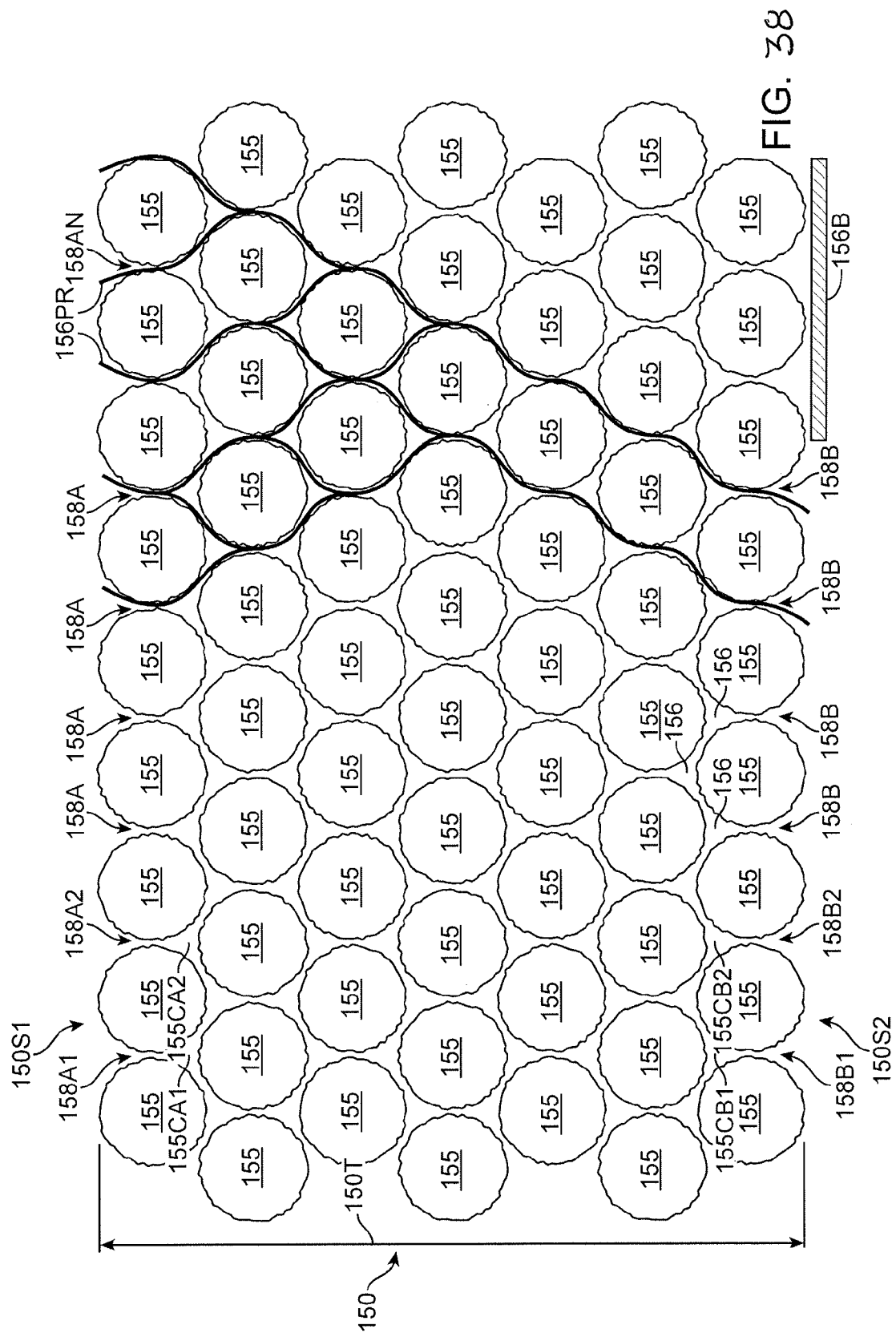
FIG. 38 shows blockage of the openings with a covering and the plurality of paths of the therapeutic agent along the interconnecting channels extending from a first side 150S1 to a second side 150S2 of the porous structure as in FIGS. 35 and 36, in accordance with embodiments.

FIG. 38 shows blockage of the openings with a covering 156B and the plurality of paths of the therapeutic agent 110 along the interconnecting channels 156 extending from a first side 150S1 to the second side 150S2 of the porous structure 150 as in FIGS. 35 and 36. A plurality of paths 156PR extend from the f first side 150S1 to second side 150S2 couple the first side 150S1 to second side 150S2 where one of the sides is covered, such that the flow rate is maintained when one of the sides is partially covered.

Figure 39:
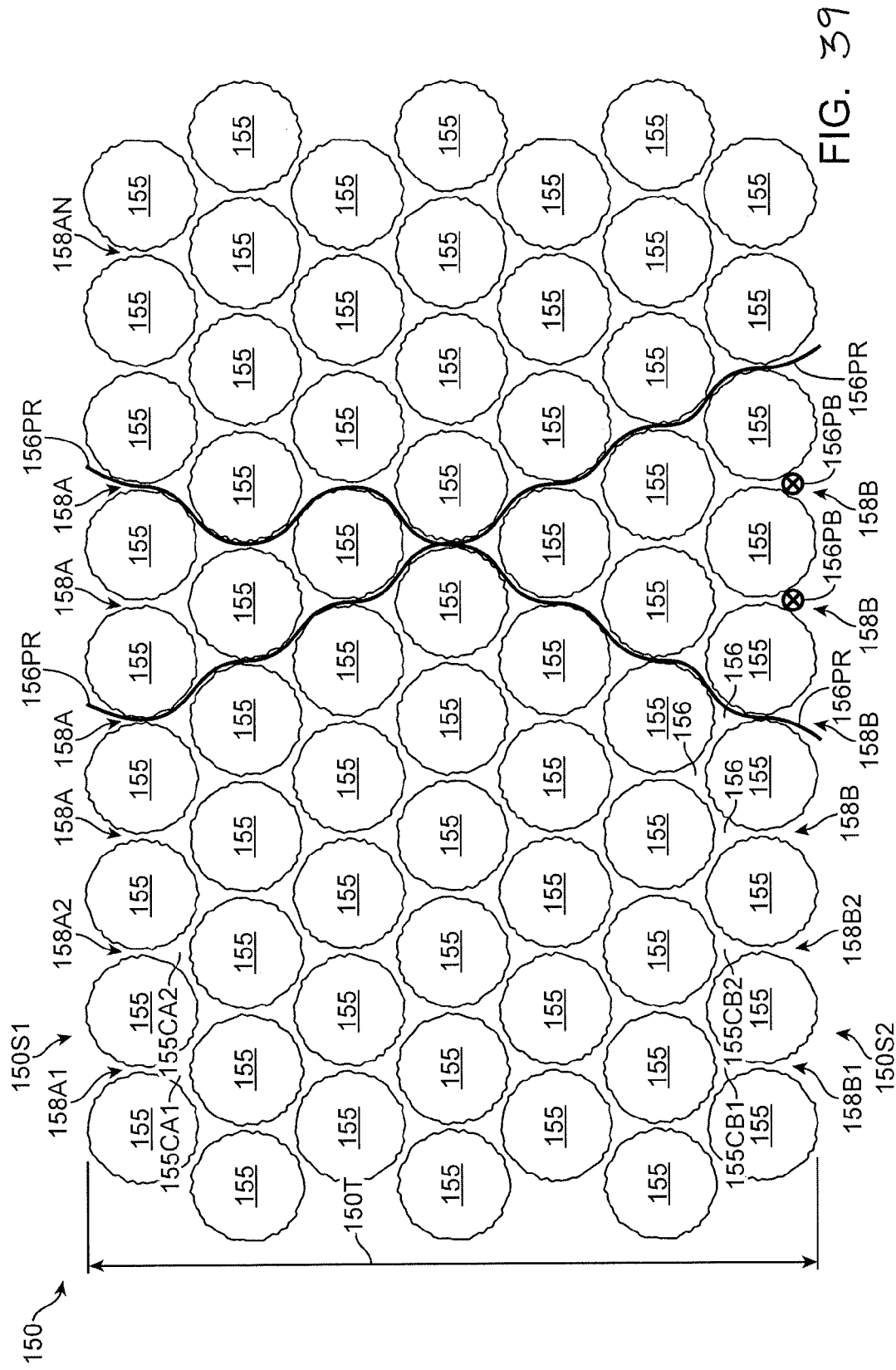
FIG. 39 shows blockage of the openings with particles and the plurality of paths of the therapeutic agent along the interconnecting channels extending from a first side 150S1 to a second side 150S2 of the porous structure as in FIGS. 35 and 36, in accordance with embodiments.

FIG. 39 shows blockage of the openings with particles 156PB and the plurality of paths of the therapeutic agent 110 along the interconnecting channels 156 extending from a first side 150S1 to a second side 150S2 of the porous structure 150 as in FIGS. 35 and 36. The plurality of paths 156PR extend from the first side 150S1 to second side 150S2 where one of the sides is covered, such that the flow rate is maintained when one of the sides is partially covered.

Figure 40:
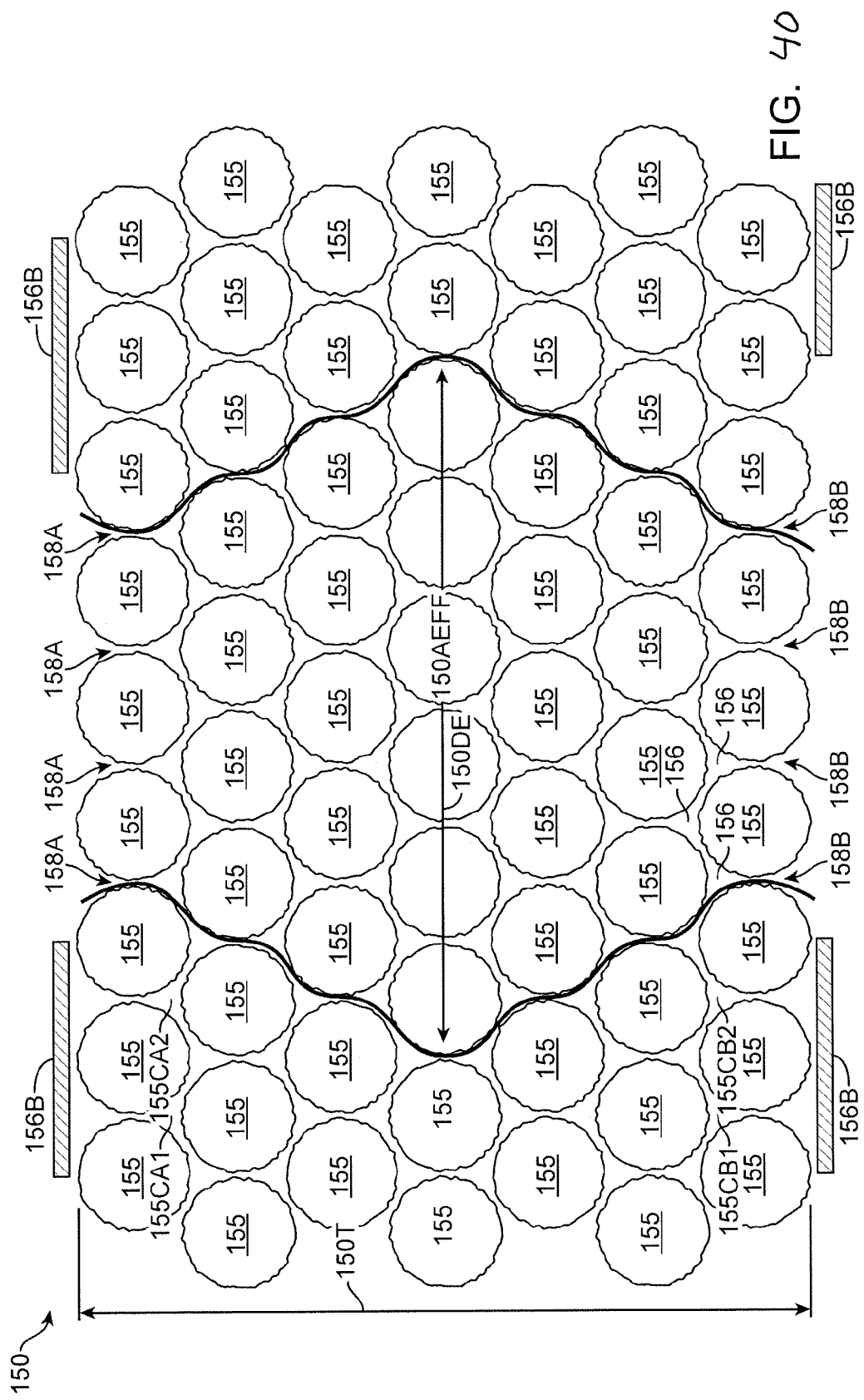
FIG. 40 shows an effective cross-sectional size and area corresponding to the plurality of paths of the therapeutic agent along the interconnecting channels extending from a first side 150S1 to a second side 150S2 of the porous structure as in FIGS. 35 and 36, in accordance with embodiments.

FIG. 40 shows an effective cross-sectional size 150DE and area 150AEFF corresponding to the plurality of paths of the therapeutic agent 110 along the interconnecting channels 156 extending from a first side 150S1 to a second side 150S2 of the porous structure 150 as in FIGS. 35 and 36. The effective cross-sectional area of the interconnecting channels 156 corresponds to the internal cross-sectional area of the porous structure 150 disposed between the openings of the first side and the openings of the second side, such that the rate of release can be substantially maintained when the channels 156 are blocked on the first side and the second side.

The rigid porous structure 150 can be shaped and molded in many ways, for example with tubular shapes, conical shapes, discs and hemispherical shapes. The rigid porous structure 150 may comprise a molded rigid porous structure 150. The molded rigid porous structure 150 may comprises at least one of a disk, a helix or a tube coupled to the reservoir and configured to release the therapeutic agent 110 for the extended period.

Figure 41:
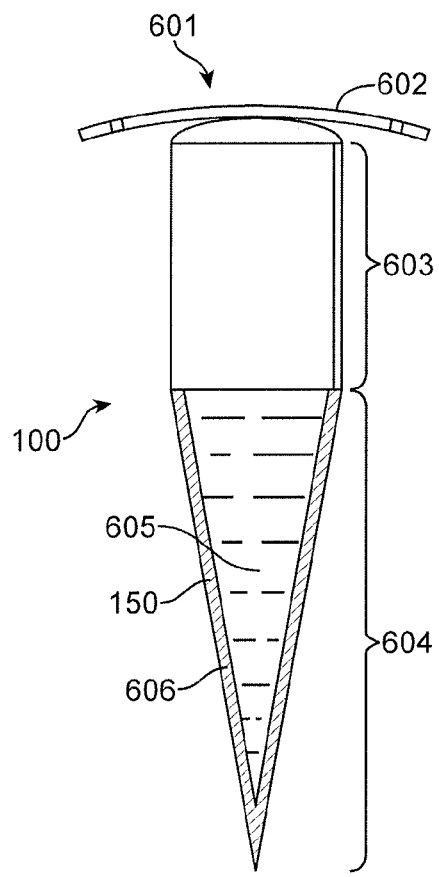
FIG. 41 shows a rigid porous structure as in FIG. 35 incorporated into a scleral tack, in accordance with embodiments.

FIG. 41 shows a rigid porous structure as in FIG. 35 incorporated into a scleral tack 601 as described in U.S. Pat. No. 5,466,233. The scleral tack comprises a head 602, a central portion 603 and a post 604. The post 604 may comprise the reservoir 605 and the rigid porous structure as described above. The porous structure 150 may comprise a molded conical structure 606 having a sharp tip configured for insertion into the patient. Alternatively or in combination, the tip may be rounded.

Figure 42:
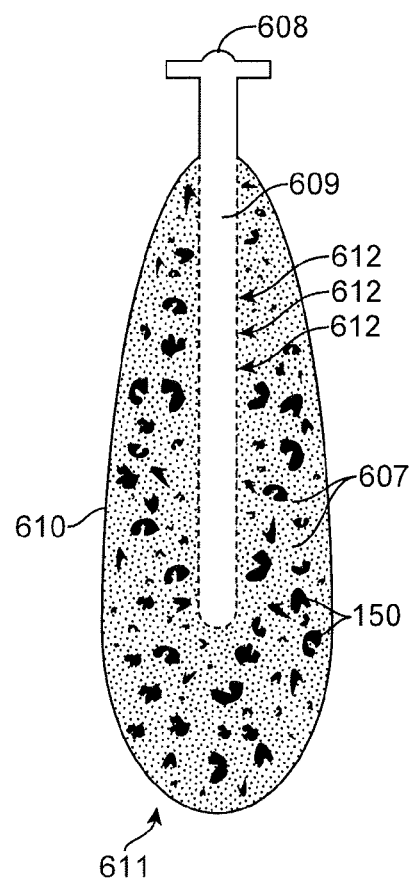
FIG. 42, shows a rigid porous structure as in FIG. 35 coupled with a reservoir for sustained release, in accordance with embodiments.

FIG. 42 shows a rigid porous structure as in FIG. 35 incorporated with a delivery device for sustained release as described in U.S. Pat. Pub. 2003/0014036 A1. The drug delivery device comprises an inlet port 608 on the proximal end and a hollow body 609 coupled to the inlet port. The hollow body 609 comprises many openings 612 that allow a solution injected into the inlet port 608 to pass from the hollow body 609 into a balloon 610. The balloon 610 comprises a distal end 611 disposed opposite the injection port. The balloon 610 comprises a plurality of the rigid porous structures 607, as described above. Each of the plurality of porous rigid structures 607 comprises a first surface exposed to the interior of the balloon 610 and a second surface configured to contact the vitreous. The calculated area can be the combined area of the plurality of porous rigid structures as noted above.

Figure 43:
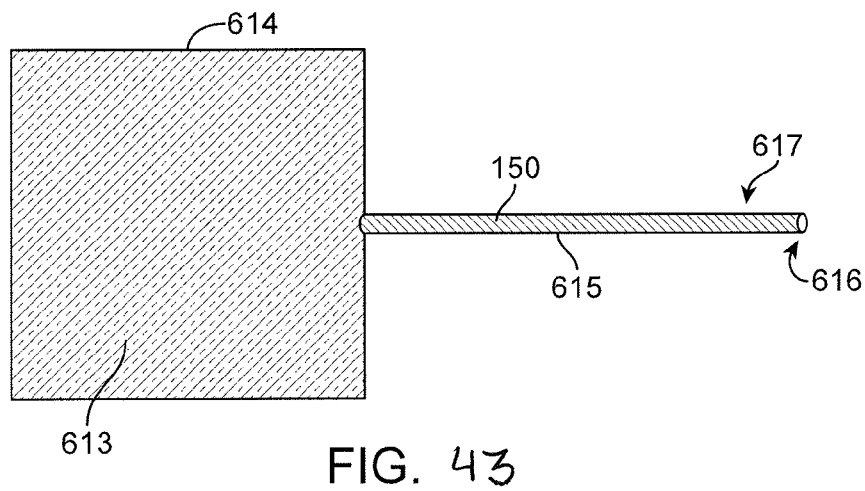
FIG. 43 shows a rigid porous structure within a hollow body or tube for sustained release, in accordance with embodiments.

FIG. 43 shows a rigid porous structure 150 incorporated with a drug delivery device for sustained release as described in U.S. Pat. No. 5,972,369. The therapeutic device 100 comprises a reservoir 613 which can contain the therapeutic agent 110 and an impermeable and non-porous outer surface 614. The reservoir 613 can be coupled to a rigid porous structure 615 that extends to a distal end 617. The rigid porous structure 615 can comprise an exposed area 616 on the distal end 617 to release the therapeutic agent 110, and the impermeable and non-porous outer surface may extend to the distal end 617.

FIG. 44 shows a rigid porous structure as in FIG. 35 incorporated with a non-linear body member 618 for sustained release as described in U.S. Pat. No. 6,719,750. The non-linear member may comprise a helical shape. The non-linear member can be coupled to a cap 619 on the proximal end 620. The non-linear member 618 may comprise a lumen 621 filled with therapeutic agent 110 so as to comprise a reservoir 622. The porous structure 623 can be disposed on a distal end 624 of the non-linear member to release the therapeutic agent 110. The porous structure may be located at additional or alternative locations of the non-linear member 618. For example a plurality of porous structures may be disposed along the non-linear member 618 at locations disposed between the cap 619 and distal end 624 so as to release therapeutic agent 110 into the vitreous humor 30 when the cap 619 is positioned against the sclera 24.

FIG. 45 shows porous nanostructures, in accordance with some embodiments. The porous structure 150 may comprise a plurality of elongate nano-channels 156NC extending from a first side 150S1 of the porous structure 150 to a second side 150S2 of the porous structure 150. The porous structure 150 may comprise a rigid material having holes formed thereon, and the holes may comprise a maximum dimension across such as a diameter. The diameter of the nano-channels 156NC may comprise a dimension across, for example from about 10 nm across, to about 1000 nm across, or larger. The channels may be formed with etching of the material, for example lithographic etching of the material. The channels may comprise substantially straight channels and the porous structure 150 may comprise interconnecting nano-channels 156NC, for example formed with a sintered nano-material. Furthermore, the injection of therapeutic agent 110 into the device 100 as described herein can be performed before implantation into the eye 10 or alternatively when the therapeutic device 100 is implanted into the eye 10.

FIG. 46 shows a therapeutic device 100 coupled to an injector 701 that removes material from the device 100 and injects therapeutic agent 702 into the device. The injector 701 picks up spent media 703 and refills the injector 701 with fresh therapeutic agent. The therapeutic agent is injected into the therapeutic device 100. The spent media is pulled up into the injector 701. The injector 701 may comprise a stopper mechanism 704.

The injector 701 may comprise a first container 702C to contain a formulation of therapeutic agent 702 and a second container 703C to receive the spent media 703. Work in relation to embodiments suggests that the removal of spent media 703 comprising material from the container reservoir of the therapeutic device 100 can remove particulate from the therapeutic device 100, for example particles comprised of aggregated therapeutic agent such as protein. The needle 189 may comprise a double lumen needle with a first lumen coupled to the first container 702C and a second lumen coupled to the second container 703C, such that spent media 703 passes from the container reservoir of device 100 to the injector. A valve 703V, for example a vent, can be disposed between the second lumen and the second container 703C. When the valve 703V is open and therapeutic agent 702 is injected, spent media 703 from the container reservoir of the therapeutic device 100 passes to the second container 703C of the injector 701, such that at least a portion of the spent media 703 within the therapeutic device 100 is exchanged with the formulation. When the valve 703V is closed and the therapeutic agent is injected, a portion of the therapeutic agent passes from the reservoir of the therapeutic device 100 into the eye 10. For example, a first portion of formulation of therapeutic agent 702 can be injected into therapeutic device 100 when the valve is open such that the first portion of the formulation is exchanged with material disposed within the reservoir; the valve is then closed and a second portion of the formulation is injected into therapeutic device 100 such that at least a portion of the first portion passes through the porous structure 150 into the eye 10. Alternatively or in combination, a portion of the second portion of injected formulation may pass through the porous structure 150 when the second portion is injected into the eye 10. The second portion of formulation injected when the valve 703V is closed may correspond to a volume of formulation that passes through the porous structure 150 into the vitreous humor 30 to treat the patient immediately. In addition, the needle 189 may comprise a dual lumen needle, for example as described with reference to FIG. 49 shown below.

Figure 47:
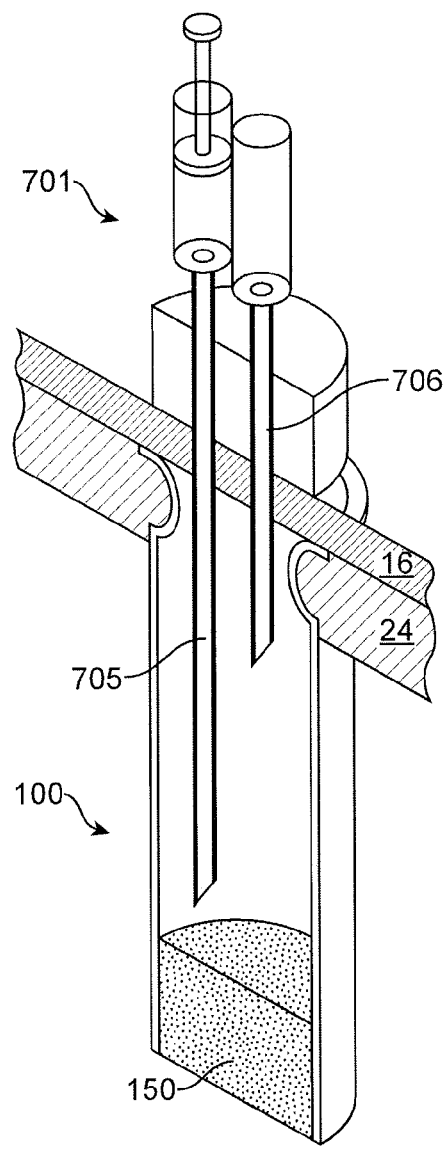
FIG. 47 shows a therapeutic device comprising a porous structure and a penetrable barrier as in FIG. 43, with the penetrable barrier coupled to an injector to inject and remove material from the device, in accordance with embodiments.

FIG. 47 shows a therapeutic device 100 coupled to an injector 701 to inject and remove material from the device 100. The injector may comprise a two needle system configured to insert into a container of the device. The injector may simultaneously inject therapeutic agent through the first needle 705 (the injection needle) while withdrawing liquid from the device through the second needle 706 (the vent needle). The injection needle 705 may be longer and/or have a smaller diameter than the vent needle 706 to facilitate removal of prior material from the device. The vent needle 706 may also be attached to a vacuum to facilitate removal of prior material from the device.

Figure 48:
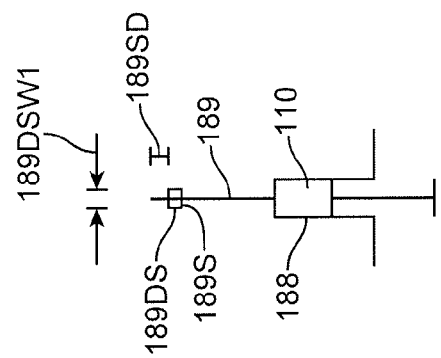
FIG. 48 shows a therapeutic device comprising a penetrable barrier coupled to an injector needle comprising a stop that positions the distal end of the needle near the proximal end of the reservoir of the device to flush the reservoir with ejection of liquid formulation through the porous frit structure, in accordance with embodiments.

FIG. 48 shows a therapeutic device 100 comprising an access port 180 with a penetrable barrier 184 coupled to an injector needle 189 comprising a stop 189S that positions the distal end of the needle near the proximal end of the reservoir 140 of the device to flush the reservoir with ejection of liquid formulation through the porous frit structure, in accordance with embodiments. For example, the injector needle 189 may comprise a single lumen needle having a bevel that extends approximately 0.5 mm along the shaft of the needle from the tip of the needle to the annular portion of the needle. The stop 189S can be sized and positioned along an axis of the needle such that the needle tip extends a stop distance 189SD into the reservoir as defined by the length of the needle from the stop to the tip and the thickness of the penetrable barrier 184, in which the stop distance is within a range from about 0.5 to about 2 mm. The reservoir may extend along an axis of the therapeutic device 100 having a distance within a range from about 4 to 8 mm. A volume comprising a quantity of liquid formulation within a range from about 20 to about 200 µL, for example about 50 µL can be injected into the therapeutic device 100 with the needle tip disposed on the distal end. The volume of the reservoir can be less than the injection volume of the formulation of therapeutic agent, such that liquid is flushed through the porous structure 150. For example, the reservoir may comprise a volume within a range from about 20 to 40 µL, and the injection volume of the liquid formulation of therapeutic agent may comprise about 40 to 100 µL, for example about 50 µL.

Figure 49:
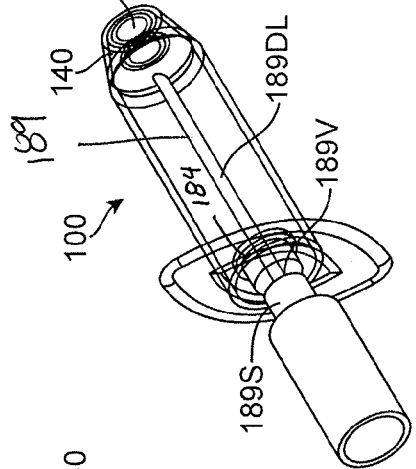
FIG. 49 shows a therapeutic device comprising a penetrable barrier coupled to a needle of an injector to inject and remove material from the device such that the liquid in the reservoir 130 is exchanged with the injected formulation, in accordance with embodiments.

FIG. 49 shows a therapeutic device 100 comprising a penetrable barrier 184 coupled to a needle 189 of an injector to inject and remove material from the device such that the liquid in the reservoir 140 is exchanged with the injected formulation. The needle comprises at least one lumen and may comprise a concentric double lumen needle 189DL with a distal end coupled to the inner lumen to inject formulation of the therapeutic agent into the therapeutic device 100 and a proximal vent 189V to receive liquid into the needle when the formulation is injected. Alternatively, the vent may correspond to an opening on the distal end of the inner lumen of the needle and the outer lumen may comprise a proximal opening to inject therapeutic agent formulation into a proximal portion of the container reservoir.

Work in relation to the injector embodiments indicates that a filling efficiency of at least about 80%, for example 90% or more can be achieved with injector apparatus and needles as described above.

Figure 50:
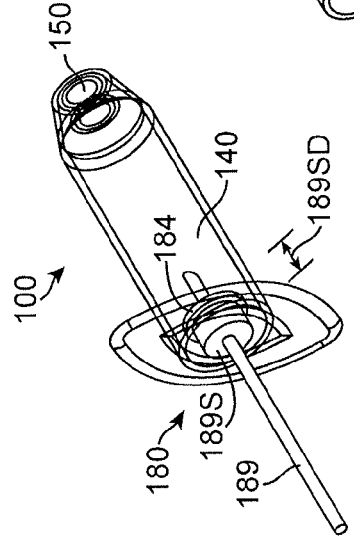
FIG. 50 shows a deformable visual indicator, in accordance with embodiments.

FIG. 50 shows a deformable visual indicator 189DS. The deformable visual indicator 189DS can be coupled to a support, for example stop 189S, such that the visual indicator can deform to indicate when the needle is positioned to an appropriate depth 189SD. The visual indicator can be used with an injector such as a syringe 188 and can be used for injections into one or more of many tissues such as dental, internal tissues during surgery and ocular tissues such as the conjunctiva 16 of the eye 10. The needle 189 may comprise a silicon needle, for example a 25 GA or more needle, for example a 30 GA needle.

The visual indicator 189DS may comprise a bright color and may comprise a soft deformable material such as silicone, and may have a Shore A hardness from about 5 to about 30, for example. The stop 189S may comprise a dark color, such that the deformable indicator becomes visible when coupled to tissue. Prior to contact with the tissue, the deformable indicator 189DS can have a first width 189DSW1.

Figure 51:
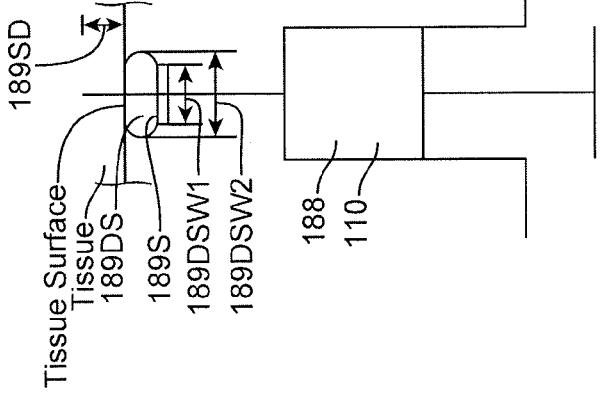
FIG. 51 shows the visual indicator coupled to soft tissue, such as tissue of an eye, for example the conjunctiva positioned over the penetrable barrier of the therapeutic device, in accordance with embodiments.

FIG. 51 shows the visual indicator 189DS coupled to soft tissue, such as tissue of an eye 10, for example the conjunctiva 16 positioned over the penetrable barrier 184 of the therapeutic device 100. The visual indicator has been deformed and comprises a second width 189DSW2 that is greater than the first width 189DSW1 such that the deformable indicator is visible when viewed when coupled to the tissue surface. Such visual indication of coupling can be helpful to ensure that the correct amount of pressure is applied by the health care provider and also so that the needle tips is located at an intended distance below the surface of the tissue.

Figure 52:
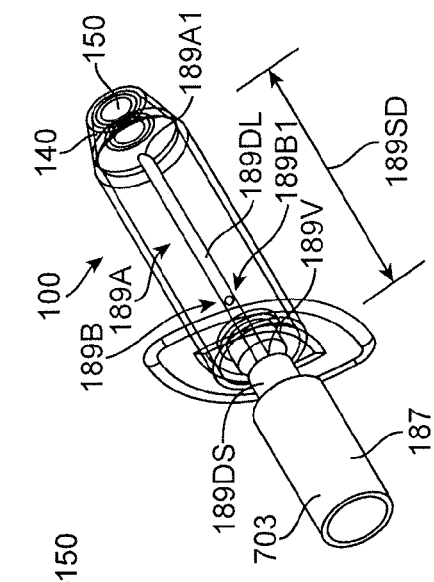
FIGS. 52 and 53 show a therapeutic device coupled to an injector, in accordance with embodiments.

FIG. 52 shows a therapeutic device 100 coupled to injector 703 or 187. As noted above, the therapeutic device 100 may provide at least some resistance to flow, and the visual indicator 189DS can indicate when operator has applied sufficient force to counter reactive force of the injection. Also, the percent mixing can be related to the accuracy of the injection, for example with a bolus injection through the therapeutic device 100, and placement of the needle tip at depth 189SD with an accuracy of better than about 1 mm or less can ensure that the mixing and/or exchange amount injections may be consistent such that the dosage of therapeutic agent can be delivered accurately.

Figure 53:
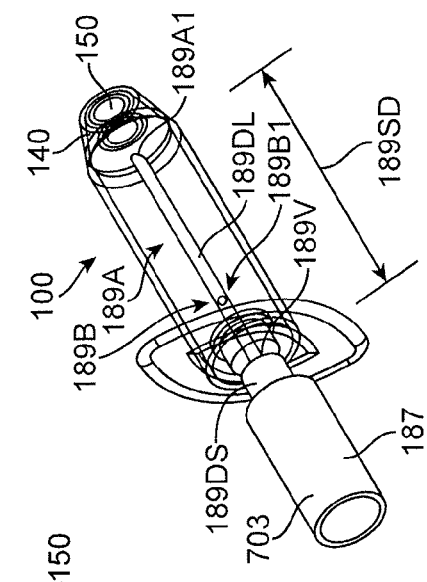

FIG. 53 shows a therapeutic device 100 coupled to injector 703 or 187. The injector can be coupled to a double lumen needle 189DL such that a first lumen 189A injects therapeutic agent through an opening 189A1 near the distal end into device 100. A second lumen 189B receives liquid from device 100 through an opening 189B1.

Figure 54:
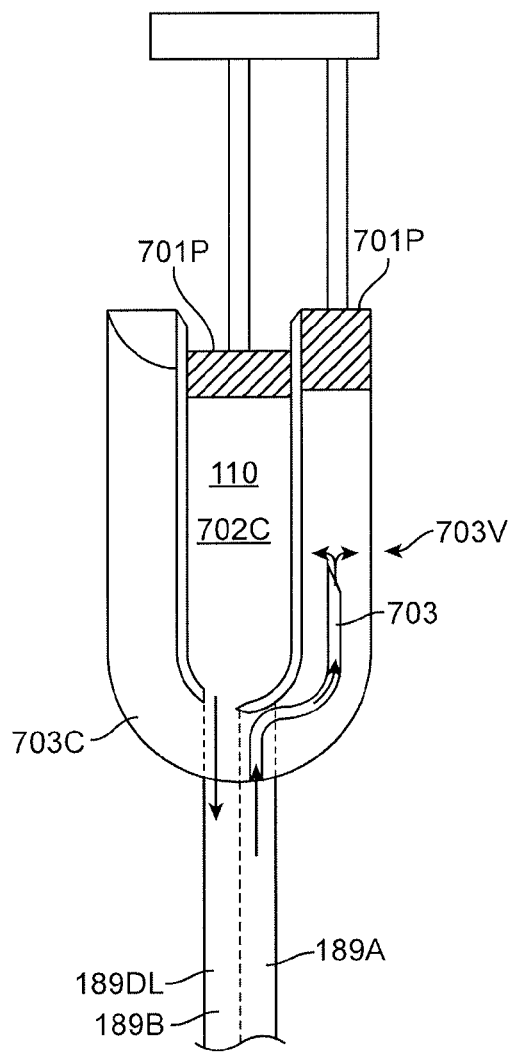
FIG. 54, FIG. 55, FIG. 56, FIG. 57, FIG. 58, and FIG. 59 show sliding coupling of a valve to a plunger coupled to a piston to exchange a first intended volume of liquid within the reservoir with a volume of formulation of therapeutic agent and close the valve so as to inject a second volume of liquid through the porous frit structure, in accordance with embodiments.
Figure 55:
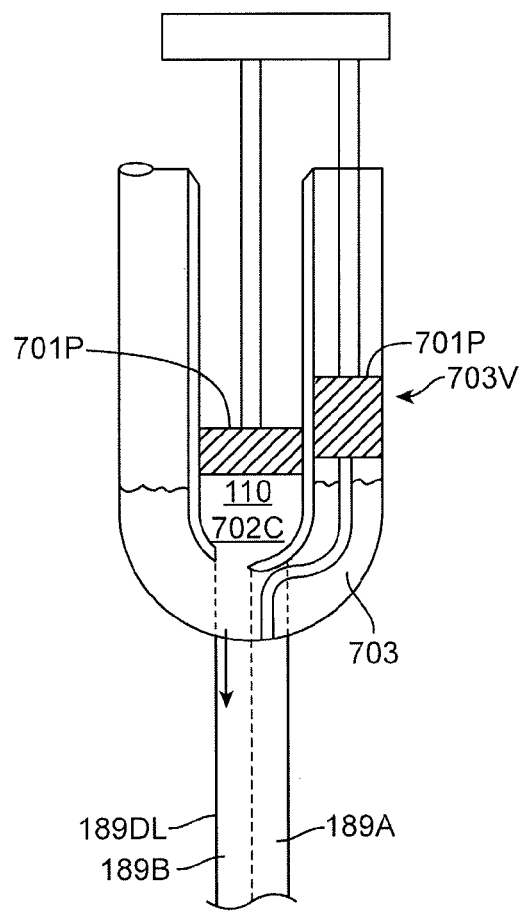
Figure 56:
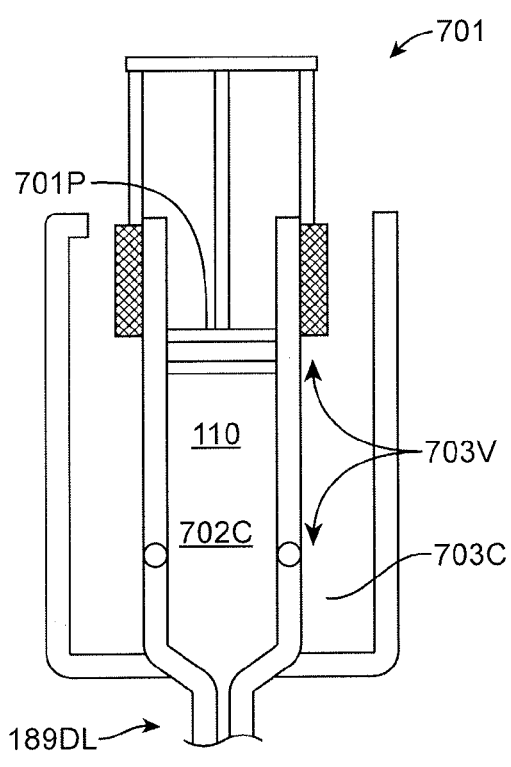
Figure 57:
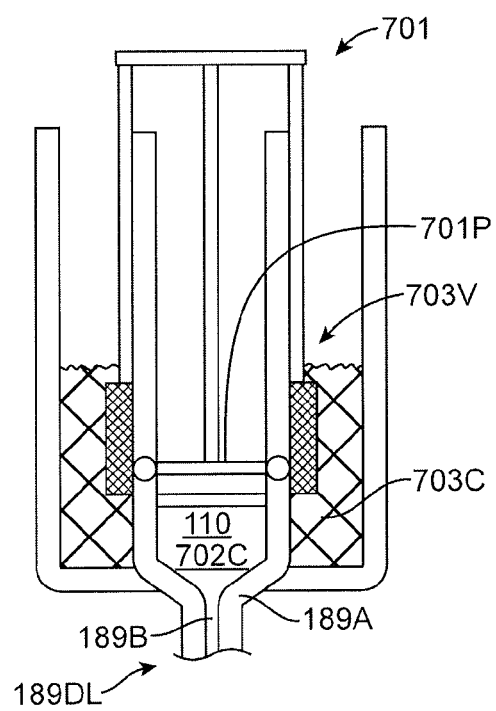
Figure 58:
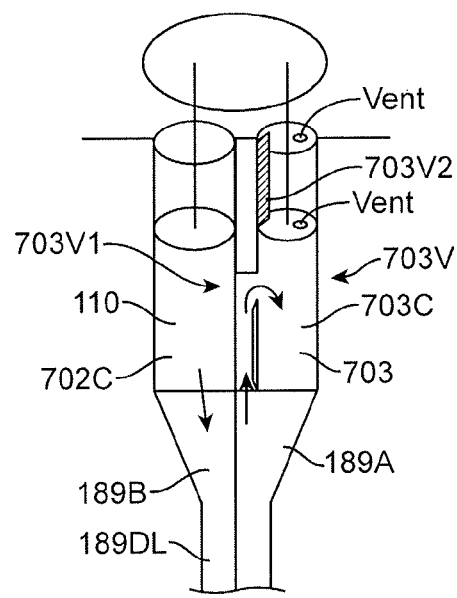
Figure 59:
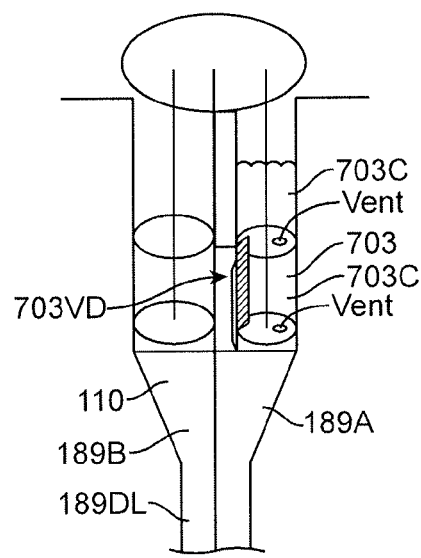

FIGS. 54 and 55 show example embodiments of sliding and coupling a valve to a plunger coupled to a piston in order to exchange a first intended volume of liquid within the reservoir with a volume of formulation of therapeutic agent and close the valve so as to inject a second volume of liquid through the porous frit structure. FIG. 54, FIG. 56, and FIG. 58 show a first configuration with the injector 701 coupled to a double lumen needle 189DL such that a second lumen 189B injects therapeutic agent 110 from a chamber of a first container 702C into device 100. A second container 703C is coupled to a first lumen 189A that extends to the chamber of the reservoir container and receives liquid from device 100, such that liquid of device 100 is exchanged. A switching valve 703V can comprise a first moving component, for example a sliding component, and a second component comprising an opening that can be blocked, for example covered, with the moving component. For example, a piston 701P can be moved toward the device 100 with a plunger, and the sliding component of switching valve 703V can be coupled to the plunger and piston 701P. When the piston 701P has advanced to exchange an intended amount of liquid and an intended amount of the formulation of the therapeutic agent 110 remains in first container 702C, the sliding component of valve 703V may cover and block the opening component of valve 703V. With valve 703V closed, an additional intended amount of therapeutic agent can be injected into device 100 as shown in FIG. 55, for example such that a bolus amount of therapeutic agent can be injected from device 100. A portion of the formulation of therapeutic agent injected into device 100 can be retained in device 100 for release for an extended time. FIGS. 57 and 59 also show example embodiments of the valve 703V in the covered configuration.

The moving component of the valve 703V may comprise one or more of many components such as a ball valve, a sleeve, a gasket, a piston having holes, or a one way pressure valve, a solenoid, or a servo, for example.

Figure 60:
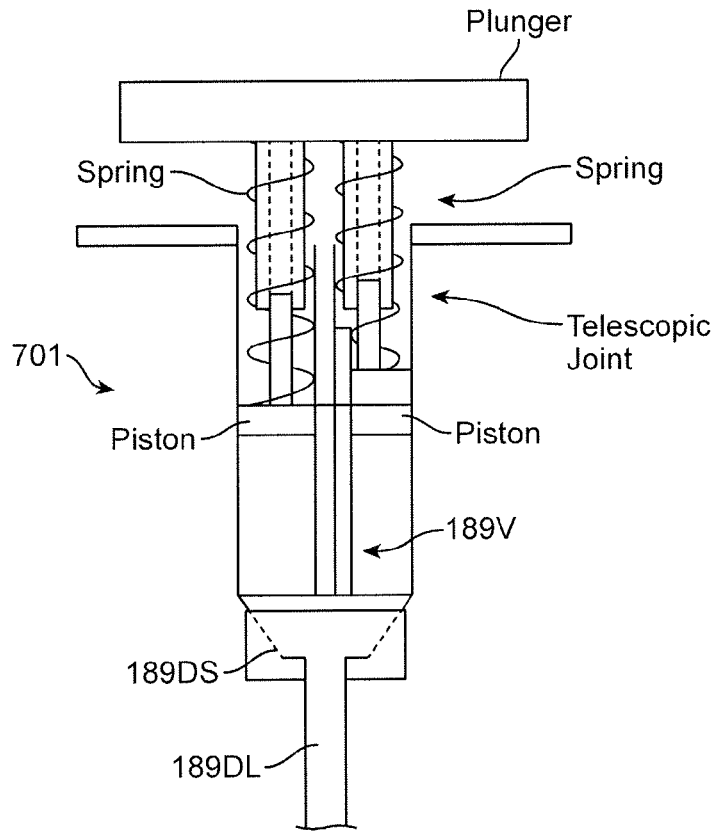
FIG. 60 and FIG. 61 show a first configuration of an injector to maintain the rate of flow into device to within about +/−50%, for example to within about +/−25%, such that the time to inject the therapeutic agent into device remains substantially constant amount devices and injections, in accordance with embodiments.
Figure 61:
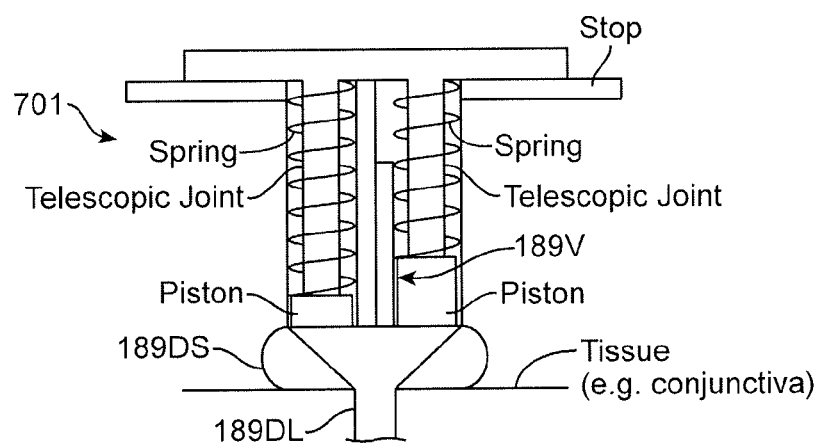

FIG. 60 and FIG. 61 show a first configuration of an injector 701 which can maintain the rate of flow into device to within about +/−50%, for example to within about +/−25%, such that the time to inject the therapeutic agent into device 100 remains substantially constant. For example, as the release rate index can be less than about 0.5, for example less than about 0.1, for example less than about 0.05, and the amount of time to inject a fully substantially fixed volume of the therapeutic device 100 can be inversely related to the release rate index.

The injector 701 can comprise a mechanism to maintain the rate of flow into the device and limit a maximum amount of flow, for example with a spring 701SP. The mechanism may comprise one or more of a mechanical mechanism, an electrical mechanism, a pneumatic mechanism, a hydraulic mechanism, or combinations thereof. Although a mechanical mechanism is shown, the above described mechanisms can provide similar results.

The visible indicator 189DS can be used to indicate to the operator that injector 701 is coupled to the therapeutic device 100 implanted in the eye 10 at a depth for injection. The operator can then depress the plunger.

The plunger 701PL can comprise a telescopic joint 701TJ and a spring 701SP, such that the joint 701TJ can be slid together such that the plunger 701PL is urged downward to contact the stop. When the plunger is urged downward, the spring may be compressed when the ends of the telescopic joint come together. The compressed spring can urge the piston toward the therapeutic device 100 such that the formulation of therapeutic agent may be injected into the therapeutic device 100 with the force of the spring. The valve 703V can close as described above (see FIG. 55, 57, or 59). The second portion of the injection corresponding to the bolus injection can be injected into the therapeutic device 100 and through porous structure 150.

Figure 62:
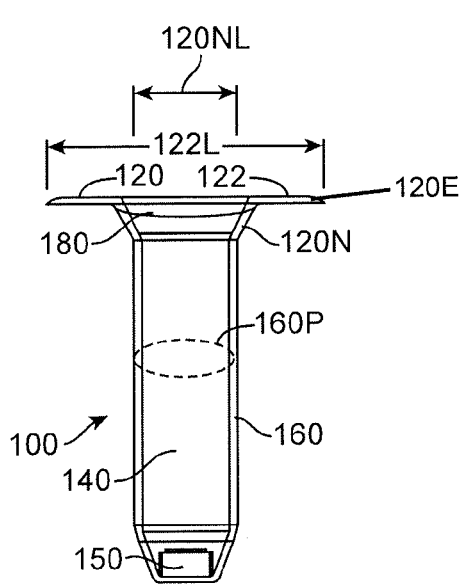
FIG. 62 shows a side cross-sectional view of a therapeutic device comprising a retention structure having a cross-section sized to fit in an elongate incision, in accordance with embodiments.

FIG. 62 shows a side cross-sectional view of therapeutic device 100 comprising a retention structure 120 having a cross-section sized to fit in an elongate incision. The cross-section sized to fit in the elongate incision may comprise a narrow portion 120N of retention structure 120 that is sized smaller than the flange 122. The narrow portion 120N sized to fit in the elongate incision may comprise an elongate cross-section 120NE sized to fit in the incision. The narrow portion 120N may comprise a cross-section having a first cross-sectional distance across, or first dimensional width 120NL, and a second cross-sectional distance across, or second dimensional width 120NS (see FIG. 63), in which the first cross-sectional distance across is greater than the second cross-sectional distance across such that the narrow portion 120N comprises an elongate cross-sectional profile 120NP.

The retention structure 120 can comprise a narrow section 120N having a short distance 120NS and a long distance 120NL so as to fit in an elongate incision along, for example, the pars plana of the eye 10. The retention structure 120 may be comprised of an extension 120E. The extension of the retention structure 120E can comprise a short distance across 122S and a long distance across 122L, aligned with the short distance 120NS and long distance 120NL of the narrow portion 120N of the retention structure 120. The narrow portion 120N may comprise an indentation 120I sized to receive the sclera 24 (see FIGS. 87 and 88).

The elongate cross-section 120NE of the narrow portion 120N can be sized in many ways to fit the incision. The elongate cross-section 120NE may comprise a first dimension longer than a second dimension and may comprise one or more of many shapes such as dilated slot, dilated slit, lentoid, oval, ovoid, or elliptical. The dilated slit shape and dilated slot shape may correspond to the shape sclera 24 tissue assumes when cut and dilated. The lentoid shape may correspond to a biconvex lens shape. The elongate cross-section of the narrow portion may comprise a first curve along a first axis and a second curve along a second axis different than the first curve.

Similar to the narrow portion 120N of the retention structure, the container reservoir may comprise a cross-sectional profile. The barrier 160 can have as a perimeter circumference 160P.

Figure 63:
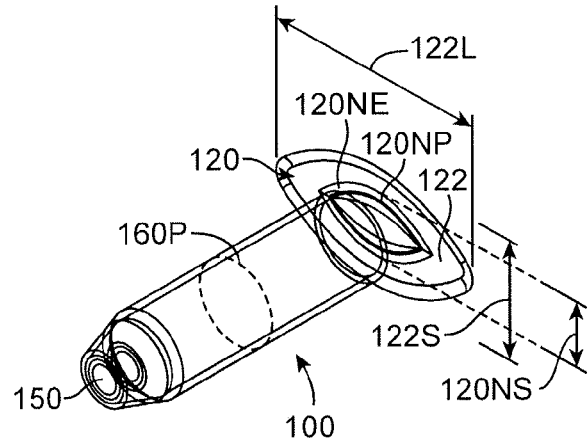
FIG. 63 shows an isometric view of the therapeutic device as in FIG. 62, in accordance with embodiments.

FIG. 63 shows an example isometric view of the therapeutic device 100 as in FIG. 62.

Figure 64:
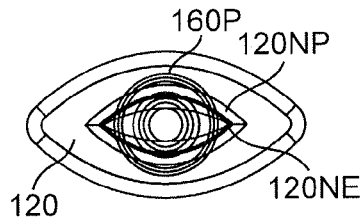
FIG. 64 shows a top view of the therapeutic device as in FIG. 62, in accordance with embodiments.

FIG. 64 shows an example top view of the therapeutic device 100 as in FIG. 62.

Figure 65:
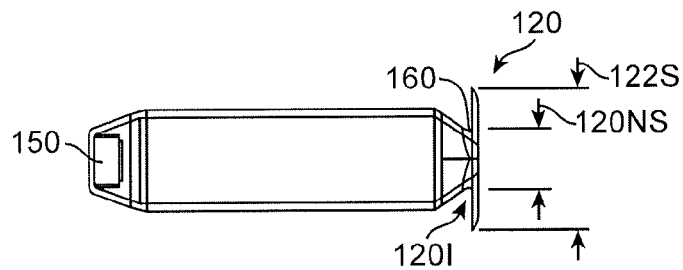
FIG. 65 shows a side cross-sectional view along the short side of the retention structure of the therapeutic device as in FIG. 62, in accordance with embodiments.

FIG. 65 shows an example side cross-sectional view along the short side of the retention structure of the therapeutic device 100 as in FIG. 62.

Figure 66:
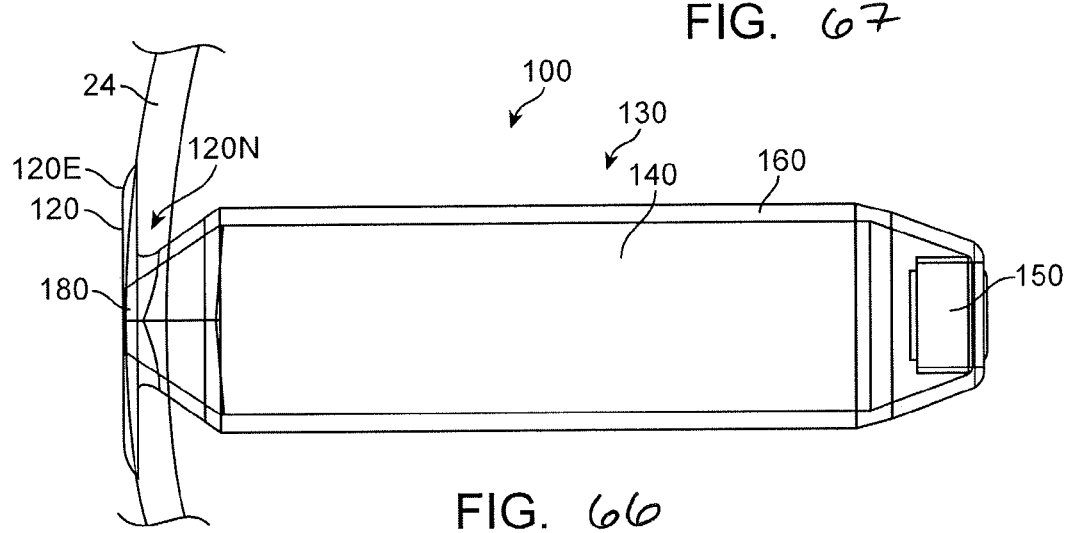
FIG. 66 shows a bottom view of the therapeutic device as in FIG. 62 implanted in the sclera, in accordance with embodiments.

FIG. 66 shows an example bottom view of the therapeutic device 100 as in FIG. 62 implanted in the sclera 24.

Figure 67:
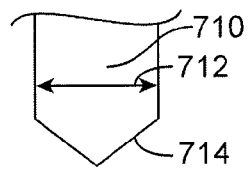
FIG. 67 shows a cutting tool comprising a blade having a width corresponding to the perimeter of the barrier and the perimeter of the narrow retention structure portion, in accordance with embodiments.

FIG. 67 shows an example cutting tool 710 comprising a blade 714 having a width 712 corresponding to perimeter 160P of the barrier 160 and the perimeter 160NP of the narrow portion. The cutting tool can be sized to the narrow portion 120N so as to seal the incision with the narrow portion when the narrow portion is positioned against the sclera 24. For example, the width 712 may comprise about one half of the perimeter 160P of the barrier 160 and about one half of the perimeter 160NP of the narrow portion. For example, the outside diameter of the tube of barrier 160 may comprise about 3 mm such that the perimeter of 160P comprises about 6 mm, and the narrow portion perimeter 160NP may comprise about 6 mm. The width 712 of the blade 714 may comprise about 3 mm such that the incision comprises an opening having a perimeter of about 6 mm so as to seal the incision with the narrow portion 160NP. Alternatively, perimeter 160P of barrier 160 may comprise a size slightly larger than the incision and the perimeter 160NP of the narrow portion.

Figure 68:
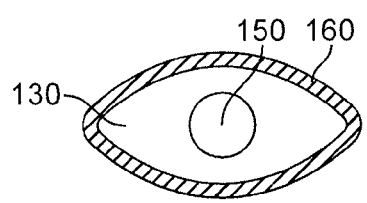
FIGS. 68 and 69 show distal cross-sectional view and a proximal cross-sectional view, respectively, of a therapeutic device comprising an elongate and non-circular cross-sectional size, in accordance with embodiments, in accordance with embodiments.
Figure 69:
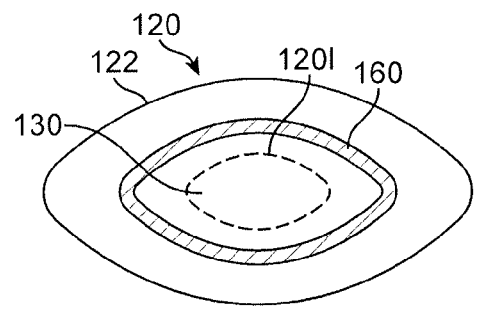

FIGS. 68 and 69 show an example distal cross-sectional view and a proximal cross-sectional view, respectively, of therapeutic device 100 comprising a non-circular cross-sectional size. The porous structure 150 can be located on a distal end portion of the therapeutic device 100, and the retention structure 120 can be located on a proximal portion of therapeutic device 100. The barrier 160 can define a size of reservoir 130. The barrier 160 and reservoir 130 may each comprise an elliptical or oval cross-sectional size, for example. The barrier 160 can comprise a first cross-sectional distance across reservoir 130, and a second cross-sectional distance across reservoir 130, and the first distance across may extend across a long (major) axis of an ellipse and the second distance across may extend across a short (minor) axis of the ellipse. This elongation of the device along one direction can allow for increased drug in the reservoir with a decrease interference in vision, for example, as the major axis of the ellipse can be aligned substantially with the circumference of the pars plana region of the eye 10 extending substantially around the cornea of the eye 10, and the minor axis of the ellipse can be aligned radially with the eye so as to decrease interference with vision as the short axis of the ellipse extends toward the optical axis of the eye 10 corresponding to the patient's line of sight through the pupil. Although reference is made to an elliptical or oval cross-section, many cross-sectional sizes and shapes can be used such as rectangular with a short dimension extending toward the pupil of the eye and the long dimension extending along the pars plana of the eye 10.

The retention structure 120 may comprise structures corresponding to a structure of the cross-sectional area. For example, the flange 122 may comprise a first distance across and a second distance across, with the first distance across greater than the second distance across. The extension may comprise many shapes, such as rectangular, oval, or elliptical, and the long distance across can correspond to the long distance of the reservoir and barrier. The retention structure 120 may comprise the narrow portion 120N having an indentation 120I (see FIGS. 87 and 88) extending around an access port to the therapeutic device 100, as described above. The indentation 120I and flange 122 may each comprise an elliptical or oval profile with a first long (major) axis of the ellipse extending in the first direction and a second short (minor) axis of the ellipse extending in the second direction. The long axis can be aligned so as to extend circumferentially along the pars plana of the eye 10, and the short axis can be aligned so as to extend toward the pupil of the eye 10, such that the orientation of device 100 can be determined with visual examination by the treating physician.

Figure 70:
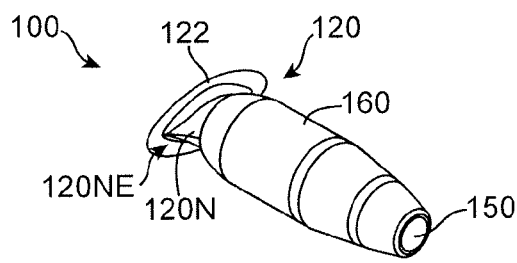
FIG. 70 shows an isometric view of the therapeutic device having a retention structure with an elongate cross-sectional size, in accordance with embodiments, in accordance with embodiments.

FIG. 70 shows an example isometric view of the therapeutic device 100 having a retention structure comprising a narrow portion 120N with an elongate cross-sectional size 120NE.

Figure 71:
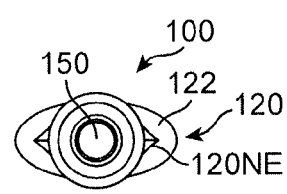
FIG. 71 shows a distal end view of the therapeutic device as in FIG. 70, in accordance with embodiments.

FIG. 71 shows an example distal end view of the therapeutic device 100 as in FIG. 70.

Figure 72:
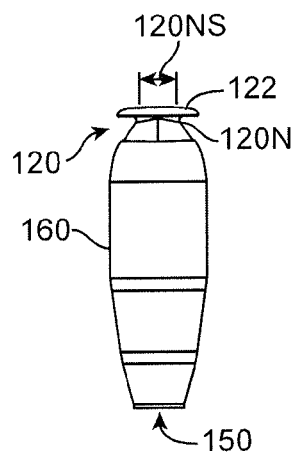
FIG. 72 shows a side view of the short axis of the narrow neck portion of the therapeutic device as in FIG. 70, in accordance with embodiments.

FIG. 72 shows an example side view of the short distance 120NS of the narrow portion 120N of the therapeutic device 100 as in FIG. 70.

Figure 73:
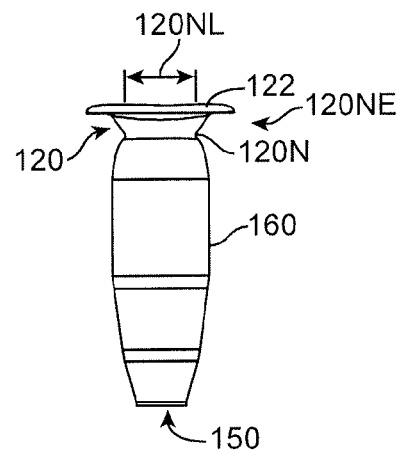
FIG. 73 shows a side view of the long axis of the narrow neck portion of the therapeutic device as in FIG. 70, in accordance with embodiments.

FIG. 73 shows a side view of the long distance 120NL of the narrow portion 120N of the therapeutic device 100 as in FIG. 70.

Figure 74:
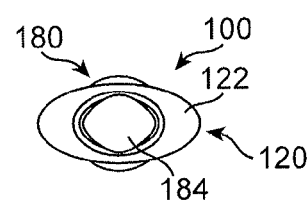
FIG. 74 shows a proximal view of the therapeutic device as in FIG. 70, in accordance with embodiments.

FIG. 74 shows a proximal view of the therapeutic device 100 as in FIG. 70.

FIG. 75 to FIG. 77 show an example exploded assembly drawings for the therapeutic device 100 as in FIGS. 70 to 74. The assembly drawings of FIG. 75, FIG. 76 and FIG. 77 show isometric and thin side profiles views, respectively, of the elongate portion 120NE of the narrow portion 120N of the retention structure 120. The therapeutic device 100 has an elongate axis 100A.

The penetrable barrier 184, for example the septum, can be inserted into the access port 180. The penetrable barrier 184 may comprise an elastic material sized such that the penetrable barrier 184 can be inserted into the access port 180. The penetrable barrier 184 may comprise one or more elastic materials, such as siloxane or rubber. The penetrable barrier 184 may comprise tabs 184T to retain the penetrable barrier 184 in the access port. The penetrable barrier 184 may comprise a beveled upper rim 184R sized to seal the access port 180. The access port 180 of the reservoir container 130 may comprise a beveled upper surface to engage the beveled rim and seal the penetrable barrier 184 against the access port 180 when the tabs 184T engage an inner annular or elongate channel of the access port 180. The penetrable barrier 184 may comprise an opaque material, for example a grey material, for example silicone, such that the penetrable barrier 184 can be visualized by the patient and treating physician.

The reservoir container 130 of the device may comprise a rigid biocompatible material that extends at least from the retention structure to the rigid porous structure 150, such that the reservoir comprises a substantially constant volume when the therapeutic agent is released with the rigid porous structure 150 so as to maintain a stable release rate profile, for example when the patient moves. Alternatively or in combination, the reservoir container 130 may comprise an optically transmissive material such that the reservoir container 130 can be translucent, for example transparent, such that the reservoir chamber 140 can be visualized when the device is loaded with therapeutic agent outside the patient prior to implantation, for example when injected with a formulation of therapeutic agent prior to implantation in the physician's office. This visualization of the reservoir chamber 140 can be helpful to ensure that the reservoir chamber 140 is properly filled with therapeutic agent by the treating physician or assistant prior to implantation. The reservoir container 130 may comprise one or more of many biocompatible materials such as acrylates, polymethylmethacrylate, siloxanes, metals, titanium stainless steel, polycarbonate, polyetheretherketone (PEEK), polyethylene, polyethylene terephthalate (PET), polyimide, polyamide-imide, polypropylene, polysulfone, polyurethane, polyvinylidene fluoride or PTFE. The biocompatible material of the reservoir container may comprise an optically transmissive material such as one or more of acrylate, polyacrylate, methlymethacrylate, polymethylmethacrylate (PMMA), polyacarbonate or siloxane. The reservoir container 130 can be machined from a piece of material, or injection molded, so as to form the retention structure 120 comprising flange 122 and the elongate narrow portion 120NE. The flange 122 may comprise a translucent material such that the physician can visualize tissue under the flange to assess the patient and to decrease appearance of the device 100 when implanted. The reservoir container 130 may comprise a channel extending along axis 100A from the access port 180 to porous structure 150, such that formulation injected into device 100 can be released in accordance with the volume of the reservoir and release rate of the porous structure 150 as described herein. The porous structure 150 can be affixed to the distal end of therapeutic device 100, for example with glue. Alternatively or in combination, the distal end of the reservoir container 130 may comprise an inner diameter sized to receive the porous structure 150, and the reservoir container 130 may comprise a stop to position the porous structure 150 at a predetermined location on the distal end so as to define a predetermined size of reservoir chamber 140.

FIG. 78 shows an expandable therapeutic device 790 comprising expandable barrier material 160 and support 160S in an expanded configuration for extended release of the therapeutic agent. The expanded configuration can store an increased amount of therapeutic agent, for example from about 30 µl, to about 100 µL. The expandable device may comprise a retention structure 120, an expandable reservoir 140. The support 160S may comprise a resilient material configured for compression, for example resilient metal or thermoplastic. Alternatively, the expandable support may be bent when expanded. The expandable device can comprise the porous structure 150 disposed on a distal end, and affixed to the expandable support. The expandable device may comprise an access port 180, for example with a penetrable barrier 184. In the expanded configuration, the device is substantially clear from a majority of the optical path OP of the patient The support 160S of the barrier 160 can provide a substantially constant volume of the reservoir in the expanded configuration. The substantially constant volume, for example +/−25%, can be combined with the release rate index of the porous structure 150 so as to tune the expanded reservoir and porous structure 150 to the volume of therapeutic agent to be injected into the therapeutic device, as described herein. The barrier 160 may comprise a thin compliant material, for example a membrane, and the support 160S can urge the barrier 160 to an expanded configuration so as to define the reservoir chamber having the substantially constant volume.

FIG. 79 shows an example of the distal end portion of the support 160S. The support 160S may comprise struts that extend to an annular flange 160SF that supports the porous structure 150 on the distal end of device 100.

FIG. 80 shows an example of the support 160S disposed inside the barrier 160 so as to provide the substantially constant expanded volume of the reservoir chamber.

FIG. 81 shows an example of the support 160S disposed along the inner surface of the barrier 160 so as to provide the substantially constant expanded volume of the reservoir chamber. The support 160S can be bonded to the barrier 160 in many ways, for example with a bonding agent such as glue or resin, or with thermal bonding. The support 160S can be disposed on the outside of barrier 160.

Figure 82:
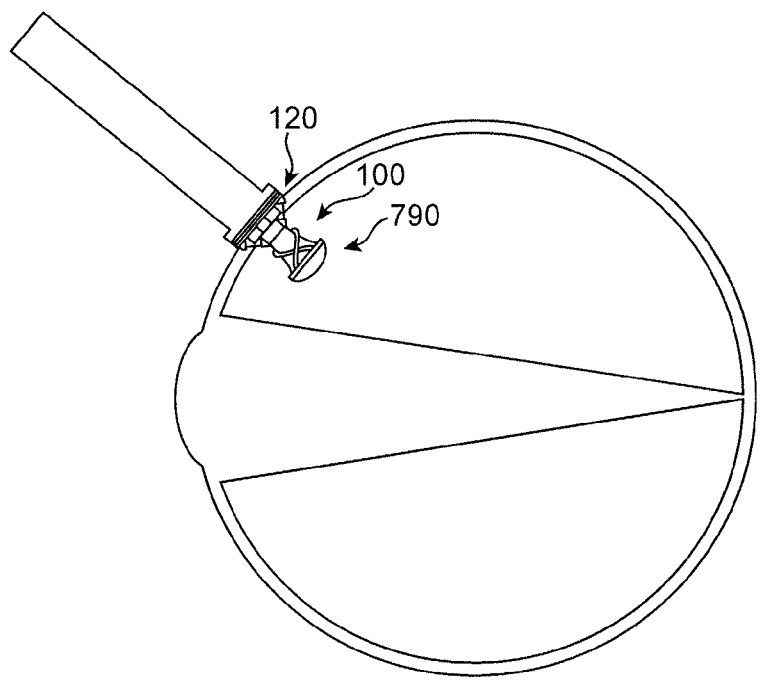
FIG. 82 shows the expandable therapeutic device as in FIG. 78 in a narrow profile configuration, in accordance with embodiments.

FIG. 82 shows the expandable therapeutic device 790 as in FIG. 78 in a narrow profile configuration suitable for use in an injection lumen.

Figure 83:
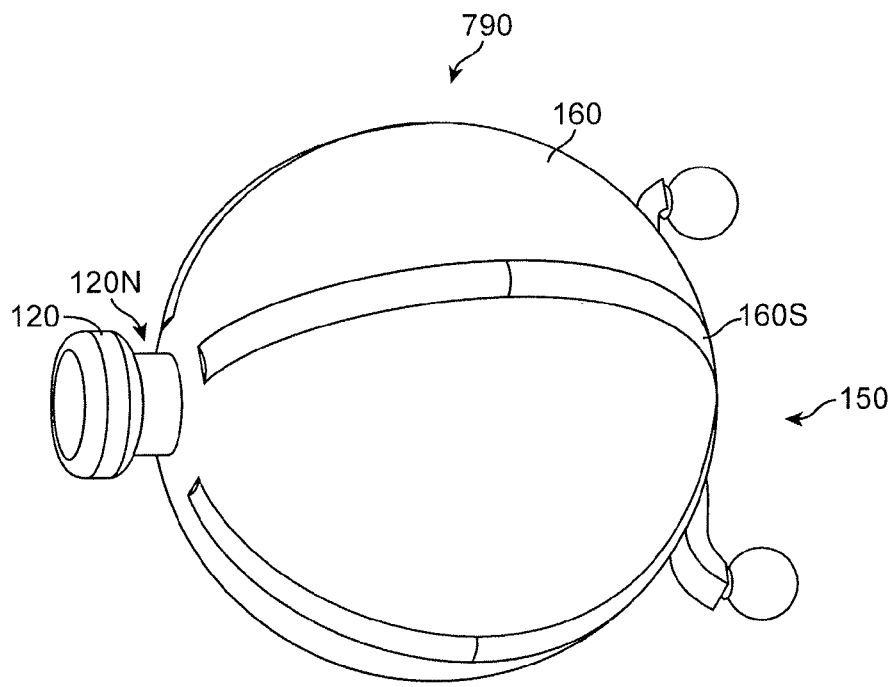
FIG. 83 shows the expandable therapeutic device as in FIG. 78 in an expanded profile configuration, in accordance with embodiments.

FIG. 83 shows the expandable therapeutic device as in FIG. 78 in an expanded profile configuration, suitable for retention, for example with the sclera 24.

Figure 84:
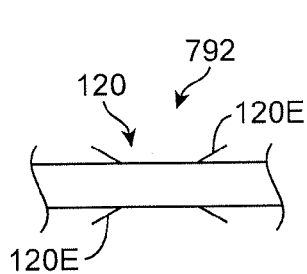
FIGS. 84 and 85 show an expandable retention structure, in accordance with embodiments.
Figure 85:
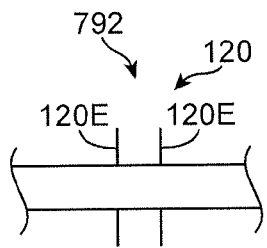

FIGS. 84 and 85 show an expandable retention structure 792. The expandable retention structure 792 can be used with the expandable therapeutic device 790, or with a substantially fixed reservoir and container device as described above. The expandable retention structure 792 comprises many compressible or expandable or resilient materials or combinations thereof. The expandable retention structure 792 comprises an extension 120E that can expand from the narrow profile configuration to the expanded configuration, for example with tabs and flanges comprising resilient material. The upper portion can be inclined proximally and the distal portion can be inclined distally, such that the retention structure expands to engage opposite sides of the sclera 24. The resilient material may comprise at least one of thermoplastic material, a resilient metal, a shape memory material, and combinations thereof.

Figure 86:
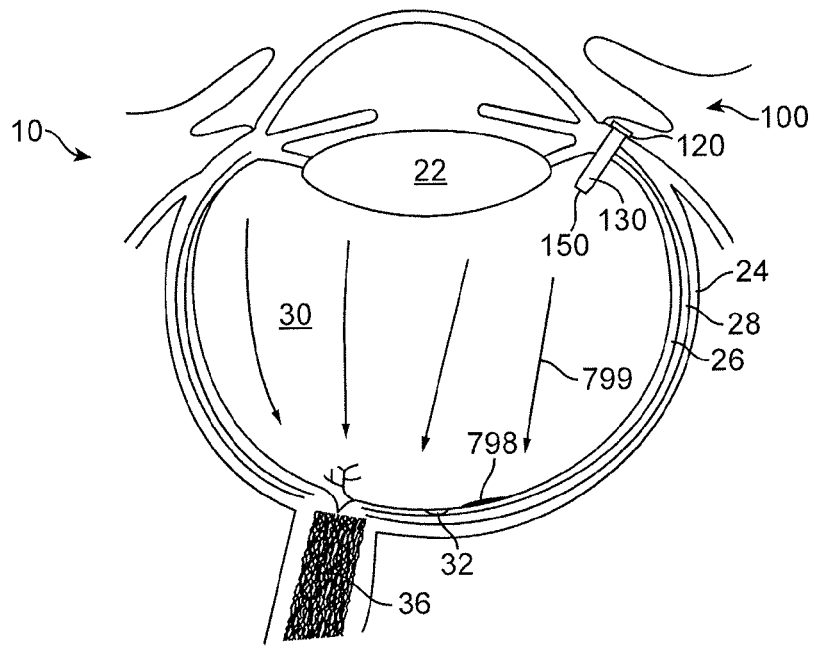
FIG. 86 shows a therapeutic device comprising a porous structure positioned in an eye to deliver a therapeutic agent to a target location on the retina, in accordance with embodiments.

FIG. 86 shows therapeutic device 100 comprising porous structure 150 positioned in an eye 10 to deliver a therapeutic agent to a target location on or near the retina 26, for example choroidal neovascularization of a lesion on or near the retina 26. For example, the lesion may comprise one or more buckling, folding, bending or separation of the retina 26 from the choroid related to neovascularization of corresponding vascular tissue associated with blood supply to the retina 26, and the neovascular tissue corresponding to the lesion of the retina 26 may be targeted. Work in relation to embodiments indicates that the vitreous humor 30 of the eye 10 may comprise convective current flows that extend along flow paths 799. The convective flow paths may comprise flow channels. Although small molecules can be delivered to a target location of the retina 26 in accordance with the flow paths, therapeutic agent comprising large molecules, for example with antibody fragments or antibodies, can be delivered substantially with the convective flow paths as the molecular diffusion of large molecules in the vitreous humor 30 can be somewhat lower than small molecules.

The therapeutic device 100 can be sized such that porous structure 150 is positioned along a flow path extending toward a target location of the retina 26. The therapeutic agent can be released along the flow path, such that the flow of vitreous humor 30 transports the therapeutic agent to the retina 26. The porous structure can be disposed on a distal portion of the therapeutic device 100, for example on a distal end, and the reservoir 130 can be sized for delivery for the extended time. The therapeutic device 100 can be sized such that the porous structure 150 is positioned such that it may correspond to the target region. The surgeon may identify a target region 798 of the retina 26, for example corresponding to a lesion, and the therapeutic device 100 can be positioned along the pars plana or other location such that the therapeutic agent is released to the target region.

Figure 87:
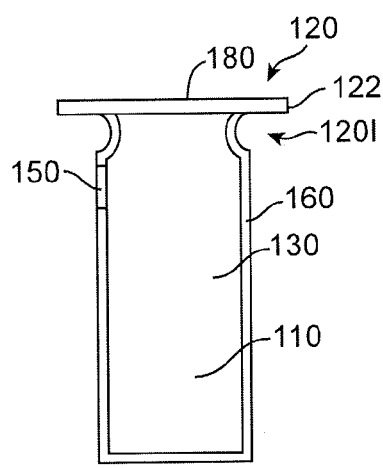
FIG. 87 shows a therapeutic device comprising a porous structure located on the device to deliver a therapeutic agent to one or more of the ciliary body or the trabecular meshwork when positioned in the eye, in accordance with embodiments.

FIG. 87 shows therapeutic device 100 comprising porous structure 150 located on a proximal portion of the device to deliver a therapeutic agent 110 to one or more of the ciliary body or the trabecular meshwork when implanted in the eye 10. The porous structure 150 can be located near retention structure 120 such that the porous structure 150 is positioned in the vitreous substantially away from the flow paths extending to retina 26, as noted above. The porous structure 150 can be located on a side of the therapeutic device 100 so as to release the therapeutic agent 110 toward a target tissue. While many therapeutic agents 110 can be used, the therapeutic agent may comprise a prostaglandin or analog, such as bimatoprost or latanoprost, such that the therapeutic agent can be released toward one or more of the ciliary body or trabecular meshwork when implanted in the vitreous humor 30 with the retention structure coupled to the sclera 24.

Figure 88:
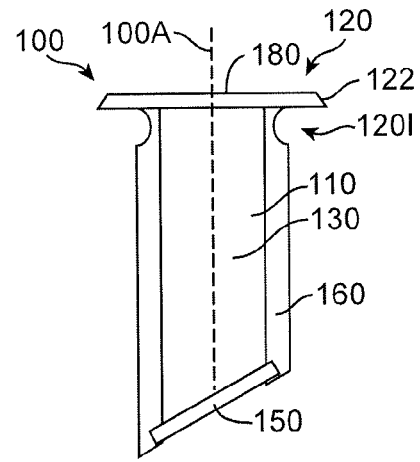
FIG. 88 shows therapeutic device comprising porous structure oriented to release the therapeutic agent away from the lens and toward the retina, in accordance with embodiments.

FIG. 88 shows therapeutic device 100 comprising porous structure 150 oriented to release the therapeutic agent 110 away from the lens and toward the retina 26. For example, the therapeutic agent 110 may comprise a steroid, and the steroid can be released from porous structure 150 away from the lens and toward the retina 26. For example, the porous structure 150 can be oriented relative to an axis 100A of the therapeutic device 100. The outer side of porous structure 150 can be oriented at least partially toward the retina 26 and away from the lens, for example along a flow path as described above so as to treat a target region of the retina 26. The barrier 160 can extend between the porous structure 150 and the lens of the eye 10 when implanted such that release of therapeutic agent toward the lens can be inhibited with barrier 160. The retention structure 120 may comprise a long distance across and a short distance across as described above. The porous structure 150 can be oriented in relation to the short and long distances of the extensions 122, such that the outer side of porous structure 150 is oriented at least partially toward the retina 26 and along the flow path when the long distance of the retention structure extends along the pars plana and the short distance extends toward the pupil.

Figure 89:
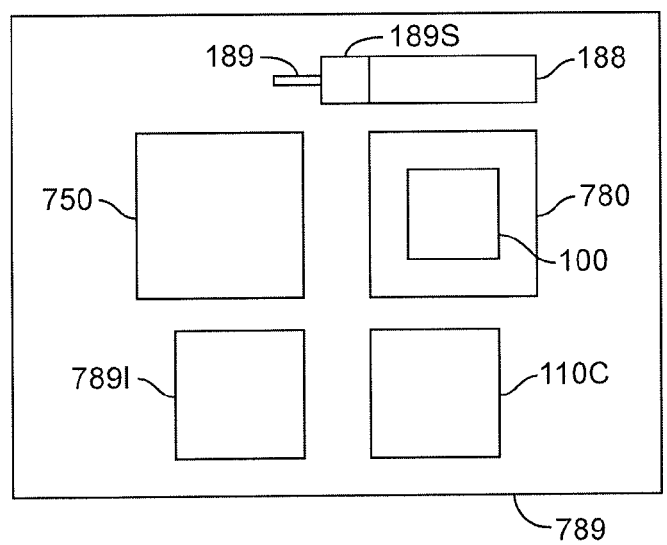
FIG. 89 shows a kit comprising a placement instrument, a container, and a therapeutic device within the container, in accordance with embodiments.

FIG. 89 shows a kit 789 comprising a placement instrument 750, a container 780, and a therapeutic device 100 disposed within the container 780. The reservoir of the therapeutic device 100 disposed in the container may comprise a non-therapeutic solution, for example saline, such that the channels 156 of the porous structure 150 comprise liquid water to inhibit bubble formation when the formulation of therapeutic agent is injected into the device 100. The kit may also comprise the syringe 188, needle 189 and stop 189S to insert the needle tip to a maximum stop distance within the reservoir as described above. The kit 789 may contain instructions for use 789I, and may contain a container 110C comprising a formulation of therapeutic agent 110. The instructions for use may comprise instructions to orient the device with the penetrable barrier 184 in relation to the porous structure 150 during injection of the therapeutic agent, for example with the penetrable barrier 184 located above the porous structure 150 when the therapeutic fluid is injected. The instructions may correspond to the configuration of the fluid displacement apparatus such as the injector as described herein.

Tuning of Therapeutic Device for Sustained Release Based on an Injection of a Formulation The therapeutic device 100 can be tuned to deliver a target therapeutic concentration profile based on the volume of formulation injected into the device. The injected volume may comprise a substantially fixed volume, for example within about +/−30% of an intended pre-determined target volume. The volume of the reservoir can be sized with the release rate index so as to release the therapeutic agent for an extended time substantially greater than the treatment time of a corresponding bolus injection. The device can also be tuned to release the therapeutic agent based on the half-life of the therapeutic agent in the eye 10. The device volume and release rate index may comprise parameters that can be tuned together based on the volume of formulation injected and a half-life of the therapeutic agent in the eye 10. The following equations can be used to determine therapeutic device 100 parameters suitable for tuning the device.

$$\text{Rate} = Vr(dCr/dt) = -D(PA/TL)Cr$$

where Rate=Rate of release of therapeutic agent from device
Cr=concentration of therapeutic agent in reservoir
Vr=volume of reservoir
D=Diffusion constant
PA/TL=RRI
P=porosity
A=area
T=tortuosity=F=channel parameter.

For a substantially fixed volume injection, $$Cr0 = (\text{Injection Volume})(\text{Concentration of Formulation})/Vr$$

Where Cr0=initial concentration in reservoir following injection of formulation For Injection Volume=50 uL $$Cr0 = (0.05 \text{ mL})(10 \text{ mg/mL})/Vr(1000 \text{ ug/1 mg}) = 500 \text{ ug}/Vr$$

$$\text{Rate} = x(500 \text{ ug})\exp(-xt)$$

where t=time $$x=(D/Vr)(PA/TL)$$

With a mass balance on the vitreous $$Vv(dCv/dt)=\text{Rate from device}=kVvCv$$

where Vv=volume of vitreous (about 4.5 ml)
Cv=concentration of therapeutic agent in vitreous
k=rate of drug from vitreous (proportional to 1/half-life of drug in vitreous)
For the situation appropriate for the embodiments as described herein where Cv remains substantially constant and changes slowly with time (i.e., dCv/dt is approximately 0), $$Cv=(\text{Rate from device})/(kVv)$$

Since kVv is substantially constant, the max value of Cv will correspond to conditions that maximize the Rate from the device. At a given time since injection into the device (e.g., 180 days), the maximum Cv is found at the value of x that provides the maximum rate. The optimal value of x satisfies $$d(\text{Rate})/dx=0 \text{ at a given time.}$$

$$\text{Rate}=500(x)\exp(-xt)=f(x)g(x) \text{ where } f(x)=500x \text{ and } g(x)=\exp(-xt)$$

$$d(\text{Rate})/dx=f'(x)g(x)+f(x)g'(x)=500(1-xt)\exp(-xt)$$

For a given time, t, d(Rate)/dx=0 when 1−xt=0 and xt=1
The rate is maximum when (D/Vr)(PA/TL)t=1.
For a given volume, optimal PA/TL=optimal RRI=Vr/(Dt)
Therefore the highest Cv at a given time, t, occurs for the optimal RRI=(PA/FL) for a given Vr.
Also, the ratio (Vr)/(RRI)=(Vr)/(PA/TL)=Dt will determine the optimal rate at the time.

The above equations can provide approximate optimized values that, when combined with numerical simulations, can provide optimal values of Vr and PA/TL. The final optimum value can depend on additional parameters, such as the filling efficiency.

The above parameters can be used to determine the optimal RRI, and the therapeutic device 100 can be tuned to the volume of formulation injected into the device with a device reservoir volume and release rate index within about +/−50% of the optimal values, for example +/−30% of the optimal values. For example, for an optimal release rate index of the porous structure 150 and an optimal reservoir volume sized to receive a predetermined quantity of therapeutic agent, e.g. 50 uL, so as to achieve therapeutic concentrations above a minimum inhibitory concentration for a predetermined extended time, such as 90 days, the maximum volume of the reservoir can be limited to no more than about twice the optimal volume. This tuning of the reservoir volume and the porous structure 150 to the injected volume of the commercially available formulation can increase the time of release of therapeutic amounts from the device as compared to a much larger reservoir volume that receives the same volume of commercially available injectable formulation. Although many examples as described herein show a porous frit structure and reservoir volume tuned together to receive a quantity of formulation and provide release for an extended time, the porous structure 150 tuned with the reservoir may comprise one or more of a porous frit, a permeable membrane, a semi-permeable membrane, a capillary tube or a tortuous channel, nano-structures, nano-channels 156 NC or sintered nano-particles, and a person of ordinary skill in the art can determine the release rate characteristics, for example a release rate index, so as to tune the one or more porous structures and the volume to receive the quantity of the formulation and release therapeutic amounts for an extended time.

As an example, the optimal RRI at 180 days can be determined for a reservoir volume of about 125 uL. Based on the above equations (Vr/Dt)=optimal RRI, such that the optimal RRI at 180 days is about 0.085 for the 50 uL formulation volume injected into the device. The corresponding Cv is about 3.19 ug/mL at 180 days based on the Rate of drug released from the device at 180 days and the rate of the drug from the vitreous (k corresponding to a half-life of about nine days). A device with a container reservoir volume of 63 uL and RRI of 0.044 will also provide the optimal Cv at 180 days since the ratio of Vr to PA/TL is also optimal. Although an optimal value can be determined, the therapeutic device 100 can be tuned to provide therapeutic amounts of drug at a targeted time, for example 180 days, with many values of the reservoir volume and many values of the release rate index near the optimal values, for example within about +/−50% of the optimal values. Although the volume of the reservoir can be substantially fixed, the volume of the reservoir can vary, for example within about +/−50% as with an expandable reservoir such as a balloon reservoir.

The half-life of the drug in the vitreous humor 30 of the eye 10 can be determined based on the therapeutic agent and the type of eye, for example human, rabbit or monkey, such that the half-life may be determined based on the species of the eye, for example. With at least some animal models the half-life of the therapeutic agent in the vitreous humor 30 can be shorter than for human eyes, for example by a factor of about two in at least some instances. For example, the half-life of the therapeutic agent Lucentis™ (ranibizumab) can be about nine days in the human eye and about two to four days in the rabbit and monkey animal models. For small molecules, the half-life in the vitreous humor 30 of the human eye can be about two to three hours and can be about one hour in the monkey and rabbit animal models. The therapeutic device 100 can be tuned to receive the volume of formulation based on the half-life of the therapeutic agent in the human vitreous humor 30, or an animal vitreous humor, or combinations thereof. Based on the teachings described herein, a person of ordinary skill in the art can determine empirically the half-life of the therapeutic agent in the eye 10 based on the type of eye and the therapeutic agent, such that the reservoir and porous structure can be tuned together so as to receive the volume of formulation and provide therapeutic amounts for the extended time.

The rate of accumulation of a component of the vitreous humor 30 of the eye can be determined based on the molecular weight of the component and the tuning of the therapeutic device 100 such as the reservoir volume and release of porous structure 150, such as a release rate index.

Figure 90:
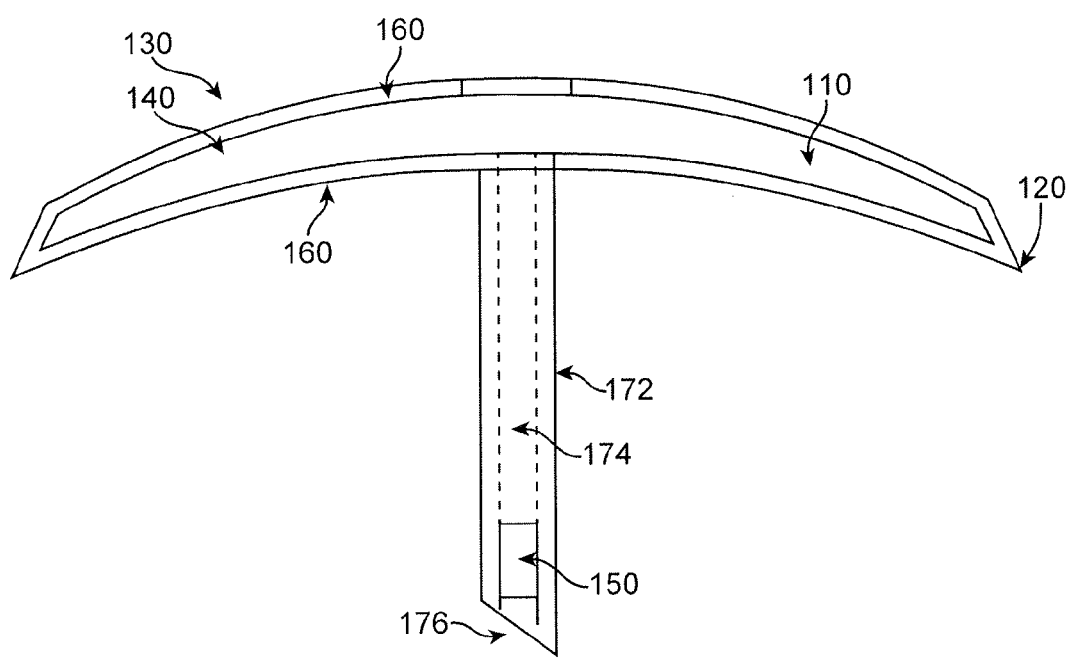
FIGS. 90 and 91 show a side cross-sectional view and a top view, respectively, of therapeutic device for placement substantially between the conjunctiva and the sclera.
Figure 91:
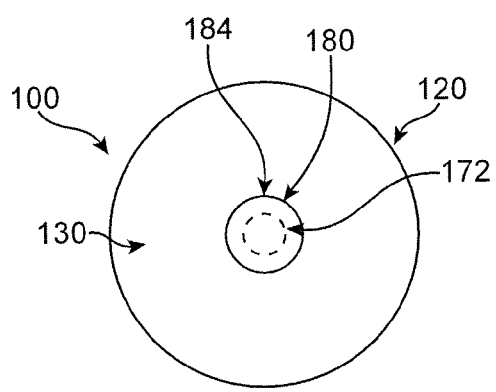

FIGS. 90 and 91 show a side cross-sectional view and a top view, respectively, of therapeutic device 100 for placement substantially between the conjunctiva 16 and the sclera 24. The therapeutic agent 110 as described herein can be injected when device 100 is implanted. The therapeutic device 100 comprises container 130 as described herein having penetrable barrier 184 as described herein disposed on an upper surface for placement against the conjunctiva 16. An elongate structure 172 is coupled to container 130. Elongate structure 172 comprises a channel 174 extending from a first opening coupled to the chamber of the container to a second opening 176 on a distal end of the elongate structure. The porous structure 150 as described herein is located on the elongate structure 172 and coupled to the container 130 so as to release therapeutic agent for an extended period, and a retention structure 120 comprising an extension protruding outward from the container 130 to couple to the sclera 24 and the conjunctiva 16. The container may comprise barrier 160 as described herein that defines at least a portion of the reservoir, and the container may comprise a width, for example a diameter. The barrier 160 may comprise a rigid material, for example rigid silicone or rigid rubber, or other material as described herein, such that the volume of the chamber of container 130 comprises a substantially constant volume as described herein. Alternatively or in combination, barrier 160 may comprise a soft material, for example when the chamber size is decreased such that the volume can be substantially constant with the decreased chamber size. A soft barrier material can be combined with a rigid material, for example a support material. The diameter can be sized within a range, for example within a range from about 1 to about 8 mm, for example within a range from about 2 to 6 mm and can be about 3 mm, for example.

The container may be coupled to elongate structure 172, and the elongate structure may have a length sized so as to extend from the conjunctiva 16 to the vitreous to release the therapeutic agent into the vitreous. The length can be sized within a range, for example within a range from about 2 to about 14 mm, for example within a range from about 4 to 10 mm and can be about 7 mm, for example. The penetrable barrier 184 may comprise a septum disposed on a proximal end of the container, in which the septum comprises a barrier that can be penetrated with a sharp object such as a needle for injection of the therapeutic agent. The porous structure 150 may comprise a cross-sectional area sized to release the therapeutic agent for the extended period. The elongate structure 172 can be located near a center of the container 130, or may be eccentric to the center. In addition, the elongate structure 172 can be inserted into the sclera 24 at the pars plana region as described herein.

The barrier 160 can have a shape profile for placement between the conjunctiva 16 and sclera 24. The lower surface can be shaped to contact the sclera 24 and may comprise a concave shape such as a concave spherical or toric surface. The upper surface can be shaped to contact the conjunctiva 16 and may comprise a convex shape, such as a convex spherical or toric surface. The barrier 160 may comprise an oval, an elliptical, or a circular shape when implanted and viewed from above, and the elongate structure 172 can be centered or eccentric to the ellipse. When implanted the long dimension of the oval can be aligned so as to extend along a circumference of the pars plana.

The cross-sectional diameter of the elongate structure 172 can be sized to decrease the invasiveness of device 100, and may comprise a diameter of no more than about 1 mm, for example no more than about 0.5 mm, for example no more than about 0.25 mm such that the penetrate sclera 24 seals substantially when elongate structure 172 is removed and the eye 10 can seal itself upon removal of elongate structure 172. The elongate structure 172 may comprise a needle, and channel 174 may comprise a lumen of the needle, for example a 30 Gauge needle.

The porous structure 150 may comprise a first side as described herein coupled to the reservoir and a second side to couple to the vitreous. The first side may comprise a first area as described herein and the second side may comprise a second area. The porous structure 150 may comprise a thickness as described herein. The porous structure 150 many comprise a diameter. The porous structure 150 may comprise a release rate index, and the chamber of container 130 that defines the volume of reservoir 140 can be sized such that the porous structure 150 and the volume are tuned to receive an amount of therapeutic agent injected with a volume of formulation of therapeutic agent and tuned to release therapeutic amounts for an extended time. Many release rate mechanisms as described herein can be used to tune the release rate and volume to the quantity of therapeutic agent injected as described herein. In addition, the volume of the reservoir 140 defined by the chamber of the container may comprise from about 5 µL to about 2000 µL of therapeutic agent, or for example from about 10 µL to about 200 µL of therapeutic agent.

The porous structure 150 may comprise a needle stop 170 that limits penetration of the needle. The porous structure 150 may comprise a plurality of channels configured for the extended release of the therapeutic agent. The porous structure may comprise a rigid sintered material having characteristics suitable for the sustained release of the material.

Figure 92:
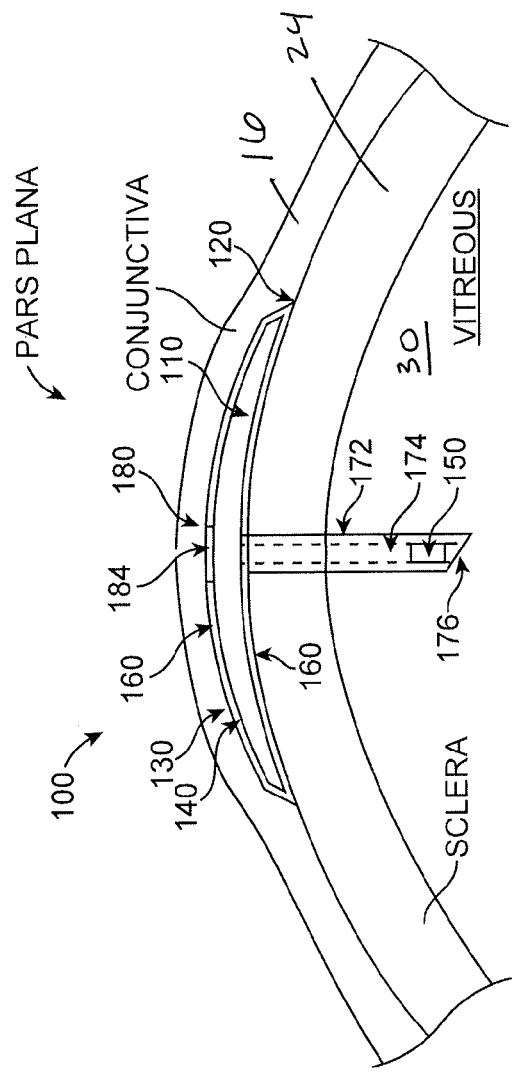
FIG. 92 shows the therapeutic device implanted with the reservoir between the conjunctiva and the sclera, such that elongate structure extends through the sclera to couple the reservoir chamber to the vitreous humor, in accordance with embodiments.

FIG. 92 shows the therapeutic device 100 implanted with the reservoir between the conjunctiva 16 and the sclera 24, such that elongate structure 172 extends through the sclera 24 to couple the reservoir chamber to the vitreous humor 30. When implanted, the porous structure 150 can be located in the vitreous humor 30, or located between the conjunctiva 16 and sclera 24, or may extend through the sclera 24, or combinations thereof.

Figure 93:
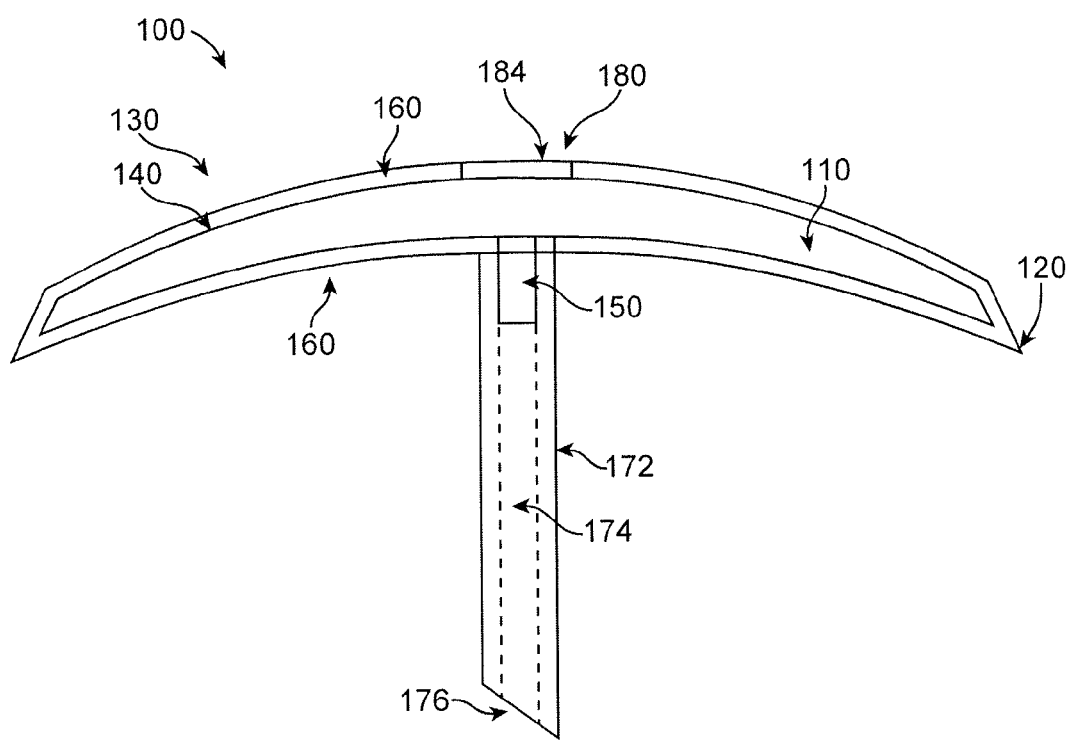
FIG. 93 shows the porous structure of therapeutic device located in channel near the opening to the chamber of the container, in accordance with embodiments.

FIG. 93 shows the porous structure 150 of therapeutic device 100 located in channel 174 near the opening to the chamber of the container 130. The porous structure 150 can extend substantially along the length of elongate structure 172.

Figure 94:
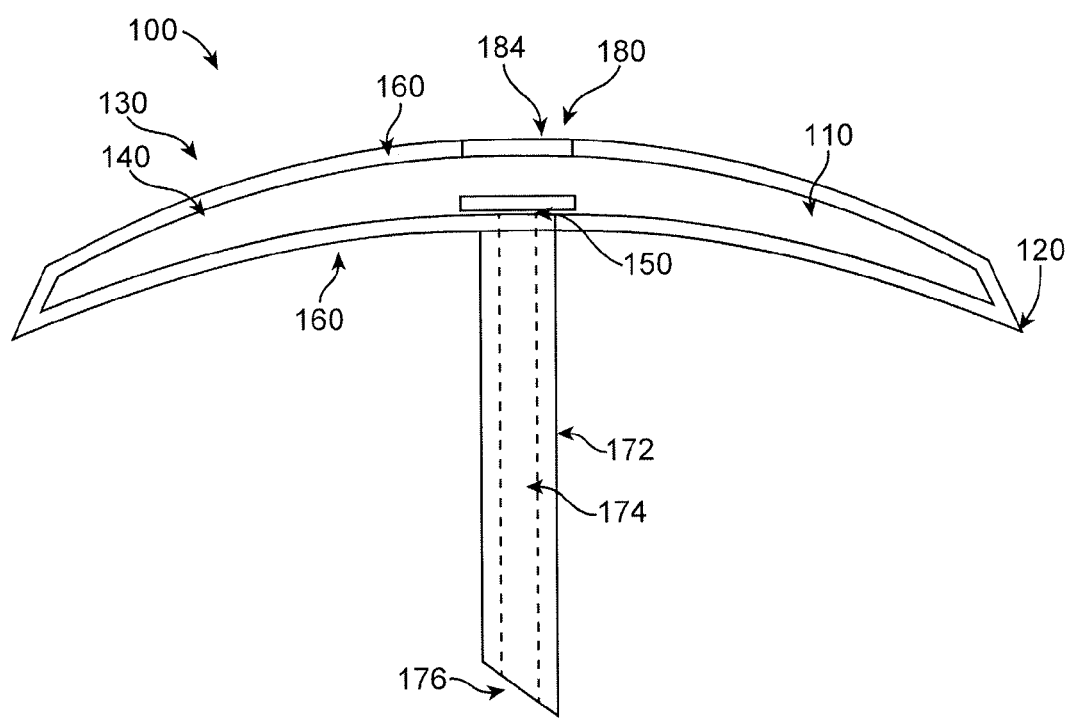
FIG. 94 shows the porous structure located within the chamber of container and coupled to the first opening of the elongate structure so as to provide the release rate profile, in accordance with embodiments.

FIG. 94 shows the porous structure 150 located within the chamber of container 130 and coupled to the first opening of the elongate structure 172 so as to provide the release rate profile. The porous structure 150 can cover the opening of elongate structure 172 such that therapeutic amounts are released for the extended time as described herein.

Figure 95:
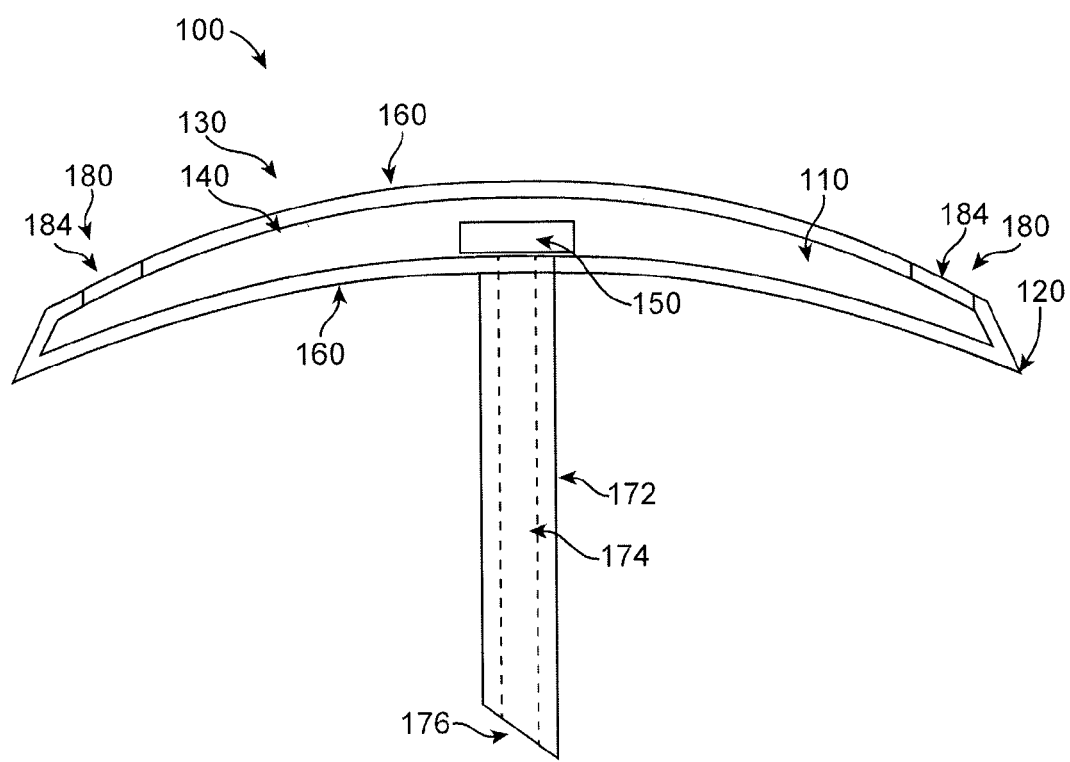
FIG. 95 shows a plurality of injection ports spaced apart so as to inject and exchange the liquid of chamber of the container and inject the therapeutic agent into the reservoir chamber of the container, in accordance with embodiments.

FIG. 95 shows a plurality of injection ports spaced apart so as to inject and exchange the liquid of chamber of the container 130 and inject the therapeutic agent into the reservoir chamber 140 of the container 130. The penetrable barrier 184 may comprise a first penetrable barrier 180 located in a first access port formed in the barrier 160 and a second penetrable barrier 180 located in a second access port formed in the barrier 160, and the first barrier can be separated from the second barrier by at least about 1 mm.

The injector 701 as described above (see FIGS. 54 through 59) can be configured to couple to the reservoir placed between the conjunctiva 16 and the sclera 24 as describe herein. The injector 701 can be coupled to a double lumen needle 189DL such that a second lumen 189B injects therapeutic agent 110 from a first container 702C into device 100, and the first lumen 189A can be spaced apart from the second lumen 189B with the distance extending therebetween sized to position the first lumen 189A in the first septum as described above and the second lumen 189B in the second septum as described above. The second container 703C can be coupled to a first lumen 189A that extends to the chamber of the reservoir container and receives liquid from device 100, such that liquid of device 100 is exchanged when the chamber of the reservoir container is positioned between the conjunctiva 16 and the sclera 24. The switching valve 703V to exchange an intended amount of liquid and an intended amount of the formulation the therapeutic agent 110, and inject an intended amount of therapeutic agent injected into device 100, for example such that a bolus amount of therapeutic agent 110 can be injected from device 100 as described above. A portion of the formulation of therapeutic agent injected into device 100 can be retained in device 100 for release for an extended time.

Figure 96:
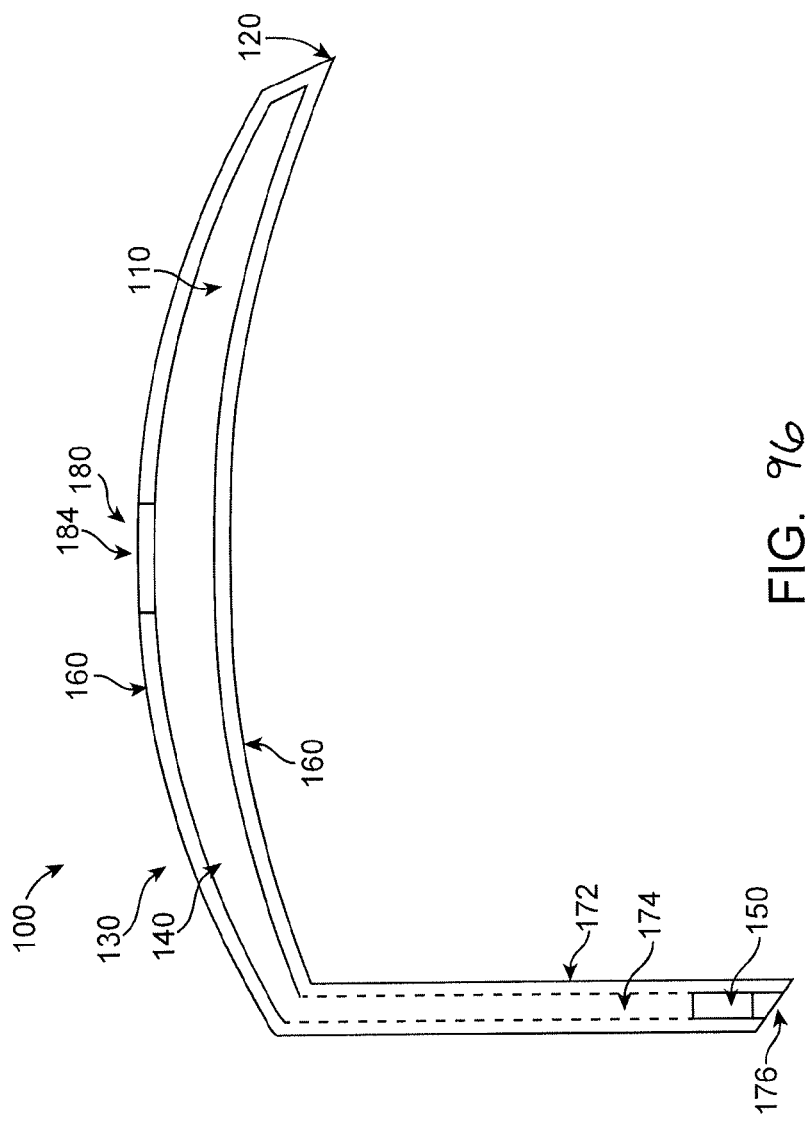
FIG. 96 shows the elongate structure coupled to the container away from the center of container and near and located near an end of the container, in accordance with embodiments.

FIG. 96 shows the elongate structure 172 coupled to the container 130 away from the center of container 130 and located near an end of the container 130.

Figure 97:
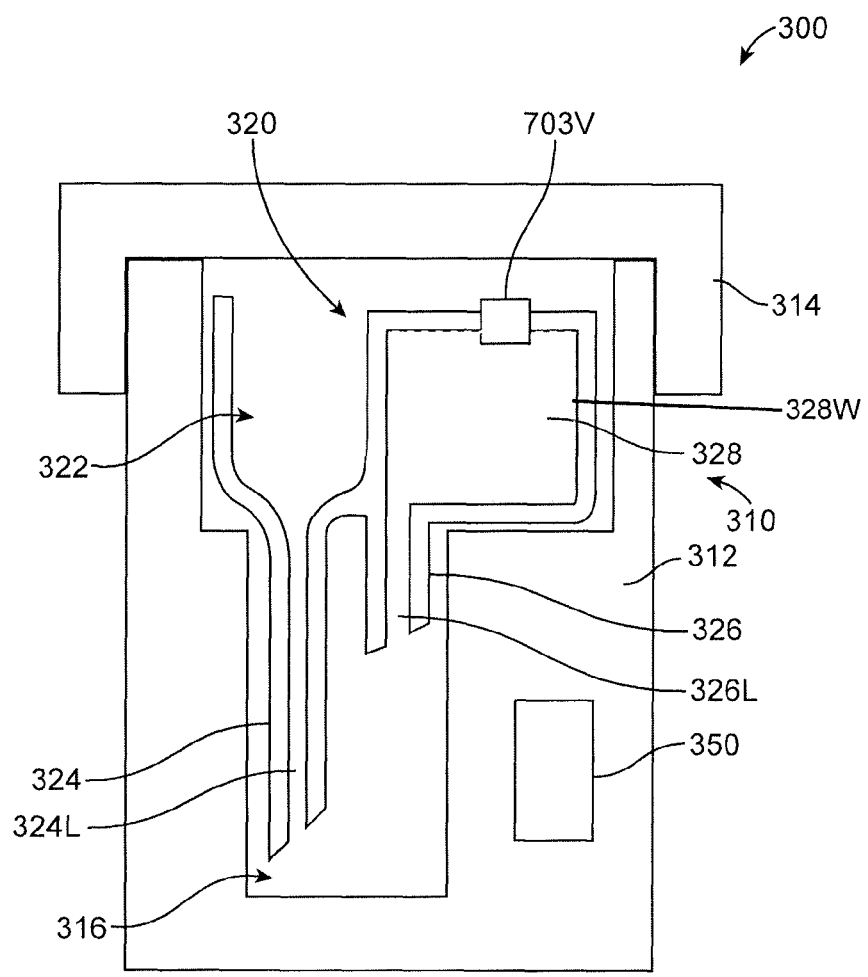
FIG. 97 shows a cartridge comprising a container to collect a sample of the fluid of the therapeutic device for analysis, in which the cartridge container is placed in a packaging container, in accordance with embodiments.

FIG. 97 shows an apparatus 300 to collect a sample of the fluid from the implanted device. The apparatus 300 comprises a cartridge 320 comprising a container 328 to collect a sample of the fluid of the therapeutic device 100 for analysis. The cartridge container 328 is placed in a packaging container 310 to protect the cartridge.

The cartridge 320 comprises a connector 322 to couple to a syringe. The connector 322 may comprise one or more standard connectors to couple to a syringe such as a Luer connector or a Hamilton connector. The cartridge 320 may comprise at least one needle such as a first needle 324 having a first lumen 324L and a second needle 326 having a second lumen 326L. The first needle and lumen are fluidically coupled to the connector 322. The second needle 326 and second lumen 326L are fluidically coupled to the container 328. The cartridge container 328 may comprise a window 328W to view the contents of container 328 and the container 328 may comprise an optically clear material. The at least one needle may comprise a double lumen needle as described herein. A valve 703V is coupled to the container 328, such that the valve 703V substantially closes when the volume of the container 328 is filled with sample fluid.

The valve 703V may comprise one or more of the valves as described herein. In many embodiments, the valve 703V may comprise a porous structure 150 having a resistance to flow of liquid greater than a resistance to a flow of air, such that the flow of liquid is substantially inhibited when liquid contacts the porous structure 150. The valve 703V may have a resistance to flow greater than porous structure 150, so as to drive liquid through porous structure 150 when liquid contact the porous structure 150 of valve 703V.

The packaging container 310 comprises a removable cover 314 and a housing 312. The housing 312 comprises a channel 316 to receive the at least one needle 324. The height of the housing 312 and channel 316 are sized to receive the cartridge 320 with the at least one needle extending along the channel 316 and the cover 314 placed on the housing 312.

The apparatus 300 comprises an identifier 350. The identifier 350 may comprise one or more of an optical bar code, a 2D bar code, a magnetic stripe, or an RFID device. The identifier 350 can be located on the housing 312. Alternatively, identifier 350 can be located on cartridge 320. The identifier 350 can be linked to a patient ID when the sample is taken to link the sample of the device to the patient.

Figure 98:
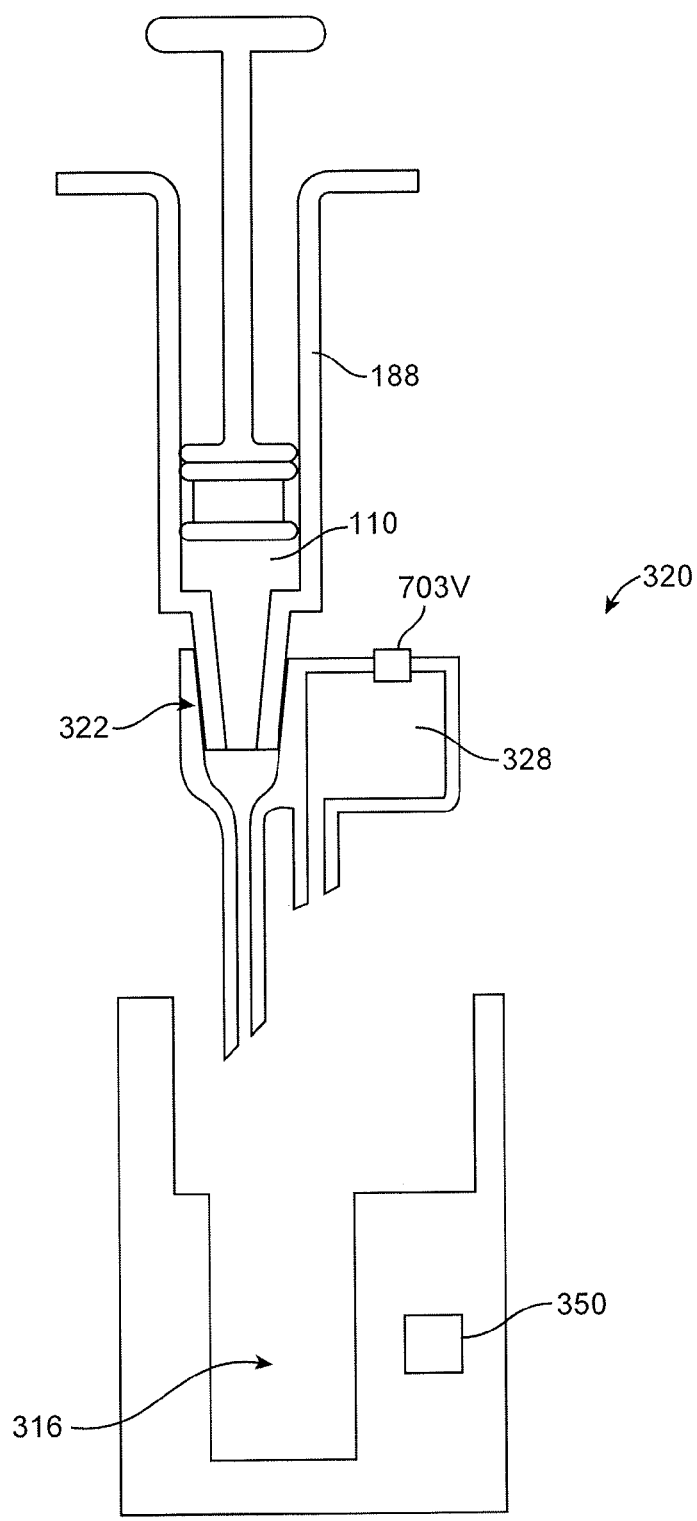
FIG. 98 shows a syringe coupled to the cartridge as in FIG. 97 to inject the formulation and collect the sample, in accordance with embodiments.

FIG. 98 shows a syringe 188 coupled to the cartridge 320 to inject formulation and collect sample. The cartridge 320 is shown by way of example as being coupled to the syringe 188, with the cartridge 320 able to be subsequently removed from the housing. The syringe 188 may comprise a standard commercially available syringe having a capacity suitable for injection of the amount of therapeutic agent. The syringe 188 may comprise an amount of the therapeutic agent 110 for injection into the device 100.

Figure 99:
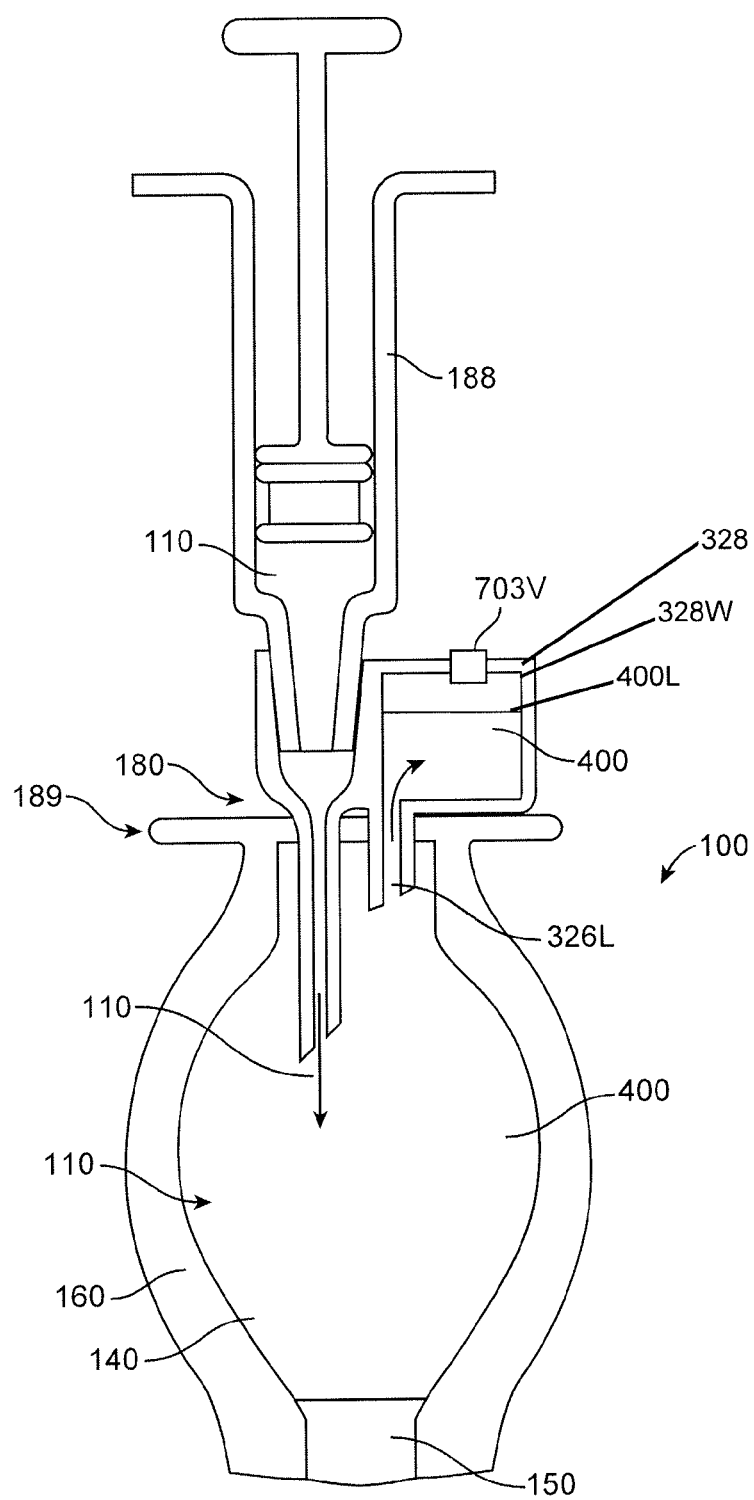
FIG. 99 shows the syringe and cartridge as in FIG. 98 coupled to the device implanted in the eye to inject the therapeutic agent and receive the fluid of the implanted device, in accordance with embodiments.

FIG. 99 shows the syringe 188 and cartridge coupled to the device 100 implanted in the eye 10 which may inject therapeutic agent and receive the fluid of the implanted device as described herein. The fluid 400 of the implanted device 100 is shown by way of example as being in container 328 extending to a level 400L which may be visible through a window 328W of the container 328.

Some embodiments suggests that the formulation of therapeutic 110 can be more dense than the fluid 400 of the device 100, and that it can be helpful to inject the formulation with the porous structure 150 below the penetrable barrier 184 of therapeutic device 100, such that the formulation of therapeutic agent 110 directed to a location of the reservoir chamber 140 is below the lumen 326L to receive fluid 400. The plunger of the syringe is depressed to urge the liquid into the device 100. When the level of fluid 400 rises to the valve 703V, the flow of liquid is substantially inhibited. The valve 703 comprising the porous structure 150 can provide a user perceptible resistance to air flow such that the formulation of agent 110 is directed to the porous structure with decreased flow that may increase gravity based separation of fluid 400 with the formulation.

Figure 100:
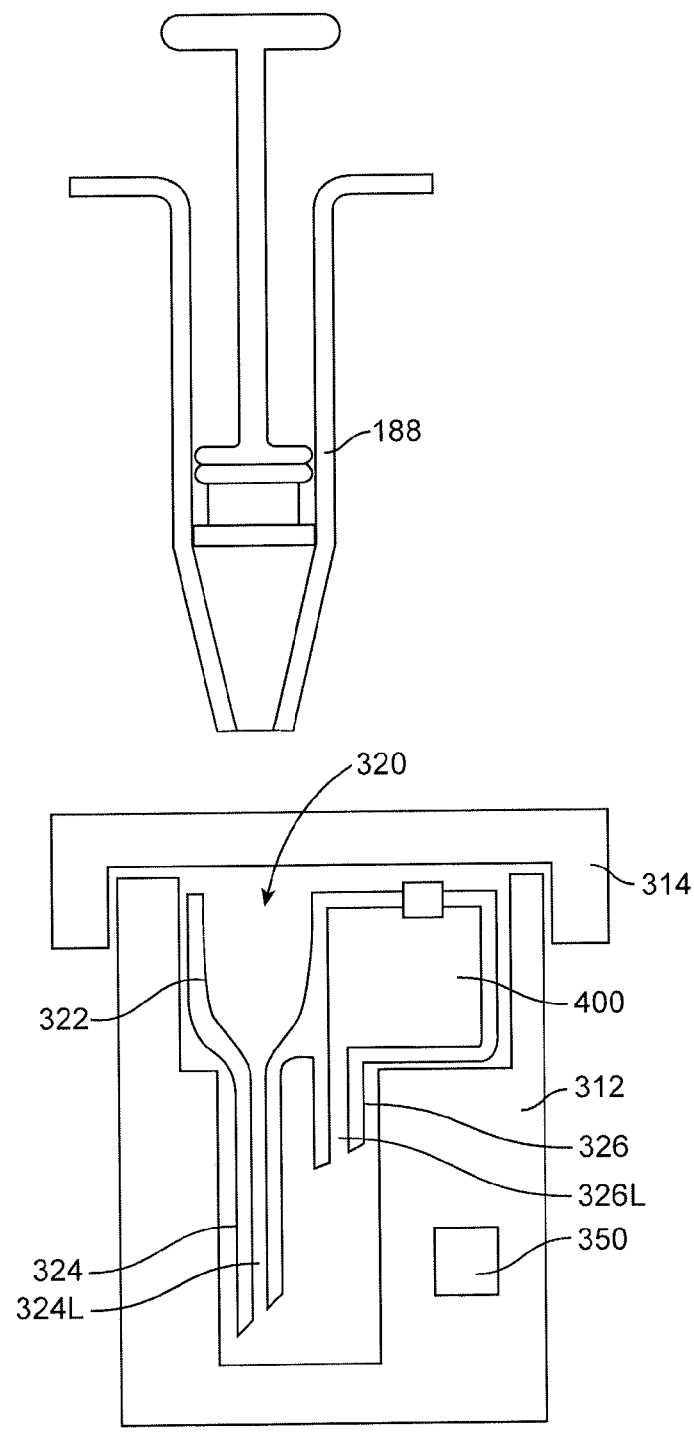
FIG. 100 shows the cartridge of FIG. 99 placed in the packaging container with the covering placed over the packaging container to inhibit evaporation of the liquid of the sample, in accordance with embodiments.

FIG. 100 shows the cartridge 320 placed in the packaging container with the covering placed over the packaging container to inhibit evaporation of the fluid 400 of the sample.

Figure 101:
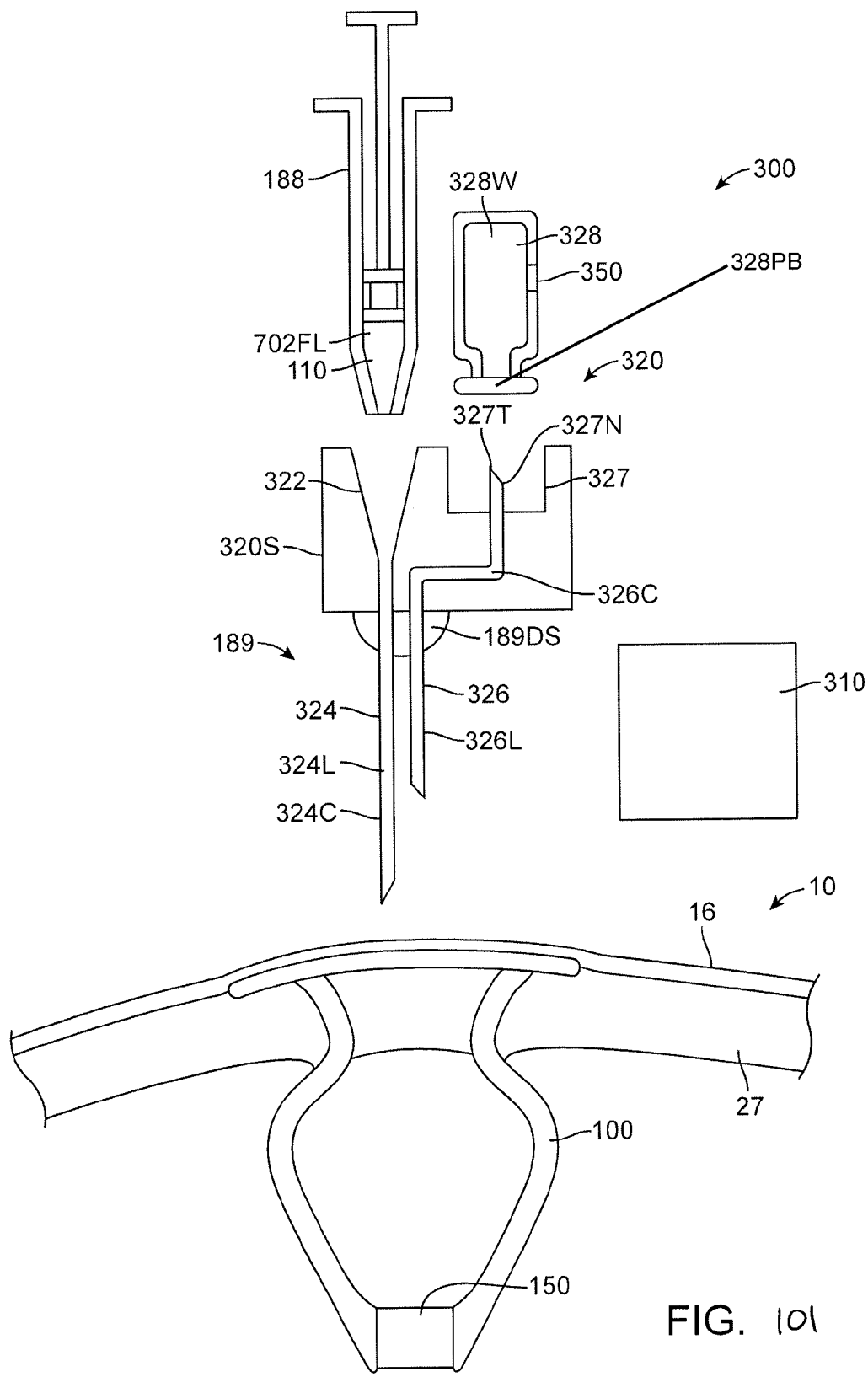
FIG. 101 shows a cartridge comprising a detachable container to collect a sample of the fluid of the therapeutic device for analysis, in which the syringe and the cartridge container can be separated from the cartridge, in accordance with embodiments.

FIG. 101 shows the cartridge 320 comprising a detachable container 310 to collect a sample of the fluid of the therapeutic device 100 for analysis. The syringe 188 and the cartridge container 328 can be separated from the cartridge. The cartridge container 328 may comprise a window 328W to view the contents of container 328. For example, the cartridge container 328 may comprise an optically clear material so as to provide the window with the container.

In many embodiments, the cartridge 320 comprises a support component 320S comprising the at least one needle 189 and deformable stop 189DS, in which the support component 320S comprises the connector 322 to couple to the syringe and a connector 327 to couple to the sample container 328 when the at least one needle 189 is placed on the eye 10. The support component 320S may comprise the at least one needle 189 such as first needle 324 having a first lumen 324L and a second needle 326 having a second lumen 326L. The support 320S can be formed in many ways and may comprise injection molded plastic, for example. A first channel 324C can extend from a distal opening near a tip of the first needle 324 to a proximal opening near connector 322 such that the first channel 324C couples the syringe to the implantable device 100 when the deformable stop 189DS couples to the conjunctiva 16 of the eye 10. A second channel 326C can extend from a distal opening near a tip of the second needle 326 to a proximal opening near connector 327 such that the second channel 326C couples the container 328 to the reservoir chamber of the implantable device 100 when the deformable stop 189DS couples to the conjunctiva 16 of the eye 10.

The connector 327 can be configured to couple to the detachable container 328 in many ways. The connector 327 may comprise an opening sized to receive a neck of the container 328. The connector 327 may comprise a needle 327N having a tip 327T. Needle 327N can be sized to extend through a penetrable barrier 328PB of the container 328 when the neck of the container 328 is placed in the opening sized to receive the neck of the container. The first channel and the second channel can be spaced apart so as to separate the syringe from the container.

Figure 102:
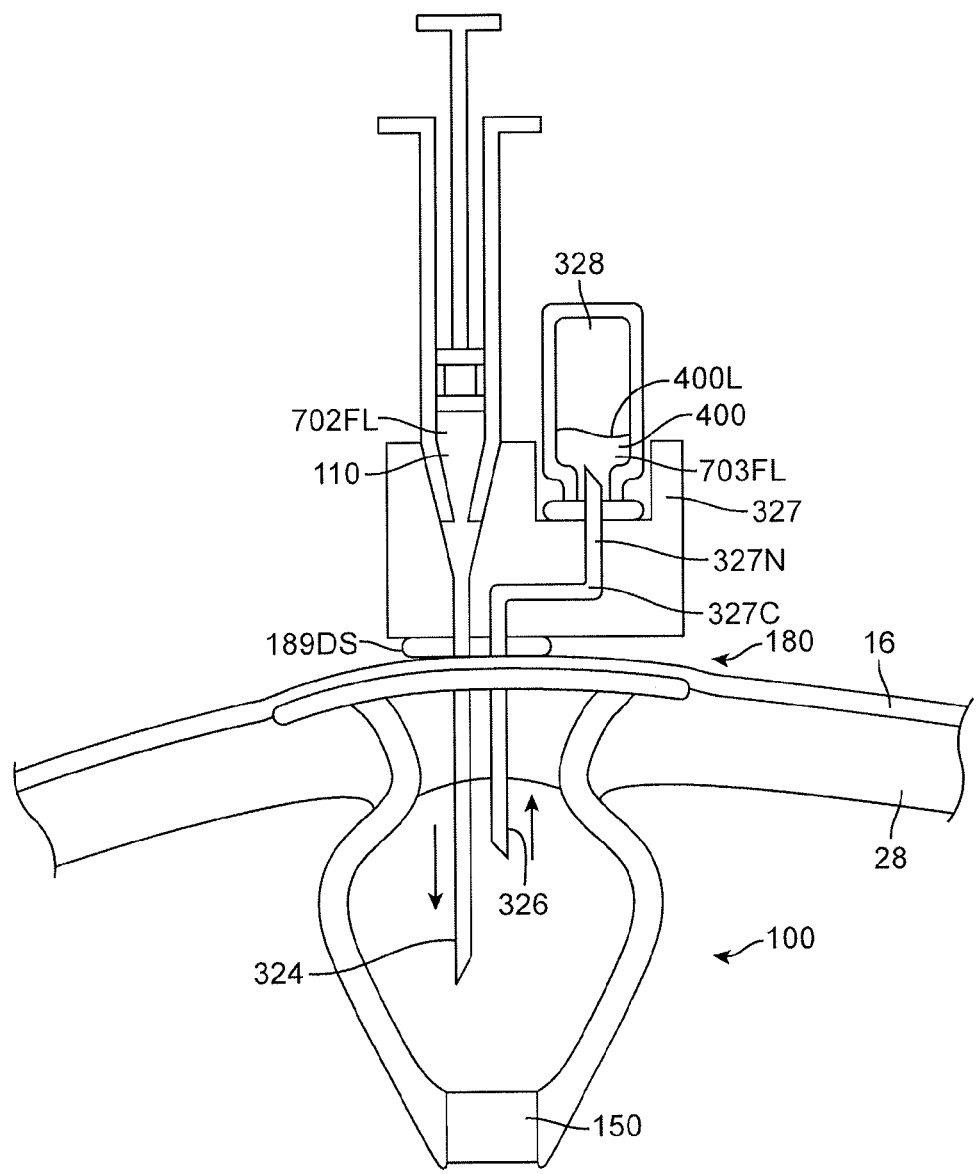
FIG. 102 shows the cartridge as in FIG. 101 to coupled to the container to inject the therapeutic fluid into the therapeutic device implanted in the eye and collect the sample of fluid from therapeutic device implanted in the eye, in accordance with embodiments.

FIG. 102 shows an example of the cartridge 320 as in FIG. 101 coupled to the syringe 188 to inject the therapeutic fluid 702FL into the therapeutic device 100 implanted in the eye 10 and collect the sample 400 comprising fluid 703FL from the therapeutic device 100 implanted in the eye 10. The therapeutic fluid 702FL comprising a formulation of therapeutic agent 110 is shown injected into the reservoir chamber of device 100, and the fluid 703FL is received in container 328. Container 328 has collected sample fluid 400 to a level 400L visible through window 328W. The deformable stop 189DS may be shown in a deformed configuration such that the stop has temporarily deformed with contact to the conjunctiva 16 so as to couple to the conjunctiva 16 and the penetrable barrier with the deformable stop to inhibit leakage of one or more of the therapeutic fluid 702FL or the displaced implanted device fluid 703FL.

FIG. 103 shows the cartridge assembly as in FIGS. 101 and 102 removed from the implanted therapeutic device 100 and the container having the fluid of the implanted sample container removed from the cartridge. The removable container may comprise the identifier 350, such that the sample fluid 400 corresponds to identifier 350. The identifier 350 can identify one or more of the patient, the eye 10 of the patient, and the day the sample was removed from the implanted device by the health care provider. The container 328 comprising sample 400 may be moved to a location having an apparatus to analyze the sample, such that sample 400 can be analyzed to one or more of diagnose or treat the patient as described herein.

Release of Stabilizers and Therapeutic Agents

The therapeutic agent may comprise one or more of the therapeutic agents as described herein, and the amount of therapeutic agent can be compared to the amount of stabilizer displaced from the device implanted in the eye 10 to one or more of diagnose or treat the patient. Examples of stabilizers and therapeutic agents released from therapeutic devices are described in U.S. Prov. Pat. App. Ser. No. 61/415,674, filed Nov. 19, 2010, entitled "THERAPEUTIC AGENT FORMULATIONS FOR IMPLANTED DEVICES"; and PCT/US11/061535, filed on Nov. 18, 2011, entitled "THERAPEUTIC AGENT FORMULATIONS FOR IMPLANTED DEVICES"; the full disclosures of which and incorporated herein by reference and suitable for combination in accordance with embodiments described herein. The stabilizer may comprise one or more of an alcohol, a polyol, a phenol, a carbohydrate, a sugar (sucrose, lactose, and glucose), amino acids (glycine, alanine, and proline), or amines (betaine and trimethylamine N-oxide), for example. The stabilizer may comprise a molecular weight corresponding to the therapeutic agent, for example at least about 20% of the molecular weight of the therapeutic agent. The molecular weight can be sufficient such that a portion of the stabilizer remains in the device 100 when a portion of the therapeutic agent is released so as to stabilize a remaining portion of the therapeutic agent. The stabilizer may comprise a high molecular weight polymer, for example at least about 2 k Daltons. The stabilizer may comprise one or more forms of cellulose (e.g., carboxymethylcellulose, hydroxyethyl cellulose, hydroxypropyl cellulose, hydroxypropyl methylcellulose, methylcellulose), chitin (e.g., chitosan), other oligosaccharides and polysaccharides, or polymeric forms of amino acids.

The diffusion constant of the stabilizer can be determined, for example, based on an estimate of hydrodynamic radius corresponding to the cube root of the molecular weight as described herein.

Table 2 shows some possible diffusion coefficients and estimates of device half-life relative to Ranibizumab.

TABLE 2 diffusion coefficients and estimates of device half-life relative to Ranibizumab Diffusion relative to Ranibizumab

| Compound | MW | Temp C. | Diff Coeff (cm^2/s) | Equiv diameter assumes unit density and is the diameter per molecule | | | Compound | MW |
|---|---|---|---|---|---|---|---|---|
| Ranibizumab | 48,000 | 37 | 1.0E−06 | | | | Ranibizumab | 48,000 |

| Example Compound | MW | mW/(Ran MW) | D/(Ran D) | Diff Coeff (cm^2/s) | Device Half-life relative to Ranibiz. | Equiv volume (nm^3) | Example Compound | MW |
|---|---|---|---|---|---|---|---|---|
| Histidine | 156 | 0.003 | 6.75 | 6.8E−06 | 0.15 | 0.3 | Histidine | 156 |
| Trehalose | 378 | 0.008 | 5.03 | 5.0E−06 | 0.20 | 0.6 | Trehalose | 378 |
| | 500 | 0.010 | 4.58 | 4.6E−06 | 0.22 | 0.8 | | 500 |
| | 1000 | 0.021 | 3.63 | 3.6E−06 | 0.28 | 1.7 | | 1000 |
| Polysorbate 20 | 1227 | 0.026 | 3.39 | 3.4E−06 | 0.29 | 2.0 | Polysorbate 20 | 1227 |
| | 2000 | 0.042 | 2.88 | 2.9E−06 | 0.35 | 3.3 | | 2000 |
| | 5000 | 0.104 | 2.13 | 2.1E−06 | 0.47 | 8.3 | | 5000 |
| | 10000 | 0.208 | 1.69 | 1.7E−06 | 0.59 | 16.6 | | 10000 |
| | 20000 | 0.417 | 1.34 | 1.3E−06 | 0.75 | 33.2 | | 20000 |
| | 30,000 | 0.625 | 1.17 | 1.2E−06 | 0.85 | 49.8 | | 30,000 |
| Ranibizumab | 48,000 | 1.000 | 1.00 | 1.0E−06 | 1.00 | 79.7 | Ranibizumab | 48,000 |
| | 50,000 | 1.042 | 0.99 | 9.9E−07 | 1.01 | 83.0 | | 50,000 |
| BSA | 66,000 | 1.375 | 0.90 | 9.0E−07 | 1.11 | 109.6 | BSA | 66,000 |
| | 100,000 | 2.083 | 0.78 | 7.8E−07 | 1.28 | 166.1 | | 100,000 |
| Bevacizumab | 149,000 | 3.104 | 0.69 | 6.9E−07 | 1.46 | 247.4 | Bevacizumab | 149,000 |
| | 200,000 | 4.167 | 0.62 | 6.2E−07 | 1.61 | 332.1 | | 200,000 |
| | 500,000 | 10.417 | 0.46 | 4.6E−07 | 2.18 | 830.3 | | 500,000 |
| | 1,000,000 | 20.833 | 0.36 | 3.6E−07 | 2.75 | 1660.6 | | 1,000,000 |
| | 2,500,000 | 52.083 | 0.27 | 2.7E−07 | 3.73 | 4151.4 | | 2,500,000 |
| | 3.94E+07 | 8.E+02 | 1.1E−01 | 1.1E−07 | 9.4 | 6.5E+04 | | 3.94E+07 |
| | 3.15E+08 | 7.E+03 | 5.3E−02 | 5.3E−08 | 18.7 | 5.2E+05 | | 3.15E+08 |
| | 2.52E+09 | 5.E+04 | 2.7E−02 | 2.7E−08 | 37.5 | 4.2E+06 | | 2.52E+09 |

TABLE 2-continued diffusion coefficients and estimates of device half-life relative to Ranibizumab

| 3.94E+10 | 8.E+05 | 1.1E−02 | 1.1E−08 | 93.6 | 6.5E+07 | 3.94E+10 |
| 3.15E+11 | 7.E+06 | 5.3E−03 | 5.3E−09 | 187.3 | 5.2E+08 | 3.15E+11 |
| 2.52E+12 | 5.E+07 | 2.7E−03 | 2.7E−09 | 374.6 | 4.2E+09 | 2.52E+12 |
| 3.94E+13 | 8.E+08 | 1.1E−03 | 1.1E−09 | 936.4 | 6.5E+10 | 3.94E+13 |

Table 2 shows that the molecular weight, diffusion coefficient, equivalent diameter of ranibizumab can be about 48 k Daltons, 1.0E-6, and 5.3 nm, respectively.

The molecular weight of the stabilizer can be provided in 1 k Dalton increments from about 1 k Dalton to about 200 k Daltons and provide in a Table having about 200 rows similar to Table 2. The parameters of Table 2 determined such as the half-life in the device, the equivalent volume, the equivalent diameter, and % in the device at the half-life of the therapeutic agent 110. The table may comprise a row for each molecular weight in 1 k Dalton increments, and the % of stabilizer in the device compared with the therapeutic agent 110. The table may include columns for two half-lives of the therapeutic agent, three half-lives of the therapeutic agent, four half-lives of the therapeutic agent, and the corresponding percentage of stabilizer remaining in the device.

The percentage at 1, 2, 3, 4 5, and 6 half-lives can be determined.

The molecular weight, diffusion coefficient and equivalent diameter of trehalose can be about 0.4 k Daltons, 5.0E-6, and 1.1 nm, respectively. The relative molecular weight of trehalose to ranibizumab can be about 0.8%, and the relative half-life of trehalose in device 100 can be about 20% of ranibizumab. The relative amount of trehalose remaining in therapeutic device 100 at the half-life of ranibizumab can be about 3.1%. This decreased half-life of trehalose and amount in the device 100 relative to ranibizumab can be related to the decreased molecular weight of trehalose relative to ranibizumab.

A disaccharide such as trehalose can be combined with one or more of micelles or polymeric proteins as described herein, so as to associate with the one or more of the micelles or the polymeric proteins so as to decrease a rate of release of the disaccharide from the reservoir chamber.

The molecular weight, diffusion coefficient and equivalent diameter of polysorbate 20 can be about 1.2 k Daltons, 3.4E-6, and 1.6 nm, respectively. The relative molecular weight of polysorbate to ranibizumab is about 2.6%, and the relative half-life of polysorbate 20 in device 100 can be about 29% of ranibizumab. The relative amount of polysorbate 20 remaining in therapeutic device 100 at the half-life of ranibizumab can be about 9.5%. This decreased half-life of polysorbate and amount in the device 100 relative to ranibizumab is related to the decreased molecular weight of polysorbate relative to ranibizumab.

The diffusion coefficients of Table 2 can be determined based on weight for molecular weights up to about 2.5 M Daltons, and based on size above about 2.5 M Daltons.

The stabilizer may comprise a molecular weight that is at least about 10% of the molecular weight of the therapeutic agent; such that the half-life of the stabilizer corresponds to at least about 50% of the half-life of the therapeutic agent. For example, a stabilizer 192 with a molecular weight of about 5 k Daltons corresponding to about 10% of the molecular weight of ranibizumab, the relative half life of the stabilizer is about half (0.47) of the half life of ranibizumab. When the half-life of the stabilizer is about half that of the therapeutic agent, about ¼ of the stabilizer may remain in the therapeutic device 100 for an extended time corresponding to the half-life of the therapeutic agent. For example, when the half-life of the therapeutic agent ranibizumab in the device is about 100 days, about ¼ of a 5 k Dalton molecular weight stabilizer may remain in the therapeutic device 100.

The stabilizer may comprise a molecular weight that is at least about 20% of the molecular weight of the therapeutic agent, such that the half life of the stabilizer corresponds to at least about 50% of the half life of the therapeutic agent. At a time of two half lives post-placement in the therapeutic device 100, the relative proportion of stabilizer to therapeutic agent is about 1 to 4. This amount of stabilizer can be sufficient to stabilize the therapeutic agent in many embodiments.

When the formulation contains a component with a substantially faster or slower diffusion coefficient than the therapeutic agent, the concentration of the formulation component in the Exchange Fluid can be utilized to determine additional information from a therapeutic device 100 refill procedure. The diffusion coefficients may differ by a factor of 2, more preferably by a factor of 5 or more, for example.

Figure 104:
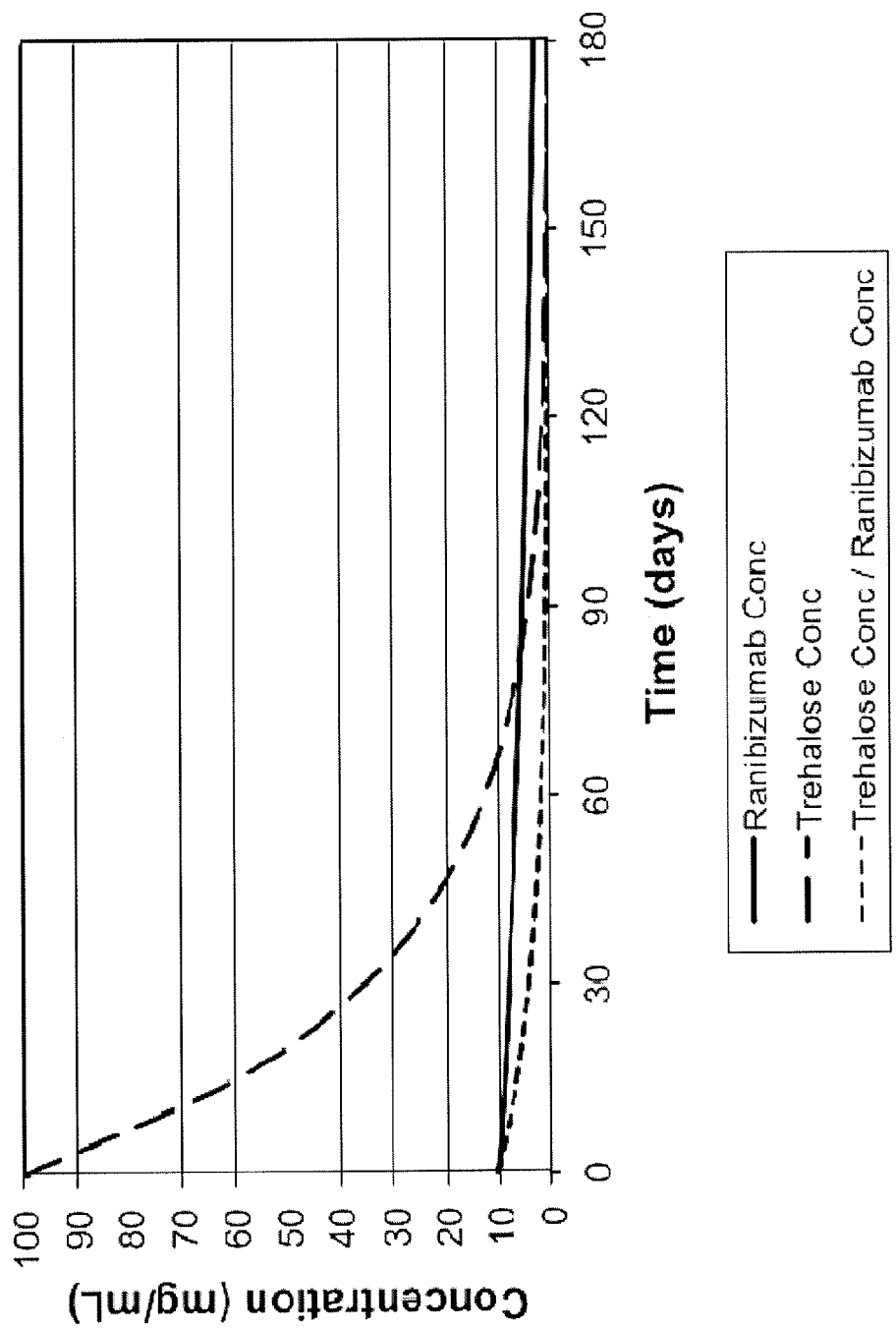
FIG. 104 shows concentrations profiles and ratios for a therapeutic agent and a stabilizer, in accordance with embodiments.

FIG. 104 and Table 3 show concentrations of therapeutic agent, stabilizer and the ratio of stabilizer to therapeutic agent in accordance with an exemplary embodiment, for example. The concentrations and rations can be determined by a person of ordinary skill in the art based on the teachings described herein. The therapeutic device 100 may comprise an RRI=0.02 mm and a reservoir chamber having a volume 25 uL that is substantially filled with Lucentis. According to the Lucentis Package Insert, the formulation contains 10 mg/mL Ranibizumab, 10 mM histidine HCl, 10% α,α-trehalose dehydrate (approx. 100 mg/mL), 0.01% polysorbate 20. Additional concentrations of the therapeutic agent can be used, for example greater amounts of therapeutic agent. Based upon the dependence of diffusion coefficient on size as described by molecular weight, the diffusion coefficient of Trehalose and rate of release through the porous structure 150 is approx. 5 times faster than the diffusion coefficient of Ranibizumab as shown in Table 3 and FIG. 104, for example. The concentrations of Ranibizumab and Trehalose in the device can be determined as a function of time using the diffusion model as described herein.

After about 90 days of delivery, the Ranibizumab concentration in the implantable device can be about 50% of the original concentration while the concentration of Trehalose is less than 5% of the original concentration. The ratio of Trehalose to Ranibizumab in the implant can continue to decline with time.

TABLE 3 concentration profiles of therapeutic agent and stabilizer.

| Time (d) | Ranibizumab Conc (mg/mL) | Trehalose Conc (mg/mL) | Conc Ratio (T/R) |
|---|---|---|---|
| 0 | 10.0 | 100.0 | 10 |
| 15 | 9.0 | 59.5 | 6.6 |

TABLE 3-continued concentration profiles of therapeutic agent and stabilizer.

| Time (d) | Ranibizumab Conc (mg/mL) | Trehalose Conc (mg/mL) | Conc Ratio (T/R) |
|---|---|---|---|
| 30 | 8.1 | 35.5 | 4.4 |
| 45 | 7.3 | 21.1 | 2.9 |
| 60 | 6.6 | 12.6 | 1.9 |
| 75 | 6.0 | 7.5 | 1.3 |
| 90 | 5.4 | 4.5 | 0.8 |
| 105 | 4.8 | 2.7 | 0.5 |
| 120 | 4.4 | 1.6 | 0.4 |
| 135 | 3.9 | 0.9 | 0.2 |
| 150 | 3.5 | 0.6 | 0.2 |
| 165 | 3.2 | 0.3 | 0.1 |
| 180 | 2.9 | 0.2 | 0.1 |

The trehalose concentration in the implantable device after refill, $C_{TT2}$, can be related to the trehalose concentration of the therapeutic fluid in the Refill Syringe, $C_{TS}$, and the Trehalose concentration in the implantable device fluid just prior to refill, $C_{TT1}$, via the following equation:

$$C_{TT2} = XC_{TS} + (1-X)C_{TT1}$$

where X denotes the fraction of the concentration in the implanted device resulting from the syringe. When the implantable device is refilled using an exchange needle after 90 or more days of delivery, the trehalose concentration in the implant just prior to refill, $C_{TT1}$, may be approximately zero and $X = C_{TT2}/C_{TS}$.

A mass balance can be performed on the trehalose in the system to yield:

$$V_S C_{TS} + V_I C_{TT1} = V_E C_{TE} + V_I C_{TT2}$$

where $V_S$=volume injected from syringe, $V_I$=volume of implantable device, $V_E$=volume of exchange fluid, and $C_{TE}$=trehalose concentration in Exchange Fluid. This can be rearranged and simplified ($C_{TT1}$, =0 and $V_S = V_E$) to yield a measure of the fraction resulting from the syringe calculated from known values ($V_S$, $V_I$, and $C_{TS}$) and the trehalose concentration measured in the exchange fluid ($C_{TE}$):

$$X = (V_S/V_I)(1-(C_{TE}/C_{TS}))$$

The ranibizumab found in the exchange fluid can be separated into ranibizumab that came from the syringe comprising the therapeutic fluid and the ranibizumab of the implantable device fluid that had been in the implant prior to refill. The ranibizumab from the syringe will have the 1:10 ratio of ranibizumab:trehalose corresponding to full strength Lucentis™. The ranibizumab from the implant will have essentially no trehalose associated with it. The fraction, X, that had been replaced by fresh solution in the implantable has been pushed into the receiver container comprising the collection chamber for the exchange fluid. The resulting mass balance can be:

$$C_{RE}V_E = (1/10)C_{TE}V_E + X \cdot C_{Ri1}V_I$$

where $C_{RE}$=ranibizumab concentration in the exchange fluid, $C_{RI1}$=ranibizumab concentration in the implant just prior to refill. This equation can be rearranged to calculate the concentration in the implant just prior to refill using a known value ($C_{TS}$) and the concentrations measured in the exchange fluid ($C_{RE}$ and $C_{TE}$):

$$C_{RI1} = (C_{RE} - (1/10)C_{TE})/(1-C_{TE}/C_{TS})$$

The ranibizumab concentration in the implant just prior to refill that can be determined using the equation above can be compared to the diffusion model predicted value to determine if the implant is performing as expected, for example.

In addition, the concentration in the implant post refill can be calculated from the following equation using parameters obtained via the method described above:

$$C_{RI2} = XC_{RS} + (1-X)C_{RI1}$$

In many embodiments, the delivery rate after refill can be proportional to the concentration in the implant post refill.

The examples described herein show measurement of the concentrations of two components in the Exchange Fluid to provide determination of the concentrations in the implant before and after the refill process, for example when the formulation component diffuses substantially faster than the therapeutic agent. Alternatively to trehalose or in combination with trehalose, other embodiments having fast diffusing formulation components include buffers such as histidine, acetate, and citrate, or other sugars such as sucrose.

The formulation component may comprise a molecular weight greater than the therapeutic agent such that the formulation component diffuse more slowly than the therapeutic agent, for example. In addition, the formulation placed in the therapeutic device 100 may comprise one or more marker components to measure device function. The one or more marker components of the formulation may comprise one or more molecules or substances that can be readily measured from the exchange sample by a person of ordinary skill in the art. The one or more marker components may comprise one or more of a therapeutic agent, a stabilizer, a second therapeutic agent, or another measurable substance provided with the formulation to determine the device function. For example, the marker may comprise one or more therapeutic agents as described herein, one or more stabilizers as described herein, a second therapeutic agent comprising a therapeutic agent as described herein, or another component such as a biocompatible dye, for example. The marker component may comprise a stabilizer added to the formulation that may not be necessary to stabilize the therapeutic agent. For example, a measurable buffer component or a measurable surfactant component can be provided in a formulation with a stable small molecule therapeutic agent, in which the small molecule therapeutic agent does not require the buffer for stabilization when placed in the therapeutic device 100. The marker component may comprise a measurable nutrient that can have therapeutic benefit, for example a vitamin.

The equations above can be applied to embodiments where the concentration of the formulation component in the implant just prior to refill was close to zero. A person of ordinary skill in the art can apply correction factors based upon the diffusion model described herein so as to allow the teachings described herein to apply to embodiments where the formulation component in the implant just prior to refill is higher than zero.

A person of ordinary skill in the art can also derive equations to extract similar information when the formulation component diffuses more slowly than the therapeutic agent based on the teachings and embodiments described herein. Examples of slowly diffusing formulation components can include carboxymethylcellulose sodium, and sodium hyaluronate, for example.

The evaluation of implanted device performance and the determination of the concentrations in the implant before and after the refill process as described herein, can be combined with the analysis of markers as described herein, to one or more of diagnose or treat the patient as described herein. For example, the measured concentrations of markers and the therapeutic agent from the sample can be adjusted based on measurements of the therapeutic agent and the stabilizer from the sample fluid collected in the receiver container as described herein.

Release of Formulation Components and Accumulation of Vitreous Components

The measurement of one or more formulation components released from the device can be combined with the measurement of one or more components of the vitreous humor 30 from the device to determine device function, diagnose the patient, or treat the patient, and combinations thereof, for example. For example, the measurement of two or more formulation components initially placed in the device and subsequently removed by exchange, such as the therapeutic agent and another component such as one or more of a stabilizer or a marker, can be combined with the measurement of one or more components of the vitreous obtained from the device, for example a bio marker and a house keeping marker as described herein. For example, the exchange fluid obtained from the device may comprise a plurality of formulation components and a plurality of vitreal components useful to determine device function, diagnose the patient, treat the patient, and combinations thereof.

The measurement of the formulation components can be used to determine the amount of one or more vitreal components in the implanted device. For example, the amount of therapeutic fluid present in the sample collected from the implanted that has mixed with the implantable device fluid during exchange can be determined and used to determine and quantify the amount of vitreal component in the therapeutic device 100 prior to exchange, for example with an adjustment to the measure amount of vitreal component.

Figure 105:
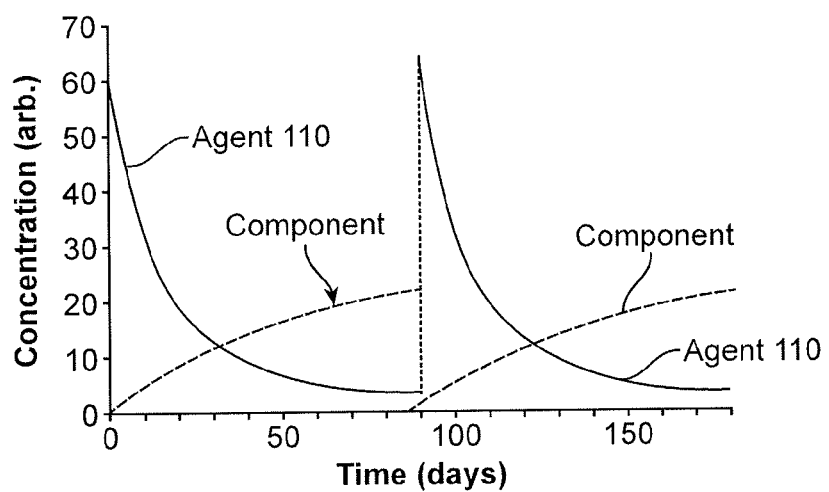
FIG. 105 shows concentration of a component of the eye in the reservoir chamber and the concentration of the therapeutic agent in the reservoir chamber over time, in accordance with embodiments.

FIG. 105 shows an example of concentrations (arbitrary units) of therapeutic agent and the component of the eye 10 over time in the reservoir chamber of device 100 as described herein. The fluid 400 of the device 100 can be exchanged with the formulation (see FIG. 99). Based on the molecular weight of the component of the eye 10 and the teachings described herein, a person of ordinary skill in the art can determine the accumulation of the component in the reservoir chamber of the device 100 based on the molecular weight of the component, the RRI and the volume of the chamber, for example. The accumulation of the component can be determined for the device tuned to deliver the amount of the therapeutic agent. The amount of the component of the eye 10 accumulated in the reservoir chamber can be compared on a relative scale, for example. The accumulation may be determined based on the molecular weight of the component of the eye and tuning of the therapeutic device 100. For example, the amount of component of the eye that has collected in the device, along with the duration of collection time, can be used to make decisions about patient treatment. Alternatively or in combination, the decision regarding treatment can be made without consideration of the amount of time that has elapsed to accumulate the marker, for example based on a ratio of a marker affected by the therapeutic agent to a marker of a house keeping gene.

The amount of component or therapeutic agent measured from the device may comprise an amount exchanged from the device. The determined amount may comprise a total mass exchanged from the device or a concentration, or both. The determined amount can be used to determine the amount of the component or agent in the reservoir chamber of the device.

The component of the eye 10 from the implanted device may comprise one or more markers corresponding to a condition of the eye 10. The component of the eye 10 from the implanted device may include an extracellular component, such as one or more of a molecule, a macromolecule, a protein, a carbohydrate, or a component of blood plasma, for example. The rate of accumulation of the marker can be related to the molecular weight of the marker and the tuning of the implanted device to release amounts of the therapeutic agent over an extended time based on a volume of the reservoir chamber and release structure, such as porous structure 150 (for example FIG. 99 and FIG. 62). Increasing the volume of the reservoir chamber can increase an amount of time for the marker to accumulate in device 100 and decreasing a release rate through porous structure 150 such as the release rate index (RRI) can increase the amount of time for the marker to accumulate in device 100. The endogenic marker can be a protein of the eye 10 or messenger RNA (hereinafter "mRNA") of the eye 10, for example. The mRNA can have a molecular weight on the order of magnitude of 100 kDa or smaller, depending on how the mRNA may fragment over time. For quantification, a person of ordinary skill in the art can assess a "house-keeping gene" and look at relative expression levels (e.g. 1× "normal" vs.>2× "pathologic") of the marker such as mRNA to the house-keeping gene, for example. Using this approach, one can determine a disease condition of the eye 10 substantially independent of time since refill and other parameters such as refill efficiency, for example. The "house-keeping-gene" may comprise a gene that is relatively unchanging with pathology of the eye 10, for example.

Figure 106:
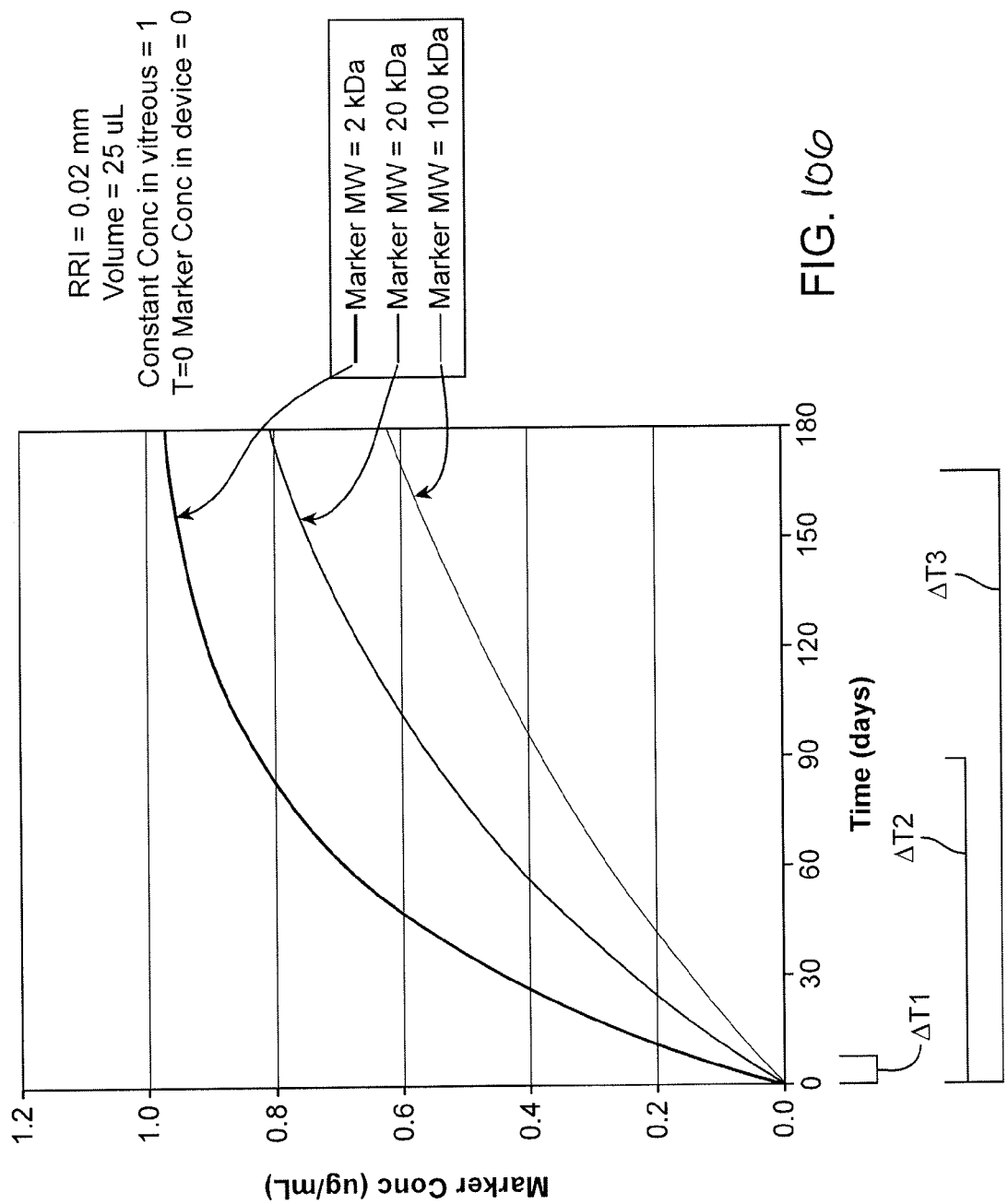
FIG. 106 shows accumulation of a plurality of components of the eye in the reservoir chamber over time, in accordance with embodiments.

FIG. 106 shows an example accumulation of a plurality of components of the eye 10 in the reservoir chamber over time. The amount of vitreous component comprising the marker within the reservoir chamber corresponds to the molecular weight of the marker and the amount of time the marker has accumulated. For a therapeutic device 100 tuned to receive an amount of therapeutic agent and release the therapeutic agent for an extended time, the corresponding accumulation rate of the marker can be used to determine the presence of the marker and in many embodiments the amount of marker in the vitreous humor 30 when the fluid of the implanted device is removed and replaced with therapeutic agent. The marker having a molecular weight of about 2 kDa may accumulate at a much faster rate than the marker having a molecular weight of about 20 kDa. The marker having the molecular weight of about 20 kDa may accumulate much faster than the marker having a molecular weight of about 100 kDa. For an initial period of time, Delta T1, the accumulation rates of each of the three markers can be substantially linear and proportional to the diffusion constant of each marker based on the molecular weight as described herein. For an intermediate period of time, Delta T2, the accumulation ratios of the amounts of the three markers can be somewhat non-linear with the higher molecular weight marker comprising a greater proportion of the concentration than the lower molecular weight marker as compared with the initial period of time, Delta T1. For the third period of time, Delta T3, the highest molecular weight marker may comprise an even greater proportion as compared with the earlier times. Based on the ratios of these markers measured from the fluid removed from the implanted device, the accumulation time in the reservoir chamber for each of the markers can be estimated.

The measured accumulation of the plurality of markers from the implantable device sample can be used in many ways to diagnose and treat the patient. The ratios of a plurality of markers to a housekeeping gene, and the ratio of markers having a substantial change in pre-treatment to post treatment amounts to each other can be used to one or more of diagnose or treat the patient. The measured markers may comprise a marker profile of the patient, for example from 10 or more markers, and the marker profile can be used to evaluate the patient or treatment or both. For example, the accumulation time of the marker can depend on when a gene switches off or on, and the measurement of the plurality of markers and corresponding ratios can be used to determine whether a therapeutic agent is appropriate for the patient, and whether an amount of the therapeutic agent should be increased or decreased or a new therapeutic agent used. The plurality of markers may correspond to intracellular RNA or DNA, or combinations thereof, for example.

Figure 107:
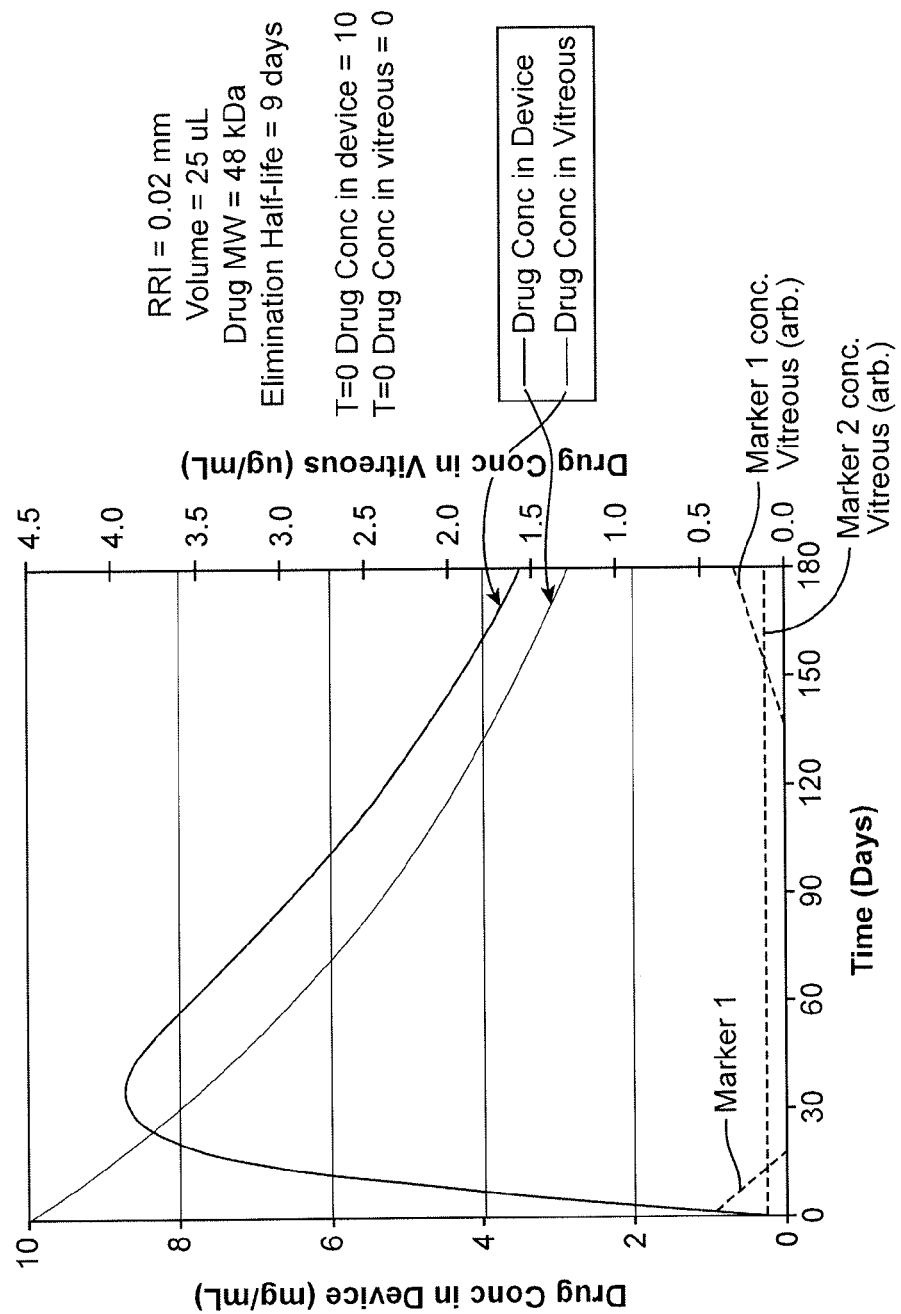
FIG. 107 shows concentrations of a first marker and a second marker in the vitreous humor over time in response to therapeutic agent, in which the second marker is less sensitive than the first marker to amounts of therapeutic agent, in accordance with embodiments.

FIG. 107 shows concentrations of a first marker and a second marker in the vitreous humor 30 over time in response to therapeutic agent, in which the second marker is less sensitive than the first marker to amounts of therapeutic agent. The second marker may comprise a "house-keeping gene", for example, that is substantially insensitive to the therapeutic agent. The marker can be expressed in response to the therapeutic agent of the vitreous humor 30 falling below a threshold amount and corresponding genomic expression. For example, the second marker may comprise a sensitivity that is no more than about 50% of the sensitivity of the first marker to the therapeutic agent, and may comprise a sensitivity that is no more than about 25% of the first marker, such that the ratio of the first marker to the second marker can be used to determine the amount of the first marker in the vitreous humor 30 of the eye 10 when the fluid of the therapeutic device 100 is removed and replaced with therapeutic fluid, for example. A ratio of the first marker to the second marker below a threshold amount can indicate a successful treatment and a ratio of the first marker to the second marker about the threshold amount can indicate a treatment that may be less than ideal, for example. Based on the teachings described herein, a person of ordinary skill in the art may be able to identify a second marker having decreased sensitivity to the therapeutic agent and the first marker having increased sensitivity to the therapeutic agent. The house-keeping genetic marker may comprise a standard marker for cell-based preparations, such as one or more of GAPDH (glyceraldehyde 3-phosphate dehydrogenase) or and beta-actin. The first marker may comprise a first marker of Table 1 and the second marker may comprise a second marker of Table I. For example, the therapeutic agent may comprise ranibizumab and the first marker may comprise one or more of VEGF and the second marker may comprise one or more of Tissue Factor. Alternatively or in combination, the second marker may comprise the standard marker for cell-based preparations, such as one or more of GAPDH (glyceraldehyde 3-phosphate dehydrogenase) or beta-actin.

Figure 108:
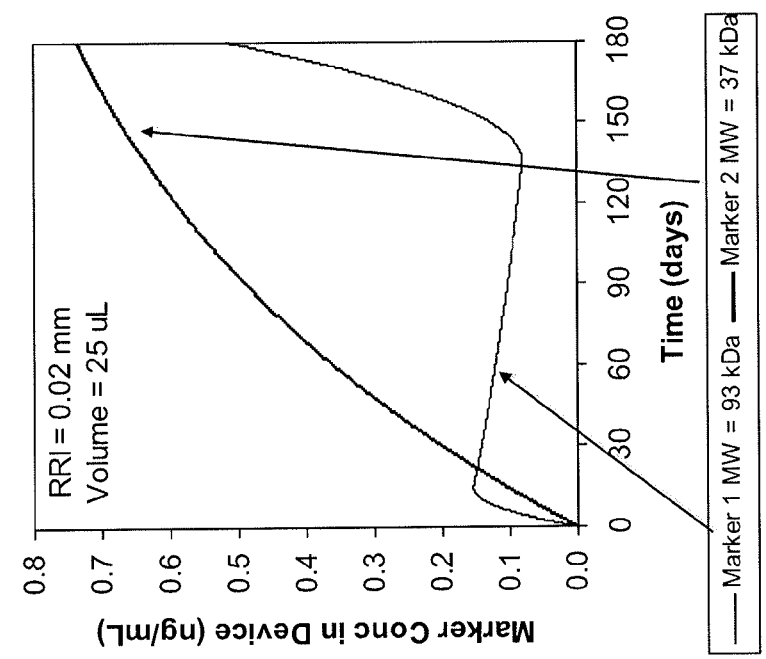
FIG. 108 shows concentrations in the vitreous humor of a first marker comprising a molecular weight corresponding to ranibizumab bound to VEGF and a second marker comprising a molecular weight corresponding to glyceraldehyde 3-phosphate dehydrogenase (hereinafter "GAPDH") in response to therapeutic agent, in accordance with embodiments.

FIG. 108 shows an example of concentrations in the vitreous humor 30 of a first marker comprising a molecular weight corresponding to ranibizumab bound to VEGF, for example, and a second marker comprising a molecular weight corresponding to GAPDH in response to therapeutic agent, for example. The RRI, reservoir volume and corresponding molecular weights are shown in the legend. The concentration of the first marker in the vitreous may change substantially in response to the therapeutic agent. For example, the ratio of post treatment VEGF to pre-treatment VEGF can be about 1.4 as shown in Table 1, and the amount of VEGF bound to a therapeutic agent sampled from the reservoir chamber may be compared with an amount of VEGF when the device is implanted, for example.

Figure 109:
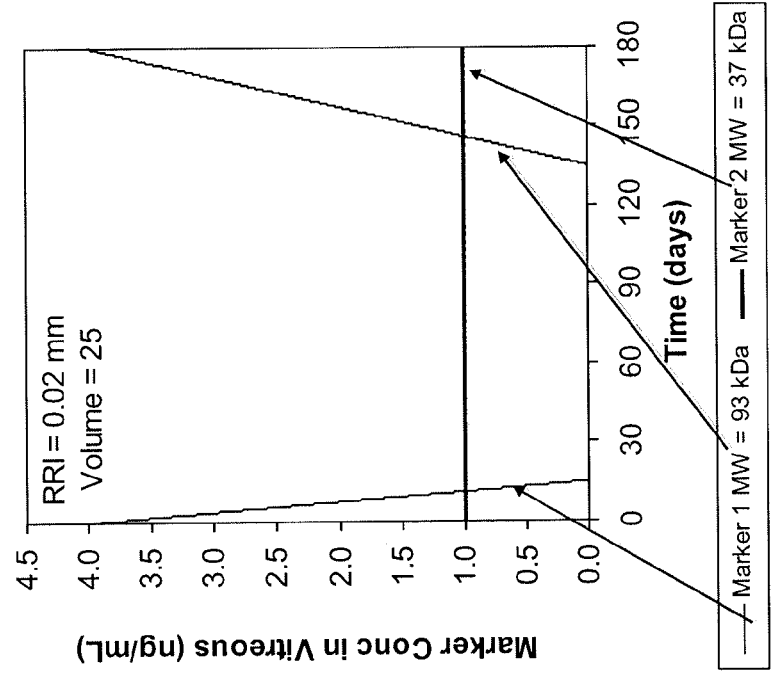
FIG. 109 shows concentrations in the reservoir chamber of the first marker and the second marker corresponding to the concentrations in the vitreous humor as in FIG. 108, in accordance with embodiments.
Figure 11O:
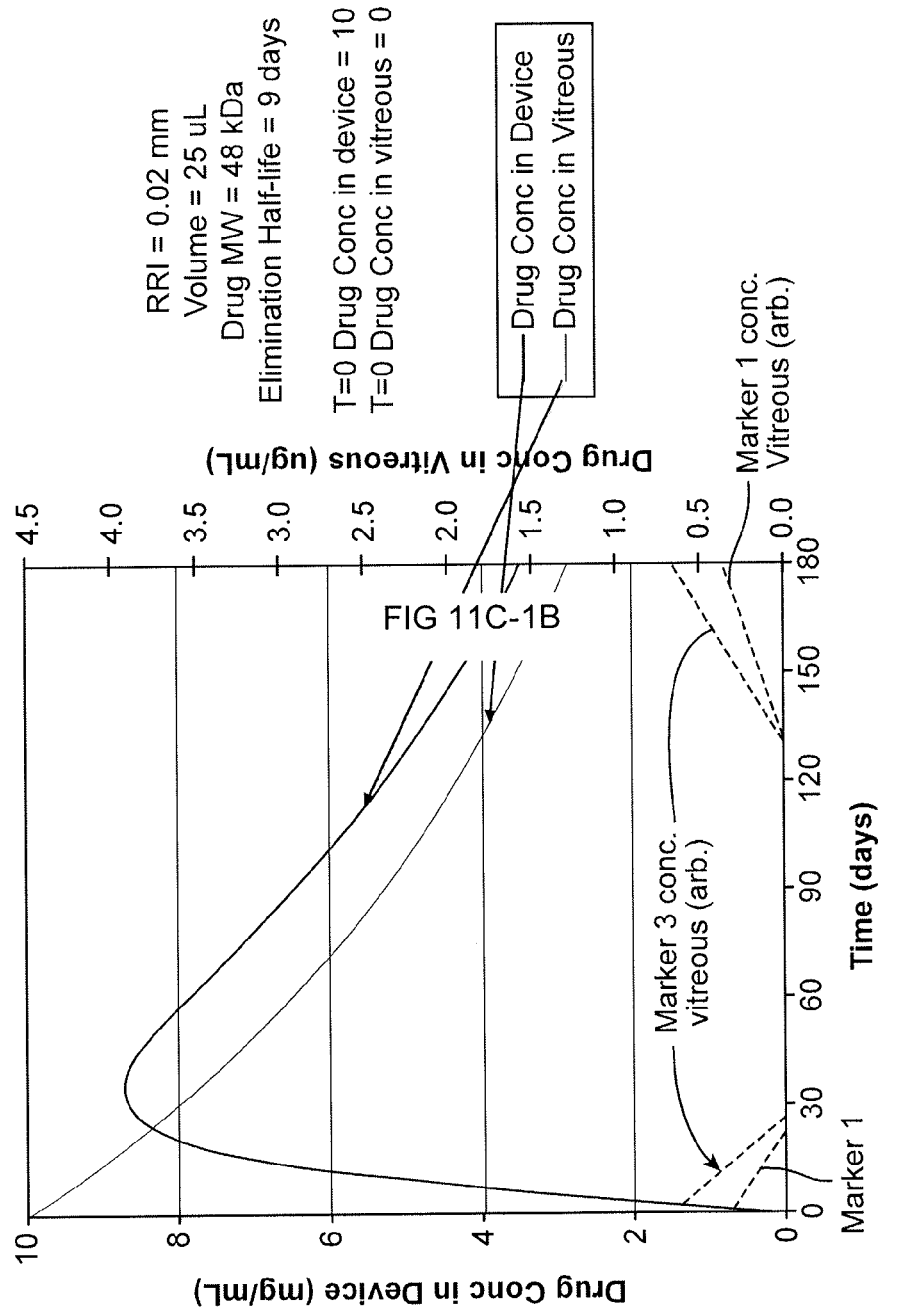

FIG. 109 shows an example of concentrations in the reservoir chamber of the first marker and the second marker corresponding to the concentrations in the vitreous humor 30 as in FIG. 108. The RRI, reservoir volume and corresponding molecular weights are shown in the legend. The amount of first marker in the reservoir chamber can be less than amount of the second marker in the reservoir chamber when the concentration of the first marker in the vitreous is greater than the second marker in the vitreous, for example. In many embodiments, the ratio of the amount of first marker to the amount of second marker within the reservoir chamber can be determined. The amount of each of the first marker and second marker may comprise one or more of a solid, a particulate, a solute, a bound marker and unbound marker, a concentration of the marker, and combinations thereof, for example. The concentration of the first marker in the vitreous may begin to increase after 100 days. The increasing slope of the first marker from days 150 to 180 within the reservoir chamber and corresponding change of the ratio of the first marker to the second marker shows that the ratio of the first marker to the second marker from the device sample can be used to determine the effectiveness of the treatment to decrease amounts of VEGF in the vitreous humor 30.

FIG. 110 shows concentrations of a first marker and a third marker in the vitreous humor 30 over time in response to therapeutic agent, in which the third marker is more sensitive than the first marker to amounts of therapeutic agent. The third marker can show greater variation in the amount of marker in response to treatment than the first marker. Each of the markers can be present initially in the vitreous humor 30 and the concentration can decrease in response to treatment and subsequently increase in response to decreased amounts of therapeutic agent in the vitreous humor 30 and so as to accumulate in the reservoir chamber of the implanted device. Based on the teachings described herein, a person of ordinary skill in the art can identify a third marker having increased sensitivity to the therapeutic agent and the first marker having decreased sensitivity to the therapeutic agent. The first marker may comprise a first marker of Table 1 and the third marker may comprise a third marker of Table 1. For example, the therapeutic agent may comprise ranibizumab and the first marker may comprise one or more of VEGF and the third marker may comprise one or more of G-CSF.

FIG. 111 shows an example of concentrations in the vitreous humor 30 of a first marker having a molecular weight corresponding to Ranibizumab bound to VEGF, a second housekeeping marker having a molecular weight corresponding to GADPH and a third marker having a molecular weight corresponding to IL-6 in response to therapeutic agent, in which the third marker is more sensitive than the first and second markers to amounts of therapeutic agent. The RRI, reservoir volume and corresponding molecular weights are shown in the legend. As shown in Table 1, the ratio of the post-treatment mean to the pre-treatment mean of IL-6 is about 7.9 and the corresponding ratio for VEGF is about 1.4, and GADPH closer to 1 than VEGF, for example.

FIG. 112 shows an example of concentrations in the reservoir chamber of the implanted device corresponding to the marker concentration in the vitreous humor 30 as in FIG. 111. The RRI, reservoir volume, and corresponding molecular weights are shown in the legend. The amounts of the first and third markers in the reservoir chamber can change substantially in response to increased amounts in the vitreous humor 30. The ratios to the housekeeping second marker also may change substantially.

Figure 113:
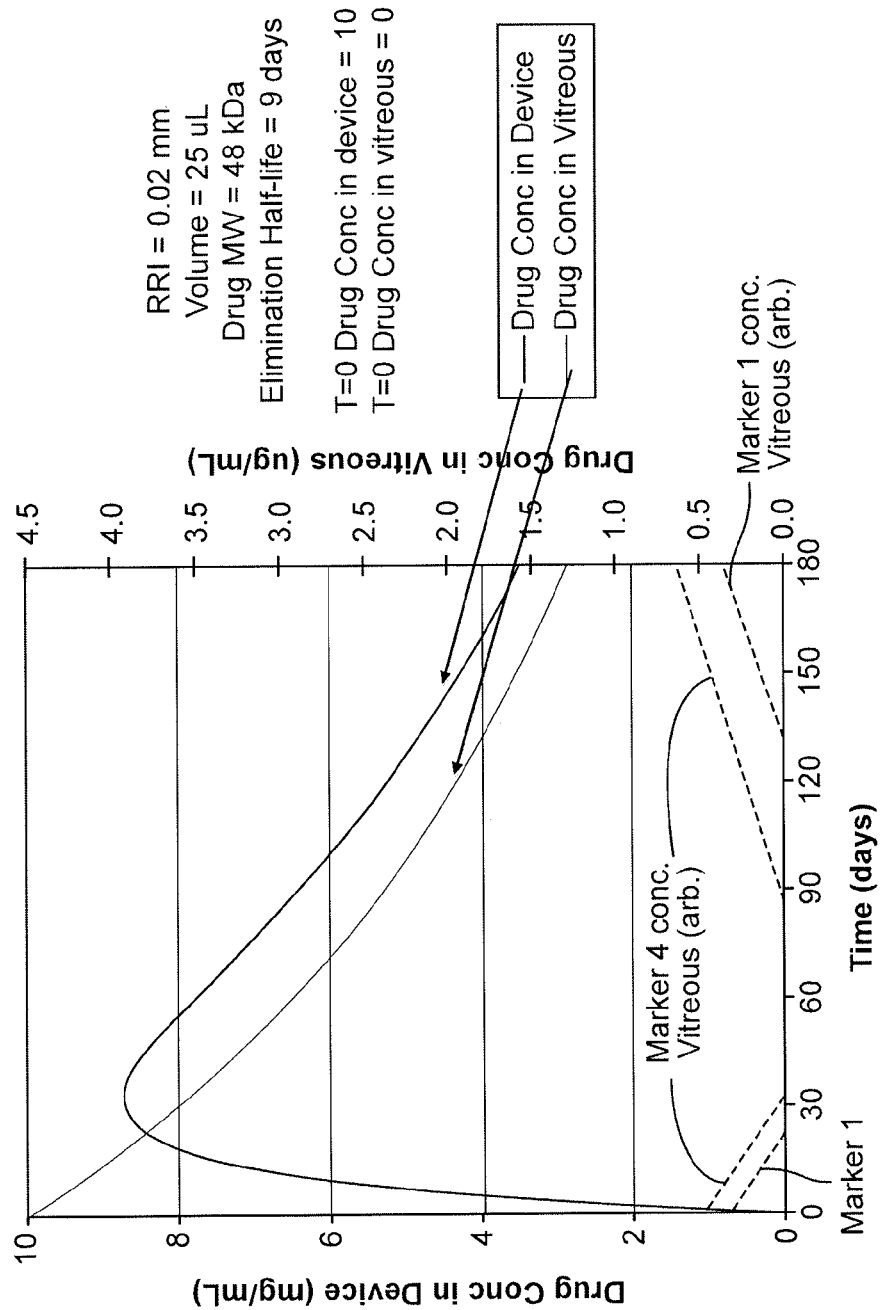
FIG. 113 shows concentrations of a first marker and a fourth marker in the vitreous humor over time in response to therapeutic agent, in which the fourth marker is more sensitive than the first marker to amounts of therapeutic agent and in which the fourth marker is released before the first marker, in accordance with embodiments.

FIG. 113 shows an example of concentrations of a first marker and a fourth marker in the vitreous humor 30 over time in response to therapeutic agent, in which the fourth marker is more sensitive than the first marker to amounts of therapeutic agent and in which the fourth marker is expressed before the first marker. The first marker can be expressed in response to the therapeutic agent below a first threshold amount and the fourth marker can be expressed in response to the therapeutic agent below a fourth threshold amount. The fourth threshold amount can be substantially greater than the first threshold amount, for example, such that the fourth marker can be expressed before the first marker.

Figure 114:
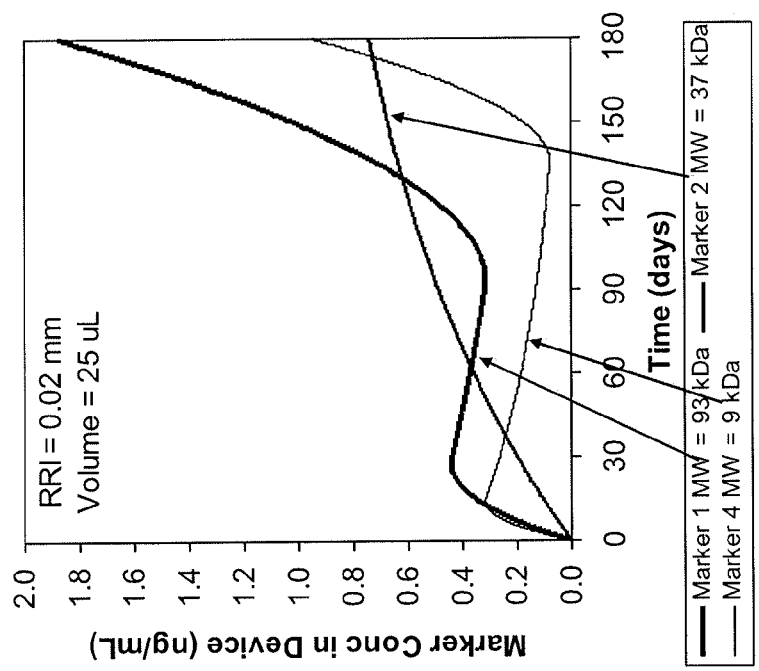
FIG. 114 shows concentrations in the vitreous humor over time of a first marker comprising ranibizumab bound to VEGF, a second housekeeping marker having comprising GAPDH and a fourth marker comprising IL-8, in which the fourth marker is released after the first marker in response to the amount of the therapeutic agent in the vitreous humor falling below a therapeutic amount, in accordance with embodiments.

FIG. 114 shows an example of concentrations in the vitreous humor 30 over time of a first marker comprising ranibizumab bound to VEGF, a second housekeeping marker having comprising GAPDH and a fourth marker comprising IL-8, in which the fourth marker is released after the first marker in response to the amount of the therapeutic agent in the vitreous humor 30 falling below a therapeutic amount. The RRI, reservoir volume, and corresponding molecular weights are shown in the legend. Work in relation to embodiments indicates that VEGF can be released in response to cell hypoxia and may be released within about one day of cell hypoxia, or sooner for example, such that VEGF may be released prior to one or more other markers as described herein when the amount of therapeutic agent released to the vitreous falls below therapeutic amounts. The plurality of markers may comprise a marker that may respond less quickly than VEGF to disease. For example, the marker may correspond to platelet growth factor or insulin production, for example one or more of platelet derived growth factor (PDGF), insulin like growth factor (IFGs) or insulin growth factor.

The ratio of VEGF to another marker having a slower response to therapeutic agent below therapeutic amounts may be compared, for example. The proportional amounts of the markers may be used to one or more of diagnose or treat an eye 10 based on a plurality of ratios of a plurality of markers, such as ratios of VEGF to GADPH, IL-8 to GADPH and VEGF to IL-8, for example.

Figure 115:
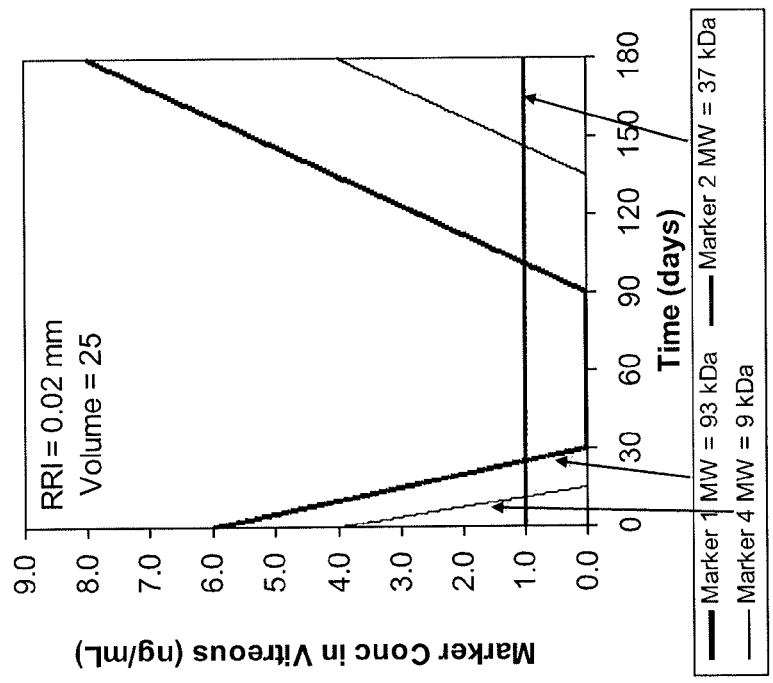
FIG. 115 shows concentrations in the reservoir chamber of the therapeutic device over time in response to the vitreal concentrations as in FIG. 114, in accordance with embodiments.

FIG. 115 shows an example of concentrations in the reservoir chamber of the therapeutic device 100 over time in response to the vitreal concentrations as in FIG. 114. The RRI, reservoir volume, and corresponding molecular weights are shown in the legend. The corresponding amounts of the therapeutic device 100 can change in proportion to the second marker.

Figure 116:
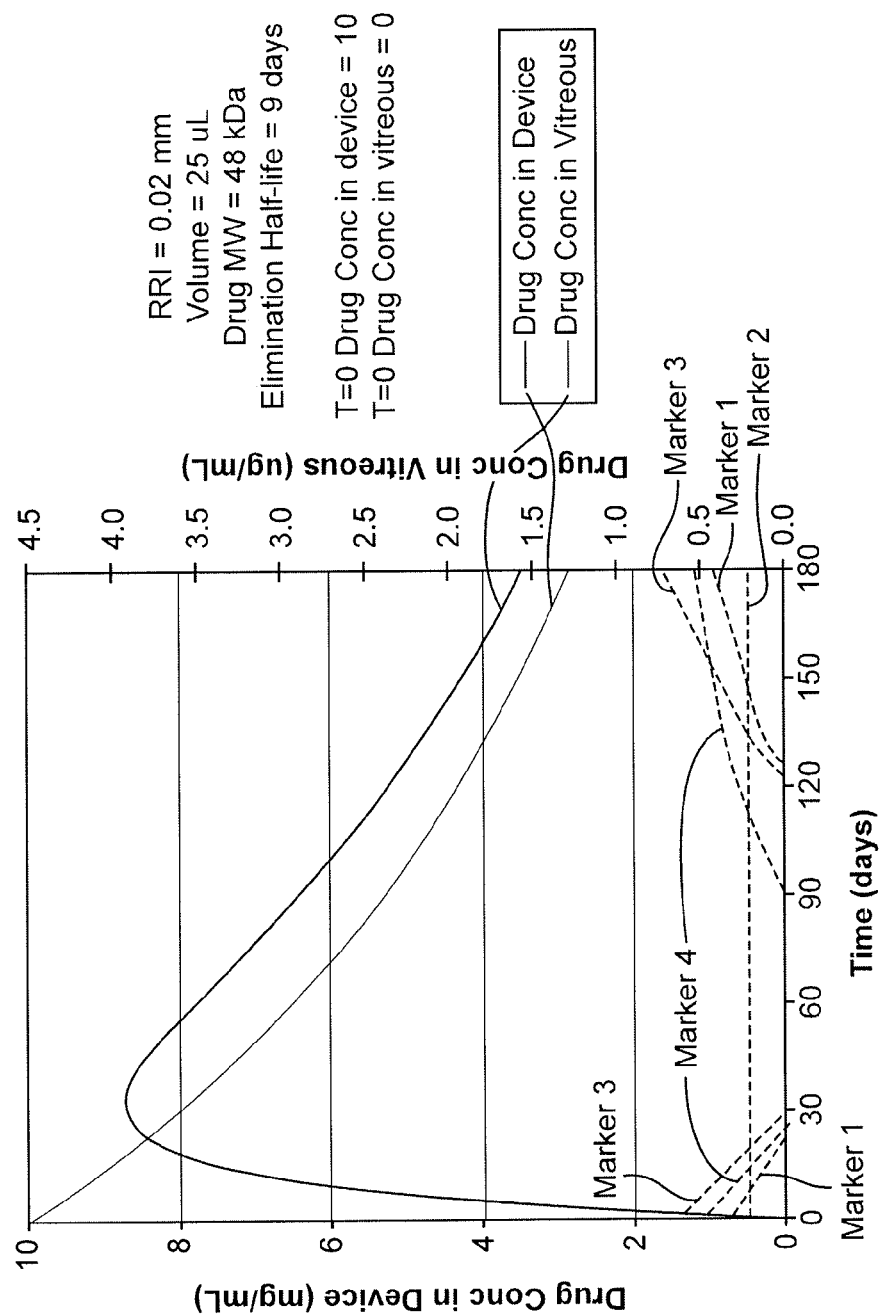
FIG. 116 shows concentrations of a first marker through fourth markers in the vitreous humor over time, in accordance with embodiments.

FIG. 116 shows concentrations of a first marker through fourth markers in the vitreous humor 30 over time. The markers can be combined and measured in many ways, and may combine known molecular weights and diffusion coefficients, such that the patient can be diagnosed based on the amount of each marker measured from the therapeutic fluid. For example, amounts of a first marker, a second marker, a third marker, and a fourth marker can be determined from a sample of the implanted device fluid removed from the therapeutic device 100 when the therapeutic fluid is placed in the implanted device. The first marker may comprise a marker targeted with the therapeutic agent. The second marker may comprise a marker having decreased sensitivity to the therapeutic agent. The third marker may comprise a marker having increased sensitivity to the therapeutic agent and a similar threshold of activation, and the fourth marker may comprise a marker having an increased sensitivity to the therapeutic agent and a higher threshold to activate in response to the therapeutic agent.

Figure 117:
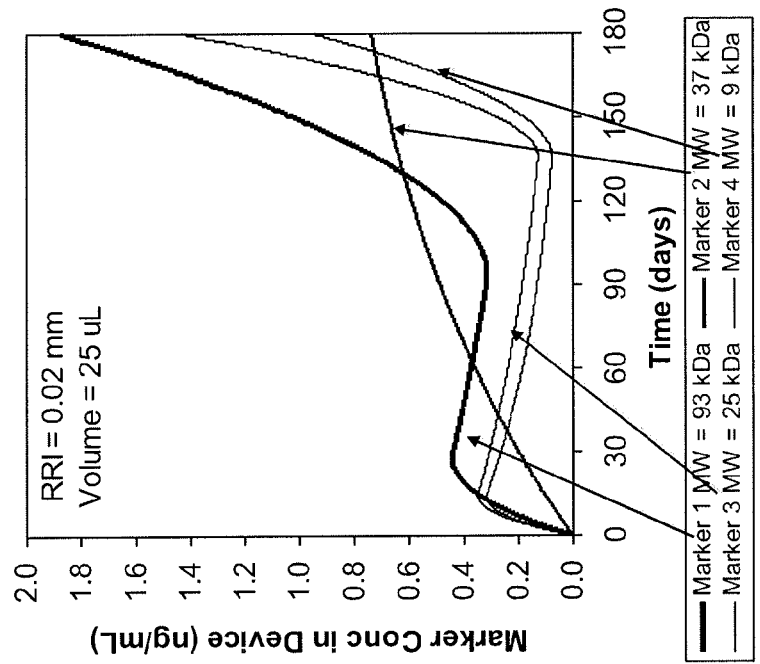
FIG. 117 shows concentrations of markers in the vitreous humor in response to a therapeutic agent, in which the first marker comprising a molecular weight corresponding ranibizumab bound to VEGF, a second marker comprising a molecular weight corresponding to GAPDA, a third marker comprising a molecular weight corresponding to IL-6, and a fourth marker comprising a molecular weight corresponding to IL-8, in accordance with embodiments.

FIG. 117 shows an example of concentrations of markers in the vitreous humor 30 in response to a therapeutic agent, in which the first marker comprising a molecular weight corresponding ranibizumab bound to VEGF, a second marker comprising a molecular weight corresponding to GAPDA, a third marker comprising a molecular weight corresponding to IL-6, and a fourth marker comprising a molecular weight corresponding to IL-8, for example. The RRI, reservoir volume, and corresponding molecular weights are shown in the legend.

Figure 118:
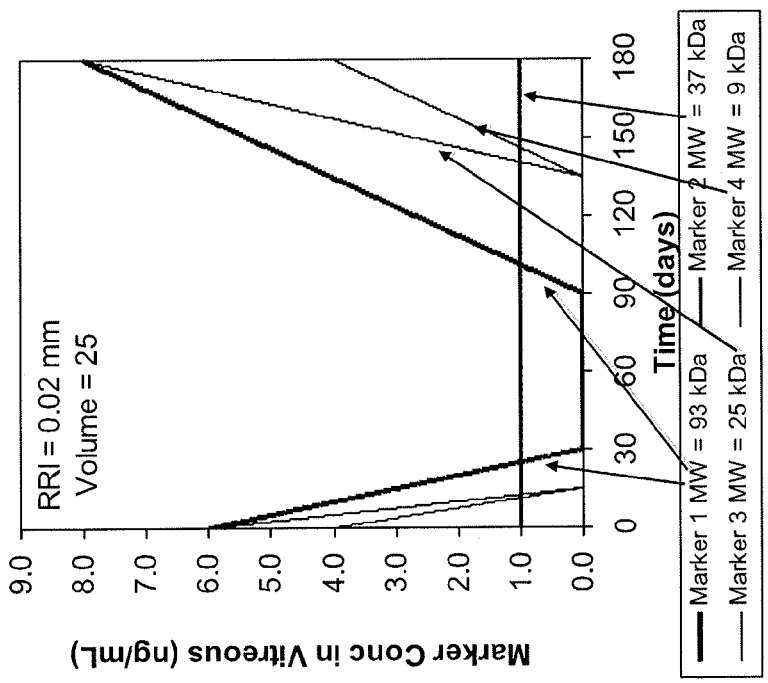
FIG. 118 shows concentrations of markers in the reservoir chamber of the therapeutic device in response to the vitreal concentrations as in FIG. 117, in accordance with embodiments.

FIG. 118 shows an example of concentrations of markers in the reservoir chamber of the therapeutic device 100 in response to the vitreal concentrations as in FIG. 117. The amounts of each marker within the reservoir chamber and corresponding ratios to the housekeeping gene and too each other can be used to one or more of diagnose or treat the eye 10. The RRI, reservoir volume and corresponding molecular weights are shown in the legend.

Figure 119:
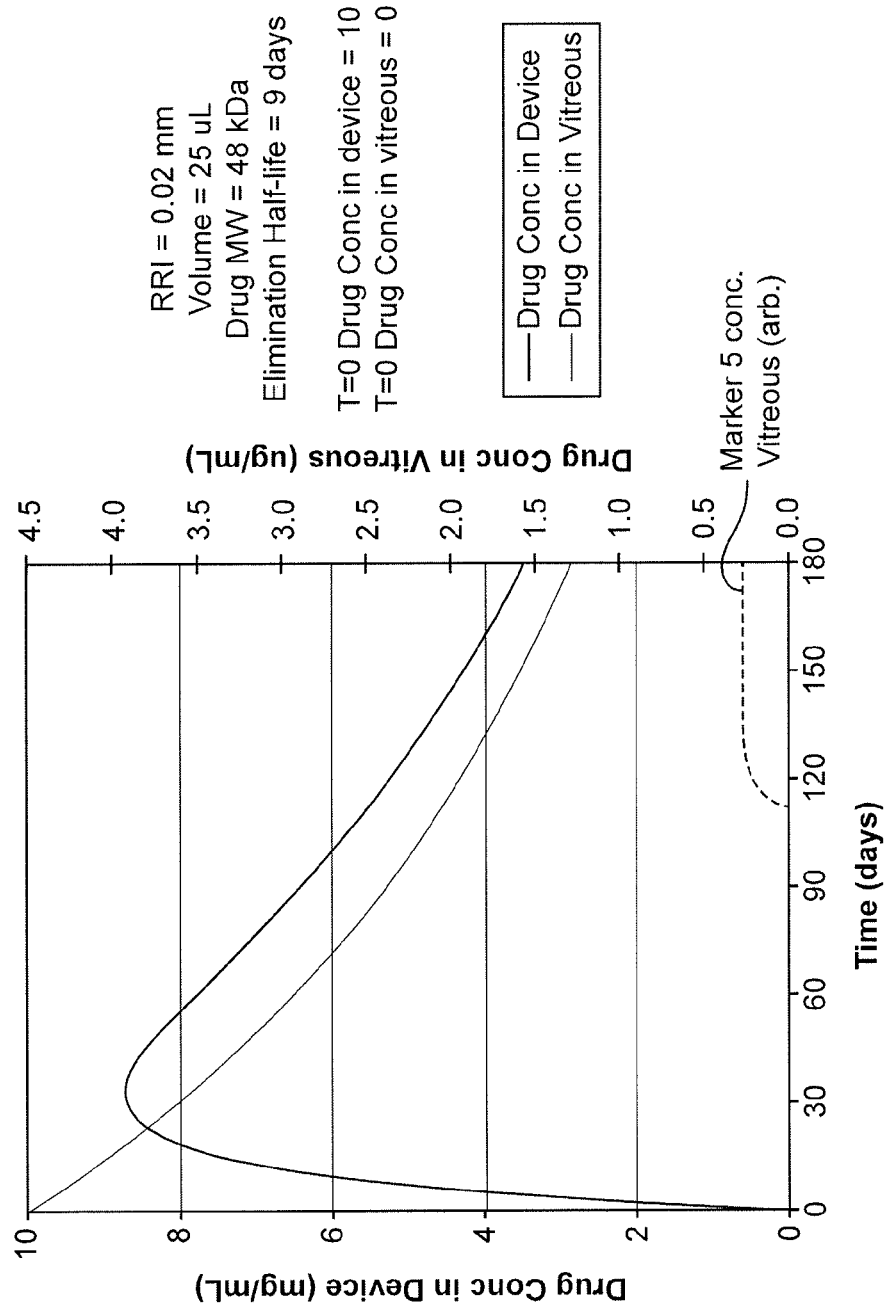
FIG. 119 shows concentrations of a fifth substantially binary marker in the vitreous humor over time, in accordance with embodiments.

FIG. 119 shows an example of concentrations of a fifth substantially binary marker in the vitreous humor 30 over time. The binary marker may correspond to a marker that switches substantially on and substantially off within a relatively narrow window of therapeutic agent, for example. Detection of the binary marker in the sample from the implanted device can indicate that the amount of therapeutic agent has fallen below a target amount, or that the treatment has proceeded in a less than ideal manner. Alternatively, a marker can be identified such that the presence of the marker can indicate a successful treatment.

Figure 120:
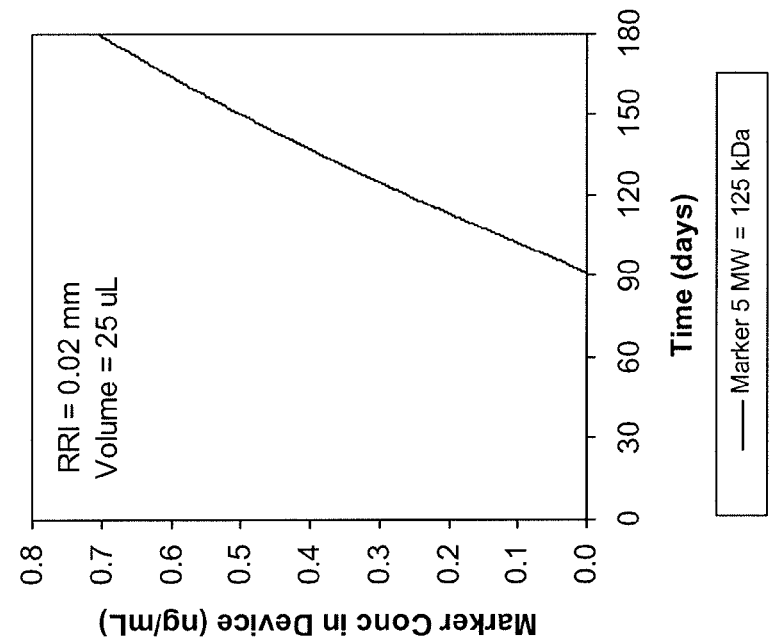
FIG. 120 shows concentrations of a substantially binary in the vitreous humor over time, in which the marker has a molecular weight corresponding to C-reactive protein, in accordance with embodiments.

FIG. 120 shows an example of concentrations of a substantially binary marker in the vitreous humor 30 over time, in which the marker has a molecular weight corresponding to C-reactive protein, for example. The RRI, reservoir volume, and corresponding molecular weights are shown in the legend.

Figure 121:
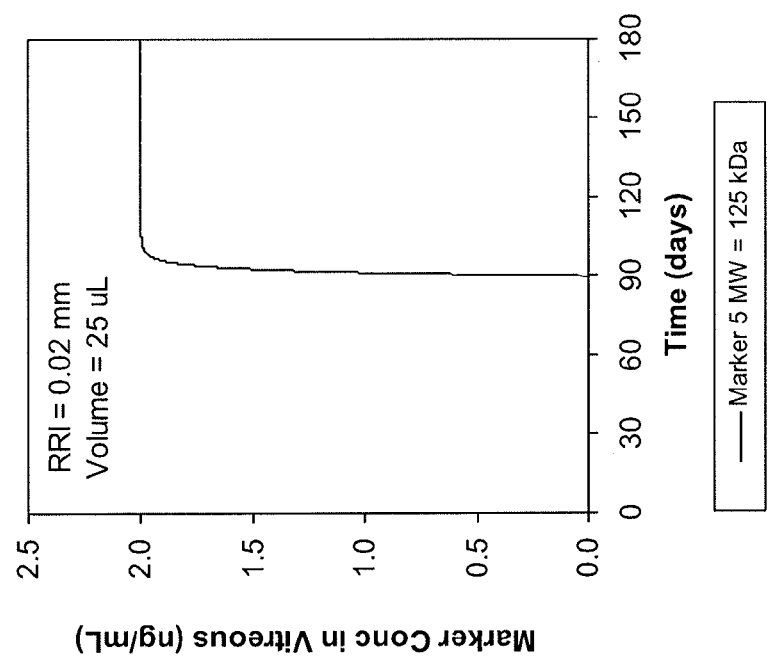
FIG. 121 shows concentrations of the substantially binary marker in the reservoir chamber of the therapeutic device in response to the vitreal concentrations as in FIG. 120, in accordance with embodiments.

FIG. 121 shows an example of concentrations of the substantially binary marker in the reservoir chamber of the therapeutic device 100 in response to the vitreal concentrations as in FIG. 120. The RRI, reservoir volume and corresponding molecular weights are shown in the legend.

Figure 122:
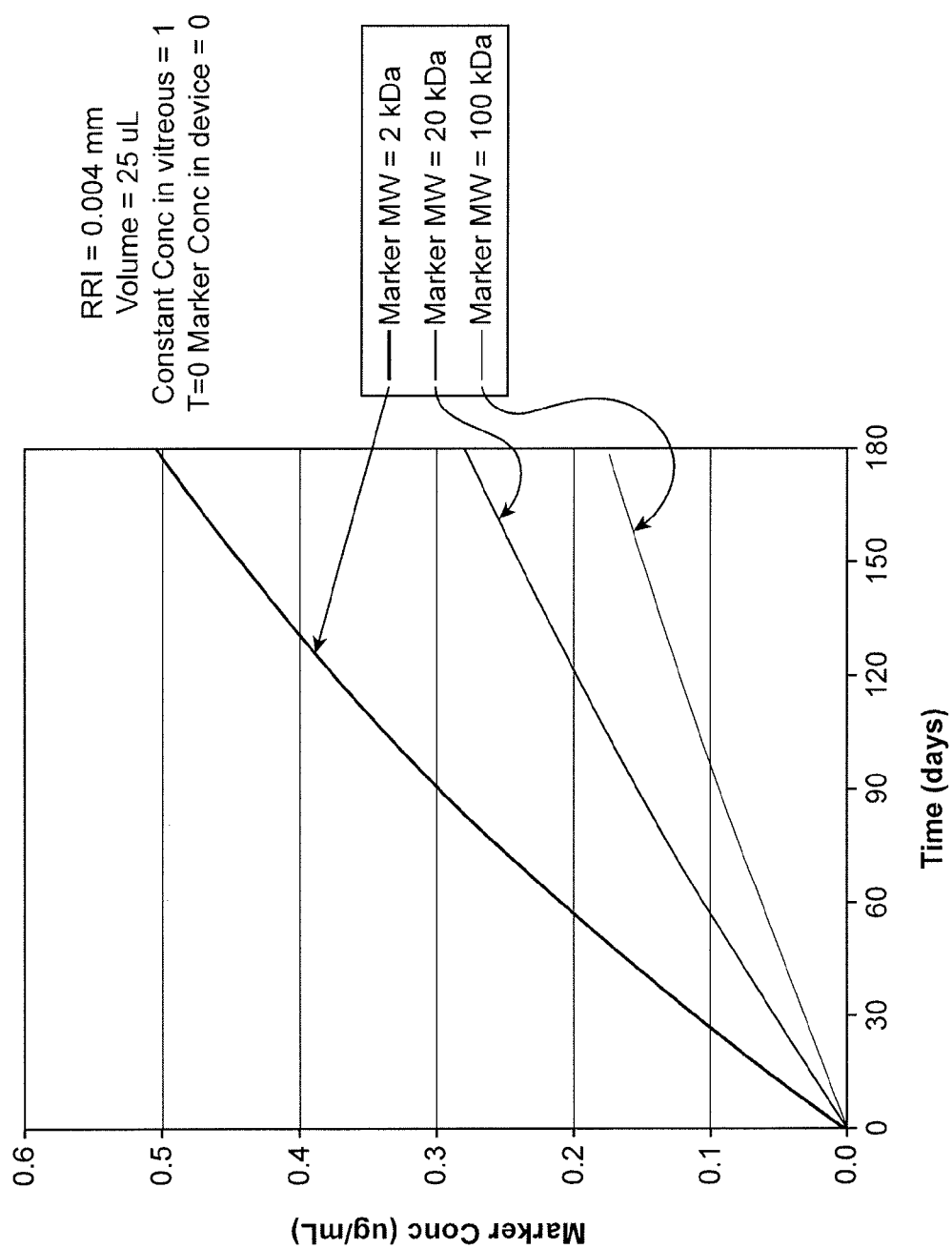
FIG. 122 concentrations of markers in a therapeutic device reservoir having a slower rate of release and a slower rate of accumulation than the therapeutic device of FIG. 106, in accordance with embodiments.

FIG. 122 shows an example of concentrations of markers in a therapeutic device 100 reservoir having a slower rate of release of therapeutic agent and a slower rate of accumulation of the marker than the therapeutic device 100 of FIG. 106. The therapeutic device 100 can be tuned in many ways to provide the rate of release of the therapeutic agent based on the porous structure 150 and the volume of the reservoir chamber as described herein. The amount of the at least one marker component of the vitreous humor 30 and at least one tuning parameter of the therapeutic device 100 can be used to diagnose the patient. For example, the volume of the reservoir chamber and the porous structure 150 can provide a time constant for release of a therapeutic agent having a diffusion coefficient, and the amount of marker component in the vitreous humor 30 may correspond to the amount of marker in the implanted device and the reservoir volume and resistance to diffusion of the porous structure 150. A release rate index of the porous structure 150 of the therapeutic device 100 can be 0.004 for a volume of 25 uL, and provide a rate of accumulation that is about $\frac{1}{5}$ (20%) of the therapeutic device 100 having a release rate index of 0.02 and a 25 uL volume of the reservoir chamber, for example.

The accumulation of the plurality of markers as described herein can be used in many ways to diagnose and treat patient. For example, each sample of the device may comprise a plurality of markers, and the plurality of markers assayed for each sample. The assay for each sample may comprise a profile of the markers. The profiles from each of the samples can be combined so as to comprise an array of marker data for the patient. The profile of marker data from a sample can be compared with an array of marker data from the same patient or a population of patients, so as to diagnose the patient. For example, an array of marker data may comprise a profile of at least about 5 markers measured from a first measurement of sample of the device implanted in the patient and at least about 5 markers from a second profile based on a second sample of the device implanted in the patient at a subsequent time. Alternatively, an array from a patient may be compared with an array corresponding to a patient population, so as to one or more of diagnose or treat the patient.

Based on the teachings described herein, the accumulation of the marker in the therapeutic device 100 can be compared with amounts in the vitreous humor 30, for example with an area under the concentration curve and many known integration methods. The accumulated marker may be compared with a pre-implantation sample such as from a vitreal tap or a sample drawn through an incision formed to place the implant in the eye 10. The amount of marker in the vitreous humor 30 can be measured with dialysis and the vitreal concentration of the component compared with the amount accumulated in the device so as to determine the corresponding rate of accumulation in the device as compared with the vitreous humor 30. Examples of experimental methods and dialysis apparatus that may be modified so as to be suitable for incorporation in accordance with the embodiments described herein are described in "Microdialysis assessment of drug delivery systems for vitreoretinal targets", *Advanced Drug Delivery Reviews*, 57(2005) 2080-2091, Sridhar Duvvuri A, Kay D. Rittenhouse B, Ashim K. Mitra, Department of Pharmaceutical Sciences, School of Pharmacy, University of Missouri-Kansas City, Kansas City, MO, 64110, USA, Pfizer Global Research and Development, La Jolla Laboratories, San Diego, CA 92121, USA Received 12 Sep. 2005; accepted 13 Sep. 2005, available online 4 Nov. 2005, which is incorporated by reference herein in its entirety.

The accumulated sample fluid removed from the implanted device may comprise or correspond to one or more biological markers as described in U.S. patent application Ser. No. 12/856,394, published as US2011/0117083, entitled "Biological Markers for Monitoring Response to VEFG Agonists" in the name of Bais et al., the full disclosure of which is incorporated herein by reference, which patent application describes genes, assays and markers suitable for incorporation and combination in accordance with embodiments described herein. For example, the biomarker measured from the reservoir chamber may comprise a biomarker of the plasma of the patient and correspond to one or more of genes, RNA or DNA of the patient, for example. Tables X, Y, Z correspond to Tables I, II and III of the above referenced Ser. No. 12/856,394 patent application previously incorporated by reference, and may describe one or more biological markers capable of diffusing into a device implanted in the patient, for example the eye, and corresponding assays suitable for incorporation in accordance with embodiments described herein.

TABLE X

| Gene | Fold Decrease in Expression |
|---|---|
| AADACL1 | 2.33 |
| ABCC9 | 2.33 |
| ACIN1 | 2.20 |

TABLE X-continued

| Gene | Fold Decrease in Expression |
|---|---|
| ACSBG2 | 2.26 |
| ADAMTS2 | 2.38 |
| ADCY4 | 2.18 |
| AFAP1L1 | 3.09 |
| AFAP1L2 | 2.47 |
| AFM | 2.61 |
| AHNAK | 2.13 |
| AKAP2 | 2.19 |
| AMBP | 2.02 |
| ANGPTL3 | 2.18 |
| ANXA1 | 2.61 |
| ANXA13 | 2.46 |
| ANXA3 | 2.15 |
| AQP4 | 2.35 |
| ARHGEF15 | 2.03 |
| ASPN | 2.72 |
| BIN2 | 2.33 |
| C10orf72 | 2.12 |
| C13orf15 | 5.04 |
| C15orf60 | 2.68 |
| C1orf54 | 6.20 |
| C6orf142 | 2.02 |
| C6orf190 | 2.48 |
| C8orf4 | 4.73 |
| CADPS2 | 2.10 |
| CALCRL | 3.98 |
| CARTPT | 3.46 |
| CAV2 | 2.44 |
| CCDC75 | 2.28 |
| CCDC88A | 2.72 |
| CCND1 | 2.20 |
| CD247 | 3.46 |
| CD34 | 6.55 |
| CD46 | 2.18 |
| CD93 | 5.15 |
| CD97 | 2.06 |
| CDC42EP1 | 3.02 |
| CDH11 | 2.49 |
| CDH5 | 2.96 |
| CENTD3 | 4.21 |
| CES7 | 5.68 |
| CFH | 2.38 |
| CGNL1 | 2.17 |
| CHCHD4 | 2.23 |
| CHD3 | 2.08 |
| CIP29 | 2.43 |
| CMTM3 | 2.05 |
| CNTNAP2 | 2.78 |
| COL13A1 | 2.69 |
| COL15A1 | 4.69 |
| COL18A1 | 3.39 |
| COL1A1 | 2.65 |
| COL1A2 | 2.13 |
| COL2A1 | 2.20 |
| COL3A1 | 2.84 |
| COL4A1 | 3.12 |
| COL4A2 | 3.49 |
| COL8A1 | 2.53 |
| CSPG4 | 3.26 |
| CTGF | 4.15 |
| CTTNBP2 | 3.00 |
| DAPK2 | 2.52 |
| DKK2 | 4.74 |
| DOPEY1 | 2.83 |
| DPP10 | 2.20 |
| DUSP6 | 2.70 |
| ECM1 | 2.04 |
| ECSM2 | 5.51 |
| EEPD1 | 2.82 |
| EFNB2 | 2.19 |
| EG214403 | 2.25 |
| EGFL7 | 2.06 |
| ELK3 | 2.73 |
| ELTD1 | 3.20 |
| EMCN | 5.32 |
| ENG | 4.47 |
| EPAS1 | 4.12 |

TABLE X-continued

| Gene | Fold Decrease in Expression |
|---|---|
| ERG | 3.53 |
| ERMN | 2.22 |
| ESAM | 2.03 |
| ESM1 | 12.54 |
| ETS1 | 2.36 |
| EXOC3L2 | 2.92 |
| EXOC4 | 2.27 |
| FABP4 | 2.75 |
| FAM170A | 2.19 |
| FAM36A | 2.03 |
| FAM38B | 4.45 |
| FAM83B | 2.58 |
| FBN1 | 2.20 |
| FBXW10 | 2.09 |
| FER1L3 | 2.09 |
| FFAR1 | 2.37 |
| FLII | 2.26 |
| FLT1 | 5.82 |
| FOXP2 | 2.93 |
| FSTL1 | 2.20 |
| GAPVD1 | 2.05 |
| GIMAP1 | 2.50 |
| GIMAP4 | 2.21 |
| GIMAP5 | 2.29 |
| GIMAP6 | 2.34 |
| GJA1 | 3.44 |
| GNAS | 2.13 |
| GNG11 | 3.38 |
| GOLGB1 | 2.01 |
| GPR116 | 2.58 |
| GPR182 | 2.06 |
| GRAP | 2.10 |
| GRIA3 | 3.55 |
| HBA1\|HBA2 | 2.18 |
| HBB | 2.72 |
| HCN1 | 2.21 |
| HSPA1A | 2.13 |
| HSPB1 | 2.22 |
| HSPG2 | 4.83 |
| ICAM2 | 5.26 |
| ID1 | 5.64 |
| IFI16 | 2.43 |
| IFI44 | 2.65 |
| IGFBP3 | 3.93 |
| IGFBP4 | 2.27 |
| IGFBP7 | 2.62 |
| INHBB | 2.50 |
| ITGB1BP1 | 2.62 |
| ITSN2 | 2.16 |
| JAG1 | 2.17 |
| KCNE3 | 3.76 |
| KCNJ8 | 2.00 |
| KCNQ5 | 2.40 |
| KDR | 3.50 |
| KIAA0644 | 2.53 |
| KITLG | 2.95 |
| KLF2 | 3.15 |
| LAMA4 | 4.65 |
| LAMB1 | 5.23 |
| LAMB2 | 2.00 |
| LGI1 | 2.47 |
| LIN52 | 2.63 |
| LOC376483 | 2.10 |
| LPHN3 | 2.72 |
| LRP4 | 3.95 |
| LUC7L | 2.02 |
| LYSMD4 | 2.15 |
| MALAT1 | 2.36 |
| MAWDBP | 2.09 |
| MCAM | 3.31 |
| MCPH1 | 2.34 |
| MEF2C | 2.46 |
| MEST | 2.51 |
| MFGE8 | 2.29 |
| MGLL | 2.78 |
| MGP | 2.64 |
| MMRN2 | 5.15 |
| MPHOSPH8 | 2.19 |
| MSLN | 2.19 |
| MYCT1 | 2.99 |
| MYL9 | 2.00 |
| MYLIP | 2.39 |
| MY018A | 2.10 |
| NDC80 | 2.17 |
| NID1 | 5.49 |
| NID2 | 10.59 |
| NKIRAS1 | 2.37 |
| NLGN1 | 2.85 |
| NOTCH4 | 2.88 |
| NR1I3 | 2.04 |
| NRP1 | 2.79 |
| NRP2 | 3.67 |
| NUDT12 | 2.14 |
| ODZ2 | 2.52 |
| OLFML2A | 2.62 |
| PABPC4L | 2.59 |
| PCDH12 | 2.85 |
| PCDH17 | 2.65 |
| PCSK5 | 2.91 |
| PDE6D | 2.28 |
| PDGFRB | 2.42 |
| PDSS2 | 2.83 |
| PHCA | 2.67 |
| PHF8 | 3.29 |
| PIP | 2.73 |
| PLAC9 | 2.64 |
| PLCB1 | 2.04 |
| PLK2 | 2.53 |
| PLK4 | 2.15 |
| PLSCR2 | 2.71 |
| PLVAP | 1.99 |
| PLXDC2 | 2.21 |
| PODXL | 2.11 |
| POSTN | 2.20 |
| PPAP2A | 2.37 |
| PPAP2B | 6.22 |
| PPIC | 3.53 |
| PRG1 | 2.44 |
| PRKAR2 | 2.95 |
| PRKCDBP | 2.72 |
| PRND | 5.55 |
| PROSC | 2.28 |
| PTBP2 | 2.65 |
| PTHR1 | 2.14 |
| PTMS | 2.03 |
| PTPRB | 4.21 |
| PTPRG | 2.01 |
| RAPGEF3 | 3.18 |
| RASGRP2 | 2.02 |
| RASGRP3 | 3.62 |
| RASIP1 | 2.73 |
| RBMY1A1 | 2.01 |
| RBP7 | 5.83 |
| RGS5 | 2.02 |
| RHOJ | 2.83 |
| RHPN2 | 2.04 |
| ROB04 | 3.05 |
| SCARF1 | 2.03 |
| SCYL3 | 2.01 |
| SEC14L3 | 2.03 |
| SERPINE1 | 2.10 |
| SERPINH1 | 4.09 |
| SGK | 2.28 |
| SH3BP5 | 2.05 |
| SH3TC1 | 2.02 |
| SLC8A1 | 2.04 |
| SMTNL1 | 1.99 |
| SOX18 | 3.18 |
| SOX7 | 2.90 |
| SPARC | 4.06 |
| SPARCL1 | 2.66 |
| SPOCK3 | 2.31 |
| SPRY4 | 3.29 |
| SPTA1 | 4.53 |

TABLE X-continued

| Gene | Fold Decrease in Expression |
|---|---|
| SRGN | 2.06 |
| STAB1 | 2.08 |
| TAGLN | 2.27 |
| TCF4 | 2.52 |
| THBD | 2.59 |
| THSD1 | 2.59 |
| TIE1 | 2.30 |
| TIMP3 | 3.03 |
| TMEM88 | 3.39 |
| TNNT2 | 2.19 |
| TRAPPC6B | 2.34 |
| TRPC6 | 2.55 |
| TSPAN18 | 2.20 |
| TTC23L | 2.28 |
| UHRF1BP1L | 3.08 |
| UNC45B | 2.42 |
| UNC5B | 2.38 |
| USHBP1 | 4.79 |
| VAV3 | 2.04 |
| VEPH1 | 2.50 |
| VIM | 2.46 |
| VTI1A | 2.44 |
| WHDC1 | 2.28 |
| WWTR1 | 2.41 |
| ZC3H13 | 2.13 |
| ZFP36L1 | 2.20 |

TABLE Y

| gene |
|---|
| ACIN1 |
| ACSBG2 |
| ADAM12 |
| ADAMTS1 |
| ADAMTS2 |
| ADCY4 |
| AFAP1L1 |
| AFAP1L2 |
| AHNAK |
| AHR |
| AKAP2 |
| AL078459.1 |
| AMBP |
| ANGPT2 |
| ANXA1 |
| ANXA2 |
| APLNR |
| AQP4 |
| ARAP3 |
| ASPN |
| BGN |
| BTNL9 |
| C13orf15 |
| C14orf73 |
| C1orf54 |
| C3orf64 |
| CADPS2 |
| CALCRL |
| CAPG |
| CCND1 |
| CD247 |
| CD34 |
| CD38 |
| CDC42EP1 |
| CFH |
| CGNL1 |
| CHD3 |
| CHST15 |
| CLEC14A |
| CLEC6A |
| CMTM3 |
| COL10A1 |
| COL13A1 |
| COL15A1 |
| COL3A1 |
| COL4A1 |
| COL4A2 |
| COL6A2 |
| CTGF |
| CXCR4 |
| CXCR7 |
| DAB2 |
| DAPK2 |
| DDAH1 |
| DUSP6 |
| EDNRB |
| EFNA1 |
| EHD4 |
| ELTD1 |
| EMCN |
| EMP1 |
| ENDOD1 |
| ENG |
| ENPP6 |
| ERG |
| ESAM |
| ETS1 |
| EXOC4 |
| FABP4 |
| FAM167B |
| FAM170A |
| FHOD1 |
| FILIP1L |
| FLI1 |
| FLT1 |
| FLT4 |
| FMOD |
| GIMAP4 |
| GIMAP5 |
| GIMAP6 |
| GJA1 |
| GJC1 |
| GNG11 |
| GPR182 |
| HBA1 |
| HBA2 |
| HIGD1B |
| HLX |
| HSPA1A |
| HSPA1B |
| ICAM2 |
| ID1 |
| IFITM1 |
| ITGA5 |
| ITGA6 |
| ITGB1BP1 |
| ITSN2 |
| KCNJ8 |
| KDM6B |
| KDR |
| KIAA0355 |
| KIAA1462 |
| KITLG |
| KLF2 |
| LAMB1 |
| LAMB2 |
| LATS2 |
| LCP1 |
| LGALS1 |
| LGI1 |
| LHFP |
| LTBP4 |
| LUC7L |
| MECOM |
| MEF2C |
| MFGE8 |
| MMP14 |
| MMRN2 |
| MNDA |
| MSN |
| MYCT1 |

TABLE Y-continued

| gene |
|---|
| MYO18A |
| MYOF |
| NAALAD2 |
| NDC80 |
| NID1 |
| NOTCH1 |
| NRARP |
| NRP1 |
| PALM2- |
| PDGFB |
| PDGFRB |
| PDSS2 |
| PHF8 |
| PLCB1 |
| PLK2 |
| PLXDC2 |
| PLXND1 |
| POSTN |
| POU4F1 |
| PPAP2A |
| PPAP2B |
| PPIC |
| PPIH |
| PRDM1 |
| PRKCDBP |
| PRND |
| PTH1R |
| PTPRB |
| PTPRE |
| PTPRG |
| RAI14 |
| RASGRP2 |
| RASIP1 |
| RBMS1 |
| RBP7 |
| REG3A |
| REG3G |
| RHOJ |
| ROBO4 |
| SCARF1 |
| SEMA3F |
| SEPT4 |
| SERPINE1 |
| SERPINH1 |
| SLC11A1 |
| SLC40A1 |
| SLFN5 |
| SMAGP |
| SMTNL1 |
| SOX18 |
| SOX7 |
| SPARC |
| SPOCK3 |
| SPTA1 |
| SRGN |
| ST8SIA6 |
| STAB1 |
| STEAP4 |
| SWAP70 |
| TAGLN |
| TEK |
| THBD |
| THSD1 |
| TIMP3 |
| TM4SF1 |
| TMEM173 |
| TMEM204 |
| TMEM88 |
| TNFAIP2 |
| TREML4 |
| TRIM5 |
| TSPAN18 |
| UHRF1BP1L |
| UNC5B |
| USHBP1 |
| VAMP5 |
| VIM |
| WISP1 |
| WWTR1 |
| ZC3H13 |
| ZFP36L1 |

TABLE Z

| Gene | 1 | 2 | 3 | 4 | 5 |
|---|---|---|---|---|---|
| ABCC9 | * |   | * |   |   |
| AC010411.1 | * | * |   |   |   |
| AC044860.2 | * | * |   |   |   |
| ACE | * |   |   |   |   |
| ACER3 | * |   |   |   |   |
| ACIN1 | * |   |   |   | * |
| ACSBG2 | * |   |   |   |   |
| ACSS1 | * |   |   |   |   |
| ADAM12 | * | * |   |   | * |
| ADAMTS1 | * | * |   |   | * |
| ADAMTS2 | * | * | * |   |   |
| ADAMTS4 | * |   |   |   |   |
| ADCY4 | * |   |   |   | * |
| AFAP1L1 | * | * | * |   | * |
| AFAP1L2 | * | * | * | * |   |
| AFM | * |   |   |   |   |
| AHNAK | * |   |   |   | * |
| AHR | * |   |   |   | * |
| AKAP2 | * |   | * |   | * |
| AL078459.1 | * |   |   |   |   |
| AMBP | * |   |   |   | * |
| ANGPT2 | * |   |   |   |   |
| ANGPTL3 | * |   |   |   |   |
| ANXA1 | * | * | * | * | * |
| ANXA2 | * | * |   |   |   |
| ANXA3 | * | * | * |   |   |
| APLNR | * | * |   |   |   |
| AQP4 | * |   |   |   | * |
| ARAP3 | * | * | * | * | * |
| ARHGAP29 | * |   |   |   |   |
| ARHGAP31 | * |   |   |   |   |
| ARHGEF15 | * |   |   |   |   |
| ASPN | * | * | * | * | * |
| BGN | * | * |   |   | * |
| BTNL9 | * | * |   |   |   |
| C10orf72 | * |   |   |   |   |
| C13orf15 | * | * | * |   | * |
| C14orf73 | * |   |   |   | * |
| C15orf60 | * |   |   |   |   |
| C1orf54 | * | * | * | * | * |
| C3orf64 | * |   |   |   | * |
| C6orf142 | * |   |   |   |   |
| C8orf4 | * | * |   |   |   |
| CADPS2 | * |   |   |   |   |
| CALCRL | * | * | * | * | * |
| CAPG | * |   |   |   |   |
| CARTPT | * |   |   |   |   |
| CAV1 | * | * |   |   |   |
| CAV2 | * | * |   |   |   |
| CCDC75 | * |   |   |   |   |
| CCDC88A | * |   |   |   |   |
| CCND1 | * | * | * | * | * |
| CD247 | * |   |   |   |   |
| CD300LG | * |   |   |   |   |
| CD34 | * | * | * | * | * |
| CD36 | * | * |   |   |   |
| CD38 | * |   |   |   | * |
| CD40 | * |   |   |   |   |
| CD93 | * | * | * | * |   |
| CD97 | * |   | * |   |   |
| CDC42EP1 | * | * |   |   |   |
| CDH11 | * | * |   |   |   |
| CDH5 | * | * | * | * |   |
| CES2 | * | * | * | * |   |
| CFH | * | * |   |   | * |
| CGNL1 | * |   |   |   | * |
| CHD3 | * |   |   |   |   |

TABLE Z-continued

| Gene | 1 | 2 | 3 | 4 | 5 |
|---|---|---|---|---|---|
| CHSTl5 | * | | | | |
| CLECl4A | * | * | | | * |
| CLEC6A | * | | | | * |
| CMTM3 | * | | | | * |
| CNN2 | * | * | | | |
| COL10A1 | * | * | | | |
| COL13Al | * | | * | | |
| COL15Al | * | * | * | * | |
| COL18Al | * | * | * | * | |
| COL1Al | * | * | * | | |
| COL1A2 | * | * | | | |
| COL2A1 | * | | | | |
| COL3A1 | * | | * | | * |
| COL4A1 | * | * | * | * | * |
| COL4A1 | * | * | * | * | * |
| COL5A2 | * | | | | |
| COL6A1 | * | * | | | |
| COL6A2 | * | * | | | * |
| COL8A1 | * | * | * | | |
| CSPG4 | * | * | | | |
| CTGF | * | * | * | * | |
| CXCR4 | * | * | | | |
| CXCR7 | * | | | | |
| DAB2 | * | | | | |
| DAPK2 | * | * | | | * |
| DCBLD1 | * | | | | |
| DDAH1 | * | | | | |
| DKK2 | * | * | * | * | |
| DLL4 | * | | | | |
| DUSP6 | * | * | | | * |
| ECM1 | * | | | | |
| EDNRB | * | * | | | |
| EFNA1 | * | * | | | * |
| EFNB2 | * | * | * | | |
| EGFL7 | * | * | | | |
| EHD4 | * | * | | | * |
| ELK3 | * | * | * | * | |
| ELTD1 | * | * | * | * | * |
| EMCN | * | * | * | * | * |
| EMP1 | * | | | | * |
| ENDOD1 | * | | | | * |
| ENG | * | * | * | * | * |
| ENPP6 | * | * | | | * |
| ERG | * | * | * | * | |
| ERMN | * | | | | |
| ESAM | * | | * | | * |
| ESM1 | * | * | * | * | |
| ETS1 | * | | | | * |
| EXOC4 | * | | | | * |
| FABP4 | * | * | | | * |
| FAMl67B | * | | * | | * |
| FAMl70A | * | | | * | |
| FAM55D | * | | | | |
| FBN1 | * | * | * | * | |
| FFAR1 | * | | | | |
| FGD5 | * | * | | | |
| FHOD1 | * | | | | |
| FILIP1L | * | | | | * |
| FKBP10 | * | | * | | |
| FLII | * | | | | |
| FLT1 | * | * | * | * | * |
| FLT4 | * | * | | * | |
| FMOD | * | | | | |
| FSTL1 | * | * | * | * | |
| GIMAP1 | * | * | | | |
| GIMAP4 | * | * | | | * |
| GIMAP5 | * | * | | | * |
| GIMAP6 | * | * | * | * | |
| GIMAP8 | * | * | | | |
| GJA1 | * | * | * | * | * |
| GJC1 | * | | | | |
| GNAS | * | | | | |
| GNG11 | * | * | * | * | |
| GOLGB1 | * | | | | |
| GPR116 | * | | | | |
| GPR182 | * | | | | * |
| GPX8 | * | * | | | |
| GRAP | * | | | | |
| GRAPL | * | | | | |
| HBA1 | * | | | | * |
| HBA2 | * | | | | * |
| HBB | * | | | | |
| HBD | * | | | | |
| HCN1 | * | | | | |
| HIGD1B | * | | | | |
| HLX | * | * | | | * |
| HMOX1 | * | | | | |
| HSPA1A | * | | | | * |
| HSPA1B | * | | | | * |
| HSPB1 | * | | | | |
| HSPG2 | * | | | | |
| ICAM2 | * | * | * | * | * |
| ID1 | * | * | | | * |
| ID3 | * | * | | | |
| IFI44 | * | | | | |
| IFITM1 | * | | | | |
| IGFBP3 | * | * | * | | |
| IGFBP4 | * | | | | |
| IGFBP7 | * | * | | | |
| IL2RG | * | | | | |
| INHBB | * | * | | | |
| ITGA5 | * | | | | |
| ITGA6 | * | | | | * |
| ITGB1BP1 | * | | | | * |
| ITSN2 | * | | | | * |
| JAG1 | * | | * | | |
| KCNE3 | * | * | * | * | |
| KCNJ8 | * | | | | * |
| KDM6B | * | | * | | |
| KDR | * | * | * | * | * |
| KIAA0355 | * | | | | * |
| KIAA1462 | * | * | * | * | * |
| KITLG | * | * | * | | |
| KLF2 | * | | | | * |
| LAMA4 | * | * | * | * | |
| LAMB1 | * | * | * | * | * |
| LAMB2 | * | | | | * |
| LAMC1 | * | * | | | |
| LATS2 | * | | | | * |
| LCPl | * | | | | * |
| LGALS1 | * | | | | * |
| LGll | * | | | | |
| LHFP | * | | | | |
| LIN52 | * | | | | |
| LRP4 | * | * | | | |
| LRRC3B | * | * | | | |
| LTBP4 | * | | | | * |
| LUC7L | * | | | | * |
| LYSMD4 | * | | | | |
| MCAM | * | | * | | |
| MCPH1 | * | | | | |
| MECOM | * | | | | * |
| MEF2C | * | * | * | * | * |
| MEST | * | * | | | |
| MFGE8 | * | * | * | | |
| MGLL | * | * | * | | |
| MGP | * | * | * | | |
| MMP14 | * | | | | |
| MMRN2 | * | * | * | * | |
| MNDA | * | | | | |
| MPHOSPH8 | * | | | | |
| MSLN | * | | | | |
| MSN | * | | | | * |
| MSRB3 | * | | | | |
| MYCT1 | * | * | * | * | * |
| MYL9 | * | | | | |
| MYLIP | * | | | | |
| MYO18A | * | | | | * |
| MYOF | * | | | | * |
| NAALAD2 | * | | | | |
| NDC80 | * | | | | * |
| NFIB | * | | * | | |
| NID1 | * | * | * | * | * |
| NID2 | * | * | * | * | |
| NKIRAS1 | * | | | | |
| NOTCH1 | * | | | | * |

TABLE Z-continued

| Gene | 1 | 2 | 3 | 4 | 5 |
|---|---|---|---|---|---|
| NOTCH4 | * | * | * | * |   |
| NR1I3 | * |   |   |   |   |
| NRARP | * |   |   |   | * |
| NRP1 | * | * | * | * | * |
| NRP2 | * | * | * | * |   |
| NUDT12 | * |   |   |   |   |
| OLFML2A | * |   |   |   |   |
| PALM2 | * |   |   |   |   |
| PALM2-AKAP2 | * |   | * |   | * |
| PCDH12 | * | * | * | * |   |
| PCDH17 | * |   |   |   |   |
| PCSK5 | * |   |   |   |   |
| PDGFB | * | * |   |   |   |
| PDGFD | * |   |   |   |   |
| PDGFRB | * | * | * |   | * |
| PDSS2 | * |   |   |   | * |
| PHF8 | * |   |   |   | * |
| PIP | * |   |   |   |   |
| PLAC9 | * |   |   |   |   |
| PLCB1 | * |   |   |   |   |
| PLK2 | * | * |   | * | * |
| PLK4 | * |   |   |   |   |
| PLSCR1 | * |   |   |   |   |
| PLSCR2 | * |   |   |   |   |
| PLVAP | * | * | * |   |   |
| PLXDC2 | * |   |   | * |   |
| PLXND1 | * | * |   | * |   |
| PODXL | * | * | * |   |   |
| POSTN | * |   | * |   |   |
| POU4F1 | * |   |   |   |   |
| PPAP2A | * |   |   |   |   |
| PPAP2B | * | * | * | * | * |
| PPIC | * | * | * | * | * |
| PPIH | * |   |   |   |   |
| PRDM1 | * | * |   | * |   |
| PRICKLE2 | * |   |   |   |   |
| PRKCDBP | * | * | * | * | * |
| PRKCH | * |   |   |   |   |
| PRND | * | * | * | * | * |
| PROSC | * |   |   |   |   |
| PRR5L | * | * |   |   |   |
| PTH1R | * |   |   | * |   |
| PTMS | * |   |   |   |   |
| PTPRB | * | * |   | * |   |
| PTPRE | * | * | * |   |   |
| PTPRG | * |   |   | * |   |
| RAI14 | * |   |   |   | * |
| RAPGEF3 | * | * |   |   |   |
| RASGRP2 | * |   |   |   |   |
| RASGRP3 | * | * | * | * |   |
| RASIP1 | * | * | * | * |   |
| RBMS1 | * |   |   |   |   |
| RBMY1A1 | * |   |   |   |   |
| RBMY1B | * |   |   |   |   |
| RBMY1D | * |   |   |   |   |
| RBMY1E | * |   |   |   |   |
| RBMY1F | * |   |   |   |   |
| RBMY1J | * |   |   |   |   |
| RBP7 | * | * |   |   |   |
| REG3A | * | * |   |   | * |
| REG3G | * | * |   |   | * |
| RGS5 | * | * |   |   |   |
| RHOJ | * | * |   |   | * |
| ROBO4 | * | * | * | * | * |
| RP4-788L13.1 | * |   |   |   |   |
| RRAS | * | * |   |   |   |
| S100A6 | * | * |   |   |   |
| S1PR1 | * |   |   |   |   |
| S1PR3 | * | * |   |   |   |
| SCARF1 | * | * |   |   |   |
| SEMA3F | * |   |   | * |   |
| SEMA6D | * | * |   |   |   |
| SEPT4 | * |   |   |   |   |
| SERPINE1 | * | * | * |   |   |
| SERPINH1 | * | * | * | * | * |
| SGK1 | * |   |   |   |   |
| SH3BP5 | * |   |   |   |   |
| SH3TC1 | * |   |   |   |   |
| SLC11A1 | * |   |   |   | * |
| SLC40A1 | * |   |   |   | * |
| SLC8A1 | * |   |   |   |   |
| SLFN5 | * |   |   |   | * |
| SMAGP | * |   |   |   |   |
| SMTNL1 | * |   |   |   |   |
| SNRK | * |   |   |   |   |
| SOX18 | * | * | * | * |   |
| SOX7 | * |   | * | * |   |
| SPARC | * | * | * | * | * |
| SPARCL1 | * |   |   |   |   |
| SPIC | * | * |   |   |   |
| SPOCK3 | * |   |   |   | * |
| SPRY4 | * | * | * |   |   |
| SPTA1 | * |   |   | * |   |
| SRGN | * |   |   |   | * |
| ST8SIA4 | * | * |   |   |   |
| ST8SIA6 | * |   |   |   |   |
| STAB1 | * |   |   |   |   |
| STEAP4 | * |   |   |   | * |
| SWAP70 | * |   |   |   |   |
| TAGLN | * |   |   |   |   |
| TBX2 | * |   |   |   |   |
| TEK | * |   |   |   | * |
| TFPI2 | * |   |   |   |   |
| TGFB1 | * |   |   |   |   |
| THBD | * | * |   |   | * |
| THBS1 | * | * |   |   |   |
| THSD1 | * | * |   |   | * |
| TIE1 | * | * | * |   |   |
| TIMP3 | * | * | * |   | * |
| TM4SF1 | * | * |   |   |   |
| TMEM173 | * |   |   |   |   |
| TMEM204 | * | * |   |   | * |
| TMEM88 | * | * | * |   | * |
| TNFAIP2 | * | * |   |   | * |
| TNNT2 | * |   | * |   |   |
| TRAPPC6B | * |   |   |   |   |
| TREML4 | * |   |   |   |   |
| TRIB2 | * |   |   |   |   |
| TRIM16 | * |   |   |   |   |
| TRIM16L | * |   |   |   |   |
| TRIM47 | * |   |   |   |   |
| TRIM5 | * |   |   |   | * |
| TSPAN18 | * |   |   |   | * |
| UHRF1BP1L | * |   |   |   | * |
| UNC45B | * | * | * |   |   |
| UNC5B | * |   |   |   | * |
| USHBP1 | * | * | * | * | * |
| VAMP5 | * |   |   |   | * |
| VIM | * | * | * | * |   |
| VTI1A | * |   |   |   |   |
| WHAMM | * |   |   |   |   |
| WISP1 | * | * |   |   | * |
| WWTR1 | * | * | * | * | * |
| ZC3H13 | * |   |   |   | * |
| ZFP36L1 | * |   | * |   | * |

The molecular weight of the biomarker corresponding to the one or more markers of Tables X, Y, and Z can be used to determine the rate of accumulation, and the fold decrease in gene expression used to one or more of diagnose or treat the patient in accordance with accumulation of the one or more markers in the reservoir chamber of the implantable device as described herein.

Figure 123:
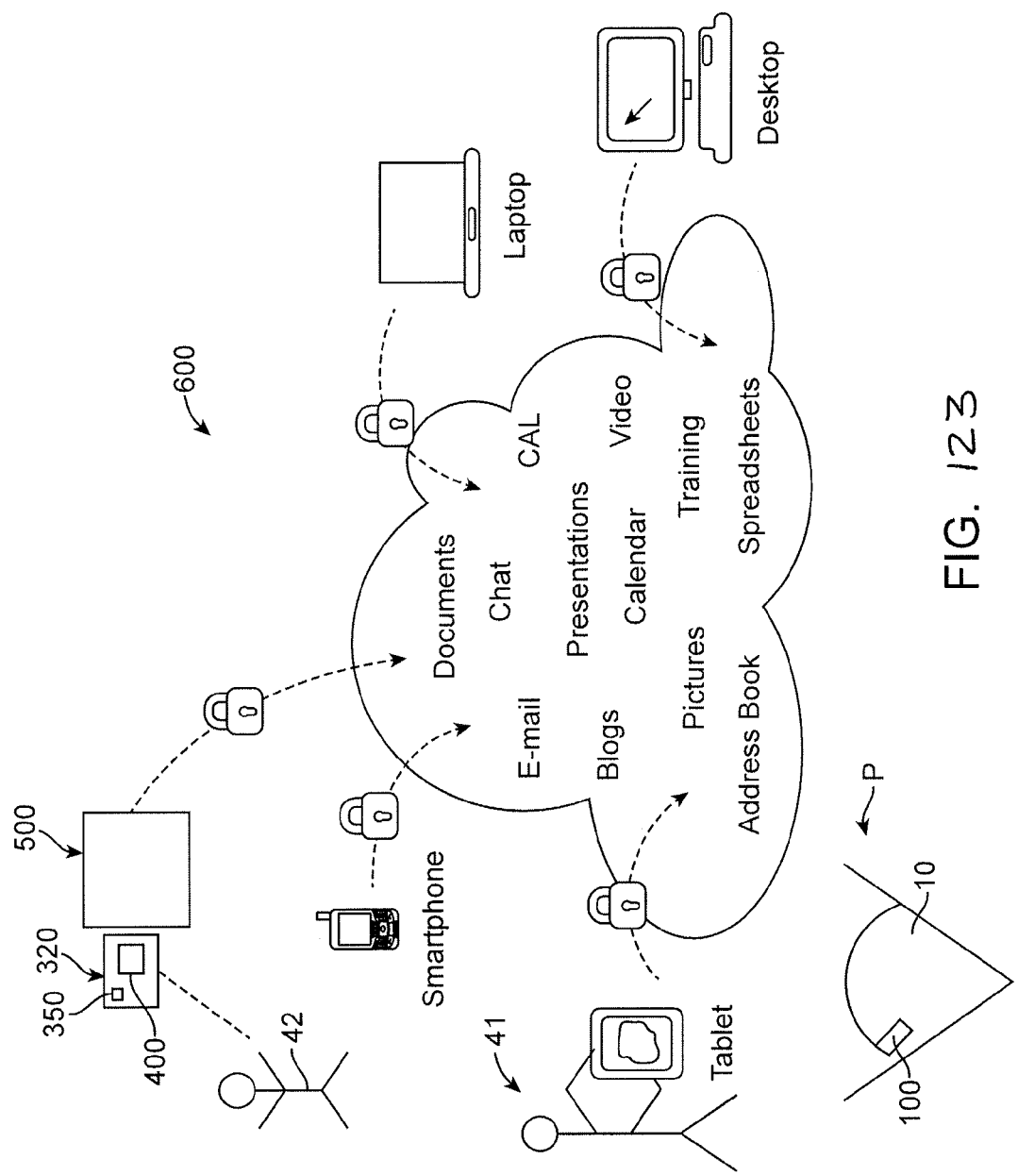
FIG. 123 shows an apparatus to analyze the sample of the implanted therapeutic device and a processor system having instructions to receive data of the fluid of the device implanted in the eye, in accordance with embodiments.

FIG. 123 shows an example of an apparatus 500 which may be used to analyze the sample of the device 100 and a processor system 600 having instructions to receive data of the fluid of the device implanted in the eye 10. The apparatus 500 may comprise an assay to determine the presence or quantify of the component of the eye 10 from the fluid 400. The processor system 600 may comprise one or more components of a cloud data storage system, for example one or more components as shown on the Wikipedia website.

The processor system may comprise one or more of many devices such as a tablet for users of the system to enter data such as data of patient P having eye 10 with device 100 implanted thereon as described herein. The processor system may include a device to scan the identifier 350 at a first location where first user 41 is located when the eye 10 is scanned, and the processor system may include a similar device to scan the identifier where the sample is measured at a second location where a second user 42 is located, for example. The first user 41 can be remote from the second user 42, for example in a different building, or the first user and the second user can be in the same building. In many embodiments, the first user and the second user can be the same user, for example when device 500 comprises a lab on a chip located in the office of the health care provider. The fluid 400 can be measured with one or more commercially available assays.

The assay may comprise a known commercially available assay such as one or more of CFH, CFB & C2 for AMD diagnostic, commercially available from Sequenom or Ophtherion. In addition, the assay may comprise genomic profiling. The sample may be frozen in the container with the identifier and sent to a remote location for analysis.

FIG. 124 shows the sample container 328 coupled to the apparatus 500 to analyze the sample of the device. The apparatus 500 may comprise a component to read the identifier of the sample container, for example. The apparatus 500 may comprise a needle to pass into container 328 and remove the sample 400 comprising fluid 703FL from the container 328. Alternatively, the apparatus 500 may comprise a port to receive the at least one needle of the cartridge 320. For example, the apparatus 500 can be configured to receive the first needle and the second needle of the cartridge and remove the sample 400 from the container 328 attached to cartridge 320 as described herein.

FIGS. 125 and 126 show sample 400 comprising fluid 703FL of the implanted device being drawn from the sample container 328 into a syringe, and the fluid 703FL from the sample container 328 being injected to a port of the apparatus 500 to analyze the sample 400 of the implanted therapeutic device 100.

Figure 127:
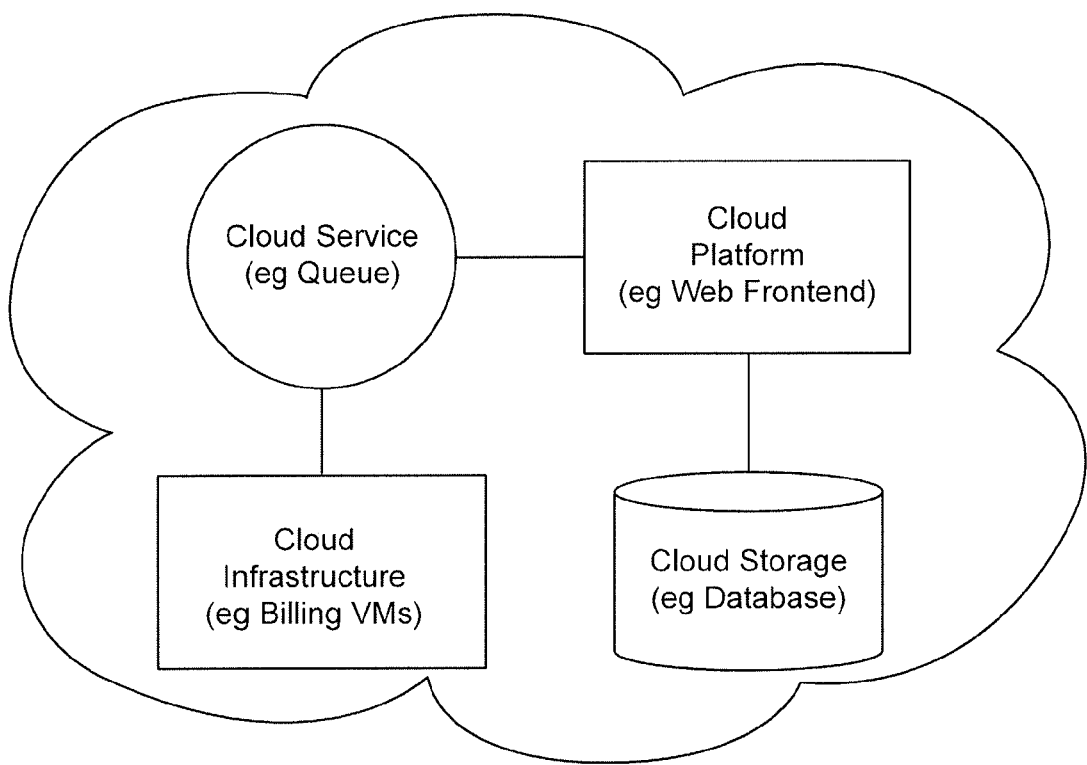
FIG. 127 shows components of the processor system of FIG. 123, in accordance with embodiments.

FIG. 127 shows components of the processor system of FIG. 123. The system of FIG. 123 may include cloud storage comprising one or more database storage devices, a cloud platform, a cloud service or a cloud infrastructure.

Figure 128:
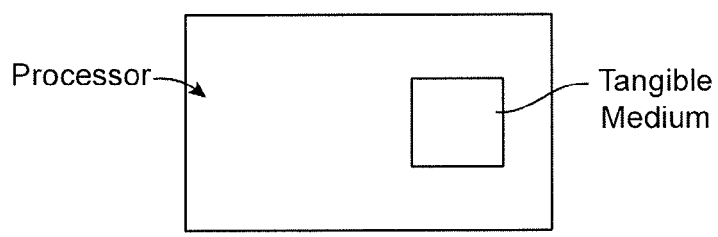
FIG. 128 shows a processor comprising a tangible medium, in accordance with embodiments.

FIG. 128 shows a processor comprising a tangible medium. Each of the plurality of devices of the processor system may comprise a processor and having tangible medium. The tangible medium may comprise a computer readable memory such as RAM, ROM, or other memory. The instructions of a computer program can be embodied on the tangible medium of one or more of the plurality of devices.

Table 4 shows an example embodiment of steps of a method 600 for diagnosing and/or treating the patient based on the data of the fluid of the device implanted in the eye 10.

| | |
|---|---|
| 601 | make incision in eye |
| 602 | obtain baseline sample through incision prior to placement of implant |
| 603 | receive baseline data of sample through incision in eye |
| 604 | receive one or more of DNA or RNA sample away from incision in eye |
| 605 | receive data of a fluid of a device implanted in an eye |
| 610 | remove component of a fluid of the eye from device 100 |
| 615 | identify the eye to modify treatment of the eye and transmit a signal to a physician. |
| 620 | transmit a signal to a physician to one or more of modify, change, adjust, or change a treatment of the eye based on the data of the fluid of the device implanted in the eye. |
| 625 | identify a therapeutic agent of the eye, a pathogen of the eye or an endogen of the eye based on the fluid of the implanted device. |
| 630 | determine amount of time for the fluid of the device comprising a component of a fluid of the eye to diffuse through the porous structure into a chamber of the device. |
| 635 | exchange fluid from the chamber of the implanted device to the container. |
| 640 | determine whether fluid of the eye comprises a one or more components of an aqueous humor of the eye or components of a vitreous humor of the eye. |
| 645 | determine that the fluid of the eye comprises a vitreous humor component and wherein the fluid of the device comprises a component of vitreous humor passed through the porous structure and determine the data of the fluid of the eye based on data of the component of the vitreous humor of the eye. |
| 650 | adjust a treatment of a therapeutic agent passed through the porous structure. |
| 655 | adjust a treatment of a therapeutic agent not passed through the porous structure. |
| 660 | receive a first identifier corresponding to first data of a first fluid of the implanted device and a second identifier corresponding to second data of a second fluid of the implanted device and compare the first data of the first fluid of the implanted device to the second data of the second fluid of the implanted device. |
| 665 | determine a function of the device implanted in the eye. |
| 670 | determine the function of the device based on one or more components of a formulation placed in the device, for example with injection. The component placed in the device may comprise one or more of a therapeutic agent, a marker to measure device function, a salt, a surfactant, a stabilizer or a particle. |
| 673 | determine the function of the device based on measurements of two or more components of a formulation placed in the device, the two or more components comprising the therapeutic agent and one or more of a marker to measure device function, a salt, a surfactant, a stabilizer or a particle. |
| 675 | determine function of the device comprising one or more of a refill efficiency, a rate of release of a therapeutic agent, or a stability of a therapeutic agent. |
| 680 | determine the refill efficiency of the therapeutic agent wherein the refill efficiency corresponds to a percentage of the therapeutic agent. |
| 690 | determine the stability of the therapeutic agent wherein the stability of the therapeutic agent corresponds to an amount of aggregated therapeutic agent of the fluid. |
| 695 | determine correspondence of data of device to a component of vitreous humor of the eye. |
| 700 | receive an input from an input device. |
| 705 | receive an identifier corresponding to the data of the fluid of the eye. |
| 710 | receive an identifier corresponding to a container to hold the fluid of the eye. |
| 715 | receive data from a fluid of a container exchanged with a chamber of a device implanted in the eye. |
| 720 | store baseline data of a baseline fluid of the eye and compare the data of the fluid of the eye baseline data of the eye. |
| 725 | baseline data corresponds to a baseline amount of therapeutic agent of a reservoir of a device implanted in the eye and wherein the data corresponds to an amount of therapeutic agent of the reservoir of the device implanted in the eye. |

| | |
|---|---|
| 730 | compare the baseline amount of the therapeutic agent of the reservoir to the amount to determine function of the device. |
| 735 | compare the baseline amount of the therapeutic agent of the reservoir to the amount to determine release of the therapeutic agent from the device. |
| 740 | determine an amount of one or more markers of the fluid of the eye to determine effectiveness of a therapeutic agent based on the one or more markers. |
| 745 | determine a susceptibility of the patient to disease progression based on the data of the fluid of the device implanted in the eye. |
| 750 | identify the patient for a change in treatment based on the data of the fluid of the device implanted in the eye. |
| 755 | identify the presence of one or more markers of the fluid of the eye. |
| 760 | determine an effectiveness of a therapeutic agent based on the one or more markers. |
| 765 | wherein the one or more markers comprises one or more of a genetic marker, genomic expression of a marker, a protein marker, a protein biomarker of ocular disease, a biomarker having a linkage to an ocular disease, a biomarker having a linkage to AMD, a biomarker associated with AMD, a biomarker corresponding to a conversion from dry AMD to wet AMD, a biomarker comprising a early predictor of conversion of wet AMD to dry AMD, or a complement cascade member. |
| 770 | wherein the one or more markers comprises a maker of expression of pro-inflammatory cytokines comprising one or more interleukin 1-beta or tissue necrosis factor alpha. |
| 775 | wherein the one or more markers comprises a marker of angiogenesis and vascular leakage such as VEGF. |
| 780 | wherein the one or more markers comprises a complement cascade member comprising one or more of complement H factor (CFH), complement factor B (CFB), complement component 2 (C2), complement component 3 (C3), complement component 5 (C5), or complement component 5a (C5A). |
| 785 | wherein the processor system comprises instructions to receive one or more of laboratory data of the fluid of the eye, microfluidics data of the fluid of the eye, chip data of the fluid of the eye, or lab on a chip data of the fluid of the eye. |
| 790 | wherein the processor system comprises instructions to the lab on the chip data and wherein the lab on the chip data corresponds to one or more of a PCR, a biochemical assay, an immunoassay based on antigen-antibody reactions, dielectrophoresis, lysed cells to extract DNA, cellular lab-on-a-chip for single-cell analysis, ion channel screening, or testing the safety and efficacy of new drug with a clinical trial. |
| 795 | wherein the processor system comprises instructions to detect one or more of bacteria, viruses or cancer based on real-time PCR of the fluid. |
| 800 | detect one or more of bacteria, viruses or cancer based on antigen-antibody reactions of the fluid of the eye. |
| 805 | detect one or more of cancer cells or bacteria based on dielectrophoresis of the fluid of the eye. |
| 810 | predict extension of an eye disease from a first eye to a second eye based on the data of the liquid of the implanted device. |
| 815 | wherein the identifier corresponds to a patient identifier corresponding to data of the patient and wherein data of the fluid of the eye is combined with the data of the patient. |
| 820 | determine a time since a prior treatment of the eye in response to the identifier. |
| 825 | determine a time since a device was last filled in response to the identifier. |
| 830 | determine a history of the patient in response to the identifier. |
| 835 | receive information of a therapeutic agent. |
| 840 | provide a library of corresponding trends of therapeutic agents and devices. |
| 845 | wherein the processor system comprises instructions of one or more of baselines, timelines, access to marker data, marker data over time, device performance profile over time, device release profile over time. |
| 850 | determine data of the patient based on the identifier and the data of the fluid and a prior identifier and prior data of a prior fluid, each from the device implanted in the eye. |
| 855 | determine a therapeutic agent of the eye, a pathogen of the eye or an endogen of the eye based on the fluid of the implant. |
| 860 | combine data of the fluid of the implanted device with a fluid of a vitreous tap of the eye and wherein the fluid of the vitreous tap comprises material having a size greater than channels of the porous structure of the implanted device. |
| 865 | identify a therapeutic agent of the eye based on the fluid of the implant. |
| 870 | identify a pathogen comprising one or more of a viral pathogen, a bacterial pathogen, or a fungal pathogen. |
| 875 | identify an endogen of the eye comprising one or more of a growth factor or an electrolyte. |
| 880 | wherein the growth factor comprises one or more of VEGF, PDGF, insulin growth factor, or insulin like growth factor. |
| 890 | adjust treatment based on an amount of the growth factor. |
| 895 | determine an output based on an interaction of the therapeutic agent of the fluid with an endogen of the eye. |
| 900 | identify the therapeutic agent, the endogen of the eye, and the therapeutic agent bound to the endogen. |
| 905 | identify the therapeutic agent, the endogen of the eye, the therapeutic agent bound to the endogen, and an aggregate of the therapeutic agent. |
| 910 | wherein the endogen comprises a growth factor and the therapeutic agent comprises an antibody fragment to bind to the growth factor. |
| 915 | wherein the growth factor comprises VEGF and the therapeutic agent comprises ranibizumab. |
| 920 | perform trend analysis of marker data and compare baseline marker amount of baseline component of eye with a plurality of follow up visits at a plurality of follow up times to determine trend of marker from baseline. |
| 925 | perform trend analysis of marker data for a plurality of markers and compare baseline marker data of the plurality of markers of eye with a plurality of follow up visits at a plurality of follow up times for each of the plurality of markers to determine trends of the plurality of markers from baseline. |

The processor system can determine changes in a marker amount over time in a patient. For example, the patient may return at approximately four month intervals for a device refill/exchange. The processor system may comprise instructions to determine and identify trends in a marker which have accumulated over that interval of time between visits. This trend analysis of marker change from baseline can provide increased sensitivity to changes in the individual patient. For example, a small and potentially relevant change can be detected within a broader band of what can be considered normal as defined by a broader patient population. For example, the normal baseline range for an amount of marker as determined with an assay of a patient population can be within a range from about 0.1 to about 1.0. The patient can present sequential values over a year's time of 0.2, 0.6, 0.9 at four months, eight months and twelve months, respectively. Although these values of the marker can be considered normal results based on comparison with the patient population, the trend can indicate early disease progression based on comparison of the values from baseline and the instructions of the processor system can be configured to identify the patient based on the trends of the marker and report the patient and the values corresponding to the trend to the health care provider, for example. The trend analysis and comparison from baseline can be performed for each of a plurality of markers as described herein at a plurality of times.

The method of Table 4 can be implemented with the processor system, and the steps shown in Table 4 may correspond to instructions of a computer program embodied on the computer readable memory of the processor system.

Although Table 4 shows a particular method in accordance with an embodiment, a person of ordinary skill in the art will recognize many adaptations and variations based on the teachings described herein. For example, the steps of the method can be removed, the order changed, or combinations thereof. Further, the steps may comprise subs-steps, and the steps may be repeated.

The embodiments as described herein can be combined in many ways including alternatively or in combination.

As used herein, like numerals and/or letters can denote like elements in the drawings as will be apparent to a person of ordinary skill in the art.

EXPERIMENTAL

Based on the teachings described herein, a person of ordinary skill in the art can conduct experiments to determine empirically assays and accumulation rates of markers of the eye 10. The amount of a marker corresponding to a clinical effect can be determined empirically with assays developed for the fluid sample from the implanted device. The assay from the implanted device may comprise one or more components from known commercially available assays. Known commercially available assays include the known ELISA assay, fluorometric binding, array assays, beads with beads combined with antibodies such as the Bioplex™ system commercially available from BioRad. Alternatively or in combination, the accumulated sample fluid removed from the implanted device may be analyzed with known methods of assay analysis suitable for combination in accordance with embodiments. U.S. patent application Ser. No. 12/856,394, published as US2011/0117083, entitled "Biological Markers for Monitoring Response to VEFG Agonists" in the name of Bais et al., the full disclosure of which has been previously incorporated herein by reference, describes genes, assays and markers suitable for incorporation and combination in accordance with embodiments described herein. For example, the biomarker measured from the reservoir chamber may comprise a biomarker of the plasma of the patient and correspond to one or more of genes, RNA or DNA of the patient, for example. Pharmokinetic studies and assays suitable for incorporation in accordance with embodiments as described herein are noted in a publication entitled, "Preclinical Pharmokinetics of Ranibizumab (rhuFabV2) after a single intravitreal administration", *Investigative Ophthalmology & Visual Science*, February 2005, Vol. 46, No. 2, for example, which is incorporated by reference in its entirety herein.

The amount of each marker can be determined empirically as part of assays developed to one or more of diagnose or treat the eye 10 based on the teachings described herein. The accumulation of the component of the vitreous can be assayed and measured in many ways, for example with assays of one or more marker components of the vitreous as described herein. For example, for each genetic marker evaluated having sensitivity to the disease of the eye 10, one could determine a corresponding comparison genetic marker that has a substantially decreased sensitivity to the therapeutic agent and also a substantially similar relative abundance so as to inhibit over amplification of one marker relative to the other marker. Alternatively or in combination, for each protein marker evaluated having sensitivity to the disease of the eye 10, one could determine a corresponding comparison protein marker that has a substantially decreased sensitivity to the therapeutic agent and also a substantially similar relative abundance. Based on the teachings described herein, one or more protein markers, genetic markers, or genomic markers can be assayed and compared to diagnose or treat the patient, or combinations thereof.

Experiments have been conducted to show displacement of fluid from an implantable device into an injector cartridge having a container to store fluid from the therapeutic device 100 suitable for analysis as described herein.

Figure 129:
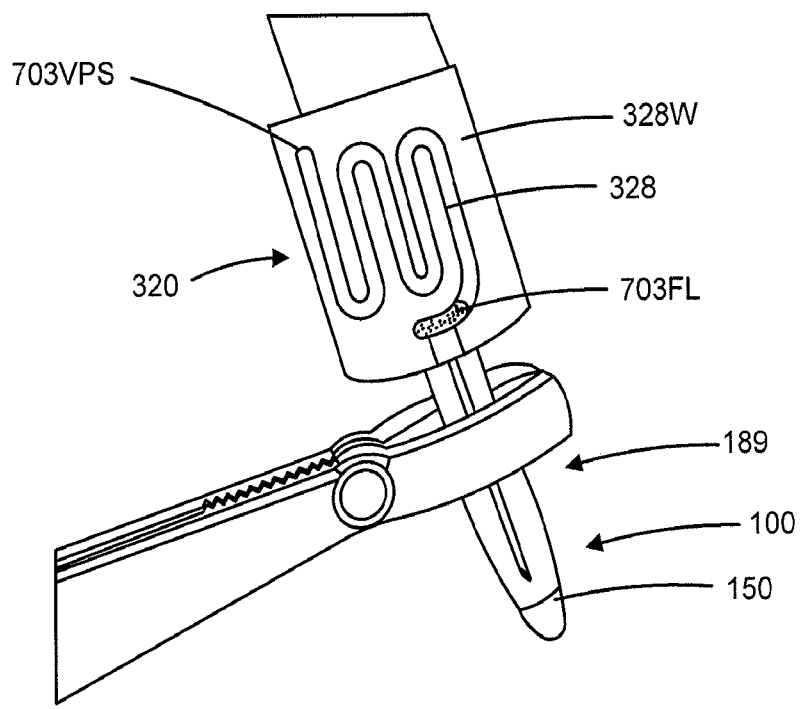
FIG. 129, FIG. 130, and FIG. 131 show an injector cartridge having a container to receive the implanted device fluid and a porous vent structure down stream of the container such that the porous structure of the cartridge comprises a valve to provide a bolus injection, in accordance with embodiments.
Figure 130:
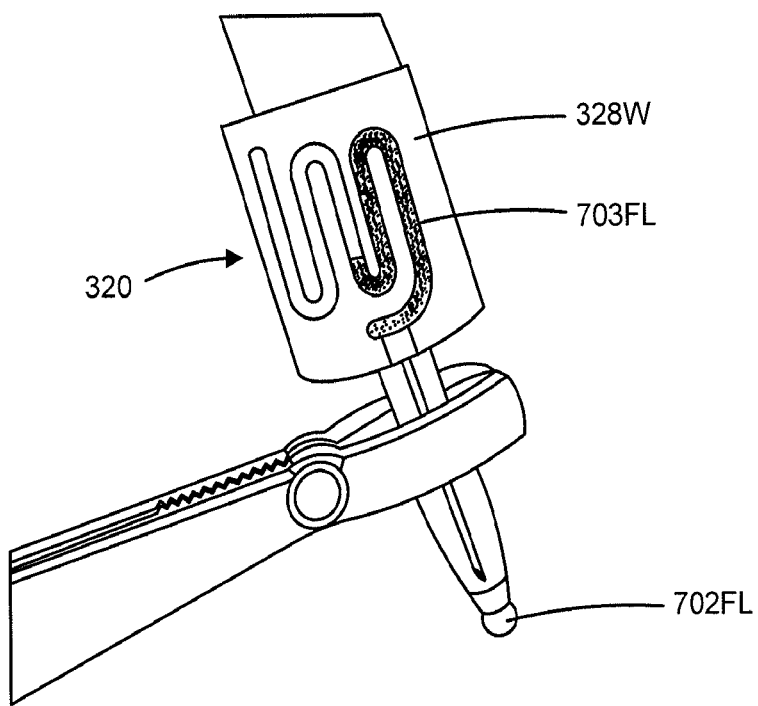
Figure 131:
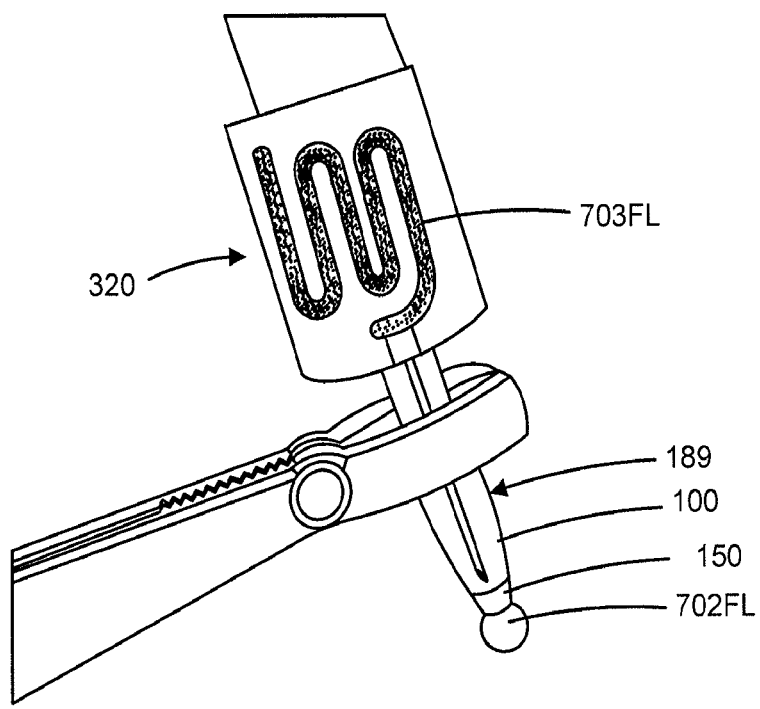

FIGS. 129 to 131 illustrate an embodiment of an injector cartridge having a container 328 to receive the implanted device fluid 703FL and a porous vent structure 703VPS downstream of the container 328 such that the porous structure 150 of the cartridge 320 comprises a valve to provide a bolus injection. The cartridge can be coupled to an injection syringe and the at least one needle comprises a first needle and a second needle. The injection lumen can extend to a distal end portion of the therapeutic device 100 and vent of the outflow channel can be located on a proximal portion of the therapeutic device 100. The injector cartridge can comprise the deformable stop 189DS to reversibly deform when coupled to the conjunctiva 16 of the eye 10. The injector cartridge comprises a window 328W to view the fluid of the implantable device received with the container.

The implantable device may include an axis that extends at an angle about 60 to 70° down off the horizontal. Red solution may be contained inside the device which may have an approximate density of 1 g/ml, while clear refill solution may have an approximate density of 1 g/ml as well. The approximate refill rate can be 1.3 µl/sec. A total of 45 µl can be injected into a device. In addition, the device capacity may be 25 µl. This device configuration and refill condition may yield an approximate refill efficiency of 60-90%.

FIG. 129 may, for example, show the fluid flow after approximately 10 µl of injection. FIG. 129 may have been taken after approximately 10 µl had been injected into the device.

FIG. 130 shows an example of the outflow of the device fluid 702FL after approximately 25 µl has been injected into the device 100. FIG. 130 may have been taken after approximately 25 µl have been injected into the device. A substantial portion of the bolus injection may have been passed through the porous structure 150 of device 100.

FIG. 131 shows an example of the outflow and bolus 702FL after approximately 45 µl has been injected. FIG. 131 may have been taken after approximately 45 µl has been injected into the device.

Figure 132:
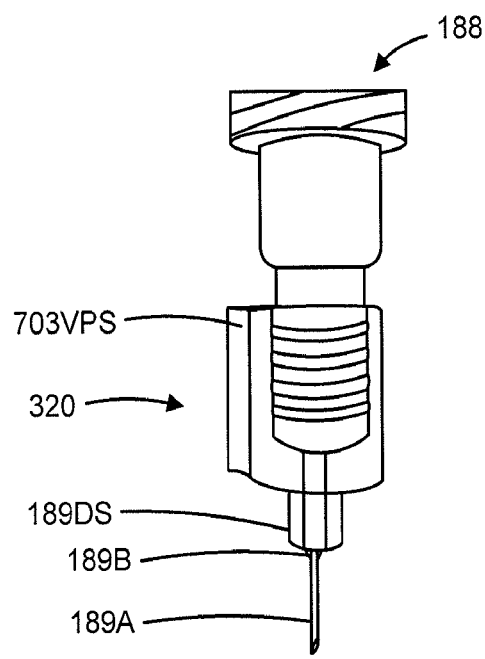
FIGS. 132 and 133 show a side view and a front view, respectively of the exchange needle apparatus. The porous structure 703VPS of the outflow path can provide a substantial resistance to flow of the fluid comprising liquid so as to provide the bolus injection, in accordance with embodiments.
Figure 133:
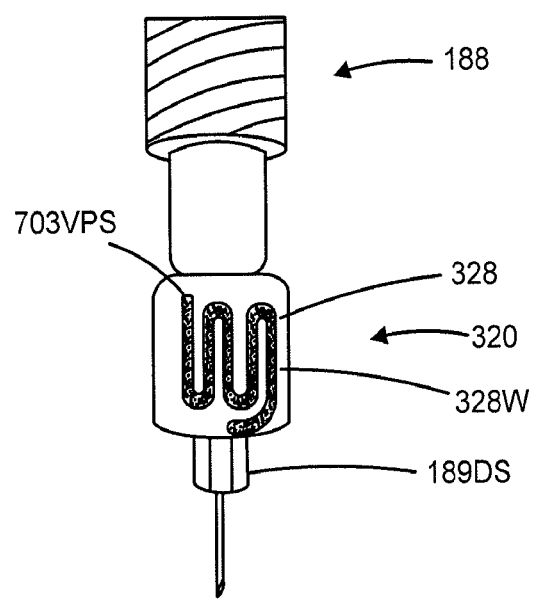

FIGS. 132 and 133 show a side view of the exchange needle apparatus and a front view, respectively, of the exchange needle apparatus. The porous structure 150 of the outflow path can provide a substantial resistance to flow of the fluid comprising liquid so as to provide the bolus injection. The cartridge comprises the deformable stop 189DS as described herein to couple to the conjunctiva 16 of the eye 10.

FIG. 132 shows an example side view of the exchange needle. This is a bi-needle system with the longer needle 189A doing the injection while the short needle 189B allows the fluid to escape into the containment track. FIG. 133 shows an example front view that shows the containment track with the porous vent at the top left end of the track. This porous vent allows for air to escape with a low amount of resistance while causing a great resistance to the fluid pass through. The resistance to air passing though can create a level of pressure in the system to cause a bolus of new exchange fluid to pass through the implantable device porous structure 150.

While the exemplary embodiments have been described in some detail, by way of example and for clarity of understanding, those of ordinary skill in the art will recognize that a variety of modifications, adaptations, and changes may be employed. Hence, the scope of the present disclosure should be limited solely by the appended claims.

APPENDIX I

Therapeutic Agent List

| Generic Name | Brands (Companies) | Category | Indication | Molecular Weight |
|---|---|---|---|---|
| 2-Methoxy-estradiol analogs | (Paloma Pharmaceuticals) | Angiogenesis inhibitors | AMD | |
| 3-aminothalidomide | | | | |
| 13-cis retinoic acid | Accutane TM (Roche Pharmaceuticals) | | | |
| A0003 | (Aqumen BioPharmaceuticals) | A0003 | AMD | |
| A5b1 integrin inhibitor | (Jerini Ophthalmic); (Ophthotech) | Inhibitors of a5b1 integrin | AMD | |
| Abarelix | Plenaxis ™ (Praecis Pharmaceuticals) | Anti-Testosterone Agents; Antineoplastic Agents | For palliative treatment of advanced prostate cancer. | 37731 |
| Abatacept | Orencia ™ (Bristol-Myers Squibb) | Antirheumatic Agents | For the second line reduction of the signs and symptoms of moderate-to-severe active rheumatoid arthritis, inducing inducing major clinical response, slowing the progression of structural damage, and improving physical function in adult patients who have | 37697 |

APPENDIX I-continued

Therapeutic Agent List

| Generic Name | Brands (Companies) | Category | Indication | Molecular Weight |
|---|---|---|---|---|
| Abciximab | ReoPro ™; ReoPro ™ (Centocor) | Anticoagulants; Antiplatelet Agents | For treatment of myocardial infarction, adjunct to percutaneous 145oronary intervention, unstable angina | 42632 |
| ABT-578 | (Abbott-Laboratories) | Limus Immunophilin Binding Compounds | | |
| Acetonide | | | | |
| Adalimumab | Humira ™ (Abbott Laboratories) | Antirheumatic Agents; Immunomodulatory Agents | Uveitis, AMD | 25645 |
| Aldesleukin | Proleukin ™; Proleukin ™ (Chiron Corp) | Antineoplastic Agents | For treatment of adults with metastatic renal cell carcinoma | 61118 |
| Alefacept | Amevive ™ | Immunomodulatory Agents; Immunosuppressive Agents | For treatment of moderate to severe chronic plaque psoriasis | 42632 |
| Alemtuzumab | Campath ™; Campath ™ (ILEX Pharmaceuticals LP); MabCampath ™ | Antineoplastic Agents | For treatment of B-cell chronic lymphocytic leukemia | 6614 |
| Alpha-1-proteinase inhibitor | Aralast ™ (Baxter); Prolastin ™ (Talecris Biotherapeutics C formerly Bayer) | Enzyme Replacement Agents | For treatment of panacinar emphysema | 28518 |
| Alteplase | Activase ™ (Genentech Inc) | Thrombolytic Agents | For management of acute myocardial infarction, acute ischemic strok and for lysis of acute pulmonary emboli | 54732 |
| AMG-1470 | | | | |
| Anakinra | Kineret ™ (Amgen Inc) | Anti-Inflammatory Agents, Non-Steroidal; Antirheumatic Agents; Immunomodulatory Agents | For the treatment of adult rheumatoid arthritis. | 65403 |

APPENDIX I-continued

Therapeutic Agent List

| Generic Name | Brands (Companies) | Category | Indication | Molecular Weight |
|---|---|---|---|---|
| Anecortave acetate | | | | |
| Angiostatin | | | | |
| Anistreplase | Eminase ™ (Wulfing Pharma GmbH) | Thrombolytic Agents | For lysis of acute pulmonary emboli, intracoronary emboli and management of myocardial infarction | 54732 |
| Anti-angiogenesis peptides | (Eyecopharm) | Anti-angiogenesis peptides | AMD | |
| Anti-angiogenesis antibodies, TRC093, TRC105 | (TRACON Pharma) | Anti-angiogenesis antibodies | AMD | |
| Anti-angiogeric bifunctional protein | Icon-1 ™ (Iconic Therapeutics) | Anti-angiogeric bifunctional protein, Icon-1 | AMD | |
| Anti-endothelial growth factor | | | | |
| Anti-hemophilic Factor | Advate ™; Alphanate ™; Bioclate ™; Helixate ™; Helixate FS ™; Hemofil M ™; Humate-P ™; Hyate: C ™; Koate-HP ™; Kogenate ™; Kogenate FS ™; Monarc-M ™; Monoclate-P ™; ReFacto ™; Xyntha ™ | Coagulants; Thrombotic Agents | For the treatment of hemophilia A, von Willebrand diseae and Factor XIII deficiency | 70037 |
| Anti-thymocyte globulin | Genzyme); Thymoglobulin ™ (SangStat Medical | Immunomodulatory Agents | For prevention of renal transplant rejection | 37173 |
| Anti-hypertensive MC1101 | (Macu-CLEAR) | Anti-hypertensive MC1101 | AMD | |
| Anti-platelet devired growth factor | | | | |
| Anti-VEGF | (Neurotech); Avastin ™ (NeoVista) | Anti-VEGF | AMD | |
| AP23841 | (Ariad) | Limus Immunophilin Binding Compounds | | |
| ARC1905 | Ophthotech | Complement Cascade Inhibitor (Factor C5) | | |
| Aprotinin | Trasylol ™ | Antifibrinolytic Agents | For prophylactic use to reduce perioperative blood loss and the need for blood transfusion in patients undergoing cardiopulmonary bypass in the course of coronary artery bypass graft surgery who are at an increased risk for blood loss and blood transfusio | 90569 |
| Arcitumomab | CEA-Scan ™ | Diagnostic Agents; Imaging Agents | For imaging colorectal tumors | 57561 |
| Asparaginase | Elspar ™ (Merck & Co. Inc) | Antineoplastic Agents | For treatment of acute lympocytic leukemia and non-Hodgkins lymphoma | 132.118 |
| Axitinib | | Tyrosine Kinase Inhibitors | | 386 |
| Basiliximab | Simulect ™ (Novartis Pharmaceuticals) | Immunomodulatory Agents; Immunosuppressive Agents | For prophylactic treatment of kidney transplant rejection | 61118 |
| Becaplermin | Regranex ™; Regranex ™ (OMJ Pharmaceuticals) | Anti-Ulcer Agents; Topical | For topical treatment of skin ulcers (from diabetes) | 123969 |
| Bevacizumab | Avastin ™; Avastin ™ (Genentech Inc) | Anti-angiogenesis Agents; Anti-neoplastic Agents | For treatment of metastatic colorectal cancer | 27043 |
| Bivalirudin | Angiomax ™; Angiomax ™ (Medicines Co or MDCO); Angiox ™ | Anti-coagulants; Anti-thrombotic Agents | For treatment of heparin-induced thrombocytopenia | 70037 |
| Bortezomib | | Proteosome Inhibitors | | |
| Bosutinib | | Tyrosine Kinase Inhibitors | | 530 |

APPENDIX I-continued

Therapeutic Agent List

| Generic Name | Brands (Companies) | Category | Indication | Molecular Weight |
|---|---|---|---|---|
| Botulinum Toxin Type A | BOTOX ™ (Allegran Inc); BOTOX Cosmetic ™ (Allegran Inc); Botox ™; Dysport ™ | Anti-Wrinkle Agents; Anti-dystonic Agents; Neuro-muscular Blocking Agents | For the treatment of cervical dystonia in adults to decrease the severity of abnormal head position and neck pain associated with cervical dystonia. Also for the treatment of severe primary axillary hyperhidrosis that is inadequately managed with topical | 23315 |
| Botulinum Toxin Type B | Myobloc ™ (Solstice Neurosciences); Neurobloc ™ (Solstice Neurosciences) | Anti-dystonic Agents | For the treatment of patients with cervical dystonia to reduce the severity of abnormal head position and neck pain associated with cervical dystonia. | 12902 |
| C5 inhibitor | (Jerini Ophthalmic); (Ophthotech) | Inhibitors of C5 | AMD | |
| Cal101 | Calistoga | PI3Kdelta Inhibitor | AMD, DME | |
| Canstatin | | | | |
| Capromab | Prosta-Scint ™ (Cytogen Corp) | Imaging Agents | For diagnosis of prostate cancer and detection of intra-pelvic metastases | 84331 |
| Captopril | | ACE Inhibitors | | |
| CCI-779 | (Wyeth) | Limus Immunophilin Binding Compounds | | |
| Cediranib | | Tyrosine Kinase Inhibitors | | 450 |
| Celecoxib | | Cyclooxygenase Inhibitors | | |
| Cetrorelix | Cetrotide ™ | Hormone Antagonists; Infertility Agents | For the inhibition of premature LH surges in women undergoing controlled ovarian stimulation | 78617 |
| Cetuximab | Erbitux ™; Erbitux ™ (ImClone Systems Inc) | Anti-neoplastic Agents | For treatment of metastatic colorectal cancer. | 42632 |
| Choriogonadotropin alfa | Novarel ™; Ovidrel ™; Pregnyl ™; Profasi ™ (Neurotech) | Fertility Agents; Gonadotropins | For the treatment of female infertility | 78617 |
| Cilary neurotrophic factor | | Cilary neurotrophic factor | AMD | |
| Coagulation Factor IX | Benefix ™ (Genetics Institute) | Coagulants; Thrombotic Agents | For treatment of hemophilia (Christmas disease). | 267012 |
| Coagulation factor VIIa | Novo-Seven ™ (Novo Nordisk) | Coagulants; Thrombotic Agents | For treatment of hemorrhagic complications in hemophilia A and B | 54732 |
| Colchicines | | | | |
| Collagenase | Cordase ™; Santyl ™ (Advance Biofactures Corp); Xiaflextm ™ (Optherion); | Anti-Ulcer Agents; Topical | For treatment of chronic dermal ulcers and severe skin burns | 138885 |
| Complement factor H recombinant | (Taligen Therapeutics) | Complement factor H recombinant | AMD, Geographic Atrophy | |
| Compstatin derivative peptide, POT-4 | (Potentia Pharmaceuticals) | Complement Factor C3 Inhibitors; Compstatin Derivative Peptides | AMD | |
| Corticotropin | ACTH ™; Acethropan ™; Acortan ™; Acthar ™; Exacthin ™; H.P. Acthar Gel ™; Isactid ™; Purified cortrophin gel ™; Reacthin ™; Solacthyl ™; Tubex | Diagnostic Agents | For use as a diagnostic agent in the screening of patients presumed to have adrenocortical insufficiency. | 33927 |
| Cosyntropin | Cortrosyn ™; Synacthen depot ™ | Diagnostic Agents | For use as a diagnostic agent in the screening of patients presumed to have adrenocortical insufficiency. | 33927 |
| Cyclophilins | | Limus Immunophilin Binding Compounds | | |

APPENDIX I-continued

Therapeutic Agent List

| Generic Name | Brands (Companies) | Category | Indication | Molecular Weight |
|---|---|---|---|---|
| Cyclosporine | Gengraf ™ (Abbott labs); Neoral ™ (Novartis); Restasis ™; Restasis ™ (Allergan Inc); Sandimmune ™ (Novartis); Sangcya ™ | Antifungal Agents; Antirheumatic Agents; Dermatologic Agents; Enzyme Inhibitors; Immunomodulatory Agents; Immunosuppressive Agents | For treatment of transplant rejection, rheumatoid arthritis, severe psoriasis | 32953 |
| Daclizumab | Zenapax ™ (Hoffmann-La Roche Inc) | Immunomodulatory Agents; Immunosuppressive Agents | For prevention of renal transplant rejection ; Uveitis | 61118 |
| Darbepoetin alfa | Aranesp ™ (Amgen Inc.) | Antianemic Agents | For the treatment of anemia (from renal transplants or certain HIV treatment) | 55066 |
| Dasatinib | | Tyrosine Kinase Inhibitors | | 488 |
| Defibrotide | Dasovas ™; Noravid ™; Prociclide ™ | Antithrombotic Agents | Defibrotide is used to treat or prevent a failure of normal blood flow (occlusive venous disease, OVD) in the liver of patients who have had bone marrow transplants or received certain drugs such as oral estrogens, mercaptopurine, and many others. | 36512 |
| Denileukin diftitox | Ontak ™ | Antineoplastic Agents | For treatment of cutaneous T-cell lymphoma | 61118 |
| Desmopressin | Adiuretin ™; Concentraid ™; Stimate ™ | Antidiuretic Agents; Hemostatic; Renal Agents | For the management of primary nocturnal enuresis and indicated as antidiuretic replacement therapy in the management of central diabetes insipidus and for the management of the temporary polyuria and polydipsia following head trauma or surgery in the pitu | 46800 |
| Dexamethasone | Ozurdex ™ (Allergan) | Glucocorticoid | DME, inflammation, macular edema following branch retinal vein occlusion (BRVO) or central retinal vein occlusion (CRVO) | 392 |
| Diclofenac | | Cyclooxygenase Inhibitors | | |
| Dithiocarbamate | | NFκB Inhibitor | | |
| Dornase Alfa | Dilor ™; Dilor-400 ™; Lufyllin ™; Lufyllin-400 ™; Neothylline ™; Pulmozyme ™ (Genentech Inc) | Enzyme Replacement Agents | For the treatment of cystic fibrosis. | 7656 (double strand) |
| Drotrecogin alfa | Xigris ™; Xigris ™ (Eli Lilly & Co) | Antisepsis Agents | For treatment of severe sepsis | 267012 |
| Eculizumab | Soliris ™; Soliris ™ (Alexion Pharmaceuticals) | Complement Cascade Inhibitor (Factor C5) | AMD | 188333 |
| Efalizumab | Raptiva ™; Raptiva ™ (Genentech Inc) | Immunomodulatory Agents; Immunosuppressive Agents | For the treatment of adult patients with moderate to severe chronic plaque psoriasis, who are candidates for phototherapy or systemic therapy. | 128771 |
| Endostatin | | | | |
| Enfuvirtide | Fuzeon ™; Fuzeon ™ (Roche Pharmaceuticals) | Anti-HIV Agents; HIV Fusion Inhibitors | For treatment of HIV AIDS | 16768 |
| Epoetin alfa | Epogen ™ (Amgen Inc.); Epogin ™ (Chugai); Epomax ™ (Elanex); Eprex ™ (Janssen-Cilag. Ortho Biologics LLC); Neo-Recormon ™ (Roche); | Antianemic Agents | For treatment of anemia (from renal transplants or certain HIV treatment) | 55066 |

APPENDIX I-continued

Therapeutic Agent List

| Generic Name | Brands (Companies) | Category | Indication | Molecular Weight |
|---|---|---|---|---|
| | Procrit ™ (Ortho Biotech); Recormon ™ (Roche) | | | |
| Eptifibatide | Integrilin ™; Integrilin ™ (Millennium Pharm) | Anti-coagulants; Antiplatelet Agents; Platelet Aggregation Inhibitors | For treatment of myocardial infarction and acute coronary syndrome. | 7128 |
| Erlotinib | | Tyrosine Kinase Inhibitors | | 393 |
| Etanercept | Enbrel ™; Enbrel ™ (Immunex Corp) | Anti-rheumatic Agents; Immuno-modulatory Agents | Uveitis, AMD | 25645 |
| Everolimus | Novartis | Limus Immuno-philin Binding Compounds, mTOR | AMD | |
| Exenatide | Byetta ™; Byetta ™ (Amylin/ Eli Lilly) | | Indicated as adjunctive therapy to improve glycemic control in patients with Type 2 diabetes mellitus who are taking metformin, a sulfonylurea, or a combination of both, but have not achieved adequate glycemic control. | 53060 |
| FCFD4514S | Genentech/ Roche | Complement Cascade Inhibitor (Factor D) | AMD, Geographic Atrophy | |
| Felypressin | Feli-presina ™ [INN-Spanish]; Feli-pressina ™ [DCIT]; Fely-pressin ™ [USAN:BAN:INN]; Fely-pressine ™ [INN-French]; Fely-pressinum ™ [INN-Latin]; Octa-pressin ™ | Renal Agents; Vaso-constrictor Agents | For use as an alternative to adrenaline as a 153calizing agent, provided that local ischaemia is not essential. | 46800 |
| Fenretinide | Sirion/ reVision Therapeutics | Binding Protein Antagonist for Oral Vitamin A | AMD, Geographic Atrophy | |
| Filgrastim | Neupogen ™ (Amgen Inc.) | Anti-Infective Agents; Anti-neutropenic Agents; Immuno-modulatory Agents | Increases leukocyte production, for treatment in non-myeloid cancer, neutropenia and bone marrow transplant | 28518 |
| FK605-binding proteins, FKBPs | | Limus Immuno philin-Binding Compounds | | |
| Fluocinolone Acetonide | Retisert ™ (Bausch & Lomb); Iluvien ™ (Alimera Sciences, Inc.) | Gluco-corticoid | Retinal inflammation, diabetic macular edema | 453 |
| Follitropin beta | Follistim ™ (Organon); Gonal F ™; Gonal-F ™ | Fertility Agents | For treatment of female infertility | 78296 |
| Fumagillin | | | | |
| Galsulfase | Na-glazyme ™; Na-glazyme ™ (BioMarin Pharma-ceuticals) | Enzyme Replacement Agents | For the treatment of adults and children with Mucopoly-saccharidosis VI. | 47047 |
| Gefitinib | | Tyrosine Kinase Inhibitors | | 447 |
| Gemtu-zumab ozogamicin | Mylotarg ™; Mylotarg ™ (Wyeth) | Anti-neoplastic Agents | For treatment of acute myeloid leukemia | 39826 |
| Glatiramer Acetate | Copaxone ™ | Adjuvants, Immuno-logic; Immuno-suppressive Agents | For reduction of the frequency of relapses in patients with Relapsing-Remitting Multiple Sclerosis. | 29914 |
| Glucagon recombinant | GlucaGen ™ (Novo Nordisk); Glucagon ™ (Eli Lilly) | Antihypo-glycemic Agents | For treatment of severe hypoglycemia, also used in gastrointestinal imaging | 54009 |
| Goserelin | Zoladex ™ | Anti-neoplastic Agents; Anti-neoplastic Agents, Hormonal | Breast cancer; Prostate carcinoma; Endometriosis | 78617 |
| Human Serum Albumin | Albutein ™ (Alpha Therapeutic Corp) | Serum substitutes | For treatment of severe blood loss, hypervolemia, hypoproteinemia | 39000 |

APPENDIX I-continued

Therapeutic Agent List

| Generic Name | Brands (Companies) | Category | Indication | Molecular Weight |
|---|---|---|---|---|
| Hyaluron-idase | Vitragan ™; Vitrase ™; Vitrase ™ (Ista Pharma) | Anesthetic Adjuvants; Permeabilizing Agents | For increase of absorption and distribution of other injected drugs and for rehydration | 69367 |
| Ibritumomab | Zevalin ™ (IDEC Pharmaceuticals) | Antineoplastic Agents | For treatment of non-Hodgkin's lymphoma | 33078 |
| Idursulfase | Elaprase ™ (Shire Pharmaceuticals) | Enzyme Replacement Agents | For the treatment of Hunter syndrome in adults and children ages 5 and older. | 47047 |
| Imatinib | | Tyrosine Kinase Inhibitors | AMD, DME | 494 |
| Immune globulin | Civacir ™; Flebogamma ™ (Instituto Grifols SA); Gamunex ™ (Talecris Biotherapeutics) | Anti-Infectives; Immunomodulatory Agents | For treatment of immunodeficiencies, thrombocytopenic purpura, Kawasaki disease, gamma-blobulinemia, leukemia, bone transplant | 42632 |
| Infliximab | Remicade ™ (Centocor Inc) | Immunomodulatory Agents; Immunosuppressive Agents | Uveitis, AMD | 25645 |
| Insulin Glargine recombinant | Lantus ™ | Hypoglycemic Agents | For treatment of diabetes (type I and II) | 156308 |
| Insulin Lyspro recombinant | Humalog ™ (Eli Lily); Insulin Lispro (Eli Lily) | Hypoglycemic Agents | For treatment of diabetes (type I and II) | 154795 |
| Insulin recombinant | Novolin R ™ (Novo Nordisk) | Hypoglycemic Agents | For treatment of diabetes (type I and II) | 156308 |
| Insulin, porcine | Iletin II ™ | Hypoglycemic Agents | For the treatment of diabetes (type I and II) | 156308 |
| Interferon | | | | |
| Interferon Alfa-2a, Recombinant | Roferon A ™ (Hoffmann-La Roche Inc); Veldona ™ (Amarillo Biosciences) | Antineoplastic Agents; Antiviral Agents | For treatment of chronic hepatitis C, hairy cell leukemia, AIDS-related Kaposi's sarcoma, and chronic myelogenous leukemia. Also for the treatment of oral warts arising from HIV infection. | 57759 |
| Interferon Alfa-2b, Recombinant | Intron A ™ (Schering Corp) | Antineoplastic Agents; Antiviral Agents; Immunomodulatory Agents | For the treatment of hairy cell leukemia, malignant melanoma, and AIDS-related Kaposi's sarcoma. | 57759 |
| Interferon alfacon-1 | Advaferon ™; Infergen ™ (InterMune Inc) | Antineoplastic Agents; Antiviral Agents; Immunomodulatory Agents | For treatment of hairy cell leukemia, malignant melanoma, and AIDS-related Kaposi's sarcoma | 57759 |
| Interferon alfa-n1 | Wellferon ™ (GlaxoSmithKline) | Antiviral Agents; Immunomodulatory Agents | For treatment of venereal or genital warts caused by the Human Papiloma Virus | 57759 |
| Interferon alfa-n3 | Alferon ™ (Interferon Sciences Inc.); Alferon LDO ™; Alferon N Injection ™ | Antineoplastic Agents; Antiviral Agents; Immunomodulatory Agents | For the intralesional treatment of refractory or recurring external condylomata 155cuminate. | 57759 |
| Interferon beta-1b | Betaseron ™ (Chiron Corp) | Antiviral Agents; Immunomodulatory Agents | For treatment of relapsing/remitting multiple sclerosis | 57759 |
| Interferon gamma-1b | Actimmune ™; Actimmune ™ (InterMune Inc) | Antiviral Agents; Immunomodulatory Agents | For treatment of Chronic granulomatous disease, Osteopetrosis | 37835 |
| Lapatinib | | Tyrosine Kinase Inhibitors | | 581 |
| Lepirudin | Refludan ™ | Anticoagulants; Antithrombotic Agents; Fibrinolytic Agents | For the treatment of heparin-induced thrombocytopenia | 70037 |
| Lestaurtinib | | Tyrosine Kinase Inhibitors | | 439 |
| Leuprolide | Eligard ™ (Atrix Labs/QLT Inc) | Anti-Estrogen Agents; Antineoplastic Agents | For treatment of prostate cancer, endometriosis, uterine fibroids and premature puberty | 37731 |
| Lutropin alfa | Luveris ™ (Serono) | Fertility Agents | For treatment of female infertility | 78617 |

APPENDIX I-continued

Therapeutic Agent List

| Generic Name | Brands (Companies) | Category | Indication | Molecular Weight |
|---|---|---|---|---|
| Mecasermin | Increlex ™; Increlex ™ (Tercica); Iplex | | For the long-term treatment of growth failure in pediatric patients with Primary IGFD or with GH gene deletion who have developed neutralizing antibodies to GH. It is not indicated to treat Secondary IGFD resulting from GH deficiency, malnutrition, hypoth | 154795 |
| Menotropins | Repronex ™ | Fertility Agents | For treatment of female infertility | 78617 |
| Methotrexate | | Immunomodulatory | Uveitis, DME | |
| mTOR inhibitors | | | | |
| Muromonab | Orthoclone OKT3 ™ (Ortho Biotech) | Immunomodulatory Agents; Immunosuppressive Agents | For treatment of organ transplant recipients, prevention of organ rejection | 23148 |
| Natalizumab | Tysabri ™ | Immunomodulatory Agents | For treatment of multiple sclerosis. | 115334 |
| Nepafenac | | Cyclooxygenase Inhibitors | | |
| Nesiritide | Natrecor ™ | Cardiac drugs | For the intravenous treatment of patients with acutely decompensated congestive heart failure who have dyspnea at rest or with minimal activity. | 118921 |
| Nilotinib | | Tyrosine Kinase Inhibitors | | 530 |
| NS398 | | Cyclooxygenase Inhibitors | | |
| Octreotide | Atrigel ™; Longastatin ™; Sandostatin ™; Sandostatin LAR ™; Sandostatin LAR ™ | Anabolic Agents; Antineoplastic Agents, Hormonal; Gastrointestinal Agents; | For treatment of acromegaly and reduction of side effects from cancer chemotherapy | 42687 |
| | (Novartis) | Hormone Replacement Agents | | |
| Omalizumab | Xolair ™ (Genentech Inc) | Anti-Asthmatic Agents; Immunomodulatory Agents | For treatment of asthma caused by allergies | 29596 |
| Oprelvekin | Neumega ™; Neumega ™ (Genetics Institute Inc) | Coagulants; Thrombotics Vaccines | Increases reduced platelet levels due to chemotherapy | 45223 |
| OspA lipoprotein | LYMErix ™ (SmithKline Beecham) | | For prophylactic treatment of Lyme Disease | 95348 |
| OT-551 | (Othera) | Antioxidant eyedrop | AMD | |
| Oxytocin | Oxytocin ™ (BAM Biotech); Pitocin ™ (Parke-Davis); Syntocinon ™ (Sandoz) | Antitocolytic Agents; Labor Induction Agents; Oxytocics | To assist in labor, elective labor induction, uterine contraction induction | 12722 |
| Palifermin | Kepivance ™ (Amgen Inc) | Antimucositis Agents | For treatment of mucositis (mouth sores) | 138885 |
| Palivizumab | Synagis ™ | Antiviral Agents | For treatment of respiratory diseases casued by respiratory syncytial virus | 63689 |
| Panitumumab | Vectibix ™; Vectibix ™ (Amgen) | Antineoplastic Agents | For the treatment of EGFR-expressing, metastatic colorectal carcinoma with disease progression on or following fluoropyrimidine-, oxaliplatin-, and irinotecan-containing chemotherapy regimens. | 134279 |
| PDGF inhibitor | (Jerini Ophthalmic); (Ophthotech) | Inhibitors of PDGF | AMD | |
| PEDF (pigment epithelium derived factor) | | | | |
| Pegademase bovine | Adagen ™ (Enzon Inc.) | Enzyme Replacement Agents | For treatment of adenosine deaminase deficiency | 36512 |
| Pegaptanib | Macugen ™ | Oligonucleotide | For the treatment of neovascular (wet) age-related macular degeneration. | 103121 |

APPENDIX I-continued

Therapeutic Agent List

| Generic Name | Brands (Companies) | Category | Indication | Molecular Weight |
|---|---|---|---|---|
| Pegaspargase | Oncaspar ™ (Enzon Inc) | Antineoplastic Agents | For treatment of acute lymphoblastic leukemia | 132.118 |
| Pegfilgrastim | Neulasta ™ (Amgen Inc.) | Anti-Infective Agents; Anti-neutropenic Agents; Immunomodulatory Agents | Increases leukocyte production, for treatment in non-myeloid cancer, neutropenia and bone marrow transplant | 28518 |
| Peginterferon alfa-2a | Pegasys ™ (Hoffman-La Roche Inc) | Antineoplastic Agents; Antiviral Agents; Immunomodulatory Agents | For treatment of hairy cell leukemia, malignant melanoma, and AIDS-related Kaposi's sarcoma. | 57759 |
| Peginterferon alfa-2b | PEG-Intron (Schering Corp); Unitron PEG ™ | Antineoplastic Agents; Antiviral Agents; Immunomodulatory Agents | For the treatment of chronic hepatitis C in patients not previously treated with interferon alpha who have compensated liver disease and are at least 18 years of age. | 57759 |
| Pegvisomant | Somavert ™ (Pfizer Inc) | Anabolic Agents; Hormone Replacement Agents | For treatment of acromegaly | 71500 |
| Pentoxifylline | | | | |
| Perindozril | | ACE Inhibitors | | |
| PI3K Inhibitor | | Inhibitor of Phosphatidylinositol 3-kinases (PI 3-kinases or PI3Ks) | Inhibit a family of enzymes involved in cellular functions such as cell growth, proliferation, differentiation, motility, and survival | |
| Pimecrolimus | | Limus Immunophilin Binding Compounds | | |
| PKC (protein kinase C) inhibitors | | | | |
| POT-4 | Potentia/Alcon | Complement Cascade Inhibitor (Factor C3) | AMD | |
| Pramlintide | Symlin ™; Symlin ™ (Amylin Pharmaceuticals) | | For the mealtime treatment of Type I and Type II diabetes in combination with standard insulin therapy, in patients who have failed to achieve adequate glucose control on insulin monotherapy. Proteosome inhibitors | 16988 |
| Proteosome inhibitors | Velcade ™ | | | |
| Pyrrolidine | | | | |
| Quinopril | | ACE Inhibitors | | |
| Ranibizumab | Lucentis ™ | | For the treatment of patients with neovascular (wet) age-related macular degeneration. | 27043 |
| Rapamycin (siroliums) | (MacuSight) | Limus Immunophilin Binding Compounds | AMD | |
| Rasburicase | Elitek ™; Elitek ™ (Sanofi-Synthelabo Inc); Fasturtec ™ | Antihyperuricemic Agents | For treatment of hyper uricemia, reduces elevated plasma uric acid levels (from chemotherapy) | 168.11 |
| Reteplase | Retavase ™ (Centocor); Retavase ™ (Roche) | Thrombolytic Agents | For lysis of acute pulmonary emboli, intracoronary emboli and management of myocardial infarction | 54732 |
| Retinal stimulant | Neurosolve ™ (Vitreoretinal Technologies) | Retinal stimulants | AMD | |
| Retinoid(s) | | | | |
| Rituximab | MabThera ™; Rituxan ™ | Antineoplastic Agents | For treatment of B-cell non-Hodgkins lymphoma (CD20 positive) | 33078 |
| RNAI (RNA interference of angiogenic factors) | | | | |
| Rofecoxib | Vioxx ™; Ceoxx ™; Ceeoxx ™ (Merck & Co.) | Cyclooxygenase Inhibitors | | |

APPENDIX I-continued

Therapeutic Agent List

| Generic Name | Brands (Companies) | Category | Indication | Molecular Weight |
|---|---|---|---|---|
| Rosiglitazone | | Thiazolidinediones | | |
| Ruboxistaurin | Eli Lilly | Protein Kinase C (PKC)-b Inhibitor | DME, diabetic peripheral retinopathy | 469 |
| Salmon Calcitonin | Calcimar ™; Miacalcin ™ (Novartis) | Antihypocalcemic Agents; Antiosteporotic Agents; Bone Density Conservation Agents | For the treatment of post-menopausal osteoporosis | 57304 |
| Sargramostim | Immunex ™; Leucomax ™ (Novartis); Leukine ™; Leukine ™ (Berlex Laboratories Inc) | Anti-Infective Agents; Antineoplastic Agents; Immunomodulatory Agents | For the treatment of cancer and bone marrow transplant | 46207 |
| SAR 1118 | SARCode | Immunomodulatory Agent | Dry eye, DME, conjunctivitis | |
| SDZ-RAD | | Limus Immunophilin Binding Compounds | | |
| Secretin | SecreFlo ™; Secremax ™, SecreFlo ™ (Repligen Corp) | Diagnostic Agents | For diagnosis of pancreatic exocrine dysfunction and gastrinoma | 50207 |
| Selective inhibitor of the factor 3 complement cascade | | | | |
| Selective inhibitor of the factor 5 complement cascade | | | | |
| Semaxanib | | Tyrosine Kinase Inhibitors | | 238 |
| Sermorelin | Geref ™ (Serono Pharma) | Anabolic Agents; Hormone Replacement Agents | For the treatment of dwarfism, prevention of HIV-induced weight loss | 47402 |
| Serum albumin iodinated | Megatope ™ (IsoTex Diagnostics) | Imaging Agents | For determination of total blood and plasma volumes | 39000 |
| SF1126 | Semafore | PI3k/mTOR Inhibition | AMD, DME | |
| Sirolimus re-formulation (rapamycin) | (MacuSight) | Limus Immunophilin Binding Compounds | AMD | |
| siRNA molecule synthetic, FTP-801i-14 | (Quark Pharmaceuticals) | siRNA molecule synthetic | AMD | |
| Somatropin recombinant | BioTropin ™ (Biotech General); Genotropin ™ (Pfizer); Humatrope ™ (Eli Lilly); Norditropin ™ (Novo Nordisk); Nutropin ™ (Genentech Inc.); NutropinAQ ™ (Genentech Inc.); Protropin ™ (Genentech Inc.); Saizen ™ (Serono SA); Serostim ™; Serostim ™ (Serono SA); Tev-Tropin ™ (GATE) | Anabolic Agents; Hormone Replacement Agents | For treatment of dwarfism, acromegaly and prevention of HIV-induced weight loss | 71500 |
| Squalamine | | | | |
| Streptokinase | Streptase ™ (Aventis Behringer GmbH) | Thrombolytic Agents | For the treatment of acute evolving transmural myocardial infarction, pulmonary embolism, deep vein thrombosis, arterial thrombosis or embolism and occlusion of arteriovenous cannulae | 90569 |
| Sunitinib | | Tyrosine Kinase Inhibitors | | 398 |
| TA106 | Taligen | Complement Cascade Inhibitor (Factor B) | AMD | |
| Tacrolimus | | Limus Immunophilin Binding Compounds | | |

APPENDIX I-continued

Therapeutic Agent List

| Generic Name | Brands (Companies) | Category | Indication | Molecular Weight |
|---|---|---|---|---|
| Tenecteplase | TNKase ™ (Genentech Inc) | Thrombolytic Agents | For treatment of myocardial infarction and lysis of intracoronary emboli | 54732 |
| Teriparatide | Apthela ™; Forsteo ™; Forteo ™; Fortessa ™; Opthia ™; Optia ™; Optiah ™; Zalectra ™; Zelletra ™ | Bone Density Conservation Agents | For the treatment of osteoporosis in men and postmenopausal women who are at high risk for having a fracture. Also used to increase bone mass in men with primary or hypogonadal osteoporosis who are at high risk for fracture. | 66361 |
| Tetrathiomolybdate | | | | |
| Thalidomide | Celgene | Anti-inflammatory, Anti-proliferative | Uveitis | |
| Thyrotropin Alfa | Thyrogen ™ (Genzyme Inc) | Diagnostic Agents | For detection of residual or recurrent thyroid cancer | 86831 |
| Tie-1 and Tie-2 kinase inhibitors | | | | |
| Toceranib | | Tyrosine Kinase Inhibitors | | 396 |
| Tositumomab | Bexxar ™ (Corixa Corp) | Anti-neoplastic Agents | For treatment of non-Hodgkin's lymphoma (CD20 positive, follicular) | 33078 |
| TPN 470 analogue | | | | |
| Trastuzumab | Herceptin ™ (Genentech) | Anti-neoplastic Agents | For treatment of HER2-positive pulmonary breast cancer | 137912 |
| Triamcinolone acetonide | Triesence ™ | Glucocorticoid | DME, For treatment of inflammation of the retina | 435 |
| Troglitazone | | Thiazolidinediones | | |
| Turnistatin | | | | |
| Urofollitropin | Fertinex ™ (Serono S.A.) | Fertility Agents | For treatment of female infertility | 78296 |
| Urokinase | Abbokinase ™; Abbokinase ™ (Abbott Laboratories) | Thrombolytic Agents | For the treatment of 163ulmonary embolism, coronary artery thrombosis and IV catheter clearance | 90569 |
| Vandetanib | | Tyrosine Kinase Inhibitors | | 475 |
| Vasopressin | Pitressin ™; Pressyn ™ | Anti-diuretics; Oxytocics; Vaso-constrictor Agents | For the treatment of enuresis, polyuria, diabetes insipidus, polydipsia and oesophageal varices with bleeding | 46800 |
| Vatalanib VEGF receptor kinase inhibitor | | Tyrosine Kinase Inhibitors | | 347 |
| VEGF Trap | Aflibercept ™ (Regneron Pharmaceuticals, Bayer HealthCare AG) | Genetically Engineered Antibodies | DME, cancer, retinal vein occlusion, choroidal neo, vascularization, delay wound healing, cancer treatment | 96600 |
| Visual Cycle Modulator ACU-4229 | (Acucela) | Visual Cycle Modulator | AMD | |
| Vitamin(s) | | | | |
| Vitronectin receptor antagonists | | | | |
| Volociximab | Ophthotech | alpha5beta1 Integrin Inhibitor | AMD | |
| XL765 | Exelixis/ Sanofi-Aventis | Pl3k/ mTOR Inhibition | AMD, DME | |

TABLE 1

List of analytes detected in pathological aqueous samples (pre-treatment) and after intravitreal bevacizumab injection (post-treatment), suitable for use as a marker in accordance with embodiments.

| Analyte | Units | Pre-treatment mean | Pre-treatment SD | Post-treatment mean | Post-treatment SD | MW (kDa) | Pre-treatment mean/Post-treatment mean |
|---|---|---|---|---|---|---|---|
| Alpha-1 Antitrypsin | mg/ml | 0.0022 | 0.0012 | 0.0025 | 0.0011 | 49-54 | 0.9 |

TABLE 1-continued

List of analytes detected in pathological aqueous samples (pre-treatment) and after intravitreal bevacizumab injection (post-treatment), suitable for use as a marker in accordance with embodiments.

| Analyte | Units | Pre-treatment mean | Pre-treatment SD | Post-treatment mean | Post-treatment SD | MW (kDa) | Pre-treatment mean/Post-treatment mean |
|---|---|---|---|---|---|---|---|
| Alpha-Fetoprotein | ng/ml | 0.2626 | 0.0569 | 0.2790 | 0.0636 | 69 | 0.9 |
| Apolipoprotein A1 | mg/ml | 0.0007 | 0.0008 | 0.0004 | 0.0004 | 28 | 1.8 |
| Apolipoprotein CIII | ug/ml | 0.0424 | 0.0188 | 0.0259 | 0.0032 | 8-11 | 1.6 |
| Apolipoprotein H | ug/ml | 0.8176 | 0.7303 | 0.6400 | 0.5762 | 40-100 | 1.3 |
| Beta-2 Microglobulin | ug/ml | 0.4088 | 0.3180 | 0.3026 | 0.1879 | 12 | 1.4 |
| C Reactive Protein | ug/ml | 0.1114 | 0.1521 | 0.0477 | 0.0514 | 23 Subunit 118-140 Aggregates | 2.3 |
| Cancer Antigen 125 | U/ml | 1.7363 | 0.4314 | 1.7225 | 0.3476 | 200-2500 | 1.0 |
| Cancer Antigen 19-9 | U/ml | 0.2952 | 0.1282 | 0.2042 | 0.1177 | — | 1.4 |
| CD40 | ng/ml | 0.0676 | 0.0598 | 0.0510 | 0.0334 | 48 | 1.3 |
| Complement 3 | mg/ml | 0.0013 | 0.0007 | 0.0014 | 0.0010 | 185 | 0.9 |
| Endothelin-1 | pg/ml | 5.4863 | 1.7494 | 5.2375 | 0.6159 | 2.5 | 1.0 |
| Eotaxin | pg/ml | 17.7750 | 4.6849 | 13.5813 | 5.1661 | 8 | 1.3 |
| Erythropoietin | pg/ml | 120.5875 | 125.032 | 111.6125 | 130.0555 | 18-45 | 1.1 |
| FGF basic | pg/ml | 52.2375 | 18.8596 | 30.8900 | 20.8668 | 16-24 | 1.7 |
| Fibrinogen | mg/ml | 0.0011 | 0.0018 | 0.0005 | 0.0005 | 330-540 | 2.2 |
| G-CSF | pg/ml | 17.2825 | 31.2826 | 3.6748 | 2.8391 | 18-30 | 4.7 |
| Glutathione S-Transferase | ng/ml | 0.1406 | 0.0164 | 0.1544 | 0.0154 | 23-55 | 0.9 |
| Haptoglobin | mg/ml | 0.0005 | 0.0005 | 0.0004 | 0.0005 | 85-180 | 1.3 |
| IgA | mg/ml | 0.0014 | 0.0011 | 0.0015 | 0.0016 | 17-160 370-1000 Aggregate | 0.9 |
| IGF-1 | ng/ml | 1.4248 | 0.7489 | 1.4285 | 0.8083 | 7-8 | 1.0 |
| IgM | mg/ml | 0.0013 | 0.0012 | 0.0009 | 0.0008 | 900 | 1.4 |
| IL-6 | pg/ml | 120.2543 | 293.001 | 15.2016 | 19.9646 | 20-30 150 Bound to sIL-GR | 7.9 |
| IL-8 | pg/ml | 22.9475 | 30.8635 | 14.9900 | 9.5664 | 8-10 | 1.5 |
| Leptin | ng/ml | 0.3806 | 0.5658 | 0.2131 | 0.3830 | 16 | 1.8 |
| MCP-1 | pg/ml | 638.0000 | 618.982 | 438.3750 | 263.5244 | 4-10 | 1.5 |
| MIP-1alpha | pg/ml | 10.3625 | 3.0867 | 9.4175 | 2.4535 | Low MW Cytokine | 1.1 |
| MIP-1beta | pg/ml | 24.8738 | 20.2587 | 21.7988 | 14.5772 | Low MW Cytokine | 1.1 |
| MMP-3 | ng/ml | 0.6362 | 1.2937 | 0.6159 | 0.4960 | 45 | 1.0 |
| PAPP-A | U/ml | 0.0526 | 0.0558 | 0.0432 | 0.0306 | 187 750-820 | 1.2 |
| Prostate Specific Antigen, Free | ng/ml | 0.0169 | 0.0066 | 0.0092 | | 28-34 96 Complexed PSA | 1.8 |
| Prostatic Acid Phosphatase | ng/ml | 0.0260 | 0.0273 | 0.0095 | 0.0054 | 50 | 2.7 |
| Serum Amyloid P | ug/ml | 0.0287 | 0.0303 | 0.0134 | 0.0081 | 25 | 2.1 |
| SGOT | ug/ml | 1.8149 | 0.6531 | 1.3488 | 0.3111 | 47 | 1.3 |
| SHBG | nmol/l | 0.5133 | 0.3151 | 0.2250 | 0.0866 | 52-90 | 2.3 |
| Stem Cell Factor | pg/ml | 19.9938 | 6.1891 | 19.4375 | 2.5757 | 18-21 | 1.0 |
| Thyroid Stimulating Hormone | U/ml | 0.0293 | 0.0252 | 0.0188 | 0.0107 | 26-30 | 1.6 |
| Thyroxine Binding Globulin | ug/ml | 0.6370 | 0.6607 | 0.3876 | 0.3822 | 61 | 1.6 |
| TIMP-1 | ng/ml | 30.9825 | 29.6818 | 22.3825 | 14.6893 | 28 | 1.4 |
| Tissue Factor | ng/ml | 0.3724 | 0.0820 | 0.3631 | 0.0698 | 31 Nonglycosylated 46 Glycosylated | 1.0 |

TABLE 1-continued

List of analytes detected in pathological aqueous samples (pre-treatment) and after intravitreal bevacizumab injection (post-treatment), suitable for use as a marker in accordance with embodiments.

| Analyte | Units | Pre-treatment mean | Pre-treatment SD | Post-treatment mean | Post-treatment SD | MW (kDa) | Pre-treatment mean/Post-treatment mean |
|---|---|---|---|---|---|---|---|
| VEGF | pg/ml | 679.6250 | 299.134 | 484.1250 | 346.3955 | 34 | 1.4 |
| | | | | | | 45 VEGF-165 | |
| ICAM-1 | ng/ml | 0.7900 | 0.7117 | 0.6971 | 0.4189 | 80-144 | 1.1 |
| | | | | | | Depending on Glycosylation | |
| | | | | | | 200 Native Dimer | |
| IL-7 | pg/ml | 11.4175 | 1.5109 | 12.3125 | 1.1753 | 17 | 0.9 |
| | | | | | | 25 Glycosylated | |

APPENDIX II

HUGO Symbols:
http://www.genenames.org/data/hgnc_data.php?hgnc_id=2367

CRP

| | |
|---|---|
| Approved Symbol± | CRP |
| Approved Name± | C-reactive protein, pentraxin-related |
| HGNC ID± | HGNC: 2367 |
| Previous Symbols & Names± | — |
| Synonyms± | "pentraxin 1", PTX1 |
| Locus Type± | gene with protein product |
| Chromosomal Location± | 1q21-q23 |

FGA

| | |
|---|---|
| Approved Symbol± | FGA |
| Approved Name± | fibrinogen alpha chain |
| HGNC ID± | HGNC: 3661 |
| Previous Symbols & Names± | "fibrinogen, A alpha polypeptide" |
| Synonyms± | — |
| Locus Type± | gene with protein product |
| Chromosomal Location± | 4q28 |

CSF3

| | |
|---|---|
| Approved Symbol± | CSF3 |
| Approved Name± | colony stimulating factor 3 (granulocyte) |
| HGNC ID± | HGNC: 2438 |
| Previous Symbols & Names± | C17orf33, "chromosome 17 open reading frame 33", G-CSF, GCSF |
| Synonyms± | "filgrastim", "granulocyte colony stimulating factor", "lenograstim", MGC45931, "pluripoietin" |
| Locus Type± | gene with protein product |
| Chromosomal Location± | 17q11.2-q12 |

VEGFA

| | |
|---|---|
| Approved Symbol± | VEGFA |
| Approved Name± | vascular endothelial growth factor A |
| HGNC ID± | HGNC: 12680 |
| Previous Symbols & Names± | "vascular endothelial growth factor", VEGF |
| Synonyms± | VEGF-A, VPF |
| Locus Type± | gene with protein product |
| Chromosomal Location± | 6p12 |

IL6

| | |
|---|---|
| Approved Symbol± | IL6 |
| Approved Name± | interleukin 6 (interferon, beta 2) |
| HGNC ID± | HGNC: 6018 |
| Previous Symbols & Names± | IFNB2 |

APPENDIX II-continued

HUGO Symbols:
http://www.genenames.org/data/hgnc_data.php?hgnc_id=2367

| | |
|---|---|
| Synonyms± | BSF2, HGF, HSF, IL-6 |
| Locus Type± | gene with protein product |
| Chromosomal Location± | 7p21-p15 |

SHBG

| | |
|---|---|
| Approved Symbol± | SHBG |
| Approved Name± | sex hormone-binding globulin |
| HGNC ID± | HGNC: 10839 |
| Previous Symbols & Names± | — |
| Synonyms± | ABP, "androgen binding protein", MGC126834, MGC138391, TEBG |
| Locus Type± | gene with protein product |
| Chromosomal Location± | 17pter-p12 |

What is claimed is:

1. An apparatus for collecting a sample of fluid from a reservoir chamber of a therapeutic device having a porous structure and configured to be implanted in an eye of a patient, the apparatus comprising:
 a cartridge comprising:
  a connector for coupling the cartridge to a syringe, the cartridge being arranged to contain therapeutic agent;
 at least one needle extending along a longitudinal axis and being operable to penetrate the implanted therapeutic device, wherein the at least one needle comprises a first lumen and a second lumen, the first lumen arranged to allow an amount of the therapeutic agent to be injected from the syringe through the first lumen into the reservoir chamber of the implanted therapeutic device;
 a visual indicator coupled to a depth stop to guide depth of penetration of the at least one needle within the reservoir chamber, wherein the visual indicator is coaxial with the longitudinal axis of the at least one needle; and
 a container coupled to the cartridge and in fluid communication with the second lumen extending through the at least one needle, the container configured to be at atmospheric pressure during use, wherein the second lumen is arranged to allow the sample of fluid to be displaced from the reservoir chamber through the second lumen into the container at the same time as the amount of therapeutic agent is injected from the syringe through the first lumen into the reservoir chamber, the container arranged to collect the displaced sample of fluid for use in one or more analyses, the container comprising a window for viewing a level of the displaced sample of fluid in the container.

2. The apparatus of claim 1, wherein the porous structure releases the therapeutic agent via diffusion out from the reservoir chamber.

3. The apparatus of claim 2, wherein the sample of fluid displaced from the reservoir chamber comprises:
liquid from the eye comprising one or more markers of the eye accumulated in the reservoir chamber through the porous structure over a period of time; and
a therapeutic agent formulation remaining in the reservoir chamber after the period of time, the therapeutic agent formulation comprising one or more non-pharmacologic components and an amount of the therapeutic agent.

4. The apparatus of claim 3, wherein the liquid from the eye comprises an aqueous humor or a vitreous humor fluid from the eye.

5. The apparatus of claim 4, wherein the one or more non-pharmacologic components comprises one or more of a marker to measure device function, a salt, a surfactant, a stabilizer, or a particle.

6. The apparatus of claim 3, wherein the therapeutic agent comprises one or more compounds of 2-Methoxyestradiol analogs, 3-aminothalidomide, 13-cis retinoic acid, A0003, A5b1 integrin inhibitor, Abarelix, Abatacept, Abciximab, ABT-578, Acetonide, Adalimumab, Aldesleukin, Alefacept, Alemtuzumab, Alpha-1-proteinase inhibitor, Alteplase, AMG-1470, Anakinra, Anecortave acetate, Angiostatin, Anistreplase, Anti-angiogenesis peptides, Anti-angiogenesis antibodies, TRC093, TRC 105, Anti-angiogeric bifunctional protein, Anti-endothelial growth factor, Antihemophilic Factor, Antithymocyte globulin, Anti-hypertensive MC1101, Anti-platelet derived growth factor, Anti-VEGF, AP23841, ARC1905 (Complement Cascade Inhibitor Factor C5), Aprotinin, Arcitumomab, Asparaginase, Axitinib, Basiliximab, Becaplermin, Bevacizumab, Bivalirudin, Bortezomib, Bosutinib, Botulinum Toxin Type A, Botulinum Toxin Type B, C5 inhibitor, Cal 101 (PI3K Delta Inhibitor), Canstatin, Capromab, Captopril, CCI-779, Cediranib, Celecoxib, Cetrorelix, Cetuximab, Choriogonadotropin alfa, Cilary neurotrophic factor, Coagulation Factor IX, Coagulation factor VIIa, Colchicines, Collagenase, Complement factor H recombinant, Compstatin derivative peptide, POT-4, Corticotropin, Cosyntropin, Cyclophilins, Cyclosporine, Daclizumab, Darbepoetin alfa, Dasatinib, Defibrotide, Denileukin diftitox, Desmopressin, Dexamethasone, Diclofenac, Dithiocarbamate, Dornase Alfa, Drotrecogin alfa, Eculizumab, Efalizumab, Endostatin, Enfuvirtide, Epoetin alfa, Eptifibatide, Erlotinib, Etanercept, Everolimus, Exenatide, FCFD4514S (Complement Cascade Inhibitor Factor D), Felypressin, Fenretinide, Filgrastim, FK605-binding proteins, FKBPs, Fluocinolone Acetonide, Follitropin beta, Fumagillin, Galsulfase, Gefitinib, Gemtuzumab ozogamicin, Glatiramer Acetate, Glucagon recombinant, Goserelin, Human Serum Albumin, Hyaluronidase, Ibritumomab, Idursulfase, Imatinib, Immune globulin, Infliximab, Insulin Glargine recombinant, Insulin Lyspro recombinant, Insulin, Interferon, Interferon Alfa-2a, Interferon Alfa-2b, Interferon alfacon-1, Interferon alfa-n1, Interferon alfa-n3, Interferon beta-1b, Interferon gamma-1b, Lapatinib, Lepirudin, Lestaurtinib, Leuprolide, Lutropin alfa, Mecasermin, Menotropins, Methotrexate, mTOR inhibitors, Muromonab, Natalizumab, Nepafenac, Nesiritide, Nilotinib, NS398, Octreotide, Omalizumab, Oprelvekin, OspA lipoprotein, OT-551, Oxytocin, Palifermin, Palivizumab, Panitumumab, PDGF inhibitor, PEDF (pigment epithelium derived factor), Pegademase bovine, Pegaptanib, Pegaspargase, Pegfilgrastim, Peginterferon alfa-2a, Peginterferon alfa-2b, Pegvisomant, Pentoxifylline, Perindozril, Pimecrolimus, PKC (protein kinase C) inhibitors, Pramlintide, Proteosome inhibitors, Pyrrolidine, Quinopril, Ranibizumab, Rapamycin (siroliums), Rasburicase, Reteplase, Retinal stimulant, Retinoid(s), Rituximab, RNAI (RNA interference of angiogenic factors), Rofecoxib, Rosiglitazone, Ruboxistaurin, Salmon Calcitonin, Sargramostim, SDZ-RAD, Secretin, Selective inhibitor of the factor 3 complement cascade, Selective inhibitor of the factor 5 complement cascade, Semaxanib, Sermorelin, Serum albumin iodinated, Sirolimus reformulation (rapamycin), siRNAi molecule synthetic FTP-801i-14, Somatropin recombinant, Squalamine, Streptokinase, Sunitinib, Complement Cascade Inhibitor (Factor B), Tacrolimus, Tenecteplase, Teriparatide, Tetrathiomolybdate, Thalidomide, Thyrotropin Alfa, Tie-1 and Tie-2 kinase inhibitors, Toceranib, Tositumomab, TPN 470 analogue, Trastuzumab, Triamcinolone acetonide, Troglitazone, Tumistatin, Urofollitropin, Urokinase, Vandetanib, Vasopressin, Vatalanib, VEGF receptor kinase inhibitor, VEGF Trap, Visual Cycle Modulator ACU-4229, Vitamin(s), Vitronectin receptor antagonists, or Volociximab.

7. The apparatus of claim 3, wherein the component comprises one or more markers of the eye to determine effectiveness treatment of a disease with a therapeutic agent, wherein the one or more markers is selected from the group consisting of one or more of a genetic marker, genomic expression of a marker, a protein marker, a protein biomarker of ocular disease, a biomarker having a linkage to an ocular disease, a biomarker having a linkage to AMD, a biomarker associated with AMD, a biomarker corresponding to a conversion from dry AMD to wet AMD, a biomarker comprising an early predictor of conversion of wet AMD to dry AMD, a complement cascade member, complement H factor (CFH), complement factor B (CFB), complement component 2 (C2), complement component 3 (C3), complement component 5 (C5) complement component 5a (C5a), C5b-9, a marker of expression of pro-inflammatory cytokines, TNF, tissue necrosis factor alpha, a marker of angiogenesis and vascular leakage, VEGF, CEP, IL-6, G-CSF, Serum Amyloid A, I CAM-1, Leptin, Glucose, lactose, C-reactive protein, PEDF, PDGF, IFG, interferon gamma, interleukin 1-beta, and IL-8.

8. The apparatus of claim 1, wherein the displaced sample of fluid comprises aqueous humor or vitreous humor fluid accumulated within the reservoir chamber from the eye through the porous structure.

9. The apparatus of claim 1, wherein the displaced sample of fluid from the reservoir chamber comprises a component accumulated within the reservoir chamber from the eye through the porous structure.

10. The apparatus of claim 9, wherein the component comprises one or more markers of the eye to determine effectiveness treatment of a disease with a therapeutic agent, wherein the one or more markers is selected from the group consisting of one or more of a genetic marker, genomic expression of a marker, a protein marker, a protein biomarker of ocular disease, a biomarker having a linkage to an ocular disease, a biomarker having a linkage to AMD, a biomarker associated with AMD, a biomarker corresponding to a conversion from dry AMD to wet AMD, a biomarker comprising an early predictor of conversion of wet AMD to dry AMD, a complement cascade member, complement H factor (CFH), complement factor B (CFB), complement component 2 (C2), complement component 3 (C3), complement component 5 (C5) complement component 5a (C5a), C5b-9, a marker of expression of pro-inflammatory cytokines, TNF, tissue necrosis factor alpha, a marker of angiogenesis and vascular leakage, VEGF, CEP, IL-6, G-CSF, Serum Amyloid A, I CAM-1, Leptin, Glucose, lactose, C-reactive protein, PEDF, PDGF, IFG, interferon gamma, interleukin 1-beta, and IL-8.

11. The apparatus of claim 1, wherein the container further comprises a penetrable barrier to access the sample of fluid contained within the container.

12. The apparatus of claim 1, where the container is detachable to release the container from the cartridge.

13. The apparatus of claim 12, further comprising a support comprising the connector to couple to the syringe, the support further comprising a second connector to couple to the container.

14. The apparatus of claim 12, wherein the cartridge further comprises an identifier coupled to the container and corresponding to data identifying the container and the patient from which the sample of fluid is collected.

15. The apparatus of claim 14, wherein the identifier comprises one or more of an optical pattern, a bar code, a one-dimensional bar code, a two-dimensional bar code, an RFID, or a magnetic code.

16. The apparatus of claim 1, further comprising a porous vent structure coupled to a proximal, downstream end of the container, the porous vent structure configured to allow air to pass through the porous vent structure while preventing liquid from passing through the porous vent structure upon being wetted by the displaced sample of fluid.

17. The apparatus of claim 1, wherein the visual indicator is formed of a deformable material.

18. The apparatus of claim 17, wherein the deformable material comprises silicone having a Shore A hardness between 5 Shore A and 30 Shore A.

* * * * *